US011680279B2

(12) United States Patent
Mijts et al.

(10) Patent No.: US 11,680,279 B2
(45) Date of Patent: Jun. 20, 2023

(54) METHOD FOR PRODUCING OBJECTIVE SUBSTANCE

(71) Applicant: AJINOMOTO CO., INC., Tokyo (JP)

(72) Inventors: Benjamin Mijts, San Carlos, CA (US); Christine Roche, Berkeley, CA (US); Rekha Murali, San Francisco, CA (US); Sayaka Asari, Kanagawa (JP); Keita Fukui, Kanagawa (JP); Miku Toyazaki, Kanagawa (JP); Keiko Noguchi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 574 days.

(21) Appl. No.: 16/200,011

(22) Filed: Nov. 26, 2018

(65) Prior Publication Data

US 2019/0161776 A1 May 30, 2019

Related U.S. Application Data

(60) Provisional application No. 62/591,910, filed on Nov. 29, 2017.

(51) Int. Cl.
| | |
|---|---|
| *C12P 13/12* | (2006.01) |
| *C12P 7/24* | (2006.01) |
| *C12N 9/10* | (2006.01) |
| *C12N 9/06* | (2006.01) |
| *C12P 7/42* | (2006.01) |
| *C12N 1/20* | (2006.01) |
| *C12R 1/15* | (2006.01) |
| *C12R 1/19* | (2006.01) |
| *C12R 1/46* | (2006.01) |

(52) U.S. Cl.
CPC .............. *C12P 7/24* (2013.01); *C12N 1/205* (2021.05); *C12N 9/0012* (2013.01); *C12N 9/1014* (2013.01); *C12N 9/1085* (2013.01); *C12P 7/42* (2013.01); *C12P 13/12* (2013.01); *C12R 2001/15* (2021.05); *C12R 2001/19* (2021.05); *C12R 2001/46* (2021.05); *C12Y 105/0102* (2013.01); *C12Y 201/02002* (2013.01); *C12Y 205/01006* (2013.01)

(58) Field of Classification Search
CPC .................................. C12P 13/12; C12P 7/24
See application file for complete search history.

(56) References Cited

U.S. PATENT DOCUMENTS

| | | | |
|---|---|---|---|
| 5,128,253 A | | 7/1992 | Labuda et al. |
| 6,372,461 B1 | | 4/2002 | Frost |
| 2006/0068476 A1 | | 3/2006 | Kroger et al. |
| 2007/0026505 A1 | * | 2/2007 | Madden ................ C07K 14/24 435/106 |
| 2009/0298136 A1 | | 12/2009 | Zelder et al. |
| 2014/0245496 A1 | * | 8/2014 | Hansen ................ A23L 33/105 514/35 |
| 2015/0225755 A1 | * | 8/2015 | Liu ....................... C07D 233/42 548/324.1 |
| 2015/0267227 A1 | | 9/2015 | Lindberg Moller et al. |
| 2016/0230200 A1 | * | 8/2016 | Zhu ....................... C12N 9/0006 |
| 2019/0161776 A1 | * | 5/2019 | Mijts ....................... C12N 1/205 |

FOREIGN PATENT DOCUMENTS

| | | |
|---|---|---|
| JP | 2009-501550 A | 1/2009 |
| JP | 2015-535181 A | 12/2015 |
| WO | WO2004/024931 A2 | 3/2004 |
| WO | WO2004/024931 A3 | 3/2004 |
| WO | WO2004/111254 A1 | 12/2004 |
| WO | WO2006/138689 A2 | 12/2006 |
| WO | WO2006/138689 A3 | 12/2006 |
| WO | WO2013/022881 A1 | 2/2013 |
| WO | WO2014100752 A1 | 6/2014 |
| WO | WO2014/106189 A2 | 7/2014 |
| WO | WO2014/106189 A3 | 7/2014 |
| WO | WO2015/032911 A1 | 3/2015 |
| WO | WO2017/073701 A2 | 5/2017 |

OTHER PUBLICATIONS

UniProt Accession No. METK_CORGL, published Oct. 1, 2000 (Year: 2000).*
Ruckert et al., "The dual transcriptional regulator CysR in Corynebacterium glutamicum ATCC 13032 controls a subset of genes of the McbR regulon in response to the availability of sulphide acceptor molecules", BMC Genomics, 2008, 9: 483 (Year: 2008).*
Venkitasubramanian et al., "Aldehyde oxidoreductase as a biocatalyst: reductions of vanillic acid", Enzyme and Microbial Technology, vol. 42, pp. 130-137, 2008 (Year: 2008).*
Kaur, B., et al., "Biotechnological and Molecular Approaches for Vanillin Production: a Review," Appl. Biochem. Biotechnol. 2013;169:1353-1372.
Extended European Search Report for European Patent App. No. 18209161.1 (dated Sep. 18, 2019).
Kunjapur, A. M., et al., "Deregulation of S-adenosylmethionine biosynthesis and regeneration improves methylation in the E. coli de novo vanillin biosynthesis pathway," Microb. Cell Fact. 2016;15(61):1-17.
Dopy of Partial European Search Report for European Patent App. No. 18209161.1 (May 22, 2019).
Han, G., et al, "Overexpression of methionine adenosyltransferase in Corynebacterium for production of S-adenosyl-L methionine," Biotechnical Appl. Biochem. 2015; 63(5); 679-689.

(Continued)

*Primary Examiner* — Tekchand Saidha
(74) *Attorney, Agent, or Firm* — Cermak Nakajima & McGowan LLP; Shelly Guest Cermak

(57) ABSTRACT

A method for producing an objective substance such as vanillin and vanillic acid is provided. An objective substance is produced from a carbon source or a precursor of the objective substance by using a microorganism that is able to produce the objective substance, which microorganism has been modified so that the activity of an enzyme involved in SAM cycle (SAM cycle enzyme) is increased.

21 Claims, No Drawings
Specification includes a Sequence Listing.

(56) References Cited

OTHER PUBLICATIONS

Wang, Y., et al., "Improving heterologous polyketide Production in *Escherichia coli* by overexpression of an S-adenosylmethionine synthetase gene," Appl. Microbiol. Biotechnol. 2007;77:367-373.

Han, G., et al., "Overexpression of methionine adenosyltransferase in Corynebacterium glutamicum for production of S-adenosyl- L methionine," Biotechnology Appl. Biochem. 2015; 63(5); 679-689.

Rückert, C. et al.; "Genome-wide Analysis of the L-methionine Biosynthetic Pathway in Corynebacterium Glutamicum by Targeted Gene Deletion and Homologous Complementation"; Journal of Biotechnology, 2003, vol. 104, p. 213-228.

* cited by examiner

SEQUENCE LISTING

<160> NUMBER OF SEQ ID NOS: 184

<210> SEQ ID NO 1
<211> LENGTH: 1053
<212> TYPE: DNA
<213> ORGANISM: Escherichia coli

<400> SEQUENCE: 1

| | | | | | |
|---|---|---|---|---|---|
| atgaattatc | agaacgacga | tttacgcatc | aaagaaatca | agagttact | tcctcctgtc | 60 |
| gcattgctgg | aaaaattccc | cgctactgaa | aatgccgcga | atacggttgc | ccatgcccga | 120 |
| aaagcgatcc | ataagatcct | gaaaggtaat | gatgatcgcc | tgttggttgt | gattggccca | 180 |
| tgctcaattc | atgatcctgt | cgcggcaaaa | gagtatgcca | ctcgcttgct | ggcgctgcgt | 240 |
| gaagagctga | aagatgagct | ggaaatcgta | atgcgcgtct | attttgaaaa | gccgcgtacc | 300 |
| acggtgggct | ggaaagggct | gattaacgat | ccgcatatgg | ataatagctt | ccagatcaac | 360 |
| gacggtctgc | gtatagcccg | taaattgctg | cttgatatta | cgacagcgg | tctgccagcg | 420 |
| gcaggtgagt | ttctcgatat | gatcacccca | caatatctcg | ctgacctgat | gagctggggc | 480 |
| gcaattggcg | cacgtaccac | cgaatcgcag | gtgcaccgcg | aactggcatc | agggctttct | 540 |
| tgtccggtcg | gcttcaaaaa | tggcaccgac | ggtacgatta | agtggctat | cgatgccatt | 600 |
| aatgccgccg | gtgcgccgca | ctgcttcctg | tccgtaacga | aatgggggca | ttcggcgatt | 660 |
| gtgaatacca | gcggtaacgg | cgattgccat | atcattctgc | gcggcggtaa | agagcctaac | 720 |
| tacagcgcga | agcacgttgc | tgaagtgaaa | gaagggctga | acaaagcagg | cctgccagca | 780 |
| caggtgatga | tcgatttcag | ccatgctaac | tcgtccaaac | aattcaaaaa | gcagatggat | 840 |
| gtttgtgctg | acgtttgcca | gcagattgcc | ggtggcgaaa | aggccattat | tggcgtgatg | 900 |
| gtggaaagcc | atctggtgga | aggcaatcag | agcctcgaga | gcggggagcc | gctggcctac | 960 |
| ggtaagagca | tcaccgatgc | ctgcatcggc | tgggaagata | ccgatgctct | gttacgtcaa | 1020 |
| ctggcgaatg | cagtaaaagc | gcgtcgcggg | taa | | | 1053 |

<210> SEQ ID NO 2
<211> LENGTH: 350
<212> TYPE: PRT
<213> ORGANISM: Escherichia coli

<400> SEQUENCE: 2

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe

```
                    130                 135                 140
Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 3
<211> LENGTH: 1089
<212> TYPE: DNA
<213> ORGANISM: Escherichia coli

<400> SEQUENCE: 3
atggagagga ttgtcgttac tctcggggaa cgtagttacc caattaccat cgcatctggt      60
ttgtttaatg aaccagcttc attcttaccg ctgaaatcgg gcgagcaggt catgttggtc     120
accaacgaaa ccctggctcc tctgtatctc gataaggtcc gcggcgtact gaacaggcg      180 ggtgttaacg tcgatagcgt tatcctccct gacggcgagc agtataaaag cctggctgta     240
ctcgataccg tctttacggc gttgttacaa aaaccgcatg gtcgcgatac tacgctggtg     300
gcgcttggcg cggcgtagt gggcgatctg accggcttcg cggcggcgag ttatcagcgc     360
ggtgtccgtt tcattcaagt cccgacgacg ttactgtcgc aggtcgattc tccgttggc      420 ggcaaaactg cggtcaacca tcccctcggt aaaaacatga ttggcgcgtt ctaccaacct     480
gcttcagtgg tggtggatct cgactgtctg aaaacgcttc ccccgcgtga gttagcgtcg     540
gggctggcag aagtcatcaa atacggcatt attcttgacg gtgcgttttt taactggctg     600
gaagagaatc tggatgcgtt gttgcgtctg acggtccgg caatggcgta ctgtattcgc      660
cgttgttgtg aactgaaggc agaagttgtc gccgccgacg agcgcgaaac cgggttacgt     720
gctttactga atctgggaca cacctttggt catgccattg aagctgaaat ggggtatggc     780
aattggttac atggtgaagc ggtcgctgcg ggtatggtga tggcggcgcg acgtcggaa      840 cgtctcgggc agtttagttc tgccgaaacg cagcgtatta taccctgctc aagcgggct     900
```

```
gggttaccgg tcaatgggcc gcgcgaaatg tccgcgcagg cgtatttacc gcatatgctg      960
cgtgacaaga aagtccttgc gggagagatg cgcttaattc ttccgttggc aattggtaag     1020
agtgaagttc gcagcggcgt ttcgcacgag cttgttctta acgccattgc cgattgtcaa     1080
tcagcgtaa                                                             1089
```

<210> SEQ ID NO 4
<211> LENGTH: 362
<212> TYPE: PRT
<213> ORGANISM: Escherichia coli

<400> SEQUENCE: 4

```
Met Glu Arg Ile Val Val Thr Leu Gly Glu Arg Ser Tyr Pro Ile Thr
1               5                   10                  15

Ile Ala Ser Gly Leu Phe Asn Glu Pro Ala Ser Phe Leu Pro Leu Lys
            20                  25                  30

Ser Gly Glu Gln Val Met Leu Val Thr Asn Glu Thr Leu Ala Pro Leu
        35                  40                  45

Tyr Leu Asp Lys Val Arg Gly Val Leu Glu Gln Ala Gly Val Asn Val
    50                  55                  60

Asp Ser Val Ile Leu Pro Asp Gly Glu Gln Tyr Lys Ser Leu Ala Val
65                  70                  75                  80

Leu Asp Thr Val Phe Thr Ala Leu Leu Gln Lys Pro His Gly Arg Asp
                85                  90                  95

Thr Thr Leu Val Ala Leu Gly Gly Gly Val Val Gly Asp Leu Thr Gly
            100                 105                 110

Phe Ala Ala Ala Ser Tyr Gln Arg Gly Val Arg Phe Ile Gln Val Pro
        115                 120                 125

Thr Thr Leu Leu Ser Gln Val Asp Ser Ser Val Gly Gly Lys Thr Ala
    130                 135                 140

Val Asn His Pro Leu Gly Lys Asn Met Ile Gly Ala Phe Tyr Gln Pro
145                 150                 155                 160

Ala Ser Val Val Val Asp Leu Asp Cys Leu Lys Thr Leu Pro Pro Arg
                165                 170                 175

Glu Leu Ala Ser Gly Leu Ala Glu Val Ile Lys Tyr Gly Ile Ile Leu
            180                 185                 190

Asp Gly Ala Phe Phe Asn Trp Leu Glu Glu Asn Leu Asp Ala Leu Leu
        195                 200                 205

Arg Leu Asp Gly Pro Ala Met Ala Tyr Cys Ile Arg Arg Cys Cys Glu
    210                 215                 220

Leu Lys Ala Glu Val Val Ala Ala Asp Glu Arg Glu Thr Gly Leu Arg
225                 230                 235                 240

Ala Leu Leu Asn Leu Gly His Thr Phe Gly His Ala Ile Glu Ala Glu
                245                 250                 255

Met Gly Tyr Gly Asn Trp Leu His Gly Glu Ala Val Ala Ala Gly Met
            260                 265                 270

Val Met Ala Ala Arg Thr Ser Glu Arg Leu Gly Gln Phe Ser Ser Ala
        275                 280                 285

Glu Thr Gln Arg Ile Ile Thr Leu Leu Lys Arg Ala Gly Leu Pro Val
    290                 295                 300

Asn Gly Pro Arg Glu Met Ser Ala Gln Ala Tyr Leu Pro His Met Leu
305                 310                 315                 320

Arg Asp Lys Lys Val Leu Ala Gly Glu Met Arg Leu Ile Leu Pro Leu
                325                 330                 335
```

```
Ala Ile Gly Lys Ser Glu Val Arg Ser Gly Val Ser His Glu Leu Val
            340                 345                 350

Leu Asn Ala Ile Ala Asp Cys Gln Ser Ala
        355                 360

<210> SEQ ID NO 5
<211> LENGTH: 759
<212> TYPE: DNA
<213> ORGANISM: Escherichia coli

<400> SEQUENCE: 5
atgaaaaccg taactgtaaa agatctcgtc attggtacgg gcgcacctaa aatcatcgtc      60
tcgctgatgg cgaaagatat cgccagcgtg aaatccgaag ctctcgccta tcgtgaagcg     120
gactttgata ttctggaatg gcgtgtggac cactatgccg acctctccaa tgtggagtct     180
gtcatggcgg cagcaaaaat tctccgtgag accatgccag aaaaaccgct gctgtttacc     240
ttccgcagtg ccaaagaagg cggcgagcag gcgatttcca ccgaggctta tattgcactc     300
aatcgtgcag ccatcgacag cggcctggtt gatatgatcg atctggagtt atttaccggt     360
gatgatcagg ttaaagaaac cgtcgcctac gcccacgcgc atgatgtgaa agtagtcatg     420
tccaaccatg acttccataa aacgccggaa gccgaagaaa tcattgcccg tctgcgcaaa     480
atgcaatcct tcgacgccga tattcctaag attgcgctga tgccgcaaag taccagcgat     540
gtgctgacgt tgcttgccgc gaccctggag atgcaggagc agtatgccga tcgtccaatt     600
atcacgatgt cgatggcaaa aactggcgta atttctcgtc tggctggtga agtatttggc     660
tcggcggcaa cttttggtgc ggtaaaaaaa gcgtctgcgc cagggcaaat ctcggtaaat     720
gatttgcgca cggtattaac tattttacac caggcataa                           759

<210> SEQ ID NO 6
<211> LENGTH: 252
<212> TYPE: PRT
<213> ORGANISM: Escherichia coli

<400> SEQUENCE: 6

Met Lys Thr Val Thr Val Lys Asp Leu Val Ile Gly Thr Gly Ala Pro
1               5                  10                  15

Lys Ile Ile Val Ser Leu Met Ala Lys Asp Ile Ala Ser Val Lys Ser
            20                  25                  30

Glu Ala Leu Ala Tyr Arg Glu Ala Asp Phe Asp Ile Leu Glu Trp Arg
        35                  40                  45

Val Asp His Tyr Ala Asp Leu Ser Asn Val Glu Ser Val Met Ala Ala
    50                  55                  60

Ala Lys Ile Leu Arg Glu Thr Met Pro Glu Lys Pro Leu Leu Phe Thr
65                  70                  75                  80

Phe Arg Ser Ala Lys Glu Gly Gly Glu Gln Ala Ile Ser Thr Glu Ala
                85                  90                  95

Tyr Ile Ala Leu Asn Arg Ala Ala Ile Asp Ser Gly Leu Val Asp Met
            100                 105                 110

Ile Asp Leu Glu Leu Phe Thr Gly Asp Asp Gln Val Lys Glu Thr Val
        115                 120                 125

Ala Tyr Ala His Ala His Asp Val Lys Val Val Met Ser Asn His Asp
    130                 135                 140

Phe His Lys Thr Pro Glu Ala Glu Glu Ile Ile Ala Arg Leu Arg Lys
145                 150                 155                 160

Met Gln Ser Phe Asp Ala Asp Ile Pro Lys Ile Ala Leu Met Pro Gln
```

```
            165                 170                 175
Ser Thr Ser Asp Val Leu Thr Leu Leu Ala Ala Thr Leu Glu Met Gln
        180                 185                 190

Glu Gln Tyr Ala Asp Arg Pro Ile Ile Thr Met Ser Met Ala Lys Thr
        195                 200                 205

Gly Val Ile Ser Arg Leu Ala Gly Glu Val Phe Gly Ser Ala Ala Thr
        210                 215                 220

Phe Gly Ala Val Lys Lys Ala Ser Ala Pro Gly Gln Ile Ser Val Asn
225                 230                 235                 240

Asp Leu Arg Thr Val Leu Thr Ile Leu His Gln Ala
                245                 250

<210> SEQ ID NO 7
<211> LENGTH: 843
<212> TYPE: DNA
<213> ORGANISM: Bacillus thuringiensis

<400> SEQUENCE: 7
atgaaatatt cgctatgtac catttcattt cgtcatcaat taatttcatt tactgatatt      60
gttcaatttg catatgaaaa cggttttgaa ggaattgaat tatggggac gcatgcacaa     120 aatttgtaca tgcaagaacg tgaaacgaca gaacgagaat tgaattttct aaaggataaa     180
aacttagaaa ttcgatgat aagtgattac ttagatatat cattatcagc agattttgaa     240
aaaacgatag agaaaagtga acaacttgta gtactagcta attggtttaa tacgaataaa     300
attcgcacgt ttgctgggca aaagggagc aaggacttct cggaacaaga gagaaaagag     360
tatgtgaagc gaatacgtaa gatttgtgat gtgtttgctc agaacaatat gtatgtgctg     420
ttagaaacac atcccaatac actaacggac acattgcctt ctactataga gttattagaa     480
gaagtaaacc atccgaattt aaaaataaat cttgattttc ttcatatatg ggagtctggc     540
gcagatccaa tagacagttt ccatcgatta aagccgtgga cactacatta ccattttaag     600
aatatatctt cagcggatta tttgcatgtg tttgaaccta ataatgtata tgctgcagca     660
ggaagtcgta taggtatggt tccgttattt gaaggtattg taaattatga tgagattatt     720
caggaagtga gaaatacgga tcttttttgct tccttagaat ggtttggaca taattcaaaa     780
gagatattaa agaagaaat gaaagtatta ataaatagaa aattagaagt agtaacttcg     840
taa                                                                   843

<210> SEQ ID NO 8
<211> LENGTH: 280
<212> TYPE: PRT
<213> ORGANISM: Bacillus thuringiensis

<400> SEQUENCE: 8

Met Lys Tyr Ser Leu Cys Thr Ile Ser Phe Arg His Gln Leu Ile Ser
1               5                  10                  15

Phe Thr Asp Ile Val Gln Phe Ala Tyr Glu Asn Gly Phe Glu Gly Ile
            20                  25                  30

Glu Leu Trp Gly Thr His Ala Gln Asn Leu Tyr Met Gln Glu Arg Glu
        35                  40                  45

Thr Thr Glu Arg Glu Leu Asn Phe Leu Lys Asp Lys Asn Leu Glu Ile
    50                  55                  60

Thr Met Ile Ser Asp Tyr Leu Asp Ile Ser Leu Ser Ala Asp Phe Glu
65                  70                  75                  80

Lys Thr Ile Glu Lys Ser Glu Gln Leu Val Val Leu Ala Asn Trp Phe
```

```
                    85                  90                  95
Asn Thr Asn Lys Ile Arg Thr Phe Ala Gly Gln Lys Gly Ser Lys Asp
            100                 105                 110

Phe Ser Glu Gln Glu Arg Lys Glu Tyr Val Lys Arg Ile Arg Lys Ile
        115                 120                 125

Cys Asp Val Phe Ala Gln Asn Met Tyr Val Leu Leu Glu Thr His
    130                 135                 140

Pro Asn Thr Leu Thr Asp Thr Leu Pro Ser Thr Ile Glu Leu Glu
145                 150                 155                 160

Glu Val Asn His Pro Asn Leu Lys Ile Asn Leu Asp Phe Leu His Ile
                165                 170                 175

Trp Glu Ser Gly Ala Asp Pro Ile Asp Ser Phe His Arg Leu Lys Pro
            180                 185                 190

Trp Thr Leu His Tyr His Phe Lys Asn Ile Ser Ser Ala Asp Tyr Leu
        195                 200                 205

His Val Phe Glu Pro Asn Val Tyr Ala Ala Ala Gly Ser Arg Ile
    210                 215                 220

Gly Met Val Pro Leu Phe Glu Gly Ile Val Asn Tyr Asp Glu Ile Ile
225                 230                 235                 240

Gln Glu Val Arg Asn Thr Asp Leu Phe Ala Ser Leu Glu Trp Phe Gly
                245                 250                 255

His Asn Ser Lys Glu Ile Leu Lys Glu Glu Met Lys Val Leu Ile Asn
            260                 265                 270

Arg Lys Leu Glu Val Val Thr Ser
        275                 280

<210> SEQ ID NO 9
<211> LENGTH: 1542
<212> TYPE: DNA
<213> ORGANISM: Escherichia coli

<400> SEQUENCE: 9
atgcgtctgg aagtcttttg tgaagaccga ctcggtctga cccgcgaatt actcgatcta    60
ctcgtgctaa gaggcattga tttacgcggt attgagattg atcccattgg gcgaatctac   120
ctcaattttg ctgaactgga gtttgagagt ttcagcagtc tgatggccga aatacgccgt   180
attgcgggtg ttaccgatgt gcgtactgtc ccgtggatgc cttccgaacg tgagcatctg   240
gcgttgagcg cgttactgga ggcgttgcct gaacctgtgc tctctgtcga tatgaaaagc   300
aaagtggata tggcgaaccc ggcgagctgt cagcttttg gcaaaaaatt ggatcgcctg   360
cgcaaccata ccgccgcaca attgattaac ggctttaatt ttttacgttg gctggaaagc   420
gaaccgcaag attcgcataa cgagcatgtc gttattaatg gcagaattt cctgatggag   480 attacgcctg tttatcttca ggatgaaaat gatcaacacg tcctgaccgg tgcggtggtg   540
atgttgcgat caacgattcg tatgggccgc cagttgcaaa atgtcgccgc ccaggacgtc   600
agcgccttca gtcaaattgt cgccgtcagc ccgaaaatga agcatgttgt cgaacaggcg   660
cagaaactgg cgatgctaag cgcgccgctg ctgattacgg gtgacacagg tacaggtaaa   720
gatctctttg cctacgcctg ccatcaggca agccccagag cgggcaaacc ttacctggcg   780
ctgaactgtg cgtctatacc ggaagatgcg gtcgagagtg aactgtttgg tcatgctccg   840
gaagggaaga aaggattctt tgagcaggcg aacggtggtt cggtgctgtt ggatgaaata   900
ggggaaatgt caccacggat gcaggcgaaa ttactgcgtt ccttaatga tggcactttc   960 cgtcggggttg gcgaagacca tgaggtgcat gtcgatgtgc gggtgatttg cgctacgcag  1020
```

-continued

```
aagaatctgg tcgaactggt gcaaaaaggc atgttccgtg aagatctcta ttatcgtctg   1080
aacgtgttga cgctcaatct gccgccgcta cgtgactgtc cgcaggacat catgccgtta   1140
actgagctgt cgtcgcccg ctttgccgac gagcagggcg tgccgcgtcc gaaactggcc    1200
gctgacctga atactgtact tacgcgttat cgtggccgg gaaatgtgcg gcagttaaag    1260
aacgctatct atcgcgcact gacacaactg gacggttatg agctgcgtcc acaggatatt   1320
ttgttgccgg attatgacgc cgcaacggta gccgtgggcg aagatgcgat ggaaggttcg   1380
ctggacgaaa tcaccagccg ttttgaacgc tcggtattaa cccagcttta tcgcaattat   1440
cccagcacgc gcaaactggc aaaacgtctc ggcgtttcac ataccgcgat tgccaataag   1500
ttgcgggaat atggtctgag tcagaagaag aacgaagagt aa                      1542
```

<210> SEQ ID NO 10
<211> LENGTH: 513
<212> TYPE: PRT
<213> ORGANISM: Escherichia coli

<400> SEQUENCE: 10

```
Met Arg Leu Glu Val Phe Cys Glu Asp Arg Leu Gly Leu Thr Arg Glu
1               5                   10                  15

Leu Leu Asp Leu Leu Val Leu Arg Gly Ile Asp Leu Arg Gly Ile Glu
            20                  25                  30

Ile Asp Pro Ile Gly Arg Ile Tyr Leu Asn Phe Ala Glu Leu Glu Phe
        35                  40                  45

Glu Ser Phe Ser Ser Leu Met Ala Glu Ile Arg Arg Ile Ala Gly Val
    50                  55                  60

Thr Asp Val Arg Thr Val Pro Trp Met Pro Ser Glu Arg Glu His Leu
65                  70                  75                  80

Ala Leu Ser Ala Leu Leu Glu Ala Leu Pro Glu Pro Val Leu Ser Val
                85                  90                  95

Asp Met Lys Ser Lys Val Asp Met Ala Asn Pro Ala Ser Cys Gln Leu
            100                 105                 110

Phe Gly Gln Lys Leu Asp Arg Leu Arg Asn His Thr Ala Ala Gln Leu
        115                 120                 125

Ile Asn Gly Phe Asn Phe Leu Arg Trp Leu Glu Ser Glu Pro Gln Asp
    130                 135                 140

Ser His Asn Glu His Val Val Ile Asn Gly Gln Asn Phe Leu Met Glu
145                 150                 155                 160

Ile Thr Pro Val Tyr Leu Gln Asp Glu Asn Asp Gln His Val Leu Thr
                165                 170                 175

Gly Ala Val Val Met Leu Arg Ser Thr Ile Arg Met Gly Arg Gln Leu
            180                 185                 190

Gln Asn Val Ala Ala Gln Asp Val Ser Ala Phe Ser Gln Ile Val Ala
        195                 200                 205

Val Ser Pro Lys Met Lys His Val Val Glu Gln Ala Gln Lys Leu Ala
    210                 215                 220

Met Leu Ser Ala Pro Leu Leu Ile Thr Gly Asp Thr Gly Thr Gly Lys
225                 230                 235                 240

Asp Leu Phe Ala Tyr Ala Cys His Gln Ala Ser Pro Arg Ala Gly Lys
                245                 250                 255

Pro Tyr Leu Ala Leu Asn Cys Ala Ser Ile Pro Glu Asp Ala Val Glu
            260                 265                 270

Ser Glu Leu Phe Gly His Ala Pro Glu Gly Lys Lys Gly Phe Phe Glu
```

```
              275                 280                 285
    Gln Ala Asn Gly Gly Ser Val Leu Leu Asp Glu Ile Gly Glu Met Ser
        290                 295                 300

Pro Arg Met Gln Ala Lys Leu Leu Arg Phe Leu Asn Asp Gly Thr Phe
    305                 310                 315                 320

Arg Arg Val Gly Glu Asp His Glu Val His Val Asp Val Arg Val Ile
                    325                 330                 335

Cys Ala Thr Gln Lys Asn Leu Val Glu Leu Val Gln Lys Gly Met Phe
                340                 345                 350

Arg Glu Asp Leu Tyr Tyr Arg Leu Asn Val Leu Thr Leu Asn Leu Pro
                355                 360                 365

Pro Leu Arg Asp Cys Pro Gln Asp Ile Met Pro Leu Thr Glu Leu Phe
    370                 375                 380

Val Ala Arg Phe Ala Asp Glu Gln Gly Val Pro Arg Pro Lys Leu Ala
    385                 390                 395                 400

Ala Asp Leu Asn Thr Val Leu Thr Arg Tyr Ala Trp Pro Gly Asn Val
                    405                 410                 415

Arg Gln Leu Lys Asn Ala Ile Tyr Arg Ala Leu Thr Gln Leu Asp Gly
                420                 425                 430

Tyr Glu Leu Arg Pro Gln Asp Ile Leu Leu Pro Asp Tyr Asp Ala Ala
                435                 440                 445

Thr Val Ala Val Gly Glu Asp Ala Met Glu Gly Ser Leu Asp Glu Ile
    450                 455                 460

Thr Ser Arg Phe Glu Arg Ser Val Leu Thr Gln Leu Tyr Arg Asn Tyr
    465                 470                 475                 480

Pro Ser Thr Arg Lys Leu Ala Lys Arg Leu Gly Val Ser His Thr Ala
                    485                 490                 495

Ile Ala Asn Lys Leu Arg Glu Tyr Gly Leu Ser Gln Lys Lys Asn Glu
                500                 505                 510

Glu

<210> SEQ ID NO 11
<211> LENGTH: 2304
<212> TYPE: DNA
<213> ORGANISM: Homo sapiens

<400> SEQUENCE: 11
cggcctgcgt ccgccaccgg aagcgccctc ctaatccccg cagcgccacc gccattgccg    60
ccatcgtcgt ggggcttctg ggcagctag  ggctgcccgc cgcgctgcct gcgccggacc   120
ggggcgggtc cagtcccggg cgggccgtcg cgggagagaa ataacatctg ctttgctgcc   180
gagctcagag gagaccccag accccctccg cagccagagg gctggagcct gctcagaggt   240
gctttgaaga tgccggaggc cccgcctctg ctgttggcag ctgtgttgct gggcctggtg   300
ctgctggtgg tgctgctgct gcttctgagg cactggggct ggggcctgtg ccttatcggc   360
tggaacgagt tcatcctgca gcccatccac aacctgctca gggtgacac caaggagcag   420 cgcatcctga ccacgtgctg cagcatgcg gagcccggga acgcacagag cgtgctggag   480
gccattgaca cctactgcga gcagaaggag tgggccatga cgtgggcga caagaaaggc   540 aagatcgtgg acgccgtgat tcaggagcac cagccctccg tgctgctgga ctggggggcc   600
tactgtggct actcagctgt gcgcatggcc cgcctgctgt caccaggggc gaggctcatc   660
accatcgaga tcaaccccga ctgtgccgcc atcacccagc ggatggtgga tttcgctggc   720
gtgaaggaca aggtcaccct gtggttgga gcgtcccagg acatcatccc ccagctgaag   780
```

| | |
|---|---|
| aagaagtatg atgtggacac actggacatg gtcttcctcg accactggaa ggaccggtac | 840 |
| ctgccggaca cgcttctctt ggaggaatgt ggcctgctgc ggaaggggac agtgctactg | 900 |
| gctgacaacg tgatctgccc aggtgcgcca gacttcctag cacacgtgcg cgggagcagc | 960 |
| tgctttgagt gcacacacta ccaatcgttc ctggaataca gggaggtggt ggacggcctg | 1020 |
| gagaaggcca tctacaaggg cccaggcagc gaagcagggc cctgactgcc ccccggccc | 1080 |
| ccctctcggg ctctctcacc cagcctggta ctgaaggtgc cagacgtgct cctgctgacc | 1140 |
| ttctgcggct ccgggctgtg tcctaaatgc aaagcacacc tcggccgagg cctgcgccct | 1200 |
| gacatgctaa cctctctgaa ctgcaacact ggattgttct tttttaagac tcaatcatga | 1260 |
| cttctttact aacactggct agctatatta tcttatatac taatatcatg ttttaaaaat | 1320 |
| ataaaataga aattaagaat ctaaatattt agatataact cgacttagta catccttctc | 1380 |
| aactgccatt cccctgctgc ccttgacttg ggcaccaaac attcaaagct ccccttgacg | 1440 |
| gacgctaacg ctaagggcgg ggcccctagc tggctgggtt ctgggtggca cgcctggccc | 1500 |
| actggcctcc cagccacagt ggtgcagagg tcagccctcc tgcagctagg ccaggggcac | 1560 |
| ctgttagccc catggggacg actgccggcc tgggaaacga agaggagtca gccagcattc | 1620 |
| acacctttct gaccaagcag gcgctgggga caggtggacc ccgcagcagc accagcccct | 1680 |
| ctgggcccca tgtggcacag agtggaagca tctccttccc tactccccac tgggccttgc | 1740 |
| ttacagaaga ggcaatggct cagaccagct cccgcatccc tgtagttgcc tccctggccc | 1800 |
| atgagtgagg atgcagtgct ggtttctgcc cacctacacc tagagctgtc cccatctcct | 1860 |
| ccaaggggtc agactgctag ccacctcaga ggctccaagg gcccagttcc caggcccagg | 1920 |
| acaggaatca accctgtgct agctgagttc acctgcaccg agaccagccc ctagccaaga | 1980 |
| ttctactcct gggctcaagg cctggctagc ccccagccag cccactccta tggatagaca | 2040 |
| gaccagtgag cccaagtgga caagtttggg gccacccagg gaccagaaac agagcctctg | 2100 |
| caggacacag cagatgggca cctggaccca cctccaccca gggccctgcc ccagacgcgc | 2160 |
| agaggcccga cacaagggag aagccagcca cttgtgccag acctgagtgg cagaaagcaa | 2220 |
| aaagttcctt tgctgcttta atttttaaat ttttcttacaa aaatttaggt gtttaccaat | 2280 |
| agtcttattt tggcttattt ttaa | 2304 |

<210> SEQ ID NO 12
<211> LENGTH: 2262
<212> TYPE: DNA
<213> ORGANISM: Homo sapiens

<400> SEQUENCE: 12

| | |
|---|---|
| ctcccacggg aggagcaaga acacagaaca gagggggcaa acagctcca ccaggagtca | 60 |
| ggagtgaatc ccctctggga acgaggcact aggaagaaga acttccagcc caggagaaat | 120 |
| aacatctgct ttgctgccga gctcagagga gaccccagac ccctcccgca gccagagggc | 180 |
| tggagcctgc tcagaggtgc tttgaagatg ccggaggccc cgcctctgct gttggcagct | 240 |
| gtgttgctgg gcctggtgct gctggtggtg ctgctgctgc ttctgaggca ctggggctgg | 300 |
| ggcctgtgcc ttatcggctg gaacgagttc atcctgcagc ccatccacaa cctgctcatg | 360 |
| ggtgacacca aggagcagcg catcctgaac cacgtgctgc agcatgcgga gcccgggaac | 420 |
| gcacagagcg tgctggaggc cattgacacc tactgcgagc agaaggagtg gccatgaac | 480 |
| gtgggcgaca agaaaggcaa gatcgtggac gccgtgattc aggagcacca gccctccgtg | 540 |

```
ctgctggagc tgggggccta ctgtggctac tcagctgtgc gcatggcccg cctgctgtca    600
ccagggccga ggctcatcac catcgagatc aacccccgact gtgccgccat cacccagcgg   660
atggtggatt tcgctggcgt gaaggacaag gtcacccttg tggttggagc gtcccaggac    720
atcatccccc agctgaagaa gaagtatgat gtggacacac tggacatggt cttcctcgac   780
cactggaagg accggtacct gccggacacg cttctcttgg aggaatgtgg cctgctgcgg   840
aaggggacag tgctactggc tgacaacgtg atctgcccag gtcgccaga cttcctagca    900 cacgtgcgcg ggagcagctg ctttgagtgc acacactacc aatcgttcct ggaatacagg   960
gaggtggtgg acggcctgga gaaggccatc tacaagggcc caggcagcga agcagggccc   1020
tgactgcccc cccggccccc ctctcgggct ctctcaccca gcctggtact gaaggtgcca   1080
gacgtgctcc tgctgacctt ctgcggctcc gggctgtgtc ctaaatgcaa agcacacctc   1140
ggccgaggcc tgcgccctga catgctaacc tctctgaact gcaacactgg attgttcttt   1200
tttaagactc aatcatgact tctttactaa cactggctag ctatattatc ttatatacta   1260
atatcatgtt ttaaaaatat aaaatagaaa ttaagaatct aaatatttag atataactcg   1320
acttagtaca tccttctcaa ctgccattcc cctgctgccc ttgacttggg caccaaacat   1380
tcaaagctcc ccttgacgga cgctaacgct aagggcgggg cccctagctg ctgggttct    1440 gggtggcacg cctggcccac tggcctccca gccacagtgg tgcagaggtc agccctcctg   1500
cagctaggcc aggggcacct gttagcccca tggggacgac tgccggcctg ggaaacgaag   1560
aggagtcagc cagcattcac accttctgga ccaagcaggc gctggggaca ggtggacccc   1620
gcagcagcac cagcccctct gggccccatg tggcacagag tggaagcatc tccttcccta   1680
ctccccactg ggccttgctt acagaagagg caatggctca gaccagctcc cgcatccctg   1740
tagttgcctc cctggcccat gagtgaggat gcagtgctgg tttctgccca cctacaccta   1800
gagctgtccc catctcctcc aaggggtcag actgctagcc acctcagagg ctccaagggc   1860
ccagttccca ggcccaggac aggaatcaac cctgtgctag ctgagttcac ctgcaccgag   1920
accagcccct agccaagatt ctactcctgg gctcaaggcc tggctagccc ccagccagcc   1980
cactcctatg gatagacaga ccagtgagcc caagtggaca agtttggggc cacccaggga   2040
ccagaaacag agcctctgca ggacacagca gatgggcacc tgggaccacc tccacccagg   2100
gccctgcccc agacgcgcag aggcccgaca caagggagaa gccagccact tgtgccagac   2160
ctgagtggca gaaagcaaaa agttcctttg ctgctttaat ttttaaattt tcttacaaaa   2220
atttaggtgt ttaccaatag tcttattttg gcttattttt aa                      2262
```

<210> SEQ ID NO 13
<211> LENGTH: 2279
<212> TYPE: DNA
<213> ORGANISM: Homo sapiens

<400> SEQUENCE: 13

```
tggagataac acggatcgct gtgtacactg tgtgctccgg ttgttgcatc cgagggttga    60
tcggatggtg gttcccatcc agatccaagt cctggcccct gatcacagag aaacacagct   120
ggacattaaa gtgaaataac atctgctttg ctgccgagct cagaggagac cccagacccc   180
tcccgcagcc agagggctgg agcctgctca gaggtgcttt gaagatgccg gaggccccgc   240
ctctgctgtt ggcagctgtg ttgctgggcc tggtgctgct ggtggtgctg ctgctgcttc   300
tgaggcactg gggctgggc ctgtgcctta tcggctggaa cgagttcatc ctgcagccca   360 tccacaaccct gctcatgggt gacaccaagg agcagcgcat cctgaaccac gtgctgcagc   420
```

| | | | | |
|---|---|---|---|---|
| atgcggagcc | cgggaacgca | cagagcgtgc | tggaggccat | tgacacctac | tgcgagcaga | 480 |
| aggagtgggc | catgaacgtg | ggcgacaaga | aaggcaagat | cgtggacgcc | gtgattcagg | 540 |
| agcaccagcc | ctccgtgctg | ctggagctgg | gggcctactg | tggctactca | gctgtgcgca | 600 |
| tggcccgcct | gctgtcacca | ggggcgaggc | tcatcaccat | cgagatcaac | ccgactgtg | 660 |
| ccgccatcac | ccagcggatg | gtggatttcg | ctggcgtgaa | ggacaaggtc | acccttgtgg | 720 |
| ttggagcgtc | ccaggacatc | atccccagc | tgaagaagaa | gtatgatgtg | acacactgg | 780 |
| acatggtctt | cctcgaccac | tggaaggacc | ggtacctgcc | ggacacgctt | ctcttggagg | 840 |
| aatgtggcct | gctgcggaag | gggacagtgc | tactggctga | aacgtgatc | tgcccaggtg | 900 |
| cgccagactt | cctagcacac | gtgcgcggga | gcagctgctt | tgagtgcaca | cactaccaat | 960 |
| cgttcctgga | atacagggag | gtggtggacg | gcctggagaa | ggccatctac | aagggcccag | 1020 |
| gcagcgaagc | agggccctga | ctgccccccc | ggccccctc | tcgggctctc | tcacccagcc | 1080 |
| tggtactgaa | ggtgccagac | gtgctcctgc | tgaccttctg | cggctccggg | ctgtgtccta | 1140 |
| aatgcaaagc | acacctcggc | cgaggcctgc | gccctgacat | gctaacctct | ctgaactgca | 1200 |
| acactggatt | gttctttttt | aagactcaat | catgacttct | ttactaacac | tggctagcta | 1260 |
| tattatctta | tatactaata | tcatgttttta | aaaatataaa | atagaaatta | agaatctaaa | 1320 |
| tatttagata | taactcgact | tagtacatcc | ttctcaactg | ccattcccct | gctgcccttg | 1380 |
| acttgggcac | caaacattca | aagctccct | tgacggacgc | taacgctaag | ggcggggccc | 1440 |
| ctagctggct | gggttctggg | tggcacgcct | ggcccactgg | cctccagcc | acagtggtgc | 1500 |
| agaggtcagc | cctcctgcag | ctaggccagg | ggcacctgtt | agcccatgg | ggacgactgc | 1560 |
| cggcctggga | aacgaagagg | agtcagccag | cattcacacc | tttctgacca | agcaggcgct | 1620 |
| ggggacaggt | ggaccccgca | gcagcaccag | ccctctggg | ccccatgtgg | cacagagtgg | 1680 |
| aagcatctcc | ttccctactc | cccactgggc | cttgcttaca | gaagaggcaa | tggctcagac | 1740 |
| cagctcccgc | atccctgtag | ttgcctccct | ggccatgag | tgaggatgca | gtgctggttt | 1800 |
| ctgcccacct | acacctagag | ctgtccccat | ctcctccaag | gggtcagact | gctagccacc | 1860 |
| tcagaggctc | caagggccca | gttcccaggc | ccaggacagg | aatcaaccct | gtgctagctg | 1920 |
| agttcacctg | caccgagacc | agcccctagc | caagattcta | ctcctgggct | caaggcctgg | 1980 |
| ctagcccca | gccagcccac | tcctatggat | agacagacca | gtgagcccaa | gtggacaagt | 2040 |
| ttggggccac | ccagggacca | gaaacagagc | ctctgcagga | cacagcagat | gggcacctgg | 2100 |
| gaccacctcc | acccagggcc | ctgccccaga | cgcgcagagg | cccgacacaa | gggagaagcc | 2160 |
| agccacttgt | gccagacctg | agtggcagaa | agcaaaaagt | tcctttgctg | ctttaatttt | 2220 |
| taaatttct | tacaaaaatt | taggtgttta | ccaatagtct | tattttggct | tatttttaa | 2279 |

<210> SEQ ID NO 14
<211> LENGTH: 2035
<212> TYPE: DNA
<213> ORGANISM: Homo sapiens

<400> SEQUENCE: 14

| | | | | |
|---|---|---|---|---|
| gctgttggca | gctgtgttgc | tgggcctggt | gctgctggtg | gtgctgctgc | tgcttctgag | 60 |
| gcactgggc | tggggcctgt | gccttatcgg | ctggaacgag | ttcatcctgc | agcccatcca | 120 |
| caacctgctc | atgggtgaca | ccaaggagca | gcgcatcctg | aaccacgtgc | tgcagcatgc | 180 |
| ggagcccggg | aacgcacaga | gcgtgctgga | ggccattgac | acctactgcg | agcagaagga | 240 |

```
gtgggccatg aacgtgggcg acaagaaagg caagatcgtg gacgccgtga ttcaggagca    300
ccagccctcc gtgctgctgg agctgggggc ctactgtggc tactcagctg tgcgcatggc    360
ccgcctgctg tcaccagggg cgaggctcat caccatcgag atcaaccccg actgtgccgc    420
catcacccag cggatggtgg atttcgctgg cgtgaaggac aaggtcaccc ttgtggttgg    480
agcgtcccag gacatcatcc cccagctgaa gaagaagtat gatgtggaca cactggacat    540
ggtcttcctc gaccactgga aggaccggta cctgccggac acgcttctct tggaggaatg    600
tggcctgctg cggaagggga cagtgctact ggctgacaac gtgatctgcc aggtgcgcc    660
agacttccta gcacacgtgc gcgggagcag ctgctttgag tgcacacact accaatcgtt    720
cctggaatac agggaggtgg tggacggcct ggagaaggcc atctacaagg gcccaggcag    780
cgaagcaggg ccctgactgc cccccggcc ccctctcgg gctctctcac ccagcctggt    840
actgaaggtg ccagacgtgc tcctgctgac cttctgcggc tccgggctgt gtcctaaatg    900
caaagcacac ctcggccgag gcctgcgccc tgacatgcta acctctctga actgcaacac    960
tggattgttc ttttttaaga ctcaatcatg acttctttac taacactggc tagctatatt   1020
atcttatata ctaatatcat gttttaaaaa tataaaatag aaattaagaa tctaaatatt   1080
tagatataac tcgacttagt acatccttct caactgccat tcccctgctg cccttgactt   1140
gggcaccaaa cattcaaagc tcccccttgac ggacgctaac gctaagggcg gggcccctag   1200
ctggctgggt tctgggtggc acgcctgccc cactggcctc ccagccacag tggtgcagag   1260
gtcagccctc ctgcagctag gccaggggca cctgttagcc ccatggggac gactgccggc   1320
ctgggaaacg aagaggagtc agccagcatt cacacctttc tgaccaagca ggcgctgggg   1380
acaggtggac cccgcagcag caccagcccc tctgggcccc atgtggcaca gagtggaagc   1440
atctccttcc ctactcccca ctgggccttg cttacagaag aggcaatggc tcagaccagc   1500
tcccgcatcc ctgtagttgc ctccctggcc catgagtgag gatgcagtgc tggtttctgc   1560
ccacctacac ctagagctgt ccccatctcc tccaagggt cagactgcta gccacctcag   1620
aggctccaag ggcccagttc ccaggcccag gacaggaatc aaccctgtgc tagctgagtt   1680
cacctgcacc gagaccagcc cctagccaag attctactcc tgggctcaag gcctggctag   1740
cccccagcca gcccactcct atggatagac agaccagtga gcccaagtgg acaagtttgg   1800
ggccacccag ggaccagaaa cagagcctct gcaggacaca gcagatgggc acctgggacc   1860
acctccaccc agggccctgc cccagacgcg cagaggcccg acacaaggga gaagccagcc   1920
acttgtgcca gacctgagtg gcagaaagca aaaagttcct ttgctgcttt aattttaaa   1980
ttttcttaca aaatttaggt gtttaccaa tagtcttatt ttggcttatt tttaa        2035
```

<210> SEQ ID NO 15
<211> LENGTH: 271
<212> TYPE: PRT
<213> ORGANISM: Homo sapiens

<400> SEQUENCE: 15

```
Met Pro Glu Ala Pro Leu Leu Leu Ala Ala Val Leu Leu Gly Leu
1               5                   10                  15

Val Leu Val Val Leu Leu Leu Leu Arg His Trp Gly Trp Gly
            20                  25                  30

Leu Cys Leu Ile Gly Trp Asn Glu Phe Ile Leu Gln Pro Ile His Asn
        35                  40                  45

Leu Leu Met Gly Asp Thr Lys Glu Gln Arg Ile Leu Asn His Val Leu
    50                  55                  60
```

```
Gln His Ala Glu Pro Gly Asn Ala Gln Ser Val Leu Glu Ala Ile Asp
 65                  70                  75                  80

Thr Tyr Cys Glu Gln Lys Glu Trp Ala Met Asn Val Gly Asp Lys Lys
             85                  90                  95

Gly Lys Ile Val Asp Ala Val Ile Gln Glu His Gln Pro Ser Val Leu
            100                 105                 110

Leu Glu Leu Gly Ala Tyr Cys Gly Tyr Ser Ala Val Arg Met Ala Arg
        115                 120                 125

Leu Leu Ser Pro Gly Ala Arg Leu Ile Thr Ile Glu Ile Asn Pro Asp
130                 135                 140

Cys Ala Ala Ile Thr Gln Arg Met Val Asp Phe Ala Gly Val Lys Asp
145                 150                 155                 160

Lys Val Thr Leu Val Val Gly Ala Ser Gln Asp Ile Ile Pro Gln Leu
                165                 170                 175

Lys Lys Lys Tyr Asp Val Asp Thr Leu Asp Met Val Phe Leu Asp His
            180                 185                 190

Trp Lys Asp Arg Tyr Leu Pro Asp Thr Leu Leu Glu Glu Cys Gly
        195                 200                 205

Leu Leu Arg Lys Gly Thr Val Leu Leu Ala Asp Asn Val Ile Cys Pro
210                 215                 220

Gly Ala Pro Asp Phe Leu Ala His Val Arg Gly Ser Ser Cys Phe Glu
225                 230                 235                 240

Cys Thr His Tyr Gln Ser Phe Leu Glu Tyr Arg Glu Val Val Asp Gly
                245                 250                 255

Leu Glu Lys Ala Ile Tyr Lys Gly Pro Gly Ser Glu Ala Gly Pro
            260                 265                 270

<210> SEQ ID NO 16
<211> LENGTH: 221
<212> TYPE: PRT
<213> ORGANISM: Homo sapiens

<400> SEQUENCE: 16

Met Gly Asp Thr Lys Glu Gln Arg Ile Leu Asn His Val Leu Gln His
  1               5                  10                  15

Ala Glu Pro Gly Asn Ala Gln Ser Val Leu Glu Ala Ile Asp Thr Tyr
             20                  25                  30

Cys Glu Gln Lys Glu Trp Ala Met Asn Val Gly Asp Lys Lys Gly Lys
         35                  40                  45

Ile Val Asp Ala Val Ile Gln Glu His Gln Pro Ser Val Leu Glu
     50                  55                  60

Leu Gly Ala Tyr Cys Gly Tyr Ser Ala Val Arg Met Ala Arg Leu Leu
 65                  70                  75                  80

Ser Pro Gly Ala Arg Leu Ile Thr Ile Glu Ile Asn Pro Asp Cys Ala
             85                  90                  95

Ala Ile Thr Gln Arg Met Val Asp Phe Ala Gly Val Lys Asp Lys Val
        100                 105                 110

Thr Leu Val Val Gly Ala Ser Gln Asp Ile Ile Pro Gln Leu Lys Lys
        115                 120                 125

Lys Tyr Asp Val Asp Thr Leu Asp Met Val Phe Leu Asp His Trp Lys
    130                 135                 140

Asp Arg Tyr Leu Pro Asp Thr Leu Leu Glu Glu Cys Gly Leu Leu
145                 150                 155                 160

Arg Lys Gly Thr Val Leu Leu Ala Asp Asn Val Ile Cys Pro Gly Ala
```

|  | 165 |  | 170 |  | 175 |  |
| --- | --- | --- | --- | --- | --- | --- |

Pro Asp Phe Leu Ala His Val Arg Gly Ser Ser Cys Phe Glu Cys Thr
    180                        185                        190

His Tyr Gln Ser Phe Leu Glu Tyr Arg Glu Val Val Asp Gly Leu Glu
      195                    200                    205

Lys Ala Ile Tyr Lys Gly Pro Gly Ser Glu Ala Gly Pro
    210                        215                    220

<210> SEQ ID NO 17
<211> LENGTH: 3453
<212> TYPE: DNA
<213> ORGANISM: Nocardia brasiliensis

<400> SEQUENCE: 17

| ttgttcgccg aggacgagca ggtgaaagcc gcggtgccgg accaggaggt ggtcgaggcg | 60 |
| atccgggcgc ccggcctgcg cctggcacag atcatggcca ccgtgatgga gcgctatgcg | 120 |
| gaccgccccg cggtgggaca gcgggcgagc gagccggtca ccgagagcgg tcgcaccacc | 180 |
| ttccggctgc tcccggaatt cgagaccctg acctaccgcg agctgtgggc gcgcgtccgc | 240 |
| gcggtggccg ccgcgtggca cggagatgcc gaaaggcctt gcgggccggg gatttcgtt | 300 |
| gctctgctgg gtttcgccgg catcgattac ggcaccctcg atctcgcgaa catccatctc | 360 |
| ggcctcgtca cggtgccgct gcaatccggc gccacgcccc gcaactcgc gcgatcctg | 420 |
| gccgagacca cgccccgggt gctggccgcg acacccgacc atctcgatat cgccgtcgaa | 480 |
| ttgctgaccg gggagcctc gccggaacgg ctggtggtat cgactaccg ccccgcggac | 540 |
| gacgatcacc gggcggcgct cgagtccgcg cgcagacggt tgagcgacgc gggcagtgcg | 600 |
| gtggtggtcg agacgctcga cgcggtccgc gcccgcggca gcgaattgcc ggccgcgccg | 660 |
| ctgttcgttc cgccgcgga cgaggacccg ctggctctgc tcatctacac ctccggcagc | 720 |
| accggcacgc ctaagggcgc catgtacacc gaaagactga accgcacgac gtggctgagc | 780 |
| ggggcgaaag gcgtcggcct cacgctcggc tacatgccga tgagtcatat tgccgggcgg | 840 |
| gcctcgttcg ccggtgtgct ggcccgcggc ggcacggtct acttcaccgc ccgcagcgat | 900 |
| atgtcgacgc tgttcgaaga tctggccctg gtgcggccga ccgagatgtt cttcgtcccg | 960 |
| cgcgtgtgcg acatgatctt ccagcgctat caggccgaac tgtcgcggcg cgcgcccgcc | 1020 |
| gcggccgcga gcccggaact cgagcaggaa ctgaagaccg aactgcgctt gtccgcggtc | 1080 |
| ggggaccgct tactcggggc gatcgcgggc agcgcgccgc tgtcggccga gatgcgggag | 1140 |
| ttcatggagt cgctgctgga tctggaactg cacgacggc acggctcgac cgaggcgggt | 1200 |
| atcggcgtac tgcaagacaa tatcgtccag cgtccgccgg tcatcgatta caagctcgtc | 1260 |
| gacgtgccga attgggcta cttccggacg accagccgc atccccgcgg tgagttgctg | 1320 |
| ttgaaaaccg aagggatgat tccgggctac ttccggcggc ccgaggtgac cgcggagatc | 1380 |
| ttcgacgagg acggtttcta caggaccggt gacatcgtcg ccgaactcga ccggatcgg | 1440 |
| ctgatctacc tggaccgccg caacaatgtg ctgaaactgg cccagggcga gttcgtcacg | 1500 |
| gtcgcccatc tggaagcggt gttcgcgacc agtccgctga tccggcagat ctacatctac | 1560 |
| ggcaacagcg agcgctcgtt cctgctggcg gtgatcgtgc ccaccgcgga cgcgctggcc | 1620 |
| gacggtgtca ccgacgcgct gaacacggcg ctgaccgaat ccttgcgaca gctcgcgaaa | 1680 |
| gaagccgggc tgcaatccta tgagctgccg cgcgagttcc tggtcgaaac cgaaccgttc | 1740 |
| accgtcgaga acggtctgct ctccggtatc gcgaaactgt tgcggcccaa gctcaaggag | 1800 |

```
cactacggcg agcgactcga gcagctgtac cgcgatatcg aggcgaaccg caacgacgag    1860
ctgatcgagc tgcggcgcac cgcggccgag ctgccggtgc tcgaaaccgt cacgcgggct    1920
gcacgttcga tgctcggact ggccgcgtcg gagttgcggc cggacgcgca tttcaccgat    1980
ctcggcggtg attcactgtc cgcgctgtcg ttttcgaccc tgctgcagga catgctcgag    2040
gtcgaggtcc cggtcggtgt catcgtgagc cccgccaact cgctcgccga tctggcgaaa    2100
tacatcgagg ccgaacggca ttcggggggtg cggcggccga gcctgatctc ggtgcacggt    2160
cccggcaccg agatccgtgc cgccgatctc accctggaca agttcatcga cgagcgcacc    2220
ctcgctgccg cgaaagcggt tccggccgcg ccggcccagg cgcagaccgt cctgctcacc    2280
ggggcgaacg gctatctcgg ccgcttcctg tgcctggaat ggctgcagcg actggaccag    2340
accggcggca cgctggtctg catcgtgcgc ggtaccgacg cggccgccgc gcggaagcgc    2400
ctggatgcgg tgttcgacag cggtgatccg gagctgctcg accactaccg gaagctggcc    2460
gccgagcacc tcgaggtgct cgcgggcgat atcgcgacc cgaatctcgg cctggacgaa    2520
gcgacttggc agcggctcgc cgcgaccgtc gacctgatcg tgcaccccgc cgccctcgtc    2580
aaccatgtgc tgccgtacag ccagctgttc gggccgaatg tggtcggcac cgccgagatc    2640
atccggctgc ccatcaccga gcgccgtaag cccgtgacgt acctgtcgac ggtcgcggtg    2700
gccgcacagg tcgatcccgc cggcttcgac gaggagcgcg atatccggga tgagcgcg    2760 gtgcgctcca tcgacgccgg gtacgcgaac ggttacggca acagcaagtg ggccggcgag    2820
gtgctgctgc gcgaggccca tgatctgtgc gggctgccgg tcgccgtgtt ccgctcggac    2880
atgatcctgg cgcacagcaa atacgtcggt cagctcaacg tccccgatgt gttcacccgg    2940
ctcatcctga gcctggcgct caccggcatc gcaccgtatt cgttctacgg gacggacagc    3000
gccgggcagc gcaggcgggc ccactacgac ggtctgcccg ccgatttcgt cgccgaggcg    3060
atcaccaccc tcggcgcgcg agccgagtcg gggttccata cctacgacgt gtggaacccg    3120
tacgacgacg gcatctcgct ggacgaattc gtcgactggc tcggcgattt cggcgtgccg    3180
atccagcgga tcgacgacta cgacgaatgg ttccggcgtt tcgagaccgc gatccgcgcg    3240
ctgcccgaaa agcagcgcga tgcttcgctg ctaccgctgc tggacgcaca ccggcggcca    3300
ctgcgcgcgg tgcgcggttc gctgttgccc gccaagaact tccaggcggc ggtgcagtcc    3360
gcgcggatcg gccccgatca ggacatcccg catctttccc cgcagttgat cgacaagtac    3420
gtcaccgacc tgcgccacct cggcctgctc tga                                3453
```

<210> SEQ ID NO 18
<211> LENGTH: 1150
<212> TYPE: PRT
<213> ORGANISM: Nocardia brasiliensis

<400> SEQUENCE: 18

```
Met Phe Ala Glu Asp Glu Gln Val Lys Ala Ala Val Pro Asp Gln Glu
1               5                   10                  15

Val Val Glu Ala Ile Arg Ala Pro Gly Leu Arg Leu Ala Gln Ile Met
            20                  25                  30

Ala Thr Val Met Glu Arg Tyr Ala Asp Arg Pro Ala Val Gly Gln Arg
        35                  40                  45

Ala Ser Glu Pro Val Thr Glu Ser Gly Arg Thr Thr Phe Arg Leu Leu
    50                  55                  60

Pro Glu Phe Glu Thr Leu Thr Tyr Arg Glu Leu Trp Ala Arg Val Arg
65                  70                  75                  80
```

```
Ala Val Ala Ala Ala Trp His Gly Asp Ala Glu Arg Pro Leu Arg Ala
                    85                  90                  95

Gly Asp Phe Val Ala Leu Leu Gly Phe Ala Gly Ile Asp Tyr Gly Thr
                100                 105                 110

Leu Asp Leu Ala Asn Ile His Leu Gly Leu Val Thr Val Pro Leu Gln
                115                 120                 125

Ser Gly Ala Thr Ala Pro Gln Leu Ala Ala Ile Leu Ala Glu Thr Thr
                130                 135                 140

Pro Arg Val Leu Ala Ala Thr Pro Asp His Leu Asp Ile Ala Val Glu
145                 150                 155                 160

Leu Leu Thr Gly Gly Ala Ser Pro Glu Arg Leu Val Val Phe Asp Tyr
                165                 170                 175

Arg Pro Ala Asp Asp His Arg Ala Ala Leu Glu Ser Ala Arg Arg
                180                 185                 190

Arg Leu Ser Asp Ala Gly Ser Ala Val Val Glu Thr Leu Asp Ala
                195                 200                 205

Val Arg Ala Arg Gly Ser Glu Leu Pro Ala Ala Pro Leu Phe Val Pro
                210                 215                 220

Ala Ala Asp Glu Asp Pro Leu Ala Leu Leu Ile Tyr Thr Ser Gly Ser
225                 230                 235                 240

Thr Gly Thr Pro Lys Gly Ala Met Tyr Thr Glu Arg Leu Asn Arg Thr
                245                 250                 255

Thr Trp Leu Ser Gly Ala Lys Gly Val Gly Leu Thr Leu Gly Tyr Met
                260                 265                 270

Pro Met Ser His Ile Ala Gly Arg Ala Ser Phe Ala Gly Val Leu Ala
                275                 280                 285

Arg Gly Gly Thr Val Tyr Phe Thr Ala Arg Ser Asp Met Ser Thr Leu
                290                 295                 300

Phe Glu Asp Leu Ala Leu Val Arg Pro Thr Glu Met Phe Phe Val Pro
305                 310                 315                 320

Arg Val Cys Asp Met Ile Phe Gln Arg Tyr Gln Ala Glu Leu Ser Arg
                325                 330                 335

Arg Ala Pro Ala Ala Ala Ser Pro Glu Leu Glu Gln Glu Leu Lys
                340                 345                 350

Thr Glu Leu Arg Leu Ser Ala Val Gly Asp Arg Leu Leu Gly Ala Ile
                355                 360                 365

Ala Gly Ser Ala Pro Leu Ser Ala Glu Met Arg Glu Phe Met Glu Ser
                370                 375                 380

Leu Leu Asp Leu Glu Leu His Asp Gly Tyr Gly Ser Thr Glu Ala Gly
385                 390                 395                 400

Ile Gly Val Leu Gln Asp Asn Ile Val Gln Arg Pro Val Ile Asp
                405                 410                 415

Tyr Lys Leu Val Asp Val Pro Glu Leu Gly Tyr Phe Arg Thr Asp Gln
                420                 425                 430

Pro His Pro Arg Gly Glu Leu Leu Lys Thr Glu Gly Met Ile Pro
                435                 440                 445

Gly Tyr Phe Arg Arg Pro Glu Val Thr Ala Glu Ile Phe Asp Glu Asp
                450                 455                 460

Gly Phe Tyr Arg Thr Gly Asp Ile Val Ala Glu Leu Glu Pro Asp Arg
465                 470                 475                 480

Leu Ile Tyr Leu Asp Arg Arg Asn Asn Val Leu Lys Leu Ala Gln Gly
                485                 490                 495

Glu Phe Val Thr Val Ala His Leu Glu Ala Val Phe Ala Thr Ser Pro
```

```
                500                 505                 510
Leu Ile Arg Gln Ile Tyr Ile Tyr Gly Asn Ser Glu Arg Ser Phe Leu
            515                 520                 525

Leu Ala Val Ile Val Pro Thr Ala Asp Ala Leu Ala Asp Gly Val Thr
            530                 535                 540

Asp Ala Leu Asn Thr Ala Leu Thr Glu Ser Leu Arg Gln Leu Ala Lys
545                 550                 555                 560

Glu Ala Gly Leu Gln Ser Tyr Glu Leu Pro Arg Glu Phe Leu Val Glu
                565                 570                 575

Thr Glu Pro Phe Thr Val Glu Asn Gly Leu Leu Ser Gly Ile Ala Lys
            580                 585                 590

Leu Leu Arg Pro Lys Leu Lys Glu His Tyr Gly Arg Leu Glu Gln
            595                 600                 605

Leu Tyr Arg Asp Ile Glu Ala Asn Arg Asn Asp Glu Leu Ile Glu Leu
            610                 615                 620

Arg Arg Thr Ala Ala Glu Leu Pro Val Leu Glu Thr Val Thr Arg Ala
625                 630                 635                 640

Ala Arg Ser Met Leu Gly Leu Ala Ala Ser Glu Leu Arg Pro Asp Ala
                645                 650                 655

His Phe Thr Asp Leu Gly Gly Asp Ser Leu Ser Ala Leu Ser Phe Ser
            660                 665                 670

Thr Leu Leu Gln Asp Met Leu Glu Val Glu Val Pro Val Gly Val Ile
            675                 680                 685

Val Ser Pro Ala Asn Ser Leu Ala Asp Leu Ala Lys Tyr Ile Glu Ala
            690                 695                 700

Glu Arg His Ser Gly Val Arg Arg Pro Ser Leu Ile Ser Val His Gly
705                 710                 715                 720

Pro Gly Thr Glu Ile Arg Ala Ala Asp Leu Thr Leu Asp Lys Phe Ile
                725                 730                 735

Asp Glu Arg Thr Leu Ala Ala Ala Lys Ala Val Pro Ala Ala Pro Ala
            740                 745                 750

Gln Ala Gln Thr Val Leu Leu Thr Gly Ala Asn Gly Tyr Leu Gly Arg
            755                 760                 765

Phe Leu Cys Leu Glu Trp Leu Gln Arg Leu Asp Gln Thr Gly Gly Thr
            770                 775                 780

Leu Val Cys Ile Val Arg Gly Thr Asp Ala Ala Ala Arg Lys Arg
785                 790                 795                 800

Leu Asp Ala Val Phe Asp Ser Gly Asp Pro Glu Leu Leu Asp His Tyr
                805                 810                 815

Arg Lys Leu Ala Ala Glu His Leu Glu Val Leu Ala Gly Asp Ile Gly
            820                 825                 830

Asp Pro Asn Leu Gly Leu Asp Glu Ala Thr Trp Gln Arg Leu Ala Ala
            835                 840                 845

Thr Val Asp Leu Ile Val His Pro Ala Ala Leu Val Asn His Val Leu
            850                 855                 860

Pro Tyr Ser Gln Leu Phe Gly Pro Asn Val Val Gly Thr Ala Glu Ile
865                 870                 875                 880

Ile Arg Leu Ala Ile Thr Glu Arg Arg Lys Pro Val Thr Tyr Leu Ser
                885                 890                 895

Thr Val Ala Val Ala Ala Gln Val Asp Pro Ala Gly Phe Asp Glu Glu
            900                 905                 910

Arg Asp Ile Arg Glu Met Ser Ala Val Arg Ser Ile Asp Ala Gly Tyr
            915                 920                 925
```

```
Ala Asn Gly Tyr Gly Asn Ser Lys Trp Ala Gly Glu Val Leu Leu Arg
        930                 935                 940

Glu Ala His Asp Leu Cys Gly Leu Pro Val Ala Val Phe Arg Ser Asp
945                 950                 955                 960

Met Ile Leu Ala His Ser Lys Tyr Val Gly Gln Leu Asn Val Pro Asp
                965                 970                 975

Val Phe Thr Arg Leu Ile Leu Ser Leu Ala Leu Thr Gly Ile Ala Pro
            980                 985                 990

Tyr Ser Phe Tyr Gly Thr Asp Ser  Ala Gly Gln Arg Arg  Arg Ala His
        995                 1000                1005

Tyr Asp  Gly Leu Pro Ala Asp  Phe Val Ala Glu Ala  Ile Thr Thr
    1010                1015                1020

Leu Gly  Ala Arg Ala Glu Ser  Gly Phe His Thr Tyr  Asp Val Trp
    1025                1030                1035

Asn Pro  Tyr Asp Asp Gly Ile  Ser Leu Asp Glu Phe  Val Asp Trp
    1040                1045                1050

Leu Gly  Asp Phe Gly Val Pro  Ile Gln Arg Ile Asp  Asp Tyr Asp
    1055                1060                1065

Glu Trp  Phe Arg Arg Phe Glu  Thr Ala Ile Arg Ala  Leu Pro Glu
    1070                1075                1080

Lys Gln  Arg Asp Ala Ser Leu  Leu Pro Leu Leu Asp  Ala His Arg
    1085                1090                1095

Arg Pro  Leu Arg Ala Val Arg  Gly Ser Leu Leu Pro  Ala Lys Asn
    1100                1105                1110

Phe Gln  Ala Ala Val Gln Ser  Ala Arg Ile Gly Pro  Asp Gln Asp
    1115                1120                1125

Ile Pro  His Leu Ser Pro Gln  Leu Ile Asp Lys Tyr  Val Thr Asp
    1130                1135                1140

Leu Arg  His Leu Gly Leu Leu
    1145                1150

<210> SEQ ID NO 19
<211> LENGTH: 3501
<212> TYPE: DNA
<213> ORGANISM: Nocardia brasiliensis

<400> SEQUENCE: 19
atggcgactg attcgcgaag cgatcggcta cggcgtcgaa ttgcacagtt gttcgccgag    60
gacgagcagg tgaaagccgc ggtgccggac caggaggtgg tcgaggcgat ccgggcgccc   120
ggcctgcgcc tggcacagat catggccacc gtgatggagc gctatgcgga ccgccccgcg   180
gtgggacagc gggcgagcga gccggtcacc gagagcggtc gcaccaccct tccggctgctc  240 ccggaattcg agaccctgac ctaccgcgag ctgtgggcgc gcgtccgcgc ggtggccgcc   300
gcgtggcacg gagatgccga aaggcctttg cgggccgggg atttcgttgc tctgctgggt   360
ttcgccggca tcgattacgg caccctcgat ctcgcgaaca tccatctcgg cctcgtcacg   420
gtgccgctgc aatccggcgc cacggccccg caactcgccg cgatcctggc cgagaccacg   480 cccgggtgc tggccgcgac acccgaccat ctcgatatcg ccgtcgaatt gctgaccggg   540
ggagcctcgc cggaacggct ggtggtattc gactaccgcc ccgcggacga cgatcaccgg   600
gcggcgctcg agtccgcgcg cagacggttg agcgacgcgg gcagtgcggt ggtggtcgag   660
acgctcgacg cggtccgcgc ccgcggcagc gaattgccgg ccgcgccgct gttcgttccc   720
gccgcggacg aggacccgct ggctctgctc atctacacct ccggcagcac cggcacgcct   780
```

```
aagggcgcca tgtacaccga aagactgaac cgcacgacgt ggctgagcgg ggcgaaaggc      840
gtcggcctca cgctcggcta catgccgatg agtcatattg ccgggcgggc ctcgttcgcc      900
ggtgtgctgg cccgcggcgg cacggtctac ttcaccgccc gcagcgatat gtcgacgctg      960
ttcgaagatc tggccctggt gcggccgacc gagatgttct tcgtcccgcg cgtgtgcgac     1020
atgatcttcc agcgctatca ggccgaactg tcgcggcgcg cgcccgccgc ggccgcgagc     1080
ccggaactcg agcaggaact gaagaccgaa ctgcgcttgt ccgcggtcgg ggaccgctta     1140
ctcggggcga tcgcgggcag cgcgccgctg tcggccgaga tgcgggagtt catggagtcg     1200
ctgctggatc tggaactgca cgacggctac ggctcgaccg aggcgggtat cggcgtactg     1260
caagacaata tcgtccagcg tccgccggtc atcgattaca agctcgtcga cgtgccggaa     1320
ttgggctact tccggacgga ccagccgcat ccccgcggtg agttgctgtt gaaaaccgaa     1380
gggatgattc cgggctactt ccggcggccc gaggtgaccg cggagatctt cgacgaggac     1440
ggtttctaca ggaccggtga catcgtcgcc gaactcgaac cggatcggct gatctacctg     1500
gaccgccgca acaatgtgct gaaactggcc cagggcgagt tcgtcacggt cgcccatctg     1560
gaagcggtgt tcgcgaccag tccgctgatc cggcagatct acatctacgg caacagcgag     1620
cgctcgttcc tgctggcggt gatcgtgccc accgcggacg cgctggccga cggtgtcacc     1680
gacgcgctga acacgcgct gaccgaatcc ttgcgacagc tcgcgaaaga agccgggctg     1740
caatcctatg agctgccgcg cgagttcctg gtcgaaaccg aaccgttcac cgtcgagaac     1800
ggtctgctct ccggtatcgc gaaactgttg cggcccaagc tcaaggagca ctacggcgag     1860
cgactcgagc agctgtaccg cgatatcgag gcgaaccgca acgacgagct gatcgagctg     1920
cggcgcaccg cggccgagct gccggtgctc gaaaccgtca cgcgggctgc acgttcgatg     1980
ctcggactgg ccgcgtcgga gttgcggccg gacgcgcatt tcaccgatct cggcggtgat     2040
tcactgtccg cgctgtcgtt ttcgaccctg ctgcaggaca tgctcgaggt cgaggtcccg     2100
gtcggtgtca tcgtgagccc cgccaactcg ctcgccgatc tggcgaaaata catcgaggcc     2160 gaacggcatt cggggggtgcg gcggccgagc ctgatctcgg tgcacggtcc cggcaccgag     2220
atccgtgccg ccgatctcac cctggacaag ttcatcgacg agcgcaccct cgctgccgcg     2280
aaagcggttc cggccgcgcc ggcccaggcg cagaccgtcc tgctcaccgg ggcgaacggc     2340
tatctcggcc gcttcctgtg cctggaatgg ctgcagcgac tggaccagac cggcggcacg     2400
ctggtctgca tcgtgcgcgg taccgacgcg gccgccgcgc ggaagcgcct ggatgcggtg     2460
ttcgacagcg gtgatccgga gctgctcgac cactaccgga agctggccgc cgagcacctc     2520
gaggtgctcg cgggcgatat cggcgacccg aatctcggcc tggacgaagc gacttggcag     2580
cggctcgccc gaccgtcga cctgatcgtg caccccgccg ccctcgtcaa ccatgtgctg     2640
ccgtacagcc agctgttcgg gccgaatgtg gtcggcaccg ccgagatcat ccggctggcc     2700
atcaccgagc gccgtaagcc cgtgacgtac ctgtcgacgg tcgcggtggc cgcacaggtc     2760
gatcccgccg gcttcgacga ggagcgcgat atccgggaga tgagcgcggt gcgctccatc     2820
gacgccgggt acgcgaacgg ttacggcaac agcaagtggg ccggcgaggt gctgctgcgc     2880
gaggcccatg atctgtgcgg gctgccggtc gccgtgttcc gctcggacat gatcctggcg     2940
cacagcaaat acgtcggtca gctcaacgtc cccgatgtgt tcacccggct catcctgagc     3000
ctggcgctca ccggcatcgc accgtattcg ttctacggga cggacagcgc cgggcagcgc     3060
aggcgggccc actacgacgg tctgcccgcc gatttcgtcg ccgaggcgat caccaccctc     3120
```

-continued

```
ggcgcgcgag ccgagtcggg gttccatacc tacgacgtgt ggaacccgta cgacgacggc      3180
atctcgctgg acgaattcgt cgactggctc ggcgatttcg gcgtgccgat ccagcggatc      3240
gacgactacg acgaatggtt ccggcgtttc gagaccgcga tccgcgcgct gcccgaaaag      3300
cagcgcgatg cttcgctgct accgctgctg gacgcacacc ggcggccact gcgcgcggtg      3360
cgcggttcgc tgttgcccgc caagaacttc caggcggcgg tgcagtccgc gcggatcggc      3420
cccgatcagg acatcccgca tctttccccg cagttgatcg acaagtacgt caccgacctg      3480
cgccacctcg gcctgctctg a                                                3501
```

<210> SEQ ID NO 20
<211> LENGTH: 1166
<212> TYPE: PRT
<213> ORGANISM: Nocardia brasiliensis

<400> SEQUENCE: 20

```
Met Ala Thr Asp Ser Arg Ser Asp Arg Leu Arg Arg Ile Ala Gln
1               5                   10                  15

Leu Phe Ala Glu Asp Glu Gln Val Lys Ala Ala Val Pro Asp Gln Glu
            20                  25                  30

Val Val Glu Ala Ile Arg Ala Pro Gly Leu Arg Leu Ala Gln Ile Met
        35                  40                  45

Ala Thr Val Met Glu Arg Tyr Ala Asp Arg Pro Ala Val Gly Gln Arg
    50                  55                  60

Ala Ser Glu Pro Val Thr Glu Ser Gly Arg Thr Thr Phe Arg Leu Leu
65                  70                  75                  80

Pro Glu Phe Glu Thr Leu Thr Tyr Arg Glu Leu Trp Ala Arg Val Arg
                85                  90                  95

Ala Val Ala Ala Ala Trp His Gly Asp Ala Glu Arg Pro Leu Arg Ala
            100                 105                 110

Gly Asp Phe Val Ala Leu Leu Gly Phe Ala Gly Ile Asp Tyr Gly Thr
        115                 120                 125

Leu Asp Leu Ala Asn Ile His Leu Gly Leu Val Thr Val Pro Leu Gln
    130                 135                 140

Ser Gly Ala Thr Ala Pro Gln Leu Ala Ala Ile Leu Ala Glu Thr Thr
145                 150                 155                 160

Pro Arg Val Leu Ala Ala Thr Pro Asp His Leu Asp Ile Ala Val Glu
                165                 170                 175

Leu Leu Thr Gly Gly Ala Ser Pro Glu Arg Leu Val Val Phe Asp Tyr
            180                 185                 190

Arg Pro Ala Asp Asp His Arg Ala Ala Leu Glu Ser Ala Arg Arg
        195                 200                 205

Arg Leu Ser Asp Ala Gly Ser Ala Val Val Glu Thr Leu Asp Ala
    210                 215                 220

Val Arg Ala Arg Gly Ser Glu Leu Pro Ala Ala Pro Leu Phe Val Pro
225                 230                 235                 240

Ala Ala Asp Glu Asp Pro Leu Ala Leu Leu Ile Tyr Thr Ser Gly Ser
                245                 250                 255

Thr Gly Thr Pro Lys Gly Ala Met Tyr Thr Glu Arg Leu Asn Arg Thr
            260                 265                 270

Thr Trp Leu Ser Gly Ala Lys Gly Val Gly Leu Thr Leu Gly Tyr Met
        275                 280                 285

Pro Met Ser His Ile Ala Gly Arg Ala Ser Phe Ala Gly Val Leu Ala
    290                 295                 300
```

```
Arg Gly Gly Thr Val Tyr Phe Thr Ala Arg Ser Asp Met Ser Thr Leu
305                 310                 315                 320

Phe Glu Asp Leu Ala Leu Val Arg Pro Thr Glu Met Phe Phe Val Pro
                325                 330                 335

Arg Val Cys Asp Met Ile Phe Gln Arg Tyr Gln Ala Glu Leu Ser Arg
                340                 345                 350

Arg Ala Pro Ala Ala Ala Ser Pro Glu Leu Glu Gln Glu Leu Lys
                355                 360                 365

Thr Glu Leu Arg Leu Ser Ala Val Gly Asp Arg Leu Leu Gly Ala Ile
    370                 375                 380

Ala Gly Ser Ala Pro Leu Ser Ala Glu Met Arg Glu Phe Met Glu Ser
385                 390                 395                 400

Leu Leu Asp Leu Glu Leu His Asp Gly Tyr Gly Ser Thr Glu Ala Gly
                405                 410                 415

Ile Gly Val Leu Gln Asp Asn Ile Val Gln Arg Pro Val Ile Asp
                420                 425                 430

Tyr Lys Leu Val Asp Val Pro Glu Leu Gly Tyr Phe Arg Thr Asp Gln
                435                 440                 445

Pro His Pro Arg Gly Glu Leu Leu Lys Thr Glu Gly Met Ile Pro
    450                 455                 460

Gly Tyr Phe Arg Arg Pro Glu Val Thr Ala Glu Ile Phe Asp Glu Asp
465                 470                 475                 480

Gly Phe Tyr Arg Thr Gly Asp Ile Val Ala Glu Leu Glu Pro Asp Arg
                485                 490                 495

Leu Ile Tyr Leu Asp Arg Arg Asn Asn Val Leu Lys Leu Ala Gln Gly
                500                 505                 510

Glu Phe Val Thr Val Ala His Leu Glu Ala Val Phe Ala Thr Ser Pro
                515                 520                 525

Leu Ile Arg Gln Ile Tyr Ile Tyr Gly Asn Ser Glu Arg Ser Phe Leu
    530                 535                 540

Leu Ala Val Ile Val Pro Thr Ala Asp Ala Leu Ala Asp Gly Val Thr
545                 550                 555                 560

Asp Ala Leu Asn Thr Ala Leu Thr Glu Ser Leu Arg Gln Leu Ala Lys
                565                 570                 575

Glu Ala Gly Leu Gln Ser Tyr Glu Leu Pro Arg Glu Phe Leu Val Glu
                580                 585                 590

Thr Glu Pro Phe Thr Val Glu Asn Gly Leu Leu Ser Gly Ile Ala Lys
    595                 600                 605

Leu Leu Arg Pro Lys Leu Lys Glu His Tyr Gly Glu Arg Leu Glu Gln
    610                 615                 620

Leu Tyr Arg Asp Ile Glu Ala Asn Arg Asn Asp Glu Leu Ile Glu Leu
625                 630                 635                 640

Arg Arg Thr Ala Ala Glu Leu Pro Val Leu Glu Thr Val Thr Arg Ala
                645                 650                 655

Ala Arg Ser Met Leu Gly Leu Ala Ala Ser Glu Leu Arg Pro Asp Ala
                660                 665                 670

His Phe Thr Asp Leu Gly Gly Asp Ser Leu Ser Ala Leu Ser Phe Ser
                675                 680                 685

Thr Leu Leu Gln Asp Met Leu Glu Val Glu Val Pro Val Gly Val Ile
    690                 695                 700

Val Ser Pro Ala Asn Ser Leu Ala Asp Leu Ala Lys Tyr Ile Glu Ala
705                 710                 715                 720

Glu Arg His Ser Gly Val Arg Arg Pro Ser Leu Ile Ser Val His Gly
```

```
                725             730             735
Pro Gly Thr Glu Ile Arg Ala Ala Asp Leu Thr Leu Asp Lys Phe Ile
                740             745             750
Asp Glu Arg Thr Leu Ala Ala Ala Lys Ala Val Pro Ala Ala Pro Ala
                755             760             765
Gln Ala Gln Thr Val Leu Leu Thr Gly Ala Asn Gly Tyr Leu Gly Arg
    770             775             780
Phe Leu Cys Leu Glu Trp Leu Gln Arg Leu Asp Gln Thr Gly Gly Thr
785             790             795             800
Leu Val Cys Ile Val Arg Gly Thr Asp Ala Ala Ala Arg Lys Arg
                805             810             815
Leu Asp Ala Val Phe Asp Ser Gly Asp Pro Glu Leu Leu Asp His Tyr
                820             825             830
Arg Lys Leu Ala Ala Glu His Leu Glu Val Leu Ala Gly Asp Ile Gly
                835             840             845
Asp Pro Asn Leu Gly Leu Asp Glu Ala Thr Trp Gln Arg Leu Ala Ala
                850             855             860
Thr Val Asp Leu Ile Val His Pro Ala Ala Leu Val Asn His Val Leu
865             870             875             880
Pro Tyr Ser Gln Leu Phe Gly Pro Asn Val Val Gly Thr Ala Glu Ile
                885             890             895
Ile Arg Leu Ala Ile Thr Glu Arg Lys Pro Val Thr Tyr Leu Ser
                900             905             910
Thr Val Ala Val Ala Ala Gln Val Asp Pro Ala Gly Phe Asp Glu Glu
                915             920             925
Arg Asp Ile Arg Glu Met Ser Ala Val Arg Ser Ile Asp Ala Gly Tyr
                930             935             940
Ala Asn Gly Tyr Gly Asn Ser Lys Trp Ala Gly Glu Val Leu Leu Arg
945             950             955             960
Glu Ala His Asp Leu Cys Gly Leu Pro Val Ala Val Phe Arg Ser Asp
                965             970             975
Met Ile Leu Ala His Ser Lys Tyr Val Gly Gln Leu Asn Val Pro Asp
                980             985             990
Val Phe Thr Arg Leu Ile Leu Ser Leu Ala Leu Thr Gly Ile Ala Pro
                995            1000            1005
Tyr Ser Phe Tyr Gly Thr Asp Ser Ala Gly Gln Arg Arg Arg Ala
                1010            1015           1020
His Tyr Asp Gly Leu Pro Ala Asp Phe Val Ala Glu Ala Ile Thr
                1025            1030           1035
Thr Leu Gly Ala Arg Ala Glu Ser Gly Phe His Thr Tyr Asp Val
                1040            1045           1050
Trp Asn Pro Tyr Asp Asp Gly Ile Ser Leu Asp Glu Phe Val Asp
                1055            1060           1065
Trp Leu Gly Asp Phe Gly Val Pro Ile Gln Arg Ile Asp Asp Tyr
                1070            1075           1080
Asp Glu Trp Phe Arg Arg Phe Glu Thr Ala Ile Arg Ala Leu Pro
                1085            1090           1095
Glu Lys Gln Arg Asp Ala Ser Leu Leu Pro Leu Leu Asp Ala His
                1100            1105           1110
Arg Arg Pro Leu Arg Ala Val Arg Gly Ser Leu Leu Pro Ala Lys
                1115            1120           1125
Asn Phe Gln Ala Ala Val Gln Ser Ala Arg Ile Gly Pro Asp Gln
                1130            1135           1140
```

Asp Ile Pro His Leu Ser Pro Gln Leu Ile Asp Lys Tyr Val Thr
1145                1150                1155

Asp Leu Arg His Leu Gly Leu Leu
1160             1165

<210> SEQ ID NO 21
<211> LENGTH: 621
<212> TYPE: DNA
<213> ORGANISM: Escherichia coli

<400> SEQUENCE: 21

```
atgaaaacta cgcatacctc cctccccttt gccggacata cgctgcattt tgttgagttc      60
gatccggcga attttgtga gcaggattta ctctggctgc cgcactacgc acaactgcaa     120
cacgctggac gtaaacgtaa aacagagcat ttagccggac ggatcgctgc tgtttatgct     180
ttgcgggaat atggctataa atgtgtgccc gcaatcggcg agctacgcca acctgtctgg     240
cctgcgaggg tatacggcag tattagccac tgtgggacta cggcattagc cgtggtatct     300
cgtcaaccga ttggcattga tatagaagaa atttttttctg tacaaaccgc aagagaattg     360
acagacaaca ttattacacc agcgaacac gagcgactcg cagactgcgg tttagccttt     420
tctctggcgc tgacactggc attttccgcc aaagagagcg catttaaggc aagtgagatc     480
caaactgatg caggttttct ggactatcag ataattagct ggaataaaca gcaggtcatc     540
attcatcgtg agaatgagat gtttgctgtg cactggcaga taaagaaaa gatagtcata     600
acgctgtgcc aacacgatta a                                              621
```

<210> SEQ ID NO 22
<211> LENGTH: 206
<212> TYPE: PRT
<213> ORGANISM: Escherichia coli

<400> SEQUENCE: 22

Met Lys Thr Thr His Thr Ser Leu Pro Phe Ala Gly His Thr Leu His
1               5                   10                  15

Phe Val Glu Phe Asp Pro Ala Asn Phe Cys Glu Gln Asp Leu Leu Trp
            20                  25                  30

Leu Pro His Tyr Ala Gln Leu Gln His Ala Gly Arg Lys Arg Lys Thr
        35                  40                  45

Glu His Leu Ala Gly Arg Ile Ala Ala Val Tyr Ala Leu Arg Glu Tyr
    50                  55                  60

Gly Tyr Lys Cys Val Pro Ala Ile Gly Glu Leu Arg Gln Pro Val Trp
65                  70                  75                  80

Pro Ala Glu Val Tyr Gly Ser Ile Ser His Cys Gly Thr Thr Ala Leu
                85                  90                  95

Ala Val Val Ser Arg Gln Pro Ile Gly Ile Asp Ile Glu Glu Ile Phe
            100                 105                 110

Ser Val Gln Thr Ala Arg Glu Leu Thr Asp Asn Ile Ile Thr Pro Ala
        115                 120                 125

Glu His Glu Arg Leu Ala Asp Cys Gly Leu Ala Phe Ser Leu Ala Leu
    130                 135                 140

Thr Leu Ala Phe Ser Ala Lys Glu Ser Ala Lys Ala Ser Glu Ile
145                 150                 155                 160

Gln Thr Asp Ala Gly Phe Leu Asp Tyr Gln Ile Ile Ser Trp Asn Lys
                165                 170                 175

Gln Gln Val Ile Ile His Arg Glu Asn Glu Met Phe Ala Val His Trp

```
                    180              185              190
Gln Ile Lys Glu Lys Ile Val Ile Thr Leu Cys Gln His Asp
            195              200              205

<210> SEQ ID NO 23
<211> LENGTH: 654
<212> TYPE: DNA
<213> ORGANISM: Corynebacterium glutamicum

<400> SEQUENCE: 23
atgctggatg agtctttgtt tccaaattcg gcaaagtttt ctttcattaa aactggcgat    60
gctgttaatt tagaccattt ccatcagttg catccgttgg aaaaggcact ggtagcgcac   120
tcggttgata ttagaaaagc agagtttgga gatgccaggt ggtgtgcaca tcaggcactc   180
caagctttgg gacgagatag cggtgatccc attttgcgtg gggaacgagg aatgccattg   240
tggccttctt cggtgtctgg ttcattgacc cacactgacg gattccgagc tgctgttgtg   300
gcgccacgat tgttggtgcg ttctatggga ttggatgccg aacctgcgga gccgttgccc   360
aaggatgttt tgggttcaat cgctcgggtg ggggagattc ctcaacttaa gcgcttggag   420
gaacaaggtg tgcactgcgc ggatcgcctg ctgttttgtg ccaaggaagc aacatacaaa   480
gcgtggttcc cgctgacgca taggtggctt ggttttgaac aagctgagat cgacttgcgt   540
gatgatggca cttttgtgtc ctatttgctg gttcgaccaa ctccagtgcc gtttatttca   600
ggtaaatggg tactgcgtga tggttatgtc atagctgcga ctgcagtgac ttga         654

<210> SEQ ID NO 24
<211> LENGTH: 217
<212> TYPE: PRT
<213> ORGANISM: Corynebacterium glutamicum

<400> SEQUENCE: 24

Met Leu Asp Glu Ser Leu Phe Pro Asn Ser Ala Lys Phe Ser Phe Ile
1               5                   10                  15

Lys Thr Gly Asp Ala Val Asn Leu Asp His Phe His Gln Leu His Pro
            20                  25                  30

Leu Glu Lys Ala Leu Val Ala His Ser Val Asp Ile Arg Lys Ala Glu
        35                  40                  45

Phe Gly Asp Ala Arg Trp Cys Ala His Gln Ala Leu Gln Ala Leu Gly
    50                  55                  60

Arg Asp Ser Gly Asp Pro Ile Leu Arg Gly Glu Arg Gly Met Pro Leu
65                  70                  75                  80

Trp Pro Ser Ser Val Ser Gly Ser Leu Thr His Thr Asp Gly Phe Arg
                85                  90                  95

Ala Ala Val Val Ala Pro Arg Leu Leu Val Arg Ser Met Gly Leu Asp
            100                 105                 110

Ala Glu Pro Ala Glu Pro Leu Pro Lys Asp Val Leu Gly Ser Ile Ala
        115                 120                 125

Arg Val Gly Glu Ile Pro Gln Leu Lys Arg Leu Glu Glu Gln Gly Val
    130                 135                 140

His Cys Ala Asp Arg Leu Leu Phe Cys Ala Lys Glu Ala Thr Tyr Lys
145                 150                 155                 160

Ala Trp Phe Pro Leu Thr His Arg Trp Leu Gly Phe Glu Gln Ala Glu
                165                 170                 175

Ile Asp Leu Arg Asp Asp Gly Thr Phe Val Ser Tyr Leu Leu Val Arg
            180                 185                 190
```

Pro Thr Pro Val Pro Phe Ile Ser Gly Lys Trp Val Leu Arg Asp Gly
          195                 200                 205

Tyr Val Ile Ala Ala Thr Ala Val Thr
          210                 215

<210> SEQ ID NO 25
<211> LENGTH: 1428
<212> TYPE: DNA
<213> ORGANISM: Corynebacterium glutamicum

<400> SEQUENCE: 25

| | | | | | |
|---|---|---|---|---|---|
| atgcgcctgc | gtgtctcgag | tagtctcctc | cccttcctcg | tccccaacct | cgaccattac | 60 |
| ggtcgccctc | tcctaaagga | gcctggcatg | gatatccgcc | aaacaattaa | cgacacagca | 120 |
| atgtcgagat | atcagtggtt | cattgtattt | atcgcagtgc | tgctcaacgc | actggacggc | 180 |
| tttgatgtcc | tcgccatgtc | ttttactgcg | aatgcagtga | ccgaagaatt | tggactgagt | 240 |
| ggcagccagc | ttggtgtgct | gctgagttcc | gcgctgttcg | gcatgaccgc | tggatctttg | 300 |
| ctgttcggtc | cgatcggtga | ccgtttcggc | cgtaagaatg | ccctgatgat | cgcgctgctg | 360 |
| ttcaacgtgg | tgggattggt | attgtccgcc | accgcgcagt | ccgcaggcca | gttgggcgtg | 420 |
| tggcgtttga | tcactggtat | cggcatcggc | ggaatcctcg | cctgcatcac | agtggtgatc | 480 |
| agtgagttct | ccaacaacaa | aaaccgcggc | atggccatgt | ccatctacgc | tgctggttac | 540 |
| ggcatcggcg | cgtccttggg | cggattcggc | gcagcgcagc | tcatcccaac | atttggatgg | 600 |
| cgctccgtgt | tcgcagccgg | tgcgatcgca | actggtatcg | ccaccatcgc | tactttcttc | 660 |
| ttcctgccag | aatccgttga | ttggctgagc | actcgccgcc | ctgcgggcgc | tcgcgacaag | 720 |
| atcaattaca | ttgcgcgccg | cctgggcaaa | gtcggtacct | tgagcttcc | aggcgaacaa | 780 |
| agcttgtcga | cgaaaaaagc | cggtctccaa | tcgtatgcag | tgctcgttaa | caaagagaac | 840 |
| cgtggaacca | gcatcaagct | gtgggttgcg | ttcggcatcg | tgatgttcgg | cttctacttc | 900 |
| gccaacactt | ggaccccgaa | gctgctcgtg | gaaaccggaa | tgtcagaaca | gcagggcatc | 960 |
| atcggtggtt | tgatgttgtc | catgggtgga | gcattcggtt | ccctgctcta | cggtttcctc | 1020 |
| accaccaagt | tcagctcccg | aaacacactg | atgaccttca | tggtgctgtc | cggcctgacg | 1080 |
| ctgatcctgt | tcatttcctc | cacctctgtt | ccatccatcg | cgtttgccag | cggcgttgtc | 1140 |
| gtgggcatgc | tgatcaatgg | ttgtgtggct | ggtctgtaca | ccctgtcccc | acagctgtac | 1200 |
| tccgctgaag | tacgcaccac | tggtgtgggc | gctgcgattg | gtatgggtcg | tgtcggtgcg | 1260 |
| atttccgcgc | cactgctggt | gggtagcctg | ctggattctg | gctggtcccc | aacgcagctg | 1320 |
| tatgttggtg | tggcagtgat | tgttattgcc | ggtgcaaccg | cattgattgg | gatgcgcact | 1380 |
| caggcagtag | ccgtcgaaaa | gcagcctgaa | gccctagcga | ccaaatag | | 1428 |

<210> SEQ ID NO 26
<211> LENGTH: 475
<212> TYPE: PRT
<213> ORGANISM: Corynebacterium glutamicum

<400> SEQUENCE: 26

Met Arg Leu Arg Val Ser Ser Ser Leu Leu Pro Phe Leu Val Pro Asn
1               5                   10                  15

Leu Asp His Tyr Gly Arg Pro Leu Leu Lys Glu Pro Gly Met Asp Ile
            20                  25                  30

Arg Gln Thr Ile Asn Asp Thr Ala Met Ser Arg Tyr Gln Trp Phe Ile
        35                  40                  45

```
Val Phe Ile Ala Val Leu Leu Asn Ala Leu Asp Gly Phe Asp Val Leu
 50                  55                  60
Ala Met Ser Phe Thr Ala Asn Ala Val Thr Glu Glu Phe Gly Leu Ser
 65                  70                  75                  80
Gly Ser Gln Leu Gly Val Leu Leu Ser Ser Ala Leu Phe Gly Met Thr
                 85                  90                  95
Ala Gly Ser Leu Leu Phe Gly Pro Ile Gly Asp Arg Phe Gly Arg Lys
                100                 105                 110
Asn Ala Leu Met Ile Ala Leu Leu Phe Asn Val Val Gly Leu Val Leu
                115                 120                 125
Ser Ala Thr Ala Gln Ser Ala Gly Gln Leu Gly Val Trp Arg Leu Ile
130                 135                 140
Thr Gly Ile Gly Ile Gly Gly Ile Leu Ala Cys Ile Thr Val Val Ile
145                 150                 155                 160
Ser Glu Phe Ser Asn Asn Lys Asn Arg Gly Met Ala Met Ser Ile Tyr
                165                 170                 175
Ala Ala Gly Tyr Gly Ile Gly Ala Ser Leu Gly Gly Phe Gly Ala Ala
                180                 185                 190
Gln Leu Ile Pro Thr Phe Gly Trp Arg Ser Val Phe Ala Ala Gly Ala
                195                 200                 205
Ile Ala Thr Gly Ile Ala Thr Ile Ala Thr Phe Phe Phe Leu Pro Glu
                210                 215                 220
Ser Val Asp Trp Leu Ser Thr Arg Arg Pro Ala Gly Ala Arg Asp Lys
225                 230                 235                 240
Ile Asn Tyr Ile Ala Arg Arg Leu Gly Lys Val Gly Thr Phe Glu Leu
                245                 250                 255
Pro Gly Glu Gln Ser Leu Ser Thr Lys Lys Ala Gly Leu Gln Ser Tyr
                260                 265                 270
Ala Val Leu Val Asn Lys Glu Asn Arg Gly Thr Ser Ile Lys Leu Trp
                275                 280                 285
Val Ala Phe Gly Ile Val Met Phe Gly Phe Tyr Phe Ala Asn Thr Trp
                290                 295                 300
Thr Pro Lys Leu Leu Val Glu Thr Gly Met Ser Glu Gln Gln Gly Ile
305                 310                 315                 320
Ile Gly Gly Leu Met Leu Ser Met Gly Gly Ala Phe Gly Ser Leu Leu
                325                 330                 335
Tyr Gly Phe Leu Thr Thr Lys Phe Ser Ser Arg Asn Thr Leu Met Thr
                340                 345                 350
Phe Met Val Leu Ser Gly Leu Thr Leu Ile Leu Phe Ile Ser Ser Thr
                355                 360                 365
Ser Val Pro Ser Ile Ala Phe Ala Ser Gly Val Val Gly Met Leu
370                 375                 380
Ile Asn Gly Cys Val Ala Gly Leu Tyr Thr Leu Ser Pro Gln Leu Tyr
385                 390                 395                 400
Ser Ala Glu Val Arg Thr Thr Gly Val Gly Ala Ala Ile Gly Met Gly
                405                 410                 415
Arg Val Gly Ala Ile Ser Ala Pro Leu Leu Val Gly Ser Leu Leu Asp
                420                 425                 430
Ser Gly Trp Ser Pro Thr Gln Leu Tyr Val Gly Val Ala Val Ile Val
                435                 440                 445
Ile Ala Gly Ala Thr Ala Leu Ile Gly Met Arg Thr Gln Ala Val Ala
450                 455                 460
Val Glu Lys Gln Pro Glu Ala Leu Ala Thr Lys
```

```
465                    470                   475
```

<210> SEQ ID NO 27
<211> LENGTH: 1296
<212> TYPE: DNA
<213> ORGANISM: Corynebacterium glutamicum

<400> SEQUENCE: 27

```
gtgtcaacga ccaccccaac ccgcgcaacc aaaagtgtcg aacagttct cgcactcctg     60
tggttcgcaa ttgtcctcga cggctttgac ctagtcgtcc tgggcgcaac aatcccgtcc   120
atgctggagg atcccgcgtg ggatctcact gctggacagg ccacacagat ttccaccatc   180
ggcctcgtcg gcatgaccat cggcgcactg accattggtt tcttaactga ccgtctgggt   240
cgacgccgcg tcatgctgtt ctctgtggca gtgttttctg tattcaccct cctgctggca   300
ttcaccacca acgtccagct cttcagcctg tggcgtttcc tcgcaggtgt tggccttggt   360
ggagcactcc ccaccgcaat tgccatggtg accgagtttc gccccggcac caaagcgggc   420
tctgcatcaa ctaccttgat gaccggatac acgtcgggg cagtagcaac cgctttcctt    480
ggtctcttcc ttatcgacgg ctttggttgg cactccatgt tcatcgcagg cgctgtgcca   540
ggactactcc tgctgccact gctgtatttc ttccttccag aatccccgca gtacctcaaa   600
atctccggca agttggatga ggcgcaggca gttgcagcat cttatggact ttccctggat   660
gatgatcttg atcgcgaaca cgaagaagaa cttggcgagt cctcctcact ttcctccctg   720
ttcaagccct cgttccgccg caacaccctg gcgatttggg gcacctcatt catgggactc   780
ctcctggtct acggcctgaa cacatggctg ccacaaatca tgcgccaagc agactacgac   840
atgggtaact ccctgggctt cctcatggtt cttaacatcg gcgcagtgat cggcctttat   900
attgcagggc gaattgccga taagaactcc cctcgcaaaa cagcactcgt atggttcgtg   960
ttctctgcat ttttcctcgc actacttgct gtccggatgc cactgatcgg tctgtatggc  1020
atcgtgctgc tcaccggcat cttgtgttc agctcccagg tactcatcta cgccttcgtt  1080
ggtgagaatc accctgccaa gatgcgtgca actgccatgg gattctccgc aggaattggt  1140
cgcctcggcg cgatctcggg tccgttgctg ggcggcctgc ttgtcagtgc caaccttgct  1200
tacccatggg gcttcttcgc cttcgctggc gttggactgc tgggcgcgct gattttctcc  1260
gcatcgaaga ctctgaggca tcgcgagaac gcttag                            1296
```

<210> SEQ ID NO 28
<211> LENGTH: 431
<212> TYPE: PRT
<213> ORGANISM: Corynebacterium glutamicum

<400> SEQUENCE: 28

```
Met Ser Thr Thr Thr Pro Thr Arg Ala Thr Lys Ser Val Gly Thr Val
 1               5                  10                  15

Leu Ala Leu Leu Trp Phe Ala Ile Val Leu Asp Gly Phe Asp Leu Val
             20                  25                  30

Val Leu Gly Ala Thr Ile Pro Ser Met Leu Glu Asp Pro Ala Trp Asp
         35                  40                  45

Leu Thr Ala Gly Gln Ala Thr Gln Ile Ser Thr Ile Gly Leu Val Gly
     50                  55                  60

Met Thr Ile Gly Ala Leu Thr Ile Gly Phe Leu Thr Asp Arg Leu Gly
 65                  70                  75                  80

Arg Arg Arg Val Met Leu Phe Ser Val Ala Val Phe Ser Val Phe Thr
                 85                  90                  95
```

Leu Leu Leu Ala Phe Thr Thr Asn Val Gln Leu Phe Ser Leu Trp Arg
            100                 105                 110

Phe Leu Ala Gly Val Gly Leu Gly Ala Leu Pro Thr Ala Ile Ala
            115                 120                 125

Met Val Thr Glu Phe Arg Pro Gly Thr Lys Ala Gly Ser Ala Ser Thr
    130                 135                 140

Thr Leu Met Thr Gly Tyr His Val Gly Val Ala Thr Ala Phe Leu
145                 150                 155                 160

Gly Leu Phe Leu Ile Asp Gly Phe Gly Trp His Ser Met Phe Ile Ala
                165                 170                 175

Gly Ala Val Pro Gly Leu Leu Leu Pro Leu Leu Tyr Phe Leu
            180                 185                 190

Pro Glu Ser Pro Gln Tyr Leu Lys Ile Ser Gly Lys Leu Asp Glu Ala
            195                 200                 205

Gln Ala Val Ala Ala Ser Tyr Gly Leu Ser Leu Asp Asp Asp Leu Asp
    210                 215                 220

Arg Glu His Glu Glu Glu Leu Gly Glu Ser Ser Ser Leu Ser Ser Leu
225                 230                 235                 240

Phe Lys Pro Ser Phe Arg Arg Asn Thr Leu Ala Ile Trp Gly Thr Ser
                245                 250                 255

Phe Met Gly Leu Leu Leu Val Tyr Gly Leu Asn Thr Trp Leu Pro Gln
            260                 265                 270

Ile Met Arg Gln Ala Asp Tyr Asp Met Gly Asn Ser Leu Gly Phe Leu
        275                 280                 285

Met Val Leu Asn Ile Gly Ala Val Ile Gly Leu Tyr Ile Ala Gly Arg
    290                 295                 300

Ile Ala Asp Lys Asn Ser Pro Arg Lys Thr Ala Leu Val Trp Phe Val
305                 310                 315                 320

Phe Ser Ala Phe Phe Leu Ala Leu Leu Ala Val Arg Met Pro Leu Ile
                325                 330                 335

Gly Leu Tyr Gly Ile Val Leu Leu Thr Gly Ile Phe Val Phe Ser Ser
            340                 345                 350

Gln Val Leu Ile Tyr Ala Phe Val Gly Glu Asn His Pro Ala Lys Met
        355                 360                 365

Arg Ala Thr Ala Met Gly Phe Ser Ala Gly Ile Gly Arg Leu Gly Ala
    370                 375                 380

Ile Ser Gly Pro Leu Leu Gly Gly Leu Leu Val Ser Ala Asn Leu Ala
385                 390                 395                 400

Tyr Pro Trp Gly Phe Phe Ala Phe Ala Gly Val Gly Leu Leu Gly Ala
                405                 410                 415

Leu Ile Phe Ser Ala Ser Lys Thr Leu Arg His Arg Glu Asn Ala
            420                 425                 430

<210> SEQ ID NO 29
<211> LENGTH: 1131
<212> TYPE: DNA
<213> ORGANISM: Corynebacterium glutamicum

<400> SEQUENCE: 29
atgacactgt ccgaacgcaa gctcaccacc accgccaaga ttcttcccca cccactcaac      60
gcctggtacg tcgccgcttg ggattatgaa gtcacatcta aaaagcccat ggccaggaca     120
atcgccaaca aaccactcgc tttgtaccgc accaaagatg gccgagccgt tgcccttgca     180
gacgcctgct ggcaccgcct cgcaccgcta tccaagggaa aactcgtggg cacagacgga     240

```
atccaatgcc cttatcacgg cttggagtac aactccgcgg ccgctgcat gaaaatgccc    300
gcgcaggaaa ccctcaaccc gtcagcagcc gtcaactcct accccgtggt ggaagcccac    360
cgctttgtgt gggtgtggct gggcgatccc acattggcag atcccaccca agtacccgat    420
atgcaccaga tgagccaccc cgaatgggca ggcgatggac gcaccatctc cgctgactgc    480
aactaccaat tagtgctgga caacttgatg gacctcaccc acgaagaatt cgtgcactcc    540
tccagcatcg gccaagacga acttagtgaa tcagagttcg tggtcaccca cactgaagat    600
tccgtgacgg tcacccgctg gatgcatgac atagatgcac caccgttttg caaaagaac     660
atgaatgata agttcccagg atttgaaggc aaggtggatc gttggcagat catccactac    720
tactaccctt ccaccatctg cattgatgtt ggtgtagcaa aggctggaac cggcgcgcag    780
gaaggcgacc gcagccaggg cgttaatggg tatgtaatga acaccattac cccagattca    840
gatcgttcct ctcattactt ctgggcattc atgcgcaact accgcctgga agccaaacc     900
atcaccaccc agctgcgcga cggtgtatcc ggtgtattca agaagacga agacatgctg      960
accgctcagc aagatgccat cgacgccaac accgactatg agttttacag cctcaacatt   1020
gatgccggtg catgtgggt gcgccgaatc ctcgaggaag cactctccaa ggaaggccga    1080
ctggatatcc ccaccacatt cccccgcgca acaccgaagc cggaggcata a            1131
```

<210> SEQ ID NO 30
<211> LENGTH: 376
<212> TYPE: PRT
<213> ORGANISM: Corynebacterium glutamicum

<400> SEQUENCE: 30

```
Met Thr Leu Ser Glu Arg Lys Leu Thr Thr Thr Ala Lys Ile Leu Pro
1               5                   10                  15

His Pro Leu Asn Ala Trp Tyr Val Ala Ala Trp Asp Tyr Glu Val Thr
            20                  25                  30

Ser Lys Lys Pro Met Ala Arg Thr Ile Ala Asn Lys Pro Leu Ala Leu
        35                  40                  45

Tyr Arg Thr Lys Asp Gly Arg Ala Val Ala Leu Ala Asp Ala Cys Trp
50                  55                  60

His Arg Leu Ala Pro Leu Ser Lys Gly Lys Leu Val Gly Thr Asp Gly
65                  70                  75                  80

Ile Gln Cys Pro Tyr His Gly Leu Glu Tyr Asn Ser Ala Gly Arg Cys
                85                  90                  95

Met Lys Met Pro Ala Gln Glu Thr Leu Asn Pro Ser Ala Ala Val Asn
            100                 105                 110

Ser Tyr Pro Val Val Glu Ala His Arg Phe Val Trp Val Trp Leu Gly
        115                 120                 125

Asp Pro Thr Leu Ala Asp Pro Thr Gln Val Pro Asp Met His Gln Met
130                 135                 140

Ser His Pro Glu Trp Ala Gly Asp Gly Arg Thr Ile Ser Ala Asp Cys
145                 150                 155                 160

Asn Tyr Gln Leu Val Leu Asp Asn Leu Met Asp Leu Thr His Glu Glu
                165                 170                 175

Phe Val His Ser Ser Ile Gly Gln Asp Glu Leu Ser Glu Ser Glu
            180                 185                 190

Phe Val Val Thr His Thr Glu Asp Ser Val Thr Val Thr Arg Trp Met
        195                 200                 205

His Asp Ile Asp Ala Pro Pro Phe Trp Gln Lys Asn Met Asn Asp Lys
```

```
                  210                215                 220
Phe Pro Gly Phe Glu Gly Lys Val Asp Arg Trp Gln Ile Ile His Tyr
225                 230                 235                 240

Tyr Tyr Pro Ser Thr Ile Cys Ile Asp Val Gly Val Ala Lys Ala Gly
                245                 250                 255

Thr Gly Ala Gln Glu Gly Asp Arg Ser Gln Gly Val Asn Gly Tyr Val
                260                 265                 270

Met Asn Thr Ile Thr Pro Asp Ser Asp Arg Ser Ser His Tyr Phe Trp
                275                 280                 285

Ala Phe Met Arg Asn Tyr Arg Leu Glu Ser Gln Thr Ile Thr Thr Gln
                290                 295                 300

Leu Arg Asp Gly Val Ser Gly Val Phe Lys Glu Asp Glu Asp Met Leu
305                 310                 315                 320

Thr Ala Gln Gln Asp Ala Ile Asp Ala Asn Thr Asp Tyr Glu Phe Tyr
                325                 330                 335

Ser Leu Asn Ile Asp Ala Gly Gly Met Trp Val Arg Arg Ile Leu Glu
                340                 345                 350

Glu Ala Leu Ser Lys Glu Gly Arg Leu Asp Ile Pro Thr Thr Phe Pro
                355                 360                 365

Arg Ala Thr Pro Lys Pro Glu Ala
                370                 375

<210> SEQ ID NO 31
<211> LENGTH: 978
<212> TYPE: DNA
<213> ORGANISM: Corynebacterium glutamicum

<400> SEQUENCE: 31
atgaactcgc aatggcaaga tgcacatgtt gtttccagcg aaatcatcgc tgcagacatt    60
cgacgaatag aactatcccc gaaatttgcg attccagtaa acccggcga acatctcaag    120
atcatggtgc ccctaaaaac tggacaggaa aagagatcgt actccatcgt tgacgctcgt    180
cacgacggtt cgactctcgc cctgagcgta ctcaaaacca gaaactcccg tggaggatct    240
gagttcatgc atacgcttcg agctggagac acagttactg tctccaggcc gtctcaggat    300
tttcctctcc gcgtgggtgc gcctgagtat gtacttgttg ccggcggaat tggaatcaca    360
gcgatccgtt caatggcatc tttattaaag aaattgggag caaactaccg cattcatttc    420
gcagcacgca gccttgatgc catggcttac aaagatgagc tcgtggcaga cacggcgac    480
aagctgcacc tgcatctaga ttctgaaggc accaccatcg atgtcccagc attgatcgaa    540
accttaaacc cccacactga gctttatatg tgcggcccca tccgcttgat ggatgccatc    600
cggcgcgcat ggaacacccg cggacttgac cccaccaatc tgcgtttcga acgtttgga    660
aacagtggat ggttctcccc agaggttttc acatccaag taccagagct ggggcttcac    720
gccacagtca acaaggatga aagcatgctg gaggctttgc aaaaggctgg ggcgaatatg    780
atgtttgatt gtcgaaaagg cgaatgtggt ttgtgccagg ttcgcgttct agaagtcgat    840
ggccaggttg atcaccgcga tgtgttcttc tctgatcgtc aaaaagaatc cgacgcaaag    900
gcatgcgcct gcgtgtctcg agtagtctcc tccccttcct cgtccccaac ctcgaccatt    960
acggtcgccc tctcctaa                                                  978

<210> SEQ ID NO 32
<211> LENGTH: 325
<212> TYPE: PRT
<213> ORGANISM: Corynebacterium glutamicum
```

<400> SEQUENCE: 32

```
Met Asn Ser Gln Trp Gln Asp Ala His Val Val Ser Ser Glu Ile Ile
1               5                   10                  15

Ala Ala Asp Ile Arg Arg Ile Glu Leu Ser Pro Lys Phe Ala Ile Pro
            20                  25                  30

Val Lys Pro Gly Glu His Leu Lys Ile Met Val Pro Leu Lys Thr Gly
        35                  40                  45

Gln Glu Lys Arg Ser Tyr Ser Ile Val Asp Ala Arg His Asp Gly Ser
    50                  55                  60

Thr Leu Ala Leu Ser Val Leu Lys Thr Arg Asn Ser Arg Gly Gly Ser
65                  70                  75                  80

Glu Phe Met His Thr Leu Arg Ala Gly Asp Thr Val Thr Val Ser Arg
                85                  90                  95

Pro Ser Gln Asp Phe Pro Leu Arg Val Gly Ala Pro Glu Tyr Val Leu
            100                 105                 110

Val Ala Gly Gly Ile Gly Ile Thr Ala Ile Arg Ser Met Ala Ser Leu
        115                 120                 125

Leu Lys Lys Leu Gly Ala Asn Tyr Arg Ile His Phe Ala Ala Arg Ser
    130                 135                 140

Leu Asp Ala Met Ala Tyr Lys Asp Glu Leu Val Ala Glu His Gly Asp
145                 150                 155                 160

Lys Leu His Leu His Leu Asp Ser Glu Gly Thr Thr Ile Asp Val Pro
                165                 170                 175

Ala Leu Ile Glu Thr Leu Asn Pro His Thr Glu Leu Tyr Met Cys Gly
            180                 185                 190

Pro Ile Arg Leu Met Asp Ala Ile Arg Arg Ala Trp Asn Thr Arg Gly
        195                 200                 205

Leu Asp Pro Thr Asn Leu Arg Phe Glu Thr Phe Gly Asn Ser Gly Trp
    210                 215                 220

Phe Ser Pro Glu Val Phe His Ile Gln Val Pro Glu Leu Gly Leu His
225                 230                 235                 240

Ala Thr Val Asn Lys Asp Glu Ser Met Leu Glu Ala Leu Gln Lys Ala
                245                 250                 255

Gly Ala Asn Met Met Phe Asp Cys Arg Lys Gly Glu Cys Gly Leu Cys
            260                 265                 270

Gln Val Arg Val Leu Glu Val Asp Gly Gln Val Asp His Arg Asp Val
        275                 280                 285

Phe Phe Ser Asp Arg Gln Lys Glu Ser Asp Ala Lys Ala Cys Ala Cys
    290                 295                 300

Val Ser Arg Val Val Ser Ser Pro Ser Ser Ser Pro Thr Ser Thr Ile
305                 310                 315                 320

Thr Val Ala Leu Ser
                325
```

<210> SEQ ID NO 33
<211> LENGTH: 615
<212> TYPE: DNA
<213> ORGANISM: Corynebacterium glutamicum

<400> SEQUENCE: 33

```
atgattgata caggaagaa cggcgagttc cgctacgagc agtcgaatat catcgatcag      60
aacgaagccg agttcggcat cactccttca cagaccgtgg gcccttacgt ccacatcggt    120
ttgacccttg aaggtgcgga gcatctcgtg gagccaggtt cggaaggcgc ggtgtccttt    180
```

```
actgtttccg caactgatgg caacggcgac cccatcgcgg atgccatgtt tgaactgtgg    240
caggccgatc cagagggcat ccacaactct gatttggatc caaaccgcac agcaccagca    300
accgcagatg gcttccgcgg gcttggtcgc gcgatggcaa acgcgcaggg tgaggcaacg    360
ttcaccactt tggttccggg agcattcgca gatgaggcac acacttcaa ggttggtgtg     420 ttcgcccgtg gcatgctgga gcgtctgtac actcgcgcat acctgccaga cgccgatttg    480
agcaccgacc cagttttggc tgtggtccca gctgatcgac gtgacctcct ggtggctcaa    540
aagaccgatg atggattccg cttcgacatc actgtccagg ctgaagacaa tgaaacccca    600
ttttttggac tctaa                                                    615
```

<210> SEQ ID NO 34
<211> LENGTH: 204
<212> TYPE: PRT
<213> ORGANISM: Corynebacterium glutamicum

<400> SEQUENCE: 34

```
Met Ile Asp Thr Gly Lys Asn Gly Glu Phe Arg Tyr Glu Gln Ser Asn
1               5                   10                  15
Ile Ile Asp Gln Asn Glu Ala Glu Phe Gly Ile Thr Pro Ser Gln Thr
            20                  25                  30
Val Gly Pro Tyr Val His Ile Gly Leu Thr Leu Glu Gly Ala Glu His
        35                  40                  45
Leu Val Glu Pro Gly Ser Glu Gly Ala Val Ser Phe Thr Val Ser Ala
    50                  55                  60
Thr Asp Gly Asn Gly Asp Pro Ile Ala Asp Ala Met Phe Glu Leu Trp
65                  70                  75                  80
Gln Ala Asp Pro Glu Gly Ile His Asn Ser Asp Leu Asp Pro Asn Arg
                85                  90                  95
Thr Ala Pro Ala Thr Ala Asp Gly Phe Arg Gly Leu Gly Arg Ala Met
            100                 105                 110
Ala Asn Ala Gln Gly Glu Ala Thr Phe Thr Thr Leu Val Pro Gly Ala
        115                 120                 125
Phe Ala Asp Glu Ala Pro His Phe Lys Val Gly Val Phe Ala Arg Gly
    130                 135                 140
Met Leu Glu Arg Leu Tyr Thr Arg Ala Tyr Leu Pro Asp Ala Asp Leu
145                 150                 155                 160
Ser Thr Asp Pro Val Leu Ala Val Val Pro Ala Asp Arg Arg Asp Leu
                165                 170                 175
Leu Val Ala Gln Lys Thr Asp Asp Gly Phe Arg Phe Asp Ile Thr Val
            180                 185                 190
Gln Ala Glu Asp Asn Glu Thr Pro Phe Phe Gly Leu
        195                 200
```

<210> SEQ ID NO 35
<211> LENGTH: 693
<212> TYPE: DNA
<213> ORGANISM: Corynebacterium glutamicum

<400> SEQUENCE: 35

```
atggacatcc cacacttcgc cccgacggga ggcgaatact ccccactgca cttcccggag    60
taccggacca ccatcaagcg caacccaagc aacgatctca tcatggttcc tagtcgcctc    120
ggcgagtcca cggacctgt cttcggcgac cgcgacttgg agacatcga caacgacatg     180 accaaggtga acgtggcga ggctatcggc cagcgcatct tcgttcacgg ccgtgtcctc    240
```

```
ggtttcgatg gcaagccagt ccgcacacc ttggtcgagg cgtggcaggc aaacgccgca      300
ggccgttacc gccacaagaa tgactcctgg ccagcgccac tggatccaca cttcaacggt      360
gttgcacgta ctctcaccga caaggacggc cagtaccact tctggaccgt tatgccaggt      420 aattacccttt ggggtaacca ccacaacgca tggcgcccgg cgcacattca cttctcgctc    480
tatggtcgtc agtttacgga gcgtctggtc acccagatgt acttcccgaa cgatccattg      540
ttcttccagg atccgatcta acgcggtgcc caaagggtgc acgtgagcg catgatcgca       600 acgttcgact atgacgagac ccgtgaaaac ttcgcgcttg gttacaagtt cgacatcgtc      660
cttcgtggcc gcaacgccac cccatttgag taa                                    693
```

<210> SEQ ID NO 36
<211> LENGTH: 230
<212> TYPE: PRT
<213> ORGANISM: Corynebacterium glutamicum

<400> SEQUENCE: 36

```
Met Asp Ile Pro His Phe Ala Pro Thr Gly Gly Glu Tyr Ser Pro Leu
1               5                   10                  15

His Phe Pro Glu Tyr Arg Thr Thr Ile Lys Arg Asn Pro Ser Asn Asp
            20                  25                  30

Leu Ile Met Val Pro Ser Arg Leu Gly Glu Ser Thr Gly Pro Val Phe
        35                  40                  45

Gly Asp Arg Asp Leu Gly Asp Ile Asp Asn Asp Met Thr Lys Val Asn
    50                  55                  60

Gly Gly Glu Ala Ile Gly Gln Arg Ile Phe Val His Gly Arg Val Leu
65                  70                  75                  80

Gly Phe Asp Gly Lys Pro Val Pro His Thr Leu Val Glu Ala Trp Gln
                85                  90                  95

Ala Asn Ala Ala Gly Arg Tyr Arg His Lys Asn Asp Ser Trp Pro Ala
            100                 105                 110

Pro Leu Asp Pro His Phe Asn Gly Val Ala Arg Thr Leu Thr Asp Lys
        115                 120                 125

Asp Gly Gln Tyr His Phe Trp Thr Val Met Pro Gly Asn Tyr Pro Trp
    130                 135                 140

Gly Asn His His Asn Ala Trp Arg Pro Ala His Ile His Phe Ser Leu
145                 150                 155                 160

Tyr Gly Arg Gln Phe Thr Glu Arg Leu Val Thr Gln Met Tyr Phe Pro
                165                 170                 175

Asn Asp Pro Leu Phe Phe Gln Asp Pro Ile Tyr Asn Ala Val Pro Lys
            180                 185                 190

Gly Ala Arg Glu Arg Met Ile Ala Thr Phe Asp Tyr Asp Glu Thr Arg
        195                 200                 205

Glu Asn Phe Ala Leu Gly Tyr Lys Phe Asp Ile Val Leu Arg Gly Arg
    210                 215                 220

Asn Ala Thr Pro Phe Glu
225                 230
```

<210> SEQ ID NO 37
<211> LENGTH: 1164
<212> TYPE: DNA
<213> ORGANISM: Escherichia coli

<400> SEQUENCE: 37

```
atgaacaact ttaatctgca cacccaacc cgcattctgt ttggtaaagg cgcaatcgct      60
```

```
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta cgccgcagc ggctaactat ccggaaaata tcgatccgtg cacattctg    360 caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa aatcatgaca ttacgttgga tgtcagccgc   1140
cgtatatacg aagccgcccg ctaa                                          1164

<210> SEQ ID NO 38
<211> LENGTH: 387
<212> TYPE: PRT
<213> ORGANISM: Escherichia coli

<400> SEQUENCE: 38

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Lys Thr Gly Val Leu Asp
            35                  40                  45

Gln Val Leu Asp Ala Leu Lys Gly Met Asp Val Leu Glu Phe Gly Gly
        50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
        130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175
```

```
Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 39
<211> LENGTH: 1062
<212> TYPE: DNA
<213> ORGANISM: Corynebacterium glutamicum

<400> SEQUENCE: 39
atgagcatcc aagtaaaagc actccagaaa accggccccg aagcaccttt cgaggtcaaa      60
atcattgagc gtcgtgagcc tcgcgctgac gacgtagtta tcgacatcaa agctgccggc     120
atctgccaca gcgatatcca caccatccgc aacgaatggg gcgaggcaca cttcccgctc     180
accgtcggcc acgaaatcgc aggcgttgtc tctgcggttg ctccgatgt aaccaagtgg      240 aaagtcggcg accgcgttgg cgtcggctgc ctagttaact cctgcggcga atgtgaacag     300
tgtgtcgcgg gatttgaaaa caactgcctt cgcggaaacg tcggaaccta caactccgac     360
gacgtcgacg gcaccatcac gcaaggtggc tacgccgaaa aggtagtggt caacgaacgt     420
ttcctctgca gcatcccaga ggaactcgac ttcgatgtcg cagcaccact gctgtgcgca     480
ggcatcacca cctactcccc gatcgctcgc tggaacgtta agaaggcga caaagtagca      540 gtcatgggcc tcggcgggct cggccacatg ggtgtccaaa tcgccgcagc caagggcgct     600
gacgttaccg ttctgtcccg ttccctgcgc aaggctgaac ttgccaagga actcggcgca     660
gctcgcacgc ttgcgacttc tgatgaggat ttcttcaccg aacacgccgg tgaattcgac     720
ttcatcctca acaccattag cgcatccatc ccagtcgaca gtacctgag ccttctcaag      780 ccacacggtg tcatggctgt tgtcggtctg ccaccagaga agcagccact gagcttcggt     840
```

-continued

```
gcgctcatcg gcggcggaaa agtcctcacc ggatccaaca ttggcggcat ccctgaaacc      900
caggaaatgc tcgacttctg tgcaaaacac ggcctcggcg cgatgatcga aactgtcggc      960
gtcaacgatg ttgatgcagc ctacgaccgc gttgttgccg gcgacgttca gttccgcgtt     1020
gtcattgata ctgcttcgtt tgcagaggta gaggcggttt ag                        1062
```

<210> SEQ ID NO 40
<211> LENGTH: 353
<212> TYPE: PRT
<213> ORGANISM: Corynebacterium glutamicum

<400> SEQUENCE: 40

```
Met Ser Ile Gln Val Lys Ala Leu Gln Lys Thr Gly Pro Glu Ala Pro
1               5                   10                  15

Phe Glu Val Lys Ile Ile Glu Arg Arg Glu Pro Arg Ala Asp Asp Val
            20                  25                  30

Val Ile Asp Ile Lys Ala Ala Gly Ile Cys His Ser Asp Ile His Thr
        35                  40                  45

Ile Arg Asn Glu Trp Gly Glu Ala His Phe Pro Leu Thr Val Gly His
    50                  55                  60

Glu Ile Ala Gly Val Val Ser Ala Val Gly Ser Asp Val Thr Lys Trp
65                  70                  75                  80

Lys Val Gly Asp Arg Val Gly Val Gly Cys Leu Val Asn Ser Cys Gly
                85                  90                  95

Glu Cys Glu Gln Cys Val Ala Gly Phe Glu Asn Asn Cys Leu Arg Gly
            100                 105                 110

Asn Val Gly Thr Tyr Asn Ser Asp Asp Val Asp Gly Thr Ile Thr Gln
        115                 120                 125

Gly Gly Tyr Ala Glu Lys Val Val Val Asn Glu Arg Phe Leu Cys Ser
    130                 135                 140

Ile Pro Glu Glu Leu Asp Phe Asp Val Ala Ala Pro Leu Leu Cys Ala
145                 150                 155                 160

Gly Ile Thr Thr Tyr Ser Pro Ile Ala Arg Trp Asn Val Lys Glu Gly
                165                 170                 175

Asp Lys Val Ala Val Met Gly Leu Gly Gly Leu Gly His Met Gly Val
            180                 185                 190

Gln Ile Ala Ala Ala Lys Gly Ala Asp Val Thr Val Leu Ser Arg Ser
        195                 200                 205

Leu Arg Lys Ala Glu Leu Ala Lys Glu Leu Gly Ala Ala Arg Thr Leu
    210                 215                 220

Ala Thr Ser Asp Glu Asp Phe Phe Thr Glu His Ala Gly Glu Phe Asp
225                 230                 235                 240

Phe Ile Leu Asn Thr Ile Ser Ala Ser Ile Pro Val Asp Lys Tyr Leu
                245                 250                 255

Ser Leu Leu Lys Pro His Gly Val Met Ala Val Gly Leu Pro Pro
            260                 265                 270

Glu Lys Gln Pro Leu Ser Phe Gly Ala Leu Ile Gly Gly Lys Val
        275                 280                 285

Leu Thr Gly Ser Asn Ile Gly Gly Ile Pro Glu Thr Gln Glu Met Leu
    290                 295                 300

Asp Phe Cys Ala Lys His Gly Leu Gly Ala Met Ile Glu Thr Val Gly
305                 310                 315                 320

Val Asn Asp Val Asp Ala Ala Tyr Asp Arg Val Val Ala Gly Asp Val
                325                 330                 335
```

```
Gln Phe Arg Val Val Ile Asp Thr Ala Ser Phe Ala Glu Glu Ala
            340                 345                 350
Val

<210> SEQ ID NO 41
<211> LENGTH: 1113
<212> TYPE: DNA
<213> ORGANISM: Corynebacterium glutamicum

<400> SEQUENCE: 41
gtgtccatga gcactgtcgt gcctggaatt gtcgccctgt ccaagggggc accggtagaa      60
aaagtaaacg ttgttgtccc tgatccaggt gctaacgatg tcatcgtcaa gattcaggcc     120
tgcggtgtgt gccacaccga cttggcctac cgcgatggcg atatttcaga tgagttccct     180
tacctcctcg gccacgaggc agcaggtatt gttgaggagg taggcgagtc cgtcacccac     240
gttgaggtcg gcgatttcgt catcttgaac tggcgtgcag tgtgcggcga gtgccgtgca     300
tgtaagaagg gcgagccaaa gtactgcttt aacacccaca acgcatctaa gaagatgacc     360
ctggaagacg gcaccgagct gtccccagca ctgggtattg gcgcgttctt ggaaaagacc     420
ctggtccacg aaggccagtg caccaaggtt aaccctgagg aagatccagc agcagctggc     480
cttctgggtt gcggcatcat ggcaggtctt ggtgctgcgg taaacaccgg tgatattaag     540
cgcggcgagt ccgtggcagt cttcggcctt ggtggcgtgg catggcagc tattgctggc     600
gccaagattg ctggtgcatc gaagattatt gctgttgata tcgatgagaa gaagttggag     660
tgggcgaagg aattcggcgc aacccacacc attaattcct ctggtcttgg tggcgagggt     720
gatgcctctg aggtcgtggc aaaggttcgt gagctcactg atggtttcgg tactgacgtc     780
tccatcgatg cggtaggcat catgccgacc tggcagcagg cgttttactc ccgtgatcat     840
gcaggccgca tggtgatggt gggcgttcca aacctgacgt ctcgcgtaga tgttcctgcg     900
attgattttt acggtcgcgg tggctctgtg cgccctgcat ggtacggcga ctgcctgcct     960
gagcgtgatt tcccaactta tgtggatctg cacctgcagg gtcgtttccc gctggataag    1020
tttgtttctg agcgtattgg tcttgatgat gttgaagagg ctttcaacac catgaaggct    1080
ggcgacgtgc tgcgttctgt ggtggagatc taa                                 1113

<210> SEQ ID NO 42
<211> LENGTH: 370
<212> TYPE: PRT
<213> ORGANISM: Corynebacterium glutamicum

<400> SEQUENCE: 42

Met Ser Met Ser Thr Val Val Pro Gly Ile Val Ala Leu Ser Lys Gly
1               5                   10                  15

Ala Pro Val Glu Lys Val Asn Val Val Pro Asp Pro Gly Ala Asn
            20                  25                  30

Asp Val Ile Val Lys Ile Gln Ala Cys Gly Val Cys His Thr Asp Leu
            35                  40                  45

Ala Tyr Arg Asp Gly Asp Ile Ser Asp Glu Phe Pro Tyr Leu Leu Gly
        50                  55                  60

His Glu Ala Ala Gly Ile Val Glu Glu Val Gly Glu Ser Val Thr His
65                  70                  75                  80

Val Glu Val Gly Asp Phe Val Ile Leu Asn Trp Arg Ala Val Cys Gly
                85                  90                  95

Glu Cys Arg Ala Cys Lys Lys Gly Glu Pro Lys Tyr Cys Phe Asn Thr
            100                 105                 110
```

```
His Asn Ala Ser Lys Lys Met Thr Leu Glu Asp Gly Thr Glu Leu Ser
        115                 120                 125
Pro Ala Leu Gly Ile Gly Ala Phe Leu Glu Lys Thr Leu Val His Glu
    130                 135                 140
Gly Gln Cys Thr Lys Val Asn Pro Glu Asp Pro Ala Ala Ala Gly
145                 150                 155                 160
Leu Leu Gly Cys Gly Ile Met Ala Gly Leu Ala Ala Val Asn Thr
                165                 170                 175
Gly Asp Ile Lys Arg Gly Glu Ser Val Ala Val Phe Gly Leu Gly
            180                 185                 190
Val Gly Met Ala Ala Ile Ala Gly Ala Lys Ile Ala Gly Ala Ser Lys
        195                 200                 205
Ile Ile Ala Val Asp Ile Asp Glu Lys Lys Leu Glu Trp Ala Lys Glu
    210                 215                 220
Phe Gly Ala Thr His Thr Ile Asn Ser Ser Gly Leu Gly Gly Glu Gly
225                 230                 235                 240
Asp Ala Ser Glu Val Val Ala Lys Val Arg Glu Leu Thr Asp Gly Phe
                245                 250                 255
Gly Thr Asp Val Ser Ile Asp Ala Val Gly Ile Met Pro Thr Trp Gln
            260                 265                 270
Gln Ala Phe Tyr Ser Arg Asp His Ala Gly Arg Met Val Met Val Gly
        275                 280                 285
Val Pro Asn Leu Thr Ser Arg Val Asp Val Pro Ala Ile Asp Phe Tyr
    290                 295                 300
Gly Arg Gly Gly Ser Val Arg Pro Ala Trp Tyr Gly Asp Cys Leu Pro
305                 310                 315                 320
Glu Arg Asp Phe Pro Thr Tyr Val Asp Leu His Leu Gln Gly Arg Phe
                325                 330                 335
Pro Leu Asp Lys Phe Val Ser Glu Arg Ile Gly Leu Asp Asp Val Glu
            340                 345                 350
Glu Ala Phe Asn Thr Met Lys Ala Gly Asp Val Leu Arg Ser Val Val
        355                 360                 365
Glu Ile
    370

<210> SEQ ID NO 43
<211> LENGTH: 1047
<212> TYPE: DNA
<213> ORGANISM: Corynebacterium glutamicum

<400> SEQUENCE: 43
gtgagtttta tgaccactgc tgcaccccaa gaatttaccg ctgctgttgt tgaaaaattc      60
ggtcatgacg tgaccgtgaa ggatattgac cttccaaagc cagggccaca ccaggcattg     120
gtgaaggtac tcacctccgg catctgccac accgacctcc acgccttgga gggcgattgg     180
ccagtaaagc cggaaccacc attcgtacca ggacacgaag gtgtaggtga agttgttgag     240
ctcggaccag gtgaacacga tgtgaaggtc ggcgatattg tcggcaatgc gtggctctgg     300
tcagcgtgcg gcacctgcga atactgcatc acaggcaggg aaactcagtg taacgaagct     360
gagtacggtg gctacaccca aaatggatcc ttcggccagt acatgctggt ggataccga      420 tacgccgctc gcatcccaga cggcgtggac tacctcgaag cagcgccaat tctgtgtgca     480
ggcgtgactg tctacaaggc actcaaagtc tctgaacccg cccgggcca attcatggtg      540 atctccggtg tcggcggact tggccacatc gcagtccaat acgcagcggc gatgggcatg     600
```

```
cgtgtcattg cggtagatat tgccgaggac aagctggaac ttgcccgtaa gcacggtgcg    660
gaatttaccg tgaatgcgcg taatgaagat ccaggcgaag ctgtacagaa gtacaccaac    720
ggtggcgcac acggcgtgct tgtgactgca gttcacgagg cagcattcgg ccaggcactg    780
gatatggctc gacgtgcagg aacaattgtg ttcaacggtc tgccaccggg agagttccca    840
gcatccgtgt tcaacatcgt attcaagggc ctgaccatcc gtggatccct cgtgggaacc    900
cgccaagact tggccgaagc gctcgatttc tttgcacgcg gactaatcaa gccaaccgtg    960
agtgagtgct ccctcgatga ggtcaatgga gttcttgacc gcatgcgaaa cggcaagatc   1020
gatggtcgtg tggcgattcg tttctaa                                       1047
```

<210> SEQ ID NO 44
<211> LENGTH: 348
<212> TYPE: PRT
<213> ORGANISM: Corynebacterium glutamicum

<400> SEQUENCE: 44

```
Met Ser Phe Met Thr Thr Ala Ala Pro Gln Glu Phe Thr Ala Ala Val
1               5                   10                  15

Val Glu Lys Phe Gly His Asp Val Thr Val Lys Asp Ile Asp Leu Pro
            20                  25                  30

Lys Pro Gly Pro His Gln Ala Leu Val Lys Val Leu Thr Ser Gly Ile
        35                  40                  45

Cys His Thr Asp Leu His Ala Leu Glu Gly Asp Trp Pro Val Lys Pro
    50                  55                  60

Glu Pro Pro Phe Val Pro Gly His Glu Gly Val Gly Glu Val Val Glu
65                  70                  75                  80

Leu Gly Pro Gly Glu His Asp Val Lys Val Gly Asp Ile Val Gly Asn
                85                  90                  95

Ala Trp Leu Trp Ser Ala Cys Gly Thr Cys Glu Tyr Cys Ile Thr Gly
            100                 105                 110

Arg Glu Thr Gln Cys Asn Glu Ala Glu Tyr Gly Gly Tyr Thr Gln Asn
        115                 120                 125

Gly Ser Phe Gly Gln Tyr Met Leu Val Asp Thr Arg Tyr Ala Ala Arg
    130                 135                 140

Ile Pro Asp Gly Val Asp Tyr Leu Glu Ala Ala Pro Ile Leu Cys Ala
145                 150                 155                 160

Gly Val Thr Val Tyr Lys Ala Leu Lys Val Ser Glu Thr Arg Pro Gly
                165                 170                 175

Gln Phe Met Val Ile Ser Gly Val Gly Gly Leu Gly His Ile Ala Val
            180                 185                 190

Gln Tyr Ala Ala Ala Met Gly Met Arg Val Ile Ala Val Asp Ile Ala
        195                 200                 205

Glu Asp Lys Leu Glu Leu Ala Arg Lys His Gly Ala Glu Phe Thr Val
    210                 215                 220

Asn Ala Arg Asn Glu Asp Pro Gly Glu Ala Val Gln Lys Tyr Thr Asn
225                 230                 235                 240

Gly Gly Ala His Gly Val Leu Val Thr Ala Val His Glu Ala Ala Phe
                245                 250                 255

Gly Gln Ala Leu Asp Met Ala Arg Arg Ala Gly Thr Ile Val Phe Asn
            260                 265                 270

Gly Leu Pro Pro Gly Glu Phe Pro Ala Ser Val Phe Asn Ile Val Phe
        275                 280                 285
```

```
Lys Gly Leu Thr Ile Arg Gly Ser Leu Val Gly Thr Arg Gln Asp Leu
    290                 295                 300

Ala Glu Ala Leu Asp Phe Phe Ala Arg Gly Leu Ile Lys Pro Thr Val
305                 310                 315                 320

Ser Glu Cys Ser Leu Asp Glu Val Asn Gly Val Leu Asp Arg Met Arg
                325                 330                 335

Asn Gly Lys Ile Asp Gly Arg Val Ala Ile Arg Phe
            340                 345
```

<210> SEQ ID NO 45
<211> LENGTH: 1020
<212> TYPE: DNA
<213> ORGANISM: Corynebacterium glutamicum

<400> SEQUENCE: 45

```
atgcccaaat acattgccat gcaggtatcc gaatccggtg caccgttagc cgcgaatctc    60
gtgcaacctg ctccgttgaa atcgagggaa gtcgcgtgg aaatcgctgc tagtggtgtg   120
tgccatgcag atattggcac ggcagcagca tcggggaagc acactgtttt cctgttacc    180
cctggtcatg agattgcagg aaccatcgcg gaaattggtg aaaacgtatc tcggtggacg   240
gttggtgatc gcgttgcaat cggttggttt ggtggcaatt gcggtgactg cgcttttgt    300
cgtgcaggtg atcctgtgca ttgcagagag cggaagattc ctggcgtttc ttatgcgggt   360
ggtgggcac agaatattgt tgttccagcg gaggctcttg ctgcgattcc agatggcatg    420
gactttacg aggccgcccc gatgggctgc gcaggtgtga acacattcaa tgcgttgcga    480
aacctgaagc tggatcccgg tgcggctgtc gcggtctttg aatcggcgg tttagtgcgc    540
ctagctattc agtttgctgc gaaaatgggt tatcgaacca tcaccatcgc ccgcggttta   600
gagcgtgagc agctagctag caacttggc gccaaccact acatcgatag caatgatctg    660
caccctggcc aggcgttatt tgaacttggc ggggctgact tgatcttgtc tactgcgtcc   720
accacggagc tctttcgga gttgtctacc ggtctttcta ttggcgggca gctaaccatt    780
atcggagttg atgggggaga tatcaccgtt tcggcagccc aattgatgat gaaccgtcag   840
atcatcacag gtcacctcac tggaagtgcg aatgacacgg aacagactat gaaatttgct   900
catctccatg gcgtgaaacc gcttattgaa cggatgcctc tcgatcaagc caacgaggct   960
attgcacgta tttcagctgg taaaccacgt ttccgtattg tcttggagcc gaattcataa  1020
```

<210> SEQ ID NO 46
<211> LENGTH: 339
<212> TYPE: PRT
<213> ORGANISM: Corynebacterium glutamicum

<400> SEQUENCE: 46

```
Met Pro Lys Tyr Ile Ala Met Gln Val Ser Glu Ser Gly Ala Pro Leu
1               5                   10                  15

Ala Ala Asn Leu Val Gln Pro Ala Pro Leu Lys Ser Arg Glu Val Arg
            20                  25                  30

Val Glu Ile Ala Ala Ser Gly Val Cys His Ala Asp Ile Gly Thr Ala
        35                  40                  45

Ala Ala Ser Gly Lys His Thr Val Phe Pro Val Thr Pro Gly His Glu
    50                  55                  60

Ile Ala Gly Thr Ile Ala Glu Ile Gly Glu Asn Val Ser Arg Trp Thr
65                  70                  75                  80

Val Gly Asp Arg Val Ala Ile Gly Trp Phe Gly Gly Asn Cys Gly Asp
                85                  90                  95
```

```
Cys Ala Phe Cys Arg Ala Gly Asp Pro Val His Cys Arg Glu Arg Lys
                100                 105                 110

Ile Pro Gly Val Ser Tyr Ala Gly Gly Trp Ala Gln Asn Ile Val Val
            115                 120                 125

Pro Ala Glu Ala Leu Ala Ala Ile Pro Asp Gly Met Asp Phe Tyr Glu
        130                 135                 140

Ala Ala Pro Met Gly Cys Ala Gly Val Thr Thr Phe Asn Ala Leu Arg
145                 150                 155                 160

Asn Leu Lys Leu Asp Pro Gly Ala Ala Val Ala Val Phe Gly Ile Gly
                165                 170                 175

Gly Leu Val Arg Leu Ala Ile Gln Phe Ala Ala Lys Met Gly Tyr Arg
            180                 185                 190

Thr Ile Thr Ile Ala Arg Gly Leu Glu Arg Glu Leu Ala Arg Gln
        195                 200                 205

Leu Gly Ala Asn His Tyr Ile Asp Ser Asn Asp Leu His Pro Gly Gln
    210                 215                 220

Ala Leu Phe Glu Leu Gly Gly Ala Asp Leu Ile Leu Ser Thr Ala Ser
225                 230                 235                 240

Thr Thr Glu Pro Leu Ser Glu Leu Ser Thr Gly Leu Ser Ile Gly Gly
                245                 250                 255

Gln Leu Thr Ile Ile Gly Val Asp Gly Gly Asp Ile Thr Val Ser Ala
            260                 265                 270

Ala Gln Leu Met Met Asn Arg Gln Ile Ile Thr Gly His Leu Thr Gly
        275                 280                 285

Ser Ala Asn Asp Thr Glu Gln Thr Met Lys Phe Ala His Leu His Gly
    290                 295                 300

Val Lys Pro Leu Ile Glu Arg Met Pro Leu Asp Gln Ala Asn Glu Ala
305                 310                 315                 320

Ile Ala Arg Ile Ser Ala Gly Lys Pro Arg Phe Arg Ile Val Leu Glu
                325                 330                 335

Pro Asn Ser
```

<210> SEQ ID NO 47
<211> LENGTH: 879
<212> TYPE: DNA
<213> ORGANISM: Corynebacterium glutamicum

<400> SEQUENCE: 47

| | | |
|---|---|---|
| atgcaaaccc ttgctgctat tgtttcgtgcc acgaagcaac cttttgagat caccaccatt | 60 |
| gatctggatg caccacgacc agatgaagtt caaatccgtg ttattgctgc cggagtgcgc | 120 |
| cacactgacg caattgttcg tgatcagatt tacccaactt ttcttcccgc agttttcggc | 180 |
| cacgaaggcg ccggagtagt tgtcgccgtg ggttctgcag tcacctcggt gaaaccagat | 240 |
| gacaaggtag tgctgggatt caactcttgt ggccagtgct tgaagtgttt gggcggtaag | 300 |
| cctgcgtact gtgagaaatt ctatgaccgc aacttcgcat gcacccgcga tgccgggcac | 360 |
| actactttgt ttacccgtgc aacaaaagag caggcagagg ccatcatcga cacccttgat | 420 |
| gatgttttct acgatgcgga tgcgggtttc ctggcatacc cagcaactcc cccagaggct | 480 |
| tcgggagtaa gcgtgttggt tgtcgcggct ggtacctctg atctcccccca agcaaaggaa | 540 |
| gcactacaca ctgcctccta cttggggcgc tccacctcac tgattgttga ttttggagtg | 600 |
| gctggcatcc accgctgct ttcatacgaa gaagaactcc gcgctgcggg cgtgctcatc | 660 |
| gttgccgctg gaatggatgg tgcgctaccc ggagttgtcg caggcttagt gtccgcacct | 720 |

```
gtcgtcgcac tgccaacctc cgtgggatac ggcgcaggtg ctggaggaat cgcaccactt      780
ctgaccatgc ttaacgcctg cgcgccggga gttggagtgg tcaacattga taacggctat      840
ggagcaggac acctggctgc gcagattgcg gcgaggtaa                              879
```

```
<210> SEQ ID NO 48
<211> LENGTH: 292
<212> TYPE: PRT
<213> ORGANISM: Corynebacterium glutamicum

<400> SEQUENCE: 48
```

```
Met Gln Thr Leu Ala Ala Ile Val Arg Ala Thr Lys Gln Pro Phe Glu
1               5                   10                  15

Ile Thr Thr Ile Asp Leu Asp Ala Pro Arg Pro Asp Glu Val Gln Ile
            20                  25                  30

Arg Val Ile Ala Ala Gly Val Arg His Thr Asp Ala Ile Val Arg Asp
        35                  40                  45

Gln Ile Tyr Pro Thr Phe Leu Pro Ala Val Phe Gly His Glu Gly Ala
    50                  55                  60

Gly Val Val Ala Val Gly Ser Ala Val Thr Ser Val Lys Pro Asp
65                  70                  75                  80

Asp Lys Val Val Leu Gly Phe Asn Ser Cys Gly Gln Cys Leu Lys Cys
                85                  90                  95

Leu Gly Gly Lys Pro Ala Tyr Cys Glu Lys Phe Tyr Asp Arg Asn Phe
            100                 105                 110

Ala Cys Thr Arg Asp Ala Gly His Thr Thr Leu Phe Thr Arg Ala Thr
        115                 120                 125

Lys Glu Gln Ala Glu Ala Ile Ile Asp Thr Leu Asp Asp Val Phe Tyr
    130                 135                 140

Asp Ala Asp Ala Gly Phe Leu Ala Tyr Pro Ala Thr Pro Pro Glu Ala
145                 150                 155                 160

Ser Gly Val Ser Val Leu Val Val Ala Ala Gly Thr Ser Asp Leu Pro
                165                 170                 175

Gln Ala Lys Glu Ala Leu His Thr Ala Ser Tyr Leu Gly Arg Ser Thr
            180                 185                 190

Ser Leu Ile Val Asp Phe Gly Val Ala Gly Ile His Arg Leu Leu Ser
        195                 200                 205

Tyr Glu Glu Glu Leu Arg Ala Ala Gly Val Leu Ile Val Ala Ala Gly
    210                 215                 220

Met Asp Gly Ala Leu Pro Gly Val Val Ala Gly Leu Val Ser Ala Pro
225                 230                 235                 240

Val Val Ala Leu Pro Thr Ser Val Gly Tyr Gly Ala Gly Ala Gly Gly
                245                 250                 255

Ile Ala Pro Leu Leu Thr Met Leu Asn Ala Cys Ala Pro Gly Val Gly
            260                 265                 270

Val Val Asn Ile Asp Asn Gly Tyr Gly Ala Gly His Leu Ala Ala Gln
        275                 280                 285

Ile Ala Ala Arg
    290
```

```
<210> SEQ ID NO 49
<211> LENGTH: 819
<212> TYPE: DNA
<213> ORGANISM: Escherichia coli

<400> SEQUENCE: 49
```

```
atggaaacct atgctgtttt tggtaatccg atagcccaca gcaaatcgcc attcattcat    60
cagcaatttg ctcagcaact gaatattgaa catccctatg ggcgcgtgtt ggcacccatc   120
aatgatttca tcaacacact gaacgctttc tttagtgctg gtggtaaagg tgcgaatgtg   180
acggtgcctt ttaaagaaga ggcttttgcc agagcggatg agcttactga acgggcagcg   240
ttggctggtg ctgttaatac cctcatgcgg ttagaagatg gacgcctgct gggtgacaat   300
accgatggtg taggcttgtt aagcgatctg gaacgtctgt cttttatccg ccctggttta   360
cgtattctgc ttatcggcgc tggtggagca tctcgcggcg tactactgcc actcctttcc   420
ctggactgtg cggtgacaat aactaatcgg acggtatccc gcgcggaaga gttggctaaa   480
ttgtttgcgc acactggcag tattcaggcg ttgagtatgg acgaactgga aggtcatgag   540
tttgatctca ttattaatgc aacatccagt ggcatcagtg gtgatattcc ggcgatcccg   600
tcatcgctca ttcatccagg catttattgc tatgacatgt tctatcagaa aggaaaaact   660
ccttttctgg catggtgtga gcagcgaggc tcaaagcgta atgctgatgg tttaggaatg   720
ctggtggcac aggcggctca tgcctttctt ctctggcacg tgttctgcc tgacgtagaa    780
ccagttataa agcaattgca ggaggaattg tccgcgtga                          819
```

<210> SEQ ID NO 50
<211> LENGTH: 272
<212> TYPE: PRT
<213> ORGANISM: Escherichia coli

<400> SEQUENCE: 50

```
Met Glu Thr Tyr Ala Val Phe Gly Asn Pro Ile Ala His Ser Lys Ser
1               5                   10                  15

Pro Phe Ile His Gln Gln Phe Ala Gln Gln Leu Asn Ile Glu His Pro
            20                  25                  30

Tyr Gly Arg Val Leu Ala Pro Ile Asn Asp Phe Ile Asn Thr Leu Asn
        35                  40                  45

Ala Phe Phe Ser Ala Gly Gly Lys Gly Ala Asn Val Thr Val Pro Phe
    50                  55                  60

Lys Glu Glu Ala Phe Ala Arg Ala Asp Glu Leu Thr Glu Arg Ala Ala
65                  70                  75                  80

Leu Ala Gly Ala Val Asn Thr Leu Met Arg Leu Glu Asp Gly Arg Leu
                85                  90                  95

Leu Gly Asp Asn Thr Asp Gly Val Gly Leu Leu Ser Asp Leu Glu Arg
            100                 105                 110

Leu Ser Phe Ile Arg Pro Gly Leu Arg Ile Leu Leu Ile Gly Ala Gly
        115                 120                 125

Gly Ala Ser Arg Gly Val Leu Leu Pro Leu Leu Ser Leu Asp Cys Ala
    130                 135                 140

Val Thr Ile Thr Asn Arg Thr Val Ser Arg Ala Glu Glu Leu Ala Lys
145                 150                 155                 160

Leu Phe Ala His Thr Gly Ser Ile Gln Ala Leu Ser Met Asp Glu Leu
                165                 170                 175

Glu Gly His Glu Phe Asp Leu Ile Ile Asn Ala Thr Ser Ser Gly Ile
            180                 185                 190

Ser Gly Asp Ile Pro Ala Ile Pro Ser Ser Leu Ile His Pro Gly Ile
        195                 200                 205

Tyr Cys Tyr Asp Met Phe Tyr Gln Lys Gly Lys Thr Pro Phe Leu Ala
    210                 215                 220
```

```
Trp Cys Glu Gln Arg Gly Ser Lys Arg Asn Ala Asp Gly Leu Gly Met
225                 230                 235                 240

Leu Val Ala Gln Ala Ala His Ala Phe Leu Leu Trp His Gly Val Leu
                245                 250                 255

Pro Asp Val Glu Pro Val Ile Lys Gln Leu Gln Glu Glu Leu Ser Ala
            260                 265                 270

<210> SEQ ID NO 51
<211> LENGTH: 35
<212> TYPE: DNA
<213> ORGANISM: Artificial Sequence
<220> FEATURE:
<223> OTHER INFORMATION: primer

<400> SEQUENCE: 51
cggtacccgg ggatccttac ttccgcgtat ccaac                          35

<210> SEQ ID NO 52
<211> LENGTH: 41
<212> TYPE: DNA
<213> ORGANISM: Artificial Sequence
<220> FEATURE:
<223> OTHER INFORMATION: primer

<400> SEQUENCE: 52
ctaggaatcg cggccggtga actcctaaag aactatataa c                   41

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
ggccgcgatt cctagcatgc                                           20

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
ccaagcttgc atgccagtca tcatcaacgg tgccg                          35

<210> SEQ ID NO 55
<211> LENGTH: 21
<212> TYPE: DNA
<213> ORGANISM: Artificial Sequence
<220> FEATURE:
<223> OTHER INFORMATION: primer

<400> SEQUENCE: 55
atctccgcag aagacgtact g                                         21

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
```

-continued tccgatcatg tatgacctcc                                          20

<210> SEQ ID NO 57
<211> LENGTH: 36
<212> TYPE: DNA
<213> ORGANISM: Artificial Sequence
<220> FEATURE:
<223> OTHER INFORMATION: primer

<400> SEQUENCE: 57
cggtacccgg ggatcggcat agtgcttcca acgctc                        36

<210> SEQ ID NO 58
<211> LENGTH: 36
<212> TYPE: DNA
<213> ORGANISM: Artificial Sequence
<220> FEATURE:
<223> OTHER INFORMATION: primer

<400> SEQUENCE: 58
tagctccact caagattcct cgatattacc tacagg                        36

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
tcttgagtgg agctagggcc                                          20

<210> SEQ ID NO 60
<211> LENGTH: 37
<212> TYPE: DNA
<213> ORGANISM: Artificial Sequence
<220> FEATURE:
<223> OTHER INFORMATION: primer

<400> SEQUENCE: 60
ccaagcttgc atgcccatat agagcccagg agctctc                       37

<210> SEQ ID NO 61
<211> LENGTH: 23
<212> TYPE: DNA
<213> ORGANISM: Artificial Sequence
<220> FEATURE:
<223> OTHER INFORMATION: primer

<400> SEQUENCE: 61
cgccgcaaag tccaaataga aag                                      23

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
ggattcttcc tgaactcagc                                          20

<210> SEQ ID NO 63
<211> LENGTH: 36
<212> TYPE: DNA
<213> ORGANISM: Artificial Sequence

```
<220> FEATURE:
<223> OTHER INFORMATION: primer

<400> SEQUENCE: 63
cggtacccgg ggatcgggct cgtcctgaaa ttgcac                              36

<210> SEQ ID NO 64
<211> LENGTH: 35
<212> TYPE: DNA
<213> ORGANISM: Artificial Sequence
<220> FEATURE:
<223> OTHER INFORMATION: primer

<400> SEQUENCE: 64
tccgtcgtga gccatgttgt gcccacgaga ctacc                               35

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
atggctcacg acggattgcg                                                20

<210> SEQ ID NO 66
<211> LENGTH: 36
<212> TYPE: DNA
<213> ORGANISM: Artificial Sequence
<220> FEATURE:
<223> OTHER INFORMATION: primer

<400> SEQUENCE: 66
ccaagcttgc atgcccggtt gcagccttca taaacg                              36

<210> SEQ ID NO 67
<211> LENGTH: 21
<212> TYPE: DNA
<213> ORGANISM: Artificial Sequence
<220> FEATURE:
<223> OTHER INFORMATION: primer

<400> SEQUENCE: 67
agaccaatga gtacccaacc g                                              21

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
tcagcgtctg gctcagctac                                                20

<210> SEQ ID NO 69
<211> LENGTH: 36
<212> TYPE: DNA
<213> ORGANISM: Artificial Sequence
<220> FEATURE:
<223> OTHER INFORMATION: primer

<400> SEQUENCE: 69
cggtacccgg ggatcaaccc cagctcaaat aacacc                              36
```

```
<210> SEQ ID NO 70
<211> LENGTH: 37
<212> TYPE: DNA
<213> ORGANISM: Artificial Sequence
<220> FEATURE:
<223> OTHER INFORMATION: primer

<400> SEQUENCE: 70
tttcaacaca atccgtcctt ctcgcttgga ttacttg                              37

<210> SEQ ID NO 71
<211> LENGTH: 23
<212> TYPE: DNA
<213> ORGANISM: Artificial Sequence
<220> FEATURE:
<223> OTHER INFORMATION: primer

<400> SEQUENCE: 71
cggattgtgt tgaaattgct ctg                                             23

<210> SEQ ID NO 72
<211> LENGTH: 35
<212> TYPE: DNA
<213> ORGANISM: Artificial Sequence
<220> FEATURE:
<223> OTHER INFORMATION: primer

<400> SEQUENCE: 72
ccaagcttgc atgcctcacc acgggaatct tcagg                                35

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
ccggactggg gtgtgttttg                                                 20

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
cccggaaaat acggtatagc                                                 20

<210> SEQ ID NO 75
<211> LENGTH: 35
<212> TYPE: DNA
<213> ORGANISM: Artificial Sequence
<220> FEATURE:
<223> OTHER INFORMATION: primer

<400> SEQUENCE: 75
ccaagcttgc atgccccatc gcattgccga aaagc                                35

<210> SEQ ID NO 76
<211> LENGTH: 35
<212> TYPE: DNA
<213> ORGANISM: Artificial Sequence
<220> FEATURE:
<223> OTHER INFORMATION: primer
```

```
<400> SEQUENCE: 76
aaagatcggg tcaatgcagt tcgcggggcg aacat                               35

<210> SEQ ID NO 77
<211> LENGTH: 35
<212> TYPE: DNA
<213> ORGANISM: Artificial Sequence
<220> FEATURE:
<223> OTHER INFORMATION: primer

<400> SEQUENCE: 77
cgccccgcga actgcattga cccgatcttt atacc                               35

<210> SEQ ID NO 78
<211> LENGTH: 35
<212> TYPE: DNA
<213> ORGANISM: Artificial Sequence
<220> FEATURE:
<223> OTHER INFORMATION: primer

<400> SEQUENCE: 78
cggtacccgg ggatcaacgt tgacggtgat gccat                               35

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
gaaatgtcat acttcagcca tcagg                                          25

<210> SEQ ID NO 80
<211> LENGTH: 25
<212> TYPE: DNA
<213> ORGANISM: Artificial Sequence
<220> FEATURE:
<223> OTHER INFORMATION: primer

<400> SEQUENCE: 80
tgcgagtgat gaaatcctga aactt                                          25

<210> SEQ ID NO 81
<211> LENGTH: 35
<212> TYPE: DNA
<213> ORGANISM: Artificial Sequence
<220> FEATURE:
<223> OTHER INFORMATION: primer

<400> SEQUENCE: 81
ccaagcttgc atgcctttcg cggtgaatca accca                               35

<210> SEQ ID NO 82
<211> LENGTH: 35
<212> TYPE: DNA
<213> ORGANISM: Artificial Sequence
<220> FEATURE:
<223> OTHER INFORMATION: primer

<400> SEQUENCE: 82
caggtcaaag ctaaggcatt gtctgtaaat gggca                               35

<210> SEQ ID NO 83
```

```
<210> SEQ ID NO 83
<211> LENGTH: 35
<212> TYPE: DNA
<213> ORGANISM: Artificial Sequence
<220> FEATURE:
<223> OTHER INFORMATION: primer

<400> SEQUENCE: 83
ctaaggggtt tagcaatgcc caatcaggcc cactt                               35

<210> SEQ ID NO 84
<211> LENGTH: 35
<212> TYPE: DNA
<213> ORGANISM: Artificial Sequence
<220> FEATURE:
<223> OTHER INFORMATION: primer

<400> SEQUENCE: 84
cggtacccgg ggatcttagg gtacgagggt aagtg                               35

<210> SEQ ID NO 85
<211> LENGTH: 93
<212> TYPE: DNA
<213> ORGANISM: Artificial Sequence
<220> FEATURE:
<223> OTHER INFORMATION: DNA fragment of P2 promoter

<400> SEQUENCE: 85
cttagctttg acctgcacaa atagttgcaa attgtcccac atacacataa agtagcttgc    60
gtatttaaaa ttatgaacct aaggggttta gca                                 93

<210> SEQ ID NO 86
<211> LENGTH: 35
<212> TYPE: DNA
<213> ORGANISM: Artificial Sequence
<220> FEATURE:
<223> OTHER INFORMATION: primer

<400> SEQUENCE: 86
atttacagac aatgccttag ctttgacctg cacaa                               35

<210> SEQ ID NO 87
<211> LENGTH: 31
<212> TYPE: DNA
<213> ORGANISM: Artificial Sequence
<220> FEATURE:
<223> OTHER INFORMATION: primer

<400> SEQUENCE: 87
ggcctgattg ggcattgcta aaccccttag g                                   31

<210> SEQ ID NO 88
<211> LENGTH: 1686
<212> TYPE: DNA
<213> ORGANISM: Corynebacterium glutamicum

<400> SEQUENCE: 88
atgacaacaa ccaccggaag tgcccggcca gcacgtgccg ccaggaagcc taagcccgaa    60
ggccaatgga aatcgacgg caccgagccg cttaaccatg ccgaggaaat taagcaagaa   120
gaacccgctt ttgctgtcaa gcagcgggtc attgatattt actccaagca gggttttttct  180 tccattgcac cggatgacat tgccccacgc tttaagtggt tgggcatttta cacccagcgt   240 aagcaggatc tgggcggtga actgaccggt cagcttcctg atgatgagct gcaggatgag   300
tacttcatga tgcgtgtgcg ttttgatggc ggactggctt cccctgagcg cctgcgtgcc   360
```

```
gtgggtgaaa tttctaggga ttatgctcgt tccaccgcgg acttcaccga ccgccagaac    420
attcagctgc actggattcg tattgaagat gtgcctgcga tctgggagaa gctagaaacc    480
gtcggactgt ccaccatgct tggttgcggt gacgttccac gtgttatctt gggctcccca    540
gtttctggcg tagctgctga agagctgatc gatgccaccc cggctatcga tgcgattcgt    600
gagcgctacc tagacaagga agagttccac aaccttcctc gtaagtttaa gactgctatc    660
actggcaacc agcgccagga tgttacccac gaaatccagg acgtttcctt cgttccttcg    720
attcacccag aattcggccc aggatttgag tgctttgtgg gcggcggcct gtccaccaac    780
ccaatgcttg ctcagccact tggttcttgg attccacttg atgaggttcc agaagtgtgg    840
gctggcgtcg ccggaatttt ccgcgactac ggcttccgac gcctgcgtaa ccgtgctcgc    900
ctcaagttct tggtggcaca gtggggtatt gagaagttcc gtgaagttct tgagaccgaa    960
tacctcgagc gcaagctgat tgatggccca gttgttacca ccaaccctgg ctaccgtgac   1020
cacattggca ttcacccaca aaaggacggc aagttctacc tcggtgtgaa gccaaccgtt   1080
ggacacacca ccggtgagca gctcattgcc attgctgatg ttgcagaaaa gcacggcatc   1140
accaggattc gtaccacggc ggaaaaggaa ctgctcttcc tcgatattga gcgagagaac   1200
cttactaccg ttgcacgtga cctggatgaa atcggactgt actcttcacc ttccgagttc   1260
cgccgcggca tcatttcctg caccggcttg gagttctgca agcttgcgca cgcaaccacc   1320
aagtcacgag caattgagct tgtggacgaa ctggaagagc gactcggcga tttggatgtt   1380
cccatcaaga ttgccctgaa cggttgccct aactcttgtg cacgcaccca ggtttccgac   1440
atcggattca agggacagac cgtcactgat gctgacggca accgcgttga aggtttccag   1500
gttcacctgg gcggttccat gaacttggat ccaaacttcg gacgcaagct caagggccac   1560
aaggttattg ccgatgaagt gggagagtac gtcactcgcg ttgttaccca cttcaaggaa   1620
cagcgccacg aggacgagca cttccgcgat tgggtccagc gggccgctga ggaagatttg   1680
gtgtga                                                              1686
```

<210> SEQ ID NO 89
<211> LENGTH: 561
<212> TYPE: PRT
<213> ORGANISM: Corynebacterium glutamicum

<400> SEQUENCE: 89

Met Thr Thr Thr Thr Gly Ser Ala Arg Pro Ala Arg Ala Ala Arg Lys
1               5                   10                  15

Pro Lys Pro Glu Gly Gln Trp Lys Ile Asp Gly Thr Glu Pro Leu Asn
            20                  25                  30

His Ala Glu Glu Ile Lys Gln Glu Pro Ala Phe Ala Val Lys Gln
        35                  40                  45

Arg Val Ile Asp Ile Tyr Ser Lys Gln Gly Phe Ser Ser Ile Ala Pro
    50                  55                  60

Asp Asp Ile Ala Pro Arg Phe Lys Trp Leu Gly Ile Tyr Thr Gln Arg
65                  70                  75                  80

Lys Gln Asp Leu Gly Gly Glu Leu Thr Gly Gln Leu Pro Asp Asp Glu
                85                  90                  95

Leu Gln Asp Glu Tyr Phe Met Met Arg Val Arg Phe Asp Gly Gly Leu
            100                 105                 110

Ala Ser Pro Glu Arg Leu Arg Ala Val Gly Glu Ile Ser Arg Asp Tyr
        115                 120                 125

```
Ala Arg Ser Thr Ala Asp Phe Thr Asp Arg Gln Asn Ile Gln Leu His
    130                 135                 140

Trp Ile Arg Ile Glu Asp Val Pro Ala Ile Trp Glu Lys Leu Glu Thr
145                 150                 155                 160

Val Gly Leu Ser Thr Met Leu Gly Cys Gly Asp Val Pro Arg Val Ile
                165                 170                 175

Leu Gly Ser Pro Val Ser Gly Val Ala Ala Glu Glu Leu Ile Asp Ala
                180                 185                 190

Thr Pro Ala Ile Asp Ala Ile Arg Glu Arg Tyr Leu Asp Lys Glu Glu
            195                 200                 205

Phe His Asn Leu Pro Arg Lys Phe Lys Thr Ala Ile Thr Gly Asn Gln
    210                 215                 220

Arg Gln Asp Val Thr His Glu Ile Gln Asp Val Ser Phe Val Pro Ser
225                 230                 235                 240

Ile His Pro Glu Phe Gly Pro Gly Phe Glu Cys Phe Val Gly Gly Gly
                245                 250                 255

Leu Ser Thr Asn Pro Met Leu Ala Gln Pro Leu Gly Ser Trp Ile Pro
                260                 265                 270

Leu Asp Glu Val Pro Glu Val Trp Ala Gly Val Ala Gly Ile Phe Arg
    275                 280                 285

Asp Tyr Gly Phe Arg Arg Leu Arg Asn Arg Ala Arg Leu Lys Phe Leu
    290                 295                 300

Val Ala Gln Trp Gly Ile Glu Lys Phe Arg Glu Val Leu Glu Thr Glu
305                 310                 315                 320

Tyr Leu Glu Arg Lys Leu Ile Asp Gly Pro Val Val Thr Thr Asn Pro
                325                 330                 335

Gly Tyr Arg Asp His Ile Gly Ile His Pro Gln Lys Asp Gly Lys Phe
                340                 345                 350

Tyr Leu Gly Val Lys Pro Thr Val Gly His Thr Thr Gly Glu Gln Leu
            355                 360                 365

Ile Ala Ile Ala Asp Val Ala Glu Lys His Gly Ile Thr Arg Ile Arg
    370                 375                 380

Thr Thr Ala Glu Lys Glu Leu Leu Phe Leu Asp Ile Glu Arg Glu Asn
385                 390                 395                 400

Leu Thr Thr Val Ala Arg Asp Leu Asp Glu Ile Gly Leu Tyr Ser Ser
                405                 410                 415

Pro Ser Glu Phe Arg Arg Gly Ile Ile Ser Cys Thr Gly Leu Glu Phe
                420                 425                 430

Cys Lys Leu Ala His Ala Thr Thr Lys Ser Arg Ala Ile Glu Leu Val
    435                 440                 445

Asp Glu Leu Glu Glu Arg Leu Gly Asp Leu Asp Val Pro Ile Lys Ile
    450                 455                 460

Ala Leu Asn Gly Cys Pro Asn Ser Cys Ala Arg Thr Gln Val Ser Asp
465                 470                 475                 480

Ile Gly Phe Lys Gly Gln Thr Val Thr Asp Ala Asp Gly Asn Arg Val
                485                 490                 495

Glu Gly Phe Gln Val His Leu Gly Gly Ser Met Asn Leu Asp Pro Asn
                500                 505                 510

Phe Gly Arg Lys Leu Lys Gly His Lys Val Ile Ala Asp Glu Val Gly
            515                 520                 525

Glu Tyr Val Thr Arg Val Val Thr His Phe Lys Glu Gln Arg His Glu
    530                 535                 540

Asp Glu His Phe Arg Asp Trp Val Gln Arg Ala Ala Glu Glu Asp Leu
```

-continued

```
545            550            555            560
Val

<210> SEQ ID NO 90
<211> LENGTH: 249
<212> TYPE: DNA
<213> ORGANISM: Corynebacterium glutamicum

<400> SEQUENCE: 90
gtgagtcttc ggaggaaacc caatcccaac cgcaaccacc ctctgtactg cccatactgc    60
gcgggagaag ttcttttccc cgatgagcaa acagaattcg cgtggttgtg tgcggattgc   120
accagagttt ttgaagtgaa atatcacggc caggacgatc cagtgcacag gccagcacca   180
gcaaagtcca catcgcaagc attaaaagaa tctctcgaaa gacacaaaag aggtgagtcg   240
caacaatga                                                          249

<210> SEQ ID NO 91
<211> LENGTH: 82
<212> TYPE: PRT
<213> ORGANISM: Corynebacterium glutamicum

<400> SEQUENCE: 91

Met Ser Leu Arg Arg Lys Pro Asn Pro Asn Arg Asn His Pro Leu Tyr
1               5                   10                  15

Cys Pro Tyr Cys Ala Gly Glu Val Leu Phe Pro Asp Glu Gln Thr Glu
            20                  25                  30

Phe Ala Trp Leu Cys Ala Asp Cys Thr Arg Val Phe Gly Val Lys Tyr
        35                  40                  45

His Gly Gln Asp Asp Pro Val His Arg Pro Ala Pro Ala Lys Ser Thr
    50                  55                  60

Ser Gln Ala Leu Lys Glu Ser Leu Glu Arg His Lys Arg Gly Glu Ser
65                  70                  75                  80

Gln Gln

<210> SEQ ID NO 92
<211> LENGTH: 786
<212> TYPE: DNA
<213> ORGANISM: Corynebacterium glutamicum

<400> SEQUENCE: 92
atgagctttc aactagttaa cgccctgaaa atactggtt cggtaaaaga tcccgagatc    60
tcacccgaag gacctcgcac gaccacaccg ttgtcaccag aggtagcaaa acacaacgag   120
gaactcgtcg aaaagcatgc tgctgcgttg tatgacgcca gcgcaagga tcctggaa     180 tggacagccg agcacacgcc gggcgctatt gcagtgacct tgagcatgga aaacaccgtg   240
ctggcggagc tggctgcgcg gcacctgccg gaagctgatt tcctcttttt ggacaccggt   300
taccacttca aggaaactct tgaagttgcc cgccaggtag atgagcgtta ttcccagaag   360
cttgtcaccg cgctgccaat cctcaagcgc acggagcagg attccattta tggtctcaac   420
ctgtaccgca gcaacccagc ggcgtgctgc cgaatgcgca agttgaacc gctggcggcg   480 tcgttaagcc catacgctgg ctggatcacc ggcctgcgcc gcgctgatgg cccaacccgt   540
gctcaagccc ctgcgctgag cttggatgcc accggcaggc tcaagatttc tccaattatc   600
acctggtcat tggaggaaac caacgagttc attgcggaca caacctcat cgatcaccca   660 cttacccatc agggttatcc atcaattgga tgcgaaacct gcaccttcc tgttgctgaa   720
```

```
ggacaagacc ctagggccgg ccgttgggct ggaaacgcca agacagaatg cggacttcac    780
tcatga                                                              786

<210> SEQ ID NO 93
<211> LENGTH: 261
<212> TYPE: PRT
<213> ORGANISM: Corynebacterium glutamicum

<400> SEQUENCE: 93

Met Ser Phe Gln Leu Val Asn Ala Leu Lys Asn Thr Gly Ser Val Lys
1               5                   10                  15

Asp Pro Glu Ile Ser Pro Glu Gly Pro Arg Thr Thr Pro Leu Ser
            20                  25                  30

Pro Glu Val Ala Lys His Asn Glu Glu Leu Val Glu Lys His Ala Ala
        35                  40                  45

Ala Leu Tyr Asp Ala Ser Ala Gln Glu Ile Leu Glu Trp Thr Ala Glu
    50                  55                  60

His Thr Pro Gly Ala Ile Ala Val Thr Leu Ser Met Glu Asn Thr Val
65                  70                  75                  80

Leu Ala Glu Leu Ala Ala Arg His Leu Pro Glu Ala Asp Phe Leu Phe
                85                  90                  95

Leu Asp Thr Gly Tyr His Phe Lys Glu Thr Leu Glu Val Ala Arg Gln
            100                 105                 110

Val Asp Glu Arg Tyr Ser Gln Lys Leu Val Thr Ala Leu Pro Ile Leu
        115                 120                 125

Lys Arg Thr Glu Gln Asp Ser Ile Tyr Gly Leu Asn Leu Tyr Arg Ser
    130                 135                 140

Asn Pro Ala Ala Cys Cys Arg Met Arg Lys Val Glu Pro Leu Ala Ala
145                 150                 155                 160

Ser Leu Ser Pro Tyr Ala Gly Trp Ile Thr Gly Leu Arg Arg Ala Asp
                165                 170                 175

Gly Pro Thr Arg Ala Gln Ala Pro Ala Leu Ser Leu Asp Ala Thr Gly
            180                 185                 190

Arg Leu Lys Ile Ser Pro Ile Ile Thr Trp Ser Leu Glu Glu Thr Asn
        195                 200                 205

Glu Phe Ile Ala Asp Asn Asn Leu Ile Asp His Pro Leu Thr His Gln
    210                 215                 220

Gly Tyr Pro Ser Ile Gly Cys Glu Thr Cys Thr Leu Pro Val Ala Glu
225                 230                 235                 240

Gly Gln Asp Pro Arg Ala Gly Arg Trp Ala Gly Asn Ala Lys Thr Glu
                245                 250                 255

Cys Gly Leu His Ser
            260

<210> SEQ ID NO 94
<211> LENGTH: 954
<212> TYPE: DNA
<213> ORGANISM: Corynebacterium glutamicum

<400> SEQUENCE: 94
ttgggctgga aacgccaaga cagaatgcgg acttcactca tgaccacaac cgttgcatca    60
gaactttccc cacaccttaa agatcttgaa atgaatccat ccacatcct ccgcgaggta    120 gctggccagt tgataaggtc ggcctgctg ttttccggcg gtaaggattc cgtcgtggtg    180
tacgagcttg cgcgccgcgc tttcgctcca gctaacgtgc cttttgaatt gctgcacgtg    240
```

```
gacaccggcc acaacttccc agaggttttg aattccgcg acaacctggt ggagcgcacc    300
ggcgcccgcc tgcgcgtagc taaagtccag gactggatcg atcgcggtga cctgcaggaa    360
cgcccagacg gcacccgcaa cccactgcag actgtccctt tggtggagac catcgctgag    420
cagggctacg acgccgtgct tggtggcgct cgccgcgatg aggagcgtgc ccgcgccaag    480
gagcgtgtgt tctctgtgcg tgactccttc ggtggttggg atccacgccg tcagcgccca    540
gagctgtgga ccctctacaa cggtggccac ctgccaggcg aaaacatccg tgttttccca    600
atctccaact ggactgaagc tgacatctgg gagtacatcg gcgcccgtgg catcgaactt    660
ccaccgatct acttctccca cgaccgcgaa gttttcgagc gcgacggcat gtggctgacc    720
gcaggcgagt ggggtggacc aaagaagggc gaggagatcg tcaccaagac tgtccgctac    780
cgcaccgtcg gcgatatgtc ctgcaccggt gctgtgctct cagaagcccg caccattgac    840
gatgtgatcg aagagatcgc cacctccacc cttaccgaac gtggcgcaac ccgcgccgat    900
gaccgcctca gcgaatccgc aatggaagac cgcaagaagg aaggctactt ctga          954
```

<210> SEQ ID NO 95
<211> LENGTH: 317
<212> TYPE: PRT
<213> ORGANISM: Corynebacterium glutamicum

<400> SEQUENCE: 95

```
Met Gly Trp Lys Arg Gln Asp Arg Met Arg Thr Ser Leu Met Thr Thr
1               5                   10                  15

Thr Val Ala Ser Glu Leu Ser Pro His Leu Lys Asp Leu Glu Asn Glu
            20                  25                  30

Ser Ile His Ile Leu Arg Glu Val Ala Gly Gln Phe Asp Lys Val Gly
        35                  40                  45

Leu Leu Phe Ser Gly Gly Lys Asp Ser Val Val Tyr Glu Leu Ala
    50                  55                  60

Arg Arg Ala Phe Ala Pro Ala Asn Val Pro Phe Glu Leu Leu His Val
65                  70                  75                  80

Asp Thr Gly His Asn Phe Pro Glu Val Leu Glu Phe Arg Asp Asn Leu
                85                  90                  95

Val Glu Arg Thr Gly Ala Arg Leu Arg Val Ala Lys Val Gln Asp Trp
            100                 105                 110

Ile Asp Arg Gly Asp Leu Gln Glu Arg Pro Gly Thr Arg Asn Pro
        115                 120                 125

Leu Gln Thr Val Pro Leu Val Glu Thr Ile Ala Glu Gln Gly Tyr Asp
    130                 135                 140

Ala Val Leu Gly Gly Ala Arg Arg Asp Glu Glu Arg Ala Arg Ala Lys
145                 150                 155                 160

Glu Arg Val Phe Ser Val Arg Asp Ser Phe Gly Trp Asp Pro Arg
                165                 170                 175

Arg Gln Arg Pro Glu Leu Trp Thr Leu Tyr Asn Gly Gly His Leu Pro
            180                 185                 190

Gly Glu Asn Ile Arg Val Phe Pro Ile Ser Asn Trp Thr Glu Ala Asp
        195                 200                 205

Ile Trp Glu Tyr Ile Gly Ala Arg Gly Ile Glu Leu Pro Pro Ile Tyr
    210                 215                 220

Phe Ser His Asp Arg Glu Val Phe Glu Arg Asp Gly Met Trp Leu Thr
225                 230                 235                 240

Ala Gly Glu Trp Gly Gly Pro Lys Lys Gly Glu Glu Ile Val Thr Lys
                245                 250                 255
```

```
Thr Val Arg Tyr Arg Thr Val Gly Asp Met Ser Cys Thr Gly Ala Val
            260                 265                 270

Leu Ser Glu Ala Arg Thr Ile Asp Asp Val Ile Glu Ile Ala Thr
        275                 280                 285

Ser Thr Leu Thr Glu Arg Gly Ala Thr Arg Ala Asp Asp Arg Leu Ser
    290                 295                 300

Glu Ser Ala Met Glu Asp Arg Lys Lys Glu Gly Tyr Phe
305                 310                 315

<210> SEQ ID NO 96
<211> LENGTH: 1302
<212> TYPE: DNA
<213> ORGANISM: Corynebacterium glutamicum

<400> SEQUENCE: 96
atgactgctc caaccttgaa taaagcatcc gaaaagattg catcacgcga gacccttcgt     60
ctgtgcaccg caggttccgt agatgatggc aagtccacct tcgtcggccg cctcctgcac    120
gacaccaagt ctgttcttgc tgatcagcta gcttccgtag agcgcacctc cgccgaccgc    180
ggcttcgaag gcctcgacct gtccctcctc gtcgacggcc tgcgcgccga gcgtgagcag    240
ggcatcacca tcgacgttgc ctaccgctac ttcgccactg acaagcgcac cttcatcctg    300
gctgacaccc caggccacgt gcagtacacc cgcaacaccg tcaccggcgt ctccacctcc    360
caggttgtag ttttgcttgt cgacgcccgc cacggcgtcg tcgagcagac ccgccgccac    420
ctgtccgtat cggccctgct gggcgtgcgc acggtgatcc tcgcagtcaa caaaattgac    480
cttgttgatt acagcgaaga agtcttccgc aacattgaaa agaattcgt ttctttggct    540 tccgctttag atgtcaccga cacccacgtc gttccgatct ccgcactcaa gggcgacaac    600
gttgcagaac cttccaccca catggactgg tacgcgggac caaccgtgct ggaaatcctg    660
gaaaacgttg aagtttcccg cggccgtgca cacgacctgg gcttccgctt cccaatccag    720
tacgtcatcc gcgagcacgc aaccgattac cgcggctacg ccggcaccat caacgctggt    780
tccatctccg tgggcgatac cgtgcaccta cctgaaggcc gcaccaccca ggtcacccac    840
atcgattccg ctgacggatc cctccaaacc gcatcagttg agaagccgt tgtcctgcgc    900 ctagcccagg aaatcgacct catccgcggc gaactcatcg caggctccga tcgcccagaa    960
tccgttcgtt ccttcaacgc cactgtcgtt ggtctagcag atcgcactat caaaccaggt   1020
gcagcagtca aggtccgcta cggcaccgag ctggtccgcg acgcgtcgc agccatcgaa   1080 cgagtcctcg acatcgacgg cgtcaacgac aacgaagcac agaaaccta cggcctcaac   1140 gacatcgcgc acgtgcgcat cgatgttgca ggtgaattgg aagttgaaga ttacgctgct   1200
cgtggcgcaa ttggctcctt ccttcttatc gatcaatcct ccggcgacac cctcgctgcc   1260
ggtttggttg ccaccgcct acgcaataac tggtcgatct ag                        1302

<210> SEQ ID NO 97
<211> LENGTH: 433
<212> TYPE: PRT
<213> ORGANISM: Corynebacterium glutamicum

<400> SEQUENCE: 97

Met Thr Ala Pro Thr Leu Asn Lys Ala Ser Glu Lys Ile Ala Ser Arg
1               5                   10                  15

Glu Thr Leu Arg Leu Cys Thr Ala Gly Ser Val Asp Asp Gly Lys Ser
            20                  25                  30
```

Thr Phe Val Gly Arg Leu Leu His Asp Thr Lys Ser Val Leu Ala Asp
            35                  40                  45

Gln Leu Ala Ser Val Glu Arg Thr Ser Ala Asp Arg Gly Phe Glu Gly
 50                  55                  60

Leu Asp Leu Ser Leu Leu Val Asp Gly Leu Arg Ala Glu Arg Glu Gln
 65                  70                  75                  80

Gly Ile Thr Ile Asp Val Ala Tyr Arg Tyr Phe Ala Thr Asp Lys Arg
                85                  90                  95

Thr Phe Ile Leu Ala Asp Thr Pro Gly His Val Gln Tyr Thr Arg Asn
            100                 105                 110

Thr Val Thr Gly Val Ser Thr Ser Gln Val Val Leu Leu Val Asp
            115                 120                 125

Ala Arg His Gly Val Val Glu Gln Thr Arg Arg His Leu Ser Val Ser
130                 135                 140

Ala Leu Leu Gly Val Arg Thr Val Ile Leu Ala Val Asn Lys Ile Asp
145                 150                 155                 160

Leu Val Asp Tyr Ser Glu Glu Val Phe Arg Asn Ile Glu Lys Glu Phe
                165                 170                 175

Val Ser Leu Ala Ser Ala Leu Asp Val Thr Asp Thr His Val Val Pro
            180                 185                 190

Ile Ser Ala Leu Lys Gly Asp Asn Val Ala Glu Pro Ser Thr His Met
            195                 200                 205

Asp Trp Tyr Ala Gly Pro Thr Val Leu Glu Ile Leu Glu Asn Val Glu
            210                 215                 220

Val Ser Arg Gly Arg Ala His Asp Leu Gly Phe Arg Phe Pro Ile Gln
225                 230                 235                 240

Tyr Val Ile Arg Glu His Ala Thr Asp Tyr Arg Gly Tyr Ala Gly Thr
                245                 250                 255

Ile Asn Ala Gly Ser Ile Ser Val Gly Asp Thr Val His Leu Pro Glu
            260                 265                 270

Gly Arg Thr Thr Gln Val Thr His Ile Asp Ser Ala Asp Gly Ser Leu
            275                 280                 285

Gln Thr Ala Ser Val Gly Glu Ala Val Val Leu Arg Leu Ala Gln Glu
290                 295                 300

Ile Asp Leu Ile Arg Gly Glu Leu Ile Ala Gly Ser Asp Arg Pro Glu
305                 310                 315                 320

Ser Val Arg Ser Phe Asn Ala Thr Val Val Gly Leu Ala Asp Arg Thr
                325                 330                 335

Ile Lys Pro Gly Ala Ala Val Lys Val Arg Tyr Gly Thr Glu Leu Val
            340                 345                 350

Arg Gly Arg Val Ala Ala Ile Glu Arg Val Leu Asp Ile Asp Gly Val
            355                 360                 365

Asn Asp Asn Glu Ala Pro Glu Thr Tyr Gly Leu Asn Asp Ile Ala His
370                 375                 380

Val Arg Ile Asp Val Ala Gly Glu Leu Glu Val Glu Asp Tyr Ala Ala
385                 390                 395                 400

Arg Gly Ala Ile Gly Ser Phe Leu Leu Ile Asp Gln Ser Ser Gly Asp
                405                 410                 415

Thr Leu Ala Ala Gly Leu Val Gly His Arg Leu Arg Asn Asn Trp Ser
            420                 425                 430

Ile

<210> SEQ ID NO 98

-continued

```
<211> LENGTH: 900
<212> TYPE: DNA
<213> ORGANISM: Corynebacterium glutamicum

<400> SEQUENCE: 98
ttggctccct tccttcttatc gatcaatcct ccggcgacac cctcgctgcc ggtttggttg      60
gccaccgcct acgcaataac tggtcgatct agaccagttg ctgtgaaggc aaggtgccgg     120
cttagatgcc ggcgcctagc ctacatccag ctaagacccc ctttaggaca cctcatgatt     180
cccctgatta cgctttccca cggttcccgc aaaaagtccg cagctgcagg tattactgcg     240
ctgactcatg aggccggacg aatgctggaa acaccagccg tggaagcgca tttagagctt     300
gctgaacctt cccttgatca ggttgtggca acgctcagtg cggaaggcgt aaccagggca     360
gcgttggttc ctttgctgtt tagcaatgcg tatcacgcaa agattgacgt tcctgaggca     420
gtaaaagatg cttcagaaaa gtatggtgtg aacttctcg tgggtccgca tttgggcact      480
ggctccgatg tagccagcgt gcttgcgcag cggttgcgtg cggacgcccc cacagatgcc     540
catgtgattt tgtattccgt tggcagctca cacgtgtccg ccaatgaatc agtcatcgat     600
cttgcccaca ccattgctct cctcactggc ttttcggttg aggtggtgcc cgctaccggt     660
gggccaggtg ccggcggcgc cggagtaata gaggtggcct cgaaacacaa ggccgtccac     720
atcctgccgc tgtttgttac ggaaggtttg ctgctggatc gggttattga tcaatccgcc     780
aacatcgcag ctgccaccgg cacgaacttt acctattccg aacccctaac tactgacctc     840
gcaccacttg ttgcagcccg ttaccacgct gcattgagcg cactgctggc acatatctaa    900

<210> SEQ ID NO 99
<211> LENGTH: 299
<212> TYPE: PRT
<213> ORGANISM: Corynebacterium glutamicum

<400> SEQUENCE: 99
```

Met Ala Pro Ser Phe Leu Ser Ile Asn Pro Ala Thr Pro Ser Leu
1               5                   10                  15

Pro Val Trp Leu Ala Thr Ala Tyr Ala Ile Thr Gly Arg Ser Arg Pro
            20                  25                  30

Val Ala Val Lys Ala Arg Cys Arg Leu Arg Cys Arg Leu Ala Tyr
        35                  40                  45

Ile Gln Leu Arg Pro Pro Leu Gly His Leu Met Ile Pro Leu Ile Thr
    50                  55                  60

Leu Ser His Gly Ser Arg Lys Lys Ser Ala Ala Gly Ile Thr Ala
65                  70                  75                  80

Leu Thr His Glu Ala Gly Arg Met Leu Glu Thr Pro Ala Val Glu Ala
                85                  90                  95

His Leu Glu Leu Ala Glu Pro Ser Leu Asp Gln Val Val Ala Thr Leu
            100                 105                 110

Ser Ala Glu Gly Val Thr Arg Ala Ala Leu Val Pro Leu Leu Phe Ser
        115                 120                 125

Asn Ala Tyr His Ala Lys Ile Asp Val Pro Glu Ala Val Lys Asp Ala
    130                 135                 140

Ser Glu Lys Tyr Gly Val Glu Leu Leu Val Gly Pro His Leu Gly Thr
145                 150                 155                 160

Gly Ser Asp Val Ala Ser Val Leu Ala Gln Arg Leu Arg Ala Asp Ala
                165                 170                 175

Pro Thr Asp Ala His Val Ile Leu Tyr Ser Val Gly Ser Ser His Val
            180                 185                 190

```
Ser Ala Asn Glu Ser Val Ile Asp Leu Ala His Thr Ile Ala Leu Leu
        195                 200                 205

Thr Gly Phe Ser Val Glu Val Val Pro Ala Thr Gly Gly Pro Gly Ala
    210                 215                 220

Gly Gly Ala Gly Val Ile Glu Val Ala Ser Lys His Lys Ala Val His
225                 230                 235                 240

Ile Leu Pro Leu Phe Val Thr Glu Gly Leu Leu Leu Asp Arg Val Ile
                245                 250                 255

Asp Gln Ser Ala Asn Ile Ala Ala Ala Thr Gly Thr Asn Phe Thr Tyr
            260                 265                 270

Ser Glu Pro Leu Thr Thr Asp Leu Ala Pro Leu Val Ala Ala Arg Tyr
        275                 280                 285

His Ala Ala Leu Ser Ala Leu Leu Ala His Ile
        290                 295

<210> SEQ ID NO 100
<211> LENGTH: 930
<212> TYPE: DNA
<213> ORGANISM: Corynebacterium glutamicum

<400> SEQUENCE: 100
atgcagacat taatctttat cgccattgca ggcgtcgcag cacagcttgt tgatggcggc      60
ctcggcatgg ggttcggcgt cacctcaacc accatcctca tcatgctcgc aggtttaggc     120
cctgcgcagg catccgccgt cgtgcacacc gcagaggttg aaccacctt agtttctggt      180 ttaagccact ggaaatttgg caacgtggat tggaaagtag ttgtccggct cggtatcccc     240
ggcgctatcg gcgcatttgc tggcgctacc ttcttgtcca atatttccac cgaagcagca     300
gcaccgatca cctccctgat tcttgccctg atcggcatga acctagtctg gcgattcagc     360
aagggacgca tccgccgcga ctattccgat cgcccgcaca gcaagggatt cctcggcgga     420
ctcggtattg tcggtggctt cgttgacgcg tccggtggcg gcggatgggg tccagtgacc     480
acctctacgc tgctgtcttt gggacgcacc gaaccccgca agtagtcgg caccgtcaac      540 accgcagaat tcttagtctc cctagccgca acattgggct tcgtcgtggg actgtgggat     600
gacctagtag ctaacctctc tgcagttctc gcgttgctca tcggcggcgc aatcgcagca     660
ccaatcggcg cctggatgat ctctcgcgtt aatgcaaccg tcctcggcgg cttcgtgggc     720
accctgattg tcacactgaa cctgccaaag gtgctcaatg tggttggcct tgatttcatc     780
cccaccggcc tcgtccaggt caccgtcctc ctcatcggcc tgccgctgac gtacctcggc     840
ttccgccgct accgcaaaaa cctcctcaac gaaaccatct ccagcgaggt tgtctccgaa     900
ccacagggac aaaagattaa aagctcttaa                                     930

<210> SEQ ID NO 101
<211> LENGTH: 309
<212> TYPE: PRT
<213> ORGANISM: Corynebacterium glutamicum

<400> SEQUENCE: 101

Met Gln Thr Leu Ile Phe Ile Ala Ile Ala Gly Val Ala Ala Gln Leu
1               5                   10                  15

Val Asp Gly Gly Leu Gly Met Gly Phe Gly Val Thr Ser Thr Thr Ile
            20                  25                  30

Leu Ile Met Leu Ala Gly Leu Gly Pro Ala Gln Ala Ser Ala Val Val
        35                  40                  45
```

-continued

His Thr Ala Glu Val Gly Thr Thr Leu Val Ser Gly Leu Ser His Trp
    50                  55                  60

Lys Phe Gly Asn Val Asp Trp Lys Val Val Arg Leu Gly Ile Pro
65                  70                  75                  80

Gly Ala Ile Gly Ala Phe Ala Gly Ala Thr Phe Leu Ser Asn Ile Ser
                85                  90                  95

Thr Glu Ala Ala Ala Pro Ile Thr Ser Leu Ile Leu Ala Leu Ile Gly
                100                 105                 110

Met Asn Leu Val Trp Arg Phe Ser Lys Gly Arg Ile Arg Arg Asp Tyr
            115                 120                 125

Ser Asp Arg Pro His Ser Lys Gly Phe Leu Gly Gly Leu Gly Ile Val
    130                 135                 140

Gly Gly Phe Val Asp Ala Ser Gly Gly Gly Gly Trp Gly Pro Val Thr
145                 150                 155                 160

Thr Ser Thr Leu Leu Ser Leu Gly Arg Thr Glu Pro Arg Lys Val Val
                165                 170                 175

Gly Thr Val Asn Thr Ala Glu Phe Leu Val Ser Leu Ala Ala Thr Leu
            180                 185                 190

Gly Phe Val Val Gly Leu Trp Asp Asp Leu Val Ala Asn Leu Ser Ala
    195                 200                 205

Val Leu Ala Leu Leu Ile Gly Gly Ala Ile Ala Ala Pro Ile Gly Ala
    210                 215                 220

Trp Met Ile Ser Arg Val Asn Ala Thr Val Leu Gly Gly Phe Val Gly
225                 230                 235                 240

Thr Leu Ile Val Thr Leu Asn Leu Pro Lys Val Leu Asn Val Val Gly
                245                 250                 255

Leu Asp Phe Ile Pro Thr Gly Leu Val Gln Val Thr Val Leu Leu Ile
            260                 265                 270

Gly Leu Pro Leu Thr Tyr Leu Gly Phe Arg Arg Tyr Arg Lys Asn Leu
    275                 280                 285

Leu Asn Glu Thr Ile Ser Ser Glu Val Val Ser Glu Pro Gln Gly Gln
    290                 295                 300

Lys Ile Lys Ser Ser
305

<210> SEQ ID NO 102
<211> LENGTH: 1374
<212> TYPE: DNA
<213> ORGANISM: Corynebacterium glutamicum

<400> SEQUENCE: 102
atgacaactc ccctgcgcgt agccatcatc ggagctggcc ctgctggcat ttacgcatcc     60
gacctcctca tccgcaatga agagcgcgaa gtgttcgttg accttttcga gcaaatgcct    120
gcaccgttcg gactcatccg ttacggcgtt gcaccagacc acccacgcat caagggcatc    180
gttaagtccc tgcacaacgt gttggacaag ccagcctgc gcctgctcgg caacattgaa    240
atcggcaaag acatcaccgt cgaagaactc cgcgactact acgacgcagt tgtcttctcc    300
accggtgcag ttgcagaccg cgacctcaac atccccggaa ttgaagcaga aggttccttc    360
ggtgccggcg agttcgttgg cttctacgac ggcaacccac gcttcgagcg ctcctgggat    420
ctgtctgcac agtccgtcgc tgttatcggc gttggtaacg tcggcctcga tgtagcccgc    480
atcctggcta agcaggcga cgagctcaaa gtcaccgaaa tttccgacaa cgtctacgac    540
tccctcaaag aaaacaaggc cactgaagta cacgttttcg acgtcgtgg cccagcacag    600

-continued

```
gtcaagttca ccccacagga actcaaagaa ctcgaccact cccccaccat caacgtggtt    660
gttgacccag aagacatcga ctacgacggc gcctccgaag aagcccgccg cgcatccaaa    720
tcccaggacc tggtctgcca gatcctggaa cagtacgcaa tccgcgagcc aaaggacgct    780
ccgcacaccc tgcagatcca cctctttgaa aacccagttg aggttcttca aaaggacggc    840
aaggttgttg gcctgcgcac cgaacgcacc gcgctcgacg caacggtgg cgtaaacggc    900 accggcgaat tcaaggactg gccagttcag gctgtctacc gcgcagtcgg ctacaagtcc    960
gaccccatcg acggcgtccc attcgatggg aacaagcacg tcatccctaa tgacggcgga   1020
catgtcctca ccgctccagg tgcagagcca gtaccaggcc tctacgccac cggctggatc   1080
aagcgtggac caatcggtct gatcggcaac accaagtctg atgccaagga aaccaccgac   1140
atcctcatca aggatgccgt caccggtgta cttgaagccc caaagcacca gggcgaagaa   1200
gccatcatcg agcttctcga ttcccgcaac atcccattca ccacctggga aggctggtac   1260
aaactcgacg cagcagagcg cgcactcggt gaagccgaag gccgcgagcg caagaagatt   1320
gttgattggg aagaaatggt ccgccaggcc cgcgaagctc agcaattgt ctaa           1374
```

<210> SEQ ID NO 103
<211> LENGTH: 457
<212> TYPE: PRT
<213> ORGANISM: Corynebacterium glutamicum

<400> SEQUENCE: 103

```
Met Thr Thr Pro Leu Arg Val Ala Ile Ile Gly Ala Gly Pro Ala Gly
1               5                   10                  15

Ile Tyr Ala Ser Asp Leu Leu Ile Arg Asn Glu Glu Arg Glu Val Phe
            20                  25                  30

Val Asp Leu Phe Glu Gln Met Pro Ala Pro Phe Gly Leu Ile Arg Tyr
        35                  40                  45

Gly Val Ala Pro Asp His Pro Arg Ile Lys Gly Ile Val Lys Ser Leu
    50                  55                  60

His Asn Val Leu Asp Lys Pro Arg Leu Arg Leu Leu Gly Asn Ile Glu
65                  70                  75                  80

Ile Gly Lys Asp Ile Thr Val Glu Glu Leu Arg Asp Tyr Tyr Asp Ala
                85                  90                  95

Val Val Phe Ser Thr Gly Ala Val Ala Asp Arg Asp Leu Asn Ile Pro
            100                 105                 110

Gly Ile Glu Ala Glu Gly Ser Phe Gly Ala Gly Glu Phe Val Gly Phe
        115                 120                 125

Tyr Asp Gly Asn Pro Arg Phe Glu Arg Ser Trp Asp Leu Ser Ala Gln
    130                 135                 140

Ser Val Ala Val Ile Gly Val Gly Asn Val Gly Leu Asp Val Ala Arg
145                 150                 155                 160

Ile Leu Ala Lys Thr Gly Asp Glu Leu Lys Val Thr Glu Ile Ser Asp
                165                 170                 175

Asn Val Tyr Asp Ser Leu Lys Glu Asn Lys Ala Thr Glu Val His Val
            180                 185                 190

Phe Gly Arg Arg Gly Pro Ala Gln Val Lys Phe Thr Pro Gln Glu Leu
        195                 200                 205

Lys Glu Leu Asp His Ser Pro Thr Ile Asn Val Val Asp Pro Glu
    210                 215                 220

Asp Ile Asp Tyr Asp Gly Ala Ser Glu Glu Ala Arg Arg Ala Ser Lys
225                 230                 235                 240
```

```
Ser Gln Asp Leu Val Cys Gln Ile Leu Glu Gln Tyr Ala Ile Arg Glu
            245                 250                 255

Pro Lys Asp Ala Pro His Thr Leu Gln Ile His Leu Phe Glu Asn Pro
        260                 265                 270

Val Glu Val Leu Gln Lys Asp Gly Lys Val Val Gly Leu Arg Thr Glu
            275                 280                 285

Arg Thr Ala Leu Asp Gly Asn Gly Val Asn Gly Thr Gly Glu Phe
        290                 295                 300

Lys Asp Trp Pro Val Gln Ala Val Tyr Arg Val Gly Tyr Lys Ser
305                 310                 315                 320

Asp Pro Ile Asp Gly Val Pro Phe Asp Gly Asn Lys His Val Ile Pro
                325                 330                 335

Asn Asp Gly Gly His Val Leu Thr Ala Pro Gly Ala Glu Pro Val Pro
            340                 345                 350

Gly Leu Tyr Ala Thr Gly Trp Ile Lys Arg Gly Pro Ile Gly Leu Ile
        355                 360                 365

Gly Asn Thr Lys Ser Asp Ala Lys Glu Thr Thr Asp Ile Leu Ile Lys
    370                 375                 380

Asp Ala Val Thr Gly Val Leu Glu Ala Pro Lys His Gln Gly Glu Glu
385                 390                 395                 400

Ala Ile Ile Glu Leu Leu Asp Ser Arg Asn Ile Pro Phe Thr Thr Trp
                405                 410                 415

Glu Gly Trp Tyr Lys Leu Asp Ala Ala Glu Arg Ala Leu Gly Glu Ala
            420                 425                 430

Glu Gly Arg Glu Arg Lys Lys Ile Val Asp Trp Glu Glu Met Val Arg
        435                 440                 445

Gln Ala Arg Glu Ala Pro Ala Ile Val
    450                 455

<210> SEQ ID NO 104
<211> LENGTH: 1173
<212> TYPE: DNA
<213> ORGANISM: Corynebacterium glutamicum

<400> SEQUENCE: 104
ttgtctatga ttggctatgg tttacctatg cccaatcagg cccacttctc tgcgtccttt      60
gcccgcccct ctaccccggc tgcaaagtgc atgcaccata tccgcctcgg ccagcaactc     120
attagaaatg agctggtcga ggccacaggt ctgtcccaac cgactgtcac ccgcgcagtc     180
accgctttaa tgcaggcagg tttggttcgt gaacgccctg atctcacact ctcatcgggc     240
cctggtcgtc ccaatattcc tctagaactc gctccaagtc catggattca tgcaggcgtg     300
gcaatcggca ccaagtcttc ctacgtcgct ttgtttgata ccaagggtcg cacccttcgt     360
gatgccatac tggaaatctc agcagctgat ttagatccag acaccttcat cgaacacctc     420
atcgctggtg tcaaccgcct caccactggt cttgatctac cactggtagg tattggtgtg     480
gctacctcag gaaaagtcac caacgcgggc gttgtcaccg caagcaactt gggctgggat     540
ggcgttgata tcgccggccg tctgaactac caattcagcg ttccagcaac cgtggcatca     600
gcaattcctg ccatcgcagc ttctgaactg caggcttccc cacttcccca ccctgagcag     660
ccaactccca tcaccttgac cttctacgcc gatgactctg tgggcgcggc ctacagcaat     720
gatttgggag acatgtcat ggaccactg gctacaactc gtggatcagg tttggatact     780
ttgggcatgg ctgctgaaga tgcgctgagc acccaaggtt tcttaagcag ggtttctgat     840
cagggtatct ttgccaacag ccttggtgag ctagtcacca ttgctaaaga caatgaaacc     900
```

-continued

```
gcacgggaat tcctcaacga tcgcgcgacc ctgctggctc acactgccgc agaagctgct      960
gaaacagtta agccatccac cctggttctc tcgggatcgg cgttttccga agatccacaa     1020
ggtcggttgg tgttcgcttc ccaattgaag aaggaatacg acgcagacat tgagctccgc     1080
ttgatcccca cccaccggga aaatgtccgc gcagcagctc gcgcagtcgc acttgatcga     1140
ctactcaacg agccacttac cctcgtaccc taa                                  1173
```

<210> SEQ ID NO 105
<211> LENGTH: 390
<212> TYPE: PRT
<213> ORGANISM: Corynebacterium glutamicum

<400> SEQUENCE: 105

Leu Ser Met Ile Gly Tyr Gly Leu Pro Met Pro Asn Gln Ala His Phe
1               5                   10                  15

Ser Ala Ser Phe Ala Arg Pro Ser Thr Pro Ala Ala Lys Cys Met His
            20                  25                  30

His Ile Arg Leu Gly Gln Gln Leu Ile Arg Asn Glu Leu Val Glu Ala
        35                  40                  45

Thr Gly Leu Ser Gln Pro Thr Val Thr Arg Ala Val Thr Ala Leu Met
    50                  55                  60

Gln Ala Gly Leu Val Arg Glu Arg Pro Asp Leu Thr Leu Ser Ser Gly
65                  70                  75                  80

Pro Gly Arg Pro Asn Ile Pro Leu Glu Leu Ala Pro Ser Pro Trp Ile
                85                  90                  95

His Ala Gly Val Ala Ile Gly Thr Lys Ser Ser Tyr Val Ala Leu Phe
            100                 105                 110

Asp Thr Lys Gly Arg Thr Leu Arg Asp Ala Ile Leu Glu Ile Ser Ala
        115                 120                 125

Ala Asp Leu Asp Pro Asp Thr Phe Ile Glu His Leu Ile Ala Gly Val
    130                 135                 140

Asn Arg Leu Thr Thr Gly Leu Asp Leu Pro Leu Val Gly Ile Gly Val
145                 150                 155                 160

Ala Thr Ser Gly Lys Val Thr Asn Ala Gly Val Val Thr Ala Ser Asn
                165                 170                 175

Leu Gly Trp Asp Gly Val Asp Ile Ala Gly Arg Leu Asn Tyr Gln Phe
            180                 185                 190

Ser Val Pro Ala Thr Val Ala Ser Ala Ile Pro Ala Ile Ala Ala Ser
        195                 200                 205

Glu Leu Gln Ala Ser Pro Leu Pro His Pro Glu Gln Pro Thr Pro Ile
    210                 215                 220

Thr Leu Thr Phe Tyr Ala Asp Asp Ser Val Gly Ala Ala Tyr Ser Asn
225                 230                 235                 240

Asp Leu Gly Val His Val Ile Gly Pro Leu Ala Thr Thr Arg Gly Ser
                245                 250                 255

Gly Leu Asp Thr Leu Gly Met Ala Ala Glu Asp Ala Leu Ser Thr Gln
            260                 265                 270

Gly Phe Leu Ser Arg Val Ser Asp Gln Gly Ile Phe Ala Asn Ser Leu
        275                 280                 285

Gly Glu Leu Val Thr Ile Ala Lys Asp Asn Glu Thr Ala Arg Glu Phe
    290                 295                 300

Leu Asn Asp Arg Ala Thr Leu Leu Ala His Thr Ala Ala Glu Ala Ala
305                 310                 315                 320

```
Glu Thr Val Lys Pro Ser Thr Leu Val Leu Ser Gly Ser Ala Phe Ser
            325                 330                 335

Glu Asp Pro Gln Gly Arg Leu Val Phe Ala Ser Gln Leu Lys Lys Glu
        340                 345                 350

Tyr Asp Ala Asp Ile Glu Leu Arg Leu Ile Pro Thr His Arg Glu Asn
    355                 360                 365

Val Arg Ala Ala Ala Arg Ala Val Ala Leu Asp Arg Leu Leu Asn Glu
370                 375                 380

Pro Leu Thr Leu Val Pro
385                 390

<210> SEQ ID NO 106
<211> LENGTH: 1074
<212> TYPE: DNA
<213> ORGANISM: Corynebacterium glutamicum

<400> SEQUENCE: 106
gtgttcatgc ttgcacagcg aacactcccc attcacatca ccgcccccca cctgccgtc        60 gcgcgcgtat ttcaccaaat tcgcgccaca gacgccgatc gcacctcgct gcaacgcgat      120
cttgaactct cccaagctgg catcactcgg catgtatcag cgcttattga tgcaggtctc      180
gtggaggaaa cccgagtgga ttccggggcg cgctcggggc gaccgcgcac aaaattaggc      240
atcgacggcc gccatctcac cgcctgggga gtgcacattg gcctgcgcag cacggatttt      300
gcggtgtgcg atttagccgg ccgagtgatt aggtatgagc gcgtggacca tgaagtttca      360
cactccacgc cgtcggaaac gctgaatttt gtcgcacata ggttacaaac attgagcgcc      420
ggcttgcccg agccccgcaa tgtgggcgtg gcattatctg cccacttaag cgccaacggc      480
accgtcactt ccgaagatta tggctggtca gaggtggaaa ttgggataca cctcccctc       540 cccgccacca tcggatcagg tgttgcggcg atggccggtt cggaaattat caacgcgcca      600
ctgacccaat ccacgcagtc cacgctgtat ttctacgccc gcgaaatggt ctcccacgcc      660
tggattttca acggcgctgt ccaccgcccc aacagcggcc gcacgccgac ggcgttcgga      720
aatacaaata ccttaaaaga tgcttttcga cgtggactca caccaacaac tttctccgat      780
ttagtccaac tctcccacac caacccgctt gcccgacaga tcctcaacga gcgcgcccac      840
aaacttgccg acgccgtaac caccgccgtt gatgttgtcg accccgaagc cgtcgtcttc      900
gccggcgaag ccttcaccct ggatccggaa actcttcgca ttgtggtgac ccagctccga      960
gcaaacaccg gcagccaact gagaatccaa cgcgcagacg cccacattct ccgcaccgcg     1020
gccatccagg tggcgctgca tccgatccgt caagatccgt tagcatttgt gtaa          1074

<210> SEQ ID NO 107
<211> LENGTH: 357
<212> TYPE: PRT
<213> ORGANISM: Corynebacterium glutamicum

<400> SEQUENCE: 107

Met Phe Met Leu Ala Gln Arg Thr Leu Pro Ile His Ile Thr Ala Pro
1               5                   10                  15

His Leu Pro Val Ala Arg Val Phe His Gln Ile Arg Ala Thr Asp Ala
            20                  25                  30

Asp Arg Thr Ser Leu Gln Arg Asp Leu Glu Leu Ser Gln Ala Gly Ile
        35                  40                  45

Thr Arg His Val Ser Ala Leu Ile Asp Ala Gly Leu Val Glu Glu Thr
    50                  55                  60
```

Arg Val Asp Ser Gly Ala Arg Ser Gly Arg Pro Arg Thr Lys Leu Gly
65                  70                  75                  80

Ile Asp Gly Arg His Leu Thr Ala Trp Gly Val His Ile Gly Leu Arg
            85                  90                  95

Ser Thr Asp Phe Ala Val Cys Asp Leu Ala Gly Arg Val Ile Arg Tyr
            100                 105                 110

Glu Arg Val Asp His Glu Val Ser His Ser Thr Pro Ser Glu Thr Leu
        115                 120                 125

Asn Phe Val Ala His Arg Leu Gln Thr Leu Ser Ala Gly Leu Pro Glu
    130                 135                 140

Pro Arg Asn Val Gly Val Ala Leu Ser Ala His Leu Ser Ala Asn Gly
145                 150                 155                 160

Thr Val Thr Ser Glu Asp Tyr Gly Trp Ser Glu Val Glu Ile Gly Ile
                165                 170                 175

His Leu Pro Phe Pro Ala Thr Ile Gly Ser Gly Val Ala Ala Met Ala
            180                 185                 190

Gly Ser Glu Ile Ile Asn Ala Pro Leu Thr Gln Ser Thr Gln Ser Thr
        195                 200                 205

Leu Tyr Phe Tyr Ala Arg Glu Met Val Ser His Ala Trp Ile Phe Asn
    210                 215                 220

Gly Ala Val His Arg Pro Asn Ser Gly Arg Thr Pro Thr Ala Phe Gly
225                 230                 235                 240

Asn Thr Asn Thr Leu Lys Asp Ala Phe Arg Arg Gly Leu Thr Pro Thr
                245                 250                 255

Thr Phe Ser Asp Leu Val Gln Leu Ser His Thr Asn Pro Leu Ala Arg
            260                 265                 270

Gln Ile Leu Asn Glu Arg Ala His Lys Leu Ala Asp Ala Val Thr Thr
        275                 280                 285

Ala Val Asp Val Val Asp Pro Glu Ala Val Val Phe Ala Gly Glu Ala
    290                 295                 300

Phe Thr Leu Asp Pro Glu Thr Leu Arg Ile Val Val Thr Gln Leu Arg
305                 310                 315                 320

Ala Asn Thr Gly Ser Gln Leu Arg Ile Gln Arg Ala Asp Ala His Ile
                325                 330                 335

Leu Arg Thr Ala Ala Ile Gln Val Ala Leu His Pro Ile Arg Gln Asp
            340                 345                 350

Pro Leu Ala Phe Val
        355

<210> SEQ ID NO 108
<211> LENGTH: 2180
<212> TYPE: DNA
<213> ORGANISM: Artificial Sequence
<220> FEATURE:
<223> OTHER INFORMATION: promoter P2

<400> SEQUENCE: 108
tttcgcggtg aatcaaccca cccgaacggc gatccttcga agtattttgc cgattgatca      60
attagcgtcg gcaacatcac tgaatatgct gctcatgcag accggcgcaa tcgttggccc     120
gctgatcgca ggtgcgttga ttccgctgat cggtttcggg tggctgtatt ccttgatgt     180 tgtctccatc atccccacac tgtgggctgt atggtcactg ccttcaatca agccatccgg    240
caaggtcatg aaggccggtt cgccagtgt ggtggatggc ctgaagtatt tggctggcca     300
acccgtgttg ttgatggtga tggtgctgga tcttatcgcc atgattttcg gcatgccacg    360

```
tgcgctttac cccgagatcg cggaagtgaa cttcggtggt ggtgacgccg gtgcaacgat      420
gctggcgttc atgtactcat ccatggctgt tggcgcagtt cttggcggcg tgctgtctgg      480
ttgggtttcc cggattagcc gccagggtgt tgcagtttat tggtgcatca tcgcctgggg      540
cgcagccgtt gctttgggtg gcgtagcaat tgttgtcagc cccggcgctg tgaccgcgtg      600
ggcgtggatg ttcatcatca tgatggtcat tggtggcatg gctgacatgt ttagctcggc      660
tgttcgaaat gctattttgc agcagtctgc agcggaacat gtgcagggcc gaatccaagg      720
tgtgtggatc atcgtcgtgg tgggtggacc tcgtttagct gacgtccttc acggttgggc      780
cgctgagccc ttgggtgcag gttggacggt attatgggc ggagtagcgg tggttgtact       840
cactgcaatt tgtatggtgg cggtgcctaa attctggaaa tacgagaaac caaaaattac      900
cggcatctaa atacttatcc atgcccattt acagacaatg ccttagcttt gacctgcaca      960
aatagttgca aattgtccca catacacata aagtagcttg cgtatttaaa attatgaacc     1020
taagggtttt agcaatgccc aatcaggccc acttctctgc gtcctttgcc cgcccctcta     1080
ccccggctgc aaagtgcatg caccatatcc gcctcggcca gcaactcatt agaaatgagc     1140
tggtcgaggc cacaggtctg tcccaaccga ctgtcacccg cgcagtcacc gctttaatgc     1200
aggcaggttt ggttcgtgaa cgccctgatc tcacactctc atcgggccct ggtcgtccca     1260
atattcctct agaactcgct ccaagtccat ggattcatgc aggcgtggca atcggcacca     1320
agtcttccta cgtcgctttg tttgatacca agggtcgcac ccttcgtgat gccatactgg     1380
aaatctcagc agctgattta gatccagaca ccttcatcga cacctcatc gctggtgtca      1440 accgcctcac cactggtctt gatctaccac tggtaggtat tggtgtggct acctcaggaa     1500
aagtcaccaa cgcgggcgtt gtcaccgcaa gcaacttggg ctgggatggc gttgatatcg     1560
ccggccgtct gaactaccaa ttcagcgttc agcaaccgt ggcatcagca attcctgcca      1620
tcgcagcttc tgaactgcag gcttccccac ttccccaccc tgagcagcca actcccatca     1680
ccttgaccct ctacgccgat gactctgtgg gcgcggccta cagcaatgat ttgggagtac     1740
atgtcattgg accactggct acaactcgtg gatcaggttt ggatactttg gcatggctg      1800 ctgaagatgc gctgagcacc caaggtttct taagcagggt ttctgatcag ggtatctttg     1860
ccaacagcct tggtgagcta gtcaccattg ctaaagacaa tgaaaccgca cgggaattcc     1920
tcaacgatcg cgcgaccctg ctggctcaca ctgccgcaga agctgctgaa acagttaagc     1980
catccaccct ggttctctcg ggatcggcgt tttccgaaga tccacaaggt cggttggtgt     2040
tcgcttccca attgaagaag gaatacgacg cagacattga gctccgcttg atccccaccc     2100
accgggaaaa tgtccgcgca gcagctcgcg cagtcgcact tgatcgacta ctcaacgagc     2160 cacttacccct cgtaccctaa                                                2180
```

<210> SEQ ID NO 109
<211> LENGTH: 2247
<212> TYPE: DNA
<213> ORGANISM: Artificial Sequence
<220> FEATURE:
<223> OTHER INFORMATION: promoter P4

<400> SEQUENCE: 109

```
ccctcatgag ttcagggggtt agaaaagcaa tgggatttgg atgcggttcg gttttggccg      60
tcatcatggt tatctcattt gttggatggg cgcttagctt catgatgga acggcaccta       120 ttcgccaact ccagcaaatc cctgaagatg ttccgccggc gcgtggtgta aagttccgc       180 aaattgatac aggggcagat ggacgcacgt cagatcattt gcgttttggg gcggaaccaa      240
```

```
ttgctcaaga tgctggtgtg tccgctcaag cgattgcggc ttatggaaac gcagagctca    300
ttgcgagtac tgcgtggcct ggctgcaatc tggggtggaa taccttggca ggtatcggcc    360
aggtggaaac ccgtcacggt acctacaacg gcaaaatgtt cggggcagt tccctggatg     420 aaaatggagt tgcaacccct ccaatcatcg gcgttccact tgatggttca ccggggtttg    480
cggaaattcc cgacactgat ggtggggaat tagatggcga tactgaatat gatcgcgcgg    540
taggtcccat gcagttcatt ccggaaacgt ggcgacttat gggattggat gcaaacggtg    600
atggggtagc ggaccccaac caaattgatg acgcagcatt gagtgccgca aacctgttgt    660
gttccaacga tcgtgacttg tccactcctg aaggatggac cgcagctgtt cattcttaca    720
acatgtctaa tcagtatttg atggacgttc gagatgctgc cgcgtcctac gctttacgac    780
agccggcgat ctaaaactta caagcgcaa cccccgaaaa tgtgagatta tgtccggtcg     840
gacacgtgcg ggctggggat atgggtagtt taataaattt ataccacaca gtctattgca    900
atagaccaag ctgttcagta gggtgcatgg gagaagaatt tcctaataaa aactcttaag    960
gacctccaag tggctgaaat catgcacgta ttcgctcgcg aaattctcga ctcccgcggt   1020
aacccaaccg tcgaggcaga ggttttcctt gatgacggtt cccacggtgt cgcaggtgtt   1080
ccatccggcg catccaccgg cgtccacgag gctcatgagc tgcgtgacgg tggcgatcgc   1140
tacctgggca agggcgtttt gaaggcagtt gaaaacgtca acgaagaaat cggcgacgag   1200
ctcgctggcc tagaggctga cgatcagcgc ctcatcgacg aagcaatgat caagcttgat   1260
ggcaccgcca acaagtcccg cctgggtgca acgcaatcc ttggtgtttc catggctgtt    1320
gcaaaggctg ctgctgattc cgcaggcctc ccactgttcc gctacatcgg tggaccaaac   1380
gcacacgttc ttccagttcc aatgatgaac atcatcaacg gtggcgctca cgctgactcc   1440
ggtgttgacg ttcaggaatt catgatcgct ccaatcggtg cagagacctt ctctgaggct   1500
ctccgcaacg gcgcagaggt ctaccacgca ctgaagtccg tcatcaagga aaagggcctg   1560
tccaccggac ttggcgatga gggcggcttc gctccttccg tcggctccac ccgtgaggct   1620
cttgacctta tcgttgaggc aatcgagaag gctggcttca ccccaggcaa ggacatcgct   1680
cttgctctgg acgttgcttc ctctgagttc ttcaaggacg gcacctacca cttcgaaggt   1740
ggccagcact ccgcagctga gatggcaaac gtttacgctg agctcgttga cgcgtaccca   1800
atcgtctcca tcgaggaccc actgcaggaa gatgactggg agggttacac caacctcacc   1860
gcaaccatcg gcgacaaggt tcagatcgtt ggcgacgact tcttcgtcac caaccctgag   1920
cgcctgaagg agggcatcgc taagaaggct gccaactcca tcctggttaa ggtgaaccag   1980
atcggtaccc tcaccgagac cttcgacgct gtcgacatgg ctcaccgcgc aggctacacc   2040
tccatgatgt cccaccgttc cggtgagacc gaggacacca ccattgctga cctcgcagtt   2100
gcactcaact gtggccagat caagactggt gctccagcac gttccgaccg tgtcgcaaag   2160
tacaaccagc ttctccgcat cgagcagttg cttggcgacg ccggcgtcta cgcaggtcgc   2220
agcgcattcc cacgctttca gggctaa                                        2247
```

<210> SEQ ID NO 110
<211> LENGTH: 2192
<212> TYPE: DNA
<213> ORGANISM: Artificial Sequence
<220> FEATURE:
<223> OTHER INFORMATION: promoter P8

<400> SEQUENCE: 110

```
tcaccgagtc tttgatcaag ggtggcgctt tgactccct tggacacgca cgaaaaggcc      60
tcatgctggt cttcgaagat gccgttgatt ccgtcatcgc taccaaaaaa gctgctgaca     120
agggacaatt tgatctcttt gcagctttcg actcggataa caacgacgat gtggcaagtt    180
tcttccagat caccgttcct gatgacgaat gggaccgtaa gcatgagctc gcactcgagc    240
gagaaatgct gggtctgtat gtttctggac acccactcga tggctatgaa gatgccattg    300
ctgcccaggt tgatacagca ctgaccacca ttgttgccgg tgaactcaag cacggcgcag    360
aagtgaccgt gggtggcatt atctctggtg tggatcgacg gttctccaag aaggacggtt    420
ccccttgggc gattgtcacc attgaagatc acaacggcgc gtccgttgaa ttgttggtct    480
tcaacaaggt gtattccatc gttggatcca tgattgtgga agacaacatc attttggcca    540
aggcacacat ctccattcga gatgatcgta tgagccttt ctgtgatgat ctccgcgttc     600
cagagcttgg gccaggaaac gggcaaggac ttccgcttcg tttgtccatg cgtactgatc    660
agtgcaccat gtccaacatt gccaagctca agcaggtgct ggtggacaac aagggtgaat    720
ctgatgtgta cctcaatttg atcgatgggg ataactccac ggtcatgatt ttgggtgatc    780
acttaagagt caaccgatcc gcaagtttga tgggcgacct caaggcaacg atggggccag    840
gcatcctcgg ttaatcacat cacactggga ttaccccgtg taggggtgaa acccgaatg     900
tggctaaaac ttttggaaac ttaagttacc tttaatcgga aacttattga attcgggtga    960
ggcaactgca actctggact aaagcatgag ccagaaccg catcaggacc actcacgttg    1020
gttccttgcc ccgtacccca gagctacttg atgcaaacat caagcgctct aacggtgaga   1080
ttggggagga ggaattcttc cagatcctgc agtcttctgt agatgacgtg atcaagcgcc   1140
aggttgacct gggtatcgac atcctcaacg agggcgaata cggccacgtc acctccggtg   1200
cagttgactt cggtgcatgg tggaactact ccttcacccg cctgggcgga ctgaccatga   1260
ccgataccga ccgttgggca agccaggaag cagtgcgttc cacccctggc aacatcaagc   1320
tgaccagctt ctctgatcgt cgcgaccgcg cattgttcag cgaagcatac gaggatccag   1380
tatctggcat cttcaccggc cgcgcttctg tgggcaaccc agagttcacc ggacctatta   1440
cctacattgg ccaggaagaa actcagacga atgttgatct gctgaagaag ggcatgaacg   1500
cagcgggagc taccgacggc ttcgttgcag cactatcccc aggatctgca gctcgattga   1560
ccaacaagtt ctacgacact gatgaagaag tcgtcgcagc atgtgccgat gcgctttccc   1620
aggaatacaa gatcatcacc gatgcaggtc tgaccgttca gctcgacgca ccggacttgg   1680
cagaagcatg ggatcagatc aacccagagc caagcgtgaa ggattactta gactggatcg   1740
gtacacgcat cgatgccatc aacagtgcag tgaagggcct tccaaaggaa cagacccgcc   1800
tgcacatctg ctgggctct tggcacggac cacacgtcac tgacatccca ttcggtgaca    1860
tcattggtga gatcctgcgc gcagaggtcg gtggcttctc cttcgaaggc gcatctcctc   1920
gtcacgcaca cgagtggcgt gtatgggaag aaaacaagct tcctgaaggc tctgttatct   1980
accctggtgt tgtgtctcac tccatcaacg ctgtggagca cccacgcctg gttgctgatc   2040
gtatcgttca gttcgccaag cttgttggcc ctgagaacgt cattgcgtcc actgactgtg   2100
gtctgggcgg acgtctgcat tcccagatcg catgggcaaa gctggagtcc ctagtagagg   2160
gcgctcgcat tgcatcaaag gaactgttct aa                                  2192
```

<210> SEQ ID NO 111
<211> LENGTH: 97
<212> TYPE: DNA
<213> ORGANISM: Artificial Sequence
<220> FEATURE:
<223> OTHER INFORMATION: promoter P3

<400> SEQUENCE: 111

```
tgccgtttct cgcgttgtgt gtggtactac gtggggacct aagcgtgtaa gatggaaacg    60
tctgtatcgg ataagtagcg aggagtgttc gttaaaa                              97
```

<210> SEQ ID NO 112
<211> LENGTH: 35
<212> TYPE: DNA
<213> ORGANISM: Artificial Sequence
<220> FEATURE:
<223> OTHER INFORMATION: primer

<400> SEQUENCE: 112

```
ccaagcttgc atgcctcacc gagtctttga tcaag                                35
```

<210> SEQ ID NO 113
<211> LENGTH: 35
<212> TYPE: DNA
<213> ORGANISM: Artificial Sequence
<220> FEATURE:
<223> OTHER INFORMATION: primer

<400> SEQUENCE: 113

```
caaaagtttt agccacattc gggttttcac cccta                                35
```

<210> SEQ ID NO 114
<211> LENGTH: 35
<212> TYPE: DNA
<213> ORGANISM: Artificial Sequence
<220> FEATURE:
<223> OTHER INFORMATION: primer

<400> SEQUENCE: 114

```
ctctggactt aaagcatgag ccagaaccgc atcag                                35
```

<210> SEQ ID NO 115
<211> LENGTH: 35
<212> TYPE: DNA
<213> ORGANISM: Artificial Sequence
<220> FEATURE:
<223> OTHER INFORMATION: primer

<400> SEQUENCE: 115

```
cggtacccgg ggatcttaga acagttcctt tgatg                                35
```

<210> SEQ ID NO 116
<211> LENGTH: 87
<212> TYPE: DNA
<213> ORGANISM: Artificial Sequence
<220> FEATURE:
<223> OTHER INFORMATION: DNA fragment of P8 promoter

<400> SEQUENCE: 116

```
gtggctaaaa cttttggaaa cttaagttac ctttaatcgg aaacttattg aattcgggtg    60
aggcaactgc aactctggac ttaaagc                                         87
```

<210> SEQ ID NO 117
<211> LENGTH: 35
<212> TYPE: DNA
<213> ORGANISM: Artificial Sequence
<220> FEATURE:
<223> OTHER INFORMATION: primer

<400> SEQUENCE: 117
gtgaaaaccc gaatgtggct aaaactttg gaaac                                35

<210> SEQ ID NO 118
<211> LENGTH: 35
<212> TYPE: DNA
<213> ORGANISM: Artificial Sequence
<220> FEATURE:
<223> OTHER INFORMATION: primer

<400> SEQUENCE: 118
gcggttctgg ctcatgcttt aagtccagag ttgca                               35

<210> SEQ ID NO 119
<211> LENGTH: 1206
<212> TYPE: DNA
<213> ORGANISM: Corynebacterium glutamicum

<400> SEQUENCE: 119

```
atgagccaga accgcatcag gaccactcac gttggttcct tgccccgtac cccagagcta     60
cttgatgcaa acatcaagcg ttctaacggt gagattgggg aggaggaatt cttccagatt    120
ctgcagtctt ctgtagatga cgtgatcaag cgccaggttg acctgggtat cgacatcctt    180
aacgagggcg aatacggcca cgtcacctcc ggtgcagttg acttcggtgc atggtggaac    240
tactccttca cccgcctggg cggactgacc atgaccgata ccgaccgttg ggcaagccag    300
gaagcagtgc gttccacccc tggcaacatc aagctgacca gcttctctga tcgtcgcgac    360
cgcgcattgt tcagcgaagc atacgaggat ccagtatctg catcttcac cggtcgcgct    420
tctgtgggca acccagagtt caccggacct attacctaca ttggccagga agaaactcag    480
acggatgttg atctgctgaa gagggcatg aacgcagcgg gagctaccga cggcttcgtt    540
gcagcactat ccccaggatc tgcagctcga ttgaccaaca agttctacga cactgatgaa    600
gaagtcgtcg cagcatgtgc tgatgcgctt tcccaggaat acaagatcat caccgatgca    660
ggtctgaccg ttcagctcga cgcaccggac ttggcagaag catgggatca gatcaaccca    720
gagccaagcg tgaaggatta cttggactgg atcggtacac gcatcgatgc catcaacagt    780
gcagtgaagg gccttccaaa ggaacagacc cgcctgcaca tctgctgggg ctcttggcac    840
ggaccacacg tcactgacat cccattcggt gacatcattg gtgagatcct gcgcgcagag    900
gtcggtggct ctccttcga aggcgcatct cctcgtcacg cacacgagtg gcgtgtatgg    960
gaagaaaaca agcttcctga aggctctgtt atctaccctg gtgttgtgtc tcactccatc   1020
aacgctgtgg agcacccacg cctggttgct gatcgtatcg ttcagttcgc caagcttgtt   1080
ggccctgaga acgtcattgc gtccactgac tgtggtctgg gcggacgtct gcattcccag   1140
atcgcatggg caaagctgga gtccctagta gagggcgctc gcattgcatc aaaggaactg   1200
ttctaa                                                              1206
```

<210> SEQ ID NO 120
<211> LENGTH: 401
<212> TYPE: PRT
<213> ORGANISM: Corynebacterium glutamicum

<400> SEQUENCE: 120

```
Met Ser Gln Asn Arg Ile Arg Thr Thr His Val Gly Ser Leu Pro Arg
1               5                   10                  15

Thr Pro Glu Leu Leu Asp Ala Asn Ile Lys Arg Ser Asn Gly Glu Ile
            20                  25                  30
```

```
Gly Glu Glu Glu Phe Phe Gln Ile Leu Gln Ser Ser Val Asp Asp Val
            35                  40                  45

Ile Lys Arg Gln Val Asp Leu Gly Ile Asp Ile Leu Asn Glu Gly Glu
 50                  55                  60

Tyr Gly His Val Thr Ser Gly Ala Val Asp Phe Gly Ala Trp Trp Asn
 65                  70                  75                  80

Tyr Ser Phe Thr Arg Leu Gly Gly Leu Thr Met Thr Asp Thr Asp Arg
                 85                  90                  95

Trp Ala Ser Gln Glu Ala Val Arg Ser Thr Pro Gly Asn Ile Lys Leu
                100                 105                 110

Thr Ser Phe Ser Asp Arg Arg Asp Arg Ala Leu Phe Ser Glu Ala Tyr
            115                 120                 125

Glu Asp Pro Val Ser Gly Ile Phe Thr Gly Arg Ala Ser Val Gly Asn
130                 135                 140

Pro Glu Phe Thr Gly Pro Ile Thr Tyr Ile Gly Gln Glu Glu Thr Gln
145                 150                 155                 160

Thr Asp Val Asp Leu Leu Lys Lys Gly Met Asn Ala Ala Gly Ala Thr
                165                 170                 175

Asp Gly Phe Val Ala Ala Leu Ser Pro Gly Ser Ala Ala Arg Leu Thr
            180                 185                 190

Asn Lys Phe Tyr Asp Thr Asp Glu Glu Val Val Ala Ala Cys Ala Asp
            195                 200                 205

Ala Leu Ser Gln Glu Tyr Lys Ile Ile Thr Asp Ala Gly Leu Thr Val
            210                 215                 220

Gln Leu Asp Ala Pro Asp Leu Ala Glu Ala Trp Asp Gln Ile Asn Pro
225                 230                 235                 240

Glu Pro Ser Val Lys Asp Tyr Leu Asp Trp Ile Gly Thr Arg Ile Asp
                245                 250                 255

Ala Ile Asn Ser Ala Val Lys Gly Leu Pro Lys Glu Gln Thr Arg Leu
            260                 265                 270

His Ile Cys Trp Gly Ser Trp His Gly Pro His Val Thr Asp Ile Pro
            275                 280                 285

Phe Gly Asp Ile Ile Gly Glu Ile Leu Arg Ala Glu Val Gly Gly Phe
290                 295                 300

Ser Phe Glu Gly Ala Ser Pro Arg His Ala His Glu Trp Arg Val Trp
305                 310                 315                 320

Glu Glu Asn Lys Leu Pro Gly Ser Val Ile Tyr Pro Gly Val Val
                325                 330                 335

Ser His Ser Ile Asn Ala Val Glu His Pro Arg Leu Val Ala Asp Arg
            340                 345                 350

Ile Val Gln Phe Ala Lys Leu Val Gly Pro Glu Asn Val Ile Ala Ser
            355                 360                 365

Thr Asp Cys Gly Leu Gly Gly Arg Leu His Ser Gln Ile Ala Trp Ala
370                 375                 380

Lys Leu Glu Ser Leu Val Gly Ala Arg Ile Ala Ser Lys Glu Leu
385                 390                 395                 400

Phe
```

<210> SEQ ID NO 121
<211> LENGTH: 35
<212> TYPE: DNA
<213> ORGANISM: Artificial Sequence
<220> FEATURE:
<223> OTHER INFORMATION: primer

```
<400> SEQUENCE: 121
ccaagcttgc atgcccctc atgagttcag gggtt                              35

<210> SEQ ID NO 122
<211> LENGTH: 35
<212> TYPE: DNA
<213> ORGANISM: Artificial Sequence
<220> FEATURE:
<223> OTHER INFORMATION: primer

<400> SEQUENCE: 122
tggtataaat ttattaaact acccatatcc ccagc                             35

<210> SEQ ID NO 123
<211> LENGTH: 35
<212> TYPE: DNA
<213> ORGANISM: Artificial Sequence
<220> FEATURE:
<223> OTHER INFORMATION: primer

<400> SEQUENCE: 123
cttaaggacc tccaagtggc tgaaatcatg cacgt                             35

<210> SEQ ID NO 124
<211> LENGTH: 35
<212> TYPE: DNA
<213> ORGANISM: Artificial Sequence
<220> FEATURE:
<223> OTHER INFORMATION: primer

<400> SEQUENCE: 124
cggtacccgg ggatcttagc cctgaaagcg tggga                             35

<210> SEQ ID NO 125
<211> LENGTH: 98
<212> TYPE: DNA
<213> ORGANISM: Artificial Sequence
<220> FEATURE:
<223> OTHER INFORMATION: DNA fragment of P4 promoter

<400> SEQUENCE: 125
aataaattta taccacacag tctattgcaa tagaccaagc tgttcagtag ggtgcatggg    60
agaagaattt cctaataaaa actcttaagg acctccaa                           98

<210> SEQ ID NO 126
<211> LENGTH: 35
<212> TYPE: DNA
<213> ORGANISM: Artificial Sequence
<220> FEATURE:
<223> OTHER INFORMATION: primer

<400> SEQUENCE: 126
ggatatgggt agtttaataa atttatacca cacag                             35

<210> SEQ ID NO 127
<211> LENGTH: 35
<212> TYPE: DNA
<213> ORGANISM: Artificial Sequence
<220> FEATURE:
<223> OTHER INFORMATION: primer

<400> SEQUENCE: 127
catgatttca gccacttgga ggtccttaag agttt                             35
```

<210> SEQ ID NO 128
<211> LENGTH: 1278
<212> TYPE: DNA
<213> ORGANISM: Corynebacterium glutamicum

<400> SEQUENCE: 128

| | | |
|---|---|---|
| gtggctgaaa tcatgcacgt attcgctcgc gaaattctcg actcccgcgg taacccaacc | 60 |
| gtcgaggcag aggttttcct tgatgacggt tcccacggtg tcgcaggtgt tccatccggc | 120 |
| gcatccaccg gcgtccacga ggctcatgag ctgcgtgacg gtggcgatcg ctacctgggc | 180 |
| aagggcgttt tgaaggcagt tgaaaacgtc aacgaagaaa tcggcgacga gctcgctggc | 240 |
| ctagaggctg acgatcagcg cctcatcgac gaagcaatga tcaagcttga tggcaccgcc | 300 |
| aacaagtccc gcctgggtgc aaacgcaatc cttggtgttt ccatggctgt tgcaaaggct | 360 |
| gctgctgatt ccgcaggcct cccactgttc cgctacatcg gtggaccaaa cgcacacgtt | 420 |
| cttccagttc caatgatgaa catcatcaac ggtggcgctc acgctgactc cggtgttgac | 480 |
| gttcaggaat tcatgatcgc tccaatcggt gcagagacct ctctgaggc tctccgcaac | 540 |
| ggcgcagagg tctaccacgc actgaagtcc gtcatcaagg aaaagggcct gtccaccgga | 600 |
| cttggcgatg agggcggctt cgctccttcc gtcggctcca ccgtgaggc tcttgacctt | 660 |
| atcgttgagg caatcgagaa ggctggcttc accccaggca aggacatcgc tcttgctctg | 720 |
| gacgttgctt cctctgagtt cttcaaggac ggcacctacc acttcgaagg tggccagcac | 780 |
| tccgcagctg agatggcaaa cgtttacgct gagctcgttg acgcgtaccc aatcgtctcc | 840 |
| atcgaggacc cactgcagga agatgactgg gagggttaca ccaacctcac cgcaaccatc | 900 |
| ggcgacaagg ttcagatcgt tggcgacgac ttcttcgtca ccaaccctga cgcctgaag | 960 |
| gagggcatcg ctaagaaggc tgccaactcc atcctggtta aggtgaacca gatcggtacc | 1020 |
| ctcaccgaga ccttcgacgc tgtcgacatg gctcaccgcg caggctacac ctccatgatg | 1080 |
| tcccaccgtt ccggtgagac cgaggacacc accattgctg acctcgcagt tgcactcaac | 1140 |
| tgtggccaga tcaagactgg tgctccagca cgttccgacc gtgtcgcaaa gtacaaccag | 1200 |
| cttctccgca tcgagcagtt gcttggcgac gccggcgtct acgcaggtcg cagcgcattc | 1260 |
| ccacgctttc agggctaa | 1278 |

<210> SEQ ID NO 129
<211> LENGTH: 425
<212> TYPE: PRT
<213> ORGANISM: Corynebacterium glutamicum

<400> SEQUENCE: 129

Met Ala Glu Ile Met His Val Phe Ala Arg Glu Ile Leu Asp Ser Arg
1               5                   10                  15

Gly Asn Pro Thr Val Glu Ala Glu Val Phe Leu Asp Asp Gly Ser His
            20                  25                  30

Gly Val Ala Gly Val Pro Ser Gly Ala Ser Thr Gly Val His Glu Ala
        35                  40                  45

His Glu Leu Arg Asp Gly Gly Asp Arg Tyr Leu Gly Lys Gly Val Leu
    50                  55                  60

Lys Ala Val Glu Asn Val Asn Glu Glu Ile Gly Asp Glu Leu Ala Gly
65                  70                  75                  80

Leu Glu Ala Asp Asp Gln Arg Leu Ile Asp Glu Ala Met Ile Lys Leu
                85                  90                  95

Asp Gly Thr Ala Asn Lys Ser Arg Leu Gly Ala Asn Ala Ile Leu Gly

```
            100                 105                 110
Val Ser Met Ala Val Ala Lys Ala Ala Asp Ser Ala Gly Leu Pro
            115                 120                 125
Leu Phe Arg Tyr Ile Gly Gly Pro Asn Ala His Val Leu Pro Val Pro
130                 135                 140
Met Met Asn Ile Ile Asn Gly Gly Ala His Ala Asp Ser Gly Val Asp
145                 150                 155                 160
Val Gln Glu Phe Met Ile Ala Pro Ile Gly Ala Glu Thr Phe Ser Glu
                165                 170                 175
Ala Leu Arg Asn Gly Ala Glu Val Tyr His Ala Leu Lys Ser Val Ile
            180                 185                 190
Lys Glu Lys Gly Leu Ser Thr Gly Leu Gly Asp Glu Gly Gly Phe Ala
            195                 200                 205
Pro Ser Val Gly Ser Thr Arg Glu Ala Leu Asp Leu Ile Val Glu Ala
        210                 215                 220
Ile Glu Lys Ala Gly Phe Thr Pro Gly Lys Asp Ile Ala Leu Ala Leu
225                 230                 235                 240
Asp Val Ala Ser Ser Glu Phe Phe Lys Asp Gly Thr Tyr His Phe Glu
                245                 250                 255
Gly Gly Gln His Ser Ala Ala Glu Met Ala Asn Val Tyr Ala Glu Leu
            260                 265                 270
Val Asp Ala Tyr Pro Ile Val Ser Ile Glu Asp Pro Leu Gln Glu Asp
        275                 280                 285
Asp Trp Glu Gly Tyr Thr Asn Leu Thr Ala Thr Ile Gly Asp Lys Val
    290                 295                 300
Gln Ile Val Gly Asp Asp Phe Phe Val Thr Asn Pro Glu Arg Leu Lys
305                 310                 315                 320
Glu Gly Ile Ala Lys Lys Ala Ala Asn Ser Ile Leu Val Lys Val Asn
                325                 330                 335
Gln Ile Gly Thr Leu Thr Glu Thr Phe Asp Ala Val Asp Met Ala His
            340                 345                 350
Arg Ala Gly Tyr Thr Ser Met Met Ser His Arg Ser Gly Glu Thr Glu
            355                 360                 365
Asp Thr Thr Ile Ala Asp Leu Ala Val Ala Leu Asn Cys Gly Gln Ile
        370                 375                 380
Lys Thr Gly Ala Pro Ala Arg Ser Asp Arg Val Ala Lys Tyr Asn Gln
385                 390                 395                 400
Leu Leu Arg Ile Glu Gln Leu Leu Gly Asp Ala Gly Val Tyr Ala Gly
                405                 410                 415
Arg Ser Ala Phe Pro Arg Phe Gln Gly
            420                 425
```

<210> SEQ ID NO 130
<211> LENGTH: 666
<212> TYPE: DNA
<213> ORGANISM: Niastella koreensis

<400> SEQUENCE: 130

```
atgaataatc aaattttga atccgttgac cattatatca gcgatttact gggttacgaa     60
gacgatgcat tgcttgccgc caccaattca ttagccgaag caggcatgcc tgccatcagc    120
gtatcaccca accagggcaa gtttctgcaa ttactggccc aattgtgcca ggcaaaaaat    180
atcctggagc tgggcacact ggcaggctac agcaccattt ggatggcccg ggccttaccc    240
aaaaacggcc ggctcatcac ccttgaatat gaccccaaac atgcggccgt tgcacaaaaa    300
```

```
aatatcgacc gggccggcct tacttcacaa gtacagatca gaaccggtaa agcaattgac      360
atattaccgc aattagtgga agaaggcgcc ggaccttttg atatgatctt tatcgatgcc      420
gataaaccac cttacaccga atattttcaa tgggcgcttc ggttatcacg tcccggtaca      480
ctcatcgtgg ccgataatgt gatccgtgat ggcaaagtgc tggatgaaaa cagtacggag      540
cctgctgtac agggcgcaag acgtttcaat gccatgctgg gcgccaatac cgccgttgac      600
gccaccattc ttcaaatggt aggtgtaaaa gaatacgatg gaatggcttt ggccatagta      660
aaataa                                                                666
```

<210> SEQ ID NO 131
<211> LENGTH: 221
<212> TYPE: PRT
<213> ORGANISM: Niastella koreensis

<400> SEQUENCE: 131

```
Met Asn Asn Gln Ile Phe Glu Ser Val Asp His Tyr Ile Ser Asp Leu
1               5                   10                  15

Leu Gly Tyr Glu Asp Asp Ala Leu Leu Ala Ala Thr Asn Ser Leu Ala
            20                  25                  30

Glu Ala Gly Met Pro Ala Ile Ser Val Ser Pro Asn Gln Gly Lys Phe
        35                  40                  45

Leu Gln Leu Leu Ala Gln Leu Cys Gln Ala Lys Asn Ile Leu Glu Leu
    50                  55                  60

Gly Thr Leu Ala Gly Tyr Ser Thr Ile Trp Met Ala Arg Ala Leu Pro
65                  70                  75                  80

Lys Asn Gly Arg Leu Ile Thr Leu Glu Tyr Asp Pro Lys His Ala Ala
                85                  90                  95

Val Ala Gln Lys Asn Ile Asp Arg Ala Gly Leu Thr Ser Gln Val Gln
            100                 105                 110

Ile Arg Thr Gly Lys Ala Ile Asp Ile Leu Pro Gln Leu Val Glu Glu
        115                 120                 125

Gly Ala Gly Pro Phe Asp Met Ile Phe Ile Asp Ala Asp Lys Pro Pro
    130                 135                 140

Tyr Thr Glu Tyr Phe Gln Trp Ala Leu Arg Leu Ser Arg Pro Gly Thr
145                 150                 155                 160

Leu Ile Val Ala Asp Asn Val Ile Arg Asp Gly Lys Val Leu Asp Glu
                165                 170                 175

Asn Ser Thr Glu Pro Ala Val Gln Gly Ala Arg Arg Phe Asn Ala Met
            180                 185                 190

Leu Gly Ala Asn Thr Ala Val Asp Ala Thr Ile Leu Gln Met Val Gly
        195                 200                 205

Val Lys Glu Tyr Asp Gly Met Ala Leu Ala Ile Val Lys
    210                 215                 220
```

<210> SEQ ID NO 132
<211> LENGTH: 8317
<212> TYPE: DNA
<213> ORGANISM: Artificial Sequence
<220> FEATURE:
<223> OTHER INFORMATION: pVK9::PcspB-omt312

<400> SEQUENCE: 132

```
cgcagcaggc atgagcagcc cgaatatgcg cctgctggct gcaacgaccg aggaaatgac       60
ccgcgttttc ggcgctgacc aggcttttttc acataggctg agccggtggc cactgcacgt     120
```

```
ctccgacgat cccaccgcgt accgctggca tgcccagcac aatcgcgtgg atcgcctagc    180
tgatcccgaa aaagtttttg cctttttgtaa aaaacttctc ggtcgccccg caaattttcg    240
attccagatt ttttaaaaac caagccagaa atacgacaca ccgtttgcag ataatctgtc    300
tttcggaaaa atcaagtgcg atacaaaatt tttagcaccc ctgagctgcg caaagtcccg    360
cttcgtgaaa attttcgtgc cgcgtgattt ccgccaaaaa actttaacga acgttcgtta    420
taatggtgtc atgaccttca cgacgaagta ccaaaattgg cccgaatcat cagctatgga    480
tctctctgat gtcgcgctgg agtccgacgc gctcgatgct gccgtcgatt taaaaacggt    540
gatcggattt ttccgagctc tcgatacgac ggacgcgcca gcatcacgag actgggccag    600
tgccgcgagc gacctagaaa ctctcgtggc ggatcttgag gagctggctg acgagctgcg    660
tgctcggcag cgccaggagg acgcacagta gtggaggatc gaatcagttg cgcctactgc    720
ggtggcctga ttcctccccg gcctgacccg cgaggacggc gcgcaaaata ttgctcagat    780
gcgtgtcgtg ccgcagccag ccgcgagcgc gccaacaaac gccacgccga ggagctggag    840
gcggctaggt cgcaaatggc gctggaagtg cgtcccccga gcgaaatttt ggccatggtc    900
gtcacagagc tggaagcggc agcgagaatt atccgcgatc gtggcgcggt gcccgcaggc    960
atgacaaaca tcgtaaatgc cgcgtttcgt gtggccgtgg ccgcccagga cgtgtcagcg   1020
ccgccaccac ctgcaccgaa tcggcagcag cgtcgcgcgt cgaaaaagcg cacaggcggc   1080
aagaagcgat aagctgcacg aatacctgaa aaatgttgaa cgccccgtga gcggtaactc   1140
acagggcgtc ggctaacccc cagtccaaac ctgggagaaa gcgctcaaaa atgactctag   1200
cggattcacg agacattgac acaccggcct ggaaattttc cgctgatctg ttcgacaccc   1260
atcccgagct cgcgctgcga tcacgtggct ggacgagcga agaccgccgc gaattcctcg   1320
ctcacctggg cagagaaaat ttccaggcca gcaagacccg cgacttcgcc agcgcttgga   1380
tcaaagaccc ggacacggga gaaacacagc cgaagttata ccgagttggt tcaaaatcgc   1440
ttgcccggtg ccagtatgtt gctctgacgc acgcgcagca cgcagccgtg cttgtcctgg   1500
acattgatgt gccgagccac caggccggcg ggaaaatcga gcacgtaaac cccgaggtct   1560
acgcgatttt ggagcgctgg gcacgcctgg aaaaagcgcc agcttggatc ggcgtgaatc   1620
cactgagcgg gaaatgccag ctcatctggc tcattgatcc ggtgtatgcc gcagcaggca   1680
tgagcagccc gaatatgcgc ctgctggctg caacgaccga ggaaatgacc cgcgttttcg   1740
gcgctgacca ggcttttttca cataggctga gccggtggcc actgcacgtc tccgacgatc   1800
ccaccgcgta ccgctggcat gcccagcaca atcgcgtgga tcgcctagct gatcttatgg   1860
aggttgctcg catgatctca ggcacagaaa aacctaaaaa acgctatgag caggagtttt   1920
ctagcggacg ggcacgtatc gaagcggcaa gaaaagccac tgcggaagca aaagcacttg   1980
ccacgcttga agcaagcctg ccgagcgccg ctgaagcgtc tggagagctg atcgacggcg   2040
tccgtgtcct ctggactgct ccagggcgtg ccgcccgtga tgagacggct tttcgccacg   2100
ctttgactgt gggataccag ttaaaagcgg ctggtgagcg cctaaaagac accaagatca   2160
tcgacgccta cgagcgtgcc tacaccgtcg ctcaggcggt cggagcagac ggccgtgagc   2220
ctgatctgcc gccgatgcgt gaccgccaga cgatggcgcg acgtgtgcgc ggctacgtcg   2280
ctaaaggcca gccagtcgtc cctgctcgtc agacagagac gcagagcagc cgagggcgaa   2340
aagctctggc cactatggga agacgtggcg gtaaaaaggc cgcagaacgc tggaaagacc   2400
caaacagtga gtacgcccga gcacagcgag aaaaactagc taagtccagt caacgacaag   2460
ctaggaaagc taaggaaatc gcttgaccat tgcaggttg gtttatgact gttgagggag   2520
```

-continued

```
agactggctc gtggccgaca atcaatgaag ctatgtctga atttagcgtg tcacgtcaga    2580
ccgtgaatag agcacttaag tctgcgggca ttgaacttcc acgaggacgc cgtaaagctt    2640
cccagtaaat gtgccatctc gtaggcagaa aacggttccc cccgtagggg tctctctctt    2700
ggcctccttt ctaggtcggg ctgattgctc ttgaagctct ctaggggggc tcacaccata    2760
ggcagataac ggttccccac cggctcacct cgtaagcgca caaggactgc tcccaaagat    2820
cgcctagctg atcttatgga ggttgctcgc atgatccttt ttgataatct catgaccaaa    2880
atcccttaac gtgagttttc gttccactga gcgtcagacc ccgtagaaaa gatccccgtc    2940
cacctacaac aaagctctca tcaaccgtgg ctccctcact ttctggctgg atgatggggc    3000
gattcaggcc tggtatgagt cagcaacacc ttcttcacga ggcagacctc tcgacggagt    3060
tccactgagc gtcagacccc gtagaaaaga tcaaaggatc ttcttgagat ccttttttc    3120 tgcgcgtaat ctgctgcttg caaacaaaaa aaccaccgct accagcggtg gtttgtttgc    3180
cggatcaaga gctaccaact cttttccga aggtaactgg cttcagcaga gcgcagatac    3240
caaatactgt tcttctagtg tagccgtagt taggccacca cttcaagaac tctgtagcac    3300
cgcctacata cctcgctctg ctaatcctgt taccagtggc tgctgccagt ggcgataagt    3360
cgtgtcttac cgggttggac tcaagacgat agttaccgga taaggcgcag cggtcgggct    3420 gaacggggg ttcgtgcaca cagcccagct tggagcgaac gacctacacc gaactgagat    3480
acctacagcg tgagctatga gaaagcgcca cgcttcccga agggagaaag gcggacaggt    3540
atccggtaag cggcagggtc ggaacaggag agcgcacgag ggagcttcca gggggaaacg    3600
cctggtatct ttatagtcct gtcgggtttc gccacctctg acttgagcgt cgatttttgt    3660
gatgctcgtc aggggggcgg agcctatgga aaaacgccag caacgcggcc ttttacggt    3720 tcctggcctt ttgctggcct tttgctcaca tgttctttcc tgcgttatcc cctgattctg    3780
tggataaccg tattaccgcc tttgagtgag ctgataccgc tcgccgcagc cgaacgaccg    3840
agcgcagcga gtcagtgagc gaggaagcgg aagaagctcg cacattcagc agcgttttc    3900 agcgcgtttt cgatcaacgt ttcaatgttg gtatcaacac caggtttaac tttgaactta    3960
tcggcactga cggttactga ttttgaactt ttgctttgcc acggaacggt ctgcgttgtc    4020
gggaagatgc gtgatctgat ccttcaactc agcaaaagtt cccaatacgc aaaccgcctc    4080
tccccgcgcg ttggccgatt cattaatgca gctggcacga caggtttccc gactggaaag    4140
cgggcagtga gcgcaacgca attaatgtga gttagctcac tcattaggca ccccaggctt    4200
tacactttat gcttccggct cgtatgttgt gtggaattgt gagcggataa caatttcaca    4260
caggaaacag ctatgaccat gattacgcca agcttgcatg ccaaattcct gtgattagct    4320
gatttagtac ttttcggagg tgtctattct taccaaatcg tcaagttgtg ggtagagtca    4380
cctgaatatt aattgcaccg cacgggtgat atatgcttat ttgctcaagt agttcgaggt    4440
taagtgtatt ttaggtgaac aaatttcagc ttcgggtaga agactttcga tgcgcttcag    4500
agcttctatt gggaaatctg acaccacttg attaaatagc ctaccccga attggggat    4560 tggtcatttt ttgctgtgaa ggtagttttg atgcatatga cctgcgttta taagaaatg    4620 taaacgtgat cagatcgata taaagaaac agtttgtact caggtttgaa gcattttctc    4680
cgattcgcct ggcaaaaatc tcaattgtcg cttacagttt ttctcaacga caggctgcta    4740
agctgctagt tcggtggcct agtgagtggc gtttacttgg ataaaagtaa tcccatgtcg    4800
tgatcagcca ttttgggttg tttccatagc aatccaaagg tttcgtcttt cgatacctat    4860
```

```
tcaaggagcc ttcgcctcta tgaacaacca gatcttcgaa tccgtcgatc actatatttc    4920
tgatcttctg ggctacgagg atgatgcgct tttggccgcc actaattccc tggccgaggc    4980
aggtaagccg gctattagcg tttccccgaa ccagggcaaa ttttttgcaac tgctggccca   5040
actttgccaa gccaaaaaca ttttggagct tggtacgttt gccggctatt cgaccatctg    5100
gatggctcgc gctctcccca agaacggccg ccttatcacc ctggaatacg atccgaagca    5160
tgccgcggta gctcagaaga acattgatcg cgctggcttg accagccaag tgcaaatccg    5220
cacgggtaaa gcaatcgaca tcctgccgca gctggtggag gagggtgccg gtccatttga    5280
tatgatcttc attgatgccg ataagccccc atacaccgaa tactttcaat gggctctgcg    5340
actgtcccgc cccggcactc tcatcgtcgc ggataatgtc atccgcgatg aaaggtgct    5400
ggacgaaaac tccaccgagc ctgccgtcca aggtgcccgc cgttttaatg ccatgctcgg    5460
tgctaatacg gcagttgacg caaccatcct ccaaatggtg ggcgtgaaag agtacgacgg    5520
catggcgctg gccatcgtta agtaagagct ccgtcgacaa gcttgcggcc gcactcgagc    5580
accaccacca ccaccactga gatccggctg ctaacaaagc ccgaaaggaa gctgagttgg    5640
ctgctgccac cgctgagcaa taactagcat gatccccggg taccgagctc gaattcactg    5700
gccgtcgttt tacaacgtcg tgactgggaa accctggcg ttacccaact taatcgcctt    5760
gcagcacatc ccccttttcgc cagctggcgt aatagcgaag aggcccgcac cgatcgccct    5820
tcccaacagt tgcgcagcct gaatggcgaa tgcgatttat tcaacaaagc cgccgtcccg    5880
tcaagtcagc gtaatgctct gccctgatga atcccctaat gattttggta aaaatcatta    5940
agttaaggtg gatacacatc ttgtcatatg atcaaatggt ttcgcgaaaa atcaataatc    6000
agacaacaag atgtgcgaac tcgatatttt acacgactct ctttaccaat tctgccccga    6060
attacactta aaacgactca acagcttaac gttggcttgc cacgcattac ttgactgtaa    6120
aactctcact cttaccgaac ttggccgtaa cctgccaacc aaagcgagaa caaaacataa    6180
catcaaacga atcgaccgat tgttaggtaa tcgtcacctc cacaaagagc gactcgctgt    6240
ataccgttgg catgctagct ttatctgttc gggcaatacg atgcccattg tacttgttga    6300
ctggtctgat attcgtgagc aaaaacgact tatggtattg cgagcttcag tcgcactaca    6360
cggtcgttct gttactcttt atgagaaagc gttcccgctt tcagagcaat gttcaaagaa    6420
agctcatgac caatttctag ccgaccttgc gagcattcta ccgagtaaca ccacaccgct    6480
cattgtcagt gatgctggct ttaaagtgcc atggtataaa tccgttgaga agctgggttg    6540
gtactggtta agtcgagtaa gaggaaaagt acaatatgca gacctaggag cggaaaactg    6600
gaaacctatc agcaacttac atgatatgtc atctagtcac tcaaagactt taggctataa    6660
gaggctgact aaaagcaatc caatctcatg ccaaattcta ttgtataaat ctcgctctaa    6720
aggccgaaaa aatcagcgct cgacacggac tcattgtcac cacccgtcac ctaaaatcta    6780
ctcagcgtcg gcaaaggagc catgggttct agcaactaac ttacctgttg aaattcgaac    6840
acccaaacaa cttgttaata tctattcgaa gcgaatgcag attgaagaaa ccttccgaga    6900
cttgaaaagt cctgcctacg gactaggcct acgccatagc cgaacgagca gctcagagcg    6960
ttttgatatc atgctgctaa tcgccctgat gcttcaacta acatgttggc ttgcgggcgt    7020
tcatgctcag aaacaaggtt gggacaagca cttccaggct aacacagtca gaaatcgaaa    7080
cgtactctca acagttcgct taggcatgga agttttgcgg cattctggct acacaataac    7140
aagggaagac ttactcgtgg ctgcaaccct actagctcaa aatttattca cacatggtta    7200
cgctttgggg aaattatgag gggatctctc agtgctctgc cagtgttaca accaattaac    7260
```

```
caattctgat tagaaaaact catcgagcat caaatgaaac tgcaatttat tcatatcagg   7320
attatcaata ccatattttt gaaaaagccg tttctgtaat gaaggagaaa actcaccgag   7380
gcagttccat aggatggcaa gatcctggta tcggtctgcg attccgactc gtccaacatc   7440
aatacaacct attaatttcc cctcgtcaaa aataaggtta tcaagtgaga atcaccatg    7500 agtgacgact gaatccggtg agaatggcaa aagcttatgc atttctttcc agacttgttc   7560
aacaggccag ccattacgct cgtcatcaaa atcactcgca tcaaccaaac cgttattcat   7620
tcgtgattgc gcctgagcga gacgaaatac gcgatcgctg ttaaaggac aattacaaac    7680 aggaatcgaa tgcaaccggc gcaggaacac tgccagcgca tcaacaatat tttcacctga   7740
atcaggatat tcttctaata cctggaatgc tgttttcccg gggatcgcag tggtgagtaa   7800
ccatgcatca tcaggagtac ggataaaatg cttgatggtc ggaagaggca taaattccgt   7860
cagccagttt agtctgacca tctcatctgt aacatcattg gcaacgctac ctttgccatg   7920
tttcagaaac aactctggcg catcgggctt cccatacaat cgatagattg tcgcacctga   7980
ttgcccgaca ttatcgcgag cccatttata cccatataaa tcagcatcca tgttggaatt   8040
taatcgcggc ttcgagcaag acgtttcccg ttgaatatgg ctcataacac cccttgtatt   8100
actgtttatg taagcagaca gttttattgt tcatgatgat atatttttat cttgtgcaat   8160
gtaacatcag agattttgag acacaacgtg gctttgttga ataaatcgaa cttttgctga   8220
gttgaaggat cagatcacgc atcttcccga caacgcagac cgttccgtgg caaagcaaaa   8280
gttcaaaatc accaactggt cgcgatccgg tgtatgc                            8317
```

<210> SEQ ID NO 133
<211> LENGTH: 221
<212> TYPE: PRT
<213> ORGANISM: Niastella koreensis

<400> SEQUENCE: 133

```
Met Asn Asn Gln Ile Phe Glu Ser Val Asp His Tyr Ile Ser Asp Leu
1               5                   10                  15

Leu Gly Tyr Glu Asp Asp Ala Leu Leu Ala Ala Thr Asn Ser Leu Ala
            20                  25                  30

Glu Ala Gly Lys Pro Ala Ile Ser Val Ser Pro Asn Gln Gly Lys Phe
        35                  40                  45

Leu Gln Leu Leu Ala Gln Leu Cys Gln Ala Lys Asn Ile Leu Glu Leu
    50                  55                  60

Gly Thr Phe Ala Gly Tyr Ser Thr Ile Trp Met Ala Arg Ala Leu Pro
65                  70                  75                  80

Lys Asn Gly Arg Leu Ile Thr Leu Glu Tyr Asp Pro Lys His Ala Ala
                85                  90                  95

Val Ala Gln Lys Asn Ile Asp Arg Ala Gly Leu Thr Ser Gln Val Gln
            100                 105                 110

Ile Arg Thr Gly Lys Ala Ile Asp Ile Leu Pro Gln Leu Val Glu Glu
        115                 120                 125

Gly Ala Gly Pro Phe Asp Met Ile Phe Ile Asp Ala Asp Lys Pro Pro
    130                 135                 140

Tyr Thr Glu Tyr Phe Gln Trp Ala Leu Arg Leu Ser Arg Pro Gly Thr
145                 150                 155                 160

Leu Ile Val Ala Asp Asn Val Ile Arg Asp Gly Lys Val Leu Asp Glu
                165                 170                 175

Asn Ser Thr Glu Pro Ala Val Gln Gly Ala Arg Arg Phe Asn Ala Met
```

|   |   | 180 |   |   |   | 185 |   |   |   | 190 |   |
|---|---|---|---|---|---|---|---|---|---|---|---|
| Leu | Gly | Ala | Asn | Thr | Ala | Val | Asp | Ala | Thr | Ile | Leu | Gln | Met | Val | Gly |

|   | 195 |   |   |   | 200 |   |   |   | 205 |
|---|---|---|---|---|---|---|---|---|---|
| Val | Lys | Glu | Tyr | Asp | Gly | Met | Ala | Leu | Ala | Ile | Val | Lys |

|   | 210 |   |   |   | 215 |   |   |   | 220 |

<210> SEQ ID NO 134
<211> LENGTH: 1563
<212> TYPE: DNA
<213> ORGANISM: Corynebacterium glutamicum

<400> SEQUENCE: 134

```
atgagcgatg atcgtaaggc aattaaacgc gcactaatta gcgtgtatga caagactggc    60
ctggaggatc tagcccaggc acttcaccgc gcgaacgtgg aaattgtttc caccggatcc   120
actgcggcga agattgctga gcttggtatt cctgttaccc cggttgagga gctcaccggt   180
ttccctgagt gccttgaggg ccgtgtgaag acactgcatc ctaaggttca cgctggcatc   240
ttggcggaca cccgcaagga agaccacctg cgtcagctca aggaacttga ggtcgcccca   300
ttccagcttg tcgtggtgaa cctgtaccca tttgctgaga ccgttgcgtc cggcgccgat   360
ttcgatgctt gcgttgagca gatcgacatc ggaggcccat ccatggttcg tgctgcggca   420
aagaaccacc catctgtcgc tgtggttgtt tcaccaaacc gctacgagga tgtccaggaa   480
gctttgaaga ccggtggatt ctcccgcgcg gagcgcacca gttggctgc tgaggctttc   540
cgccacaccg caacctacga tgtcaccgtt gcaacctgga tgagcgagca gctggctgcc   600
gaagattctg agactgagtt cccaggttgg atcggcacca ccaacacctt gtcccgcagc   660
ttgcgttacg gtgagaaccc tcaccagtct gcagctttgt acgtgggcaa cacccgcgga   720
cttgcacagg ctaagcagtt ccacggcaag gaaatgagct acaacaacta caccgattct   780
gatgctgcat ggcgtgcagc gtgggatcac gagcgtcctt gtgtagctat catcaagcat   840
gcaaacctt gtggcattgc tgtttctgat gagtccatcg cagcggcaca ccgcgaggca   900
cacgcatgtg actctgtgtc cgcattcggt ggcgtcatcg cgtccaaccg tgaagtcagc   960
gttgagatgg ctaaccaggt tgcagagatc ttcactgagg tcatcatcgc tccttcctac  1020
gaagagggcg ctgtggagat cctgagccag aagaagaaca tccgtattct tcaggctgaa  1080
gcacctgtgc gtaagggctt tgagtcccgt gagatctccg gcggtctgct tgttcaggaa  1140
cgcgacttga tccacgctga gggcgacaac tccgcaaact ggactcttgc tgccggctct  1200
gctgtttctc ctgaggttct gaaggacctg gagttcgcgt ggactgcagt tcgttccgtg  1260
aagtccaacg caattctgtt ggctaagaac ggcgctaccg ttggcgttgg catgggacag  1320
gtcaaccgcg ttgactctgc tcgcttggct gtcgaccgtg caggtgcaga gcgcgctacc  1380
ggttccgttg ctgcttccga tgcgttcttc ccattcgctg atggctttga ggttctcgct  1440
gaggctggca tcactgctgt tgtgcagcct ggtggatcca ttcgcgacaa cgaggtcatt  1500
gaggcagcca acaaggctgg cgtgaccatg tacctgactg gtgcgcgaca cttcgctcac  1560
taa                                                                 1563
```

<210> SEQ ID NO 135
<211> LENGTH: 520
<212> TYPE: PRT
<213> ORGANISM: Corynebacterium glutamicum

<400> SEQUENCE: 135

Met Ser Asp Asp Arg Lys Ala Ile Lys Arg Ala Leu Ile Ser Val Tyr

-continued

```
1               5               10              15
Asp Lys Thr Gly Leu Glu Asp Leu Ala Gln Ala Leu His Arg Ala Asn
            20              25              30
Val Glu Ile Val Ser Thr Gly Ser Thr Ala Ala Lys Ile Ala Glu Leu
            35              40              45
Gly Ile Pro Val Thr Pro Val Glu Glu Leu Thr Gly Phe Pro Glu Cys
            50              55              60
Leu Glu Gly Arg Val Lys Thr Leu His Pro Lys Val His Ala Gly Ile
65              70              75              80
Leu Ala Asp Thr Arg Lys Glu Asp His Leu Arg Gln Leu Lys Glu Leu
            85              90              95
Glu Val Ala Pro Phe Gln Leu Val Val Asn Leu Tyr Pro Phe Ala
            100             105             110
Glu Thr Val Ala Ser Gly Ala Asp Phe Asp Ala Cys Val Glu Gln Ile
            115             120             125
Asp Ile Gly Gly Pro Ser Met Val Arg Ala Ala Lys Asn His Pro
            130             135             140
Ser Val Ala Val Val Ser Pro Asn Arg Tyr Glu Asp Val Gln Glu
145             150             155             160
Ala Leu Lys Thr Gly Gly Phe Ser Arg Ala Glu Arg Thr Lys Leu Ala
            165             170             175
Ala Glu Ala Phe Arg His Thr Ala Thr Tyr Asp Val Thr Val Ala Thr
            180             185             190
Trp Met Ser Glu Gln Leu Ala Ala Glu Asp Ser Glu Thr Glu Phe Pro
            195             200             205
Gly Trp Ile Gly Thr Thr Asn Thr Leu Ser Arg Ser Leu Arg Tyr Gly
            210             215             220
Glu Asn Pro His Gln Ser Ala Ala Leu Tyr Val Gly Asn Thr Arg Gly
225             230             235             240
Leu Ala Gln Ala Lys Gln Phe His Gly Lys Glu Met Ser Tyr Asn Asn
            245             250             255
Tyr Thr Asp Ser Asp Ala Ala Trp Arg Ala Ala Trp Asp His Glu Arg
            260             265             270
Pro Cys Val Ala Ile Ile Lys His Ala Asn Pro Cys Gly Ile Ala Val
            275             280             285
Ser Asp Glu Ser Ile Ala Ala His Arg Glu Ala His Ala Cys Asp
            290             295             300
Ser Val Ser Ala Phe Gly Gly Val Ile Ala Ser Asn Arg Glu Val Ser
305             310             315             320
Val Glu Met Ala Asn Gln Val Ala Glu Ile Phe Thr Glu Val Ile Ile
            325             330             335
Ala Pro Ser Tyr Glu Glu Gly Ala Val Glu Ile Leu Ser Gln Lys Lys
            340             345             350
Asn Ile Arg Ile Leu Gln Ala Glu Ala Pro Val Arg Lys Gly Phe Glu
            355             360             365
Ser Arg Glu Ile Ser Gly Gly Leu Leu Val Gln Glu Arg Asp Leu Ile
            370             375             380
His Ala Glu Gly Asp Asn Ser Ala Asn Trp Thr Leu Ala Gly Ser
385             390             395             400
Ala Val Ser Pro Glu Val Leu Lys Asp Leu Glu Phe Ala Trp Thr Ala
            405             410             415
Val Arg Ser Val Lys Ser Asn Ala Ile Leu Leu Ala Lys Asn Gly Ala
            420             425             430
```

```
Thr Val Gly Val Gly Met Gly Gln Val Asn Arg Val Asp Ser Ala Arg
            435                 440                 445

Leu Ala Val Asp Arg Ala Gly Ala Glu Arg Ala Thr Gly Ser Val Ala
    450                 455                 460

Ala Ser Asp Ala Phe Phe Pro Phe Ala Asp Gly Phe Glu Val Leu Ala
465                 470                 475                 480

Glu Ala Gly Ile Thr Ala Val Val Gln Pro Gly Gly Ser Ile Arg Asp
                485                 490                 495

Asn Glu Val Ile Glu Ala Ala Asn Lys Ala Gly Val Thr Met Tyr Leu
            500                 505                 510

Thr Gly Ala Arg His Phe Ala His
            515                 520

<210> SEQ ID NO 136
<211> LENGTH: 1563
<212> TYPE: DNA
<213> ORGANISM: Corynebacterium glutamicum

<400> SEQUENCE: 136
```

| | |
|---|---|
| atgagcgatg atcgtaaggc aattaaacgc gcactaatta gcgtgtatga caagactggc | 60 |
| ctggaggatc tagcccaggc acttcaccgc gcgaacgtgg aaattgtttt caccggatcc | 120 |
| actgcggcga agattgctga gcttggtatt cctgttaccc cggttgagga gctcaccggt | 180 |
| ttccctgagt gccttgaggg ccgtgtgaag acactgcatc ctaaggttca cgctggcatc | 240 |
| ttggcggaca cccgcaagga agaccacctg cgtcagctca aggaacttga ggtcgcccca | 300 |
| ttccagcttg tcgtggtgaa cctgtaccca tttgctgaga ccgttgcgtc cggcgccgat | 360 |
| ttcgatgctt gcgttgagca gatcgacatc ggaggcccat ccatggttcg tgctgcggca | 420 |
| aagaaccacc catctgtcgc tgtggttgtt tcaccaaacc gctacgagga tgtccaggaa | 480 |
| gctttgaaga ccggtggatt ctcccgcgcg gagcgcacca gttggctgc tgaggctttc | 540 |
| cgccacaccg caacctacga tgtcaccgtt gcaacctgga tgagcgagca gctggctgcc | 600 |
| gaagattctg agactgagtt cccaggttgg atcggcacca ccaacacctt gtcccgcagc | 660 |
| ttgcgttacg gtgagaaccc tcaccagtct gcagctttgt acgtgggcaa cacccgcgga | 720 |
| cttgcacagg ctaagcagtt ccacggcaag gaaatgagct acaacaacta caccgattct | 780 |
| gatgctgcat ggcgtgcagc gtgggatcac gagcgtcctt gtgtagctat catcaagcat | 840 |
| gcaaaccctt gtggcattgc tgtttctgat gagtccatcg cagcggcaca ccgcgaggca | 900 |
| cacgcatgtg actctgtgtc cgcattcggt ggcgtcatcg cgtccaaccg tgaagtcagc | 960 |
| gttgagatgg ctaaccaggt tgcagagatc ttcactgagg tcatcatcgc tccttcctac | 1020 |
| gaagagggcg ctgtggagat cctgagccag aagaagaaca tccgtattct tcaggctgaa | 1080 |
| gcacctgtgc gtaagggctt tgagtcccgt gagatctccg gcggtctgct tgttcaggaa | 1140 |
| cgcgacttga tccacgctga gggcgacaac tccgcaaact ggactcttgc tgccggctct | 1200 |
| gctgtttctc ctgaggttct gaaggacctg gagttcgcgt ggactgcagt tcgttccgtg | 1260 |
| aagtccaacg caattctgtt ggctaagaac ggcgctaccg ttggcgttgg catgggacag | 1320 |
| gtcaaccgcg ttgactctgc tcgcttggct gtcgaccgtg caggtgcaga gcgcgctacc | 1380 |
| ggttccgttg ctgcttccga tgcgttcttc ccattcgctg atggctttga ggttctcgct | 1440 |
| gaggctggca tcactgctgt tgtgcagcct ggtggatcca ttcgcgacaa cgaggtcatt | 1500 |
| gaggcagcca acaaggctgg cgtgaccatg tacctgactg gtgcgcgaca cttcgctcac | 1560 | taa                                                                    1563

<210> SEQ ID NO 137
<211> LENGTH: 520
<212> TYPE: PRT
<213> ORGANISM: Corynebacterium glutamicum

<400> SEQUENCE: 137

Met Ser Asp Asp Arg Lys Ala Ile Lys Arg Ala Leu Ile Ser Val Tyr
1               5                   10                  15

Asp Lys Thr Gly Leu Glu Asp Leu Ala Gln Ala Leu His Arg Ala Asn
            20                  25                  30

Val Glu Ile Val Phe Thr Gly Ser Thr Ala Ala Lys Ile Ala Glu Leu
        35                  40                  45

Gly Ile Pro Val Thr Pro Val Glu Glu Leu Thr Gly Phe Pro Glu Cys
    50                  55                  60

Leu Glu Gly Arg Val Lys Thr Leu His Pro Lys Val His Ala Gly Ile
65                  70                  75                  80

Leu Ala Asp Thr Arg Lys Glu Asp His Leu Arg Gln Leu Lys Glu Leu
                85                  90                  95

Glu Val Ala Pro Phe Gln Leu Val Val Asn Leu Tyr Pro Phe Ala
            100                 105                 110

Glu Thr Val Ala Ser Gly Ala Asp Phe Asp Ala Cys Val Glu Gln Ile
        115                 120                 125

Asp Ile Gly Gly Pro Ser Met Val Arg Ala Ala Ala Lys Asn His Pro
    130                 135                 140

Ser Val Ala Val Val Ser Pro Asn Arg Tyr Glu Asp Val Gln Glu
145                 150                 155                 160

Ala Leu Lys Thr Gly Gly Phe Ser Arg Ala Glu Arg Thr Lys Leu Ala
                165                 170                 175

Ala Glu Ala Phe Arg His Thr Ala Thr Tyr Asp Val Thr Val Ala Thr
            180                 185                 190

Trp Met Ser Glu Gln Leu Ala Ala Glu Asp Ser Glu Thr Glu Phe Pro
        195                 200                 205

Gly Trp Ile Gly Thr Thr Asn Thr Leu Ser Arg Ser Leu Arg Tyr Gly
    210                 215                 220

Glu Asn Pro His Gln Ser Ala Ala Leu Tyr Val Gly Asn Thr Arg Gly
225                 230                 235                 240

Leu Ala Gln Ala Lys Gln Phe His Gly Lys Glu Met Ser Tyr Asn Asn
                245                 250                 255

Tyr Thr Asp Ser Asp Ala Ala Trp Arg Ala Ala Trp Asp His Glu Arg
            260                 265                 270

Pro Cys Val Ala Ile Ile Lys His Ala Asn Pro Cys Gly Ile Ala Val
        275                 280                 285

Ser Asp Glu Ser Ile Ala Ala His Arg Glu Ala His Ala Cys Asp
    290                 295                 300

Ser Val Ser Ala Phe Gly Gly Val Ile Ala Ser Asn Arg Glu Val Ser
305                 310                 315                 320

Val Glu Met Ala Asn Gln Val Ala Glu Ile Phe Thr Glu Val Ile Ile
                325                 330                 335

Ala Pro Ser Tyr Glu Glu Gly Ala Val Glu Ile Leu Ser Gln Lys Lys
            340                 345                 350

Asn Ile Arg Ile Leu Gln Ala Glu Ala Pro Val Arg Lys Gly Phe Glu
        355                 360                 365

Ser Arg Glu Ile Ser Gly Gly Leu Leu Val Gln Glu Arg Asp Leu Ile
370                 375                 380

His Ala Glu Gly Asp Asn Ser Ala Asn Trp Thr Leu Ala Ala Gly Ser
385                 390                 395                 400

Ala Val Ser Pro Glu Val Leu Lys Asp Leu Glu Phe Ala Trp Thr Ala
                405                 410                 415

Val Arg Ser Val Lys Ser Asn Ala Ile Leu Leu Ala Lys Asn Gly Ala
            420                 425                 430

Thr Val Gly Val Gly Met Gly Gln Val Asn Arg Val Asp Ser Ala Arg
        435                 440                 445

Leu Ala Val Asp Arg Ala Gly Ala Glu Arg Ala Thr Gly Ser Val Ala
450                 455                 460

Ala Ser Asp Ala Phe Phe Pro Phe Ala Asp Gly Phe Glu Val Leu Ala
465                 470                 475                 480

Glu Ala Gly Ile Thr Ala Val Val Gln Pro Gly Gly Ser Ile Arg Asp
                485                 490                 495

Asn Glu Val Ile Glu Ala Ala Asn Lys Ala Gly Val Thr Met Tyr Leu
                500                 505                 510

Thr Gly Ala Arg His Phe Ala His
        515                 520

<210> SEQ ID NO 138
<211> LENGTH: 35
<212> TYPE: DNA
<213> ORGANISM: Artificial Sequence
<220> FEATURE:
<223> OTHER INFORMATION: primer

<400> SEQUENCE: 138
ccaagcttgc atgccggtag gtggcgtatc agact                           35

<210> SEQ ID NO 139
<211> LENGTH: 35
<212> TYPE: DNA
<213> ORGANISM: Artificial Sequence
<220> FEATURE:
<223> OTHER INFORMATION: primer

<400> SEQUENCE: 139
acgcgagaaa cggcactagt tgagggcctc taaat                           35

<210> SEQ ID NO 140
<211> LENGTH: 35
<212> TYPE: DNA
<213> ORGANISM: Artificial Sequence
<220> FEATURE:
<223> OTHER INFORMATION: primer

<400> SEQUENCE: 140
gagtgttcgt taaaaatggc acaggttatg gactt                           35

<210> SEQ ID NO 141
<211> LENGTH: 35
<212> TYPE: DNA
<213> ORGANISM: Artificial Sequence
<220> FEATURE:
<223> OTHER INFORMATION: primer

<400> SEQUENCE: 141
cggtacccgg ggatcttagt agcggtagtg ctccg                           35

<210> SEQ ID NO 142
<211> LENGTH: 35
<212> TYPE: DNA
<213> ORGANISM: Artificial Sequence
<220> FEATURE:
<223> OTHER INFORMATION: primer

<400> SEQUENCE: 142
gaggccctca actagtgccg tttctcgcgt tgtgt          35

<210> SEQ ID NO 143
<211> LENGTH: 35
<212> TYPE: DNA
<213> ORGANISM: Artificial Sequence
<220> FEATURE:
<223> OTHER INFORMATION: primer

<400> SEQUENCE: 143
cataacctgt gccatttta acgaacactc ctcgc          35

<210> SEQ ID NO 144
<211> LENGTH: 1437
<212> TYPE: DNA
<213> ORGANISM: Corynebacterium glutamicum

<400> SEQUENCE: 144

```
atggcacagg ttatggactt caaggttgcc gatctttcac tagcagaggc aggacgtcac      60
cagattcgtc ttgcagagta tgagatgcca ggtctcatgc agttgcgcaa ggaattcgca     120
gacgagcagc ctttgaaggg cgcccgaatt gctggttcca tccacatgac ggtccagacc     180
gccgtgctta ttgagaccct cactgctttg ggcgctgagg ttcgttgggc ttcctgcaac     240
attttctcca cccaggatga ggctgcagcg gctatcgttg tcggctccgg caccgtcgaa     300
gagccagctg gtgttccagt attcgcgtgg aagggtgagt cactggagga gtactggtgg     360
tgcatcaacc agatcttcag ctggggcgat gagctgccaa acatgatcct cgacgacggc     420
ggtgacgcca ccatggctgt tattcgcggt cgcgaatacg agcaggctgg tctggttcca     480
ccagcagagg ccaacgattc cgatgagtac atcgcattct tgggcatgct gcgtgaggtt     540
cttgctgcag agcctggcaa gtggggcaag atcgctgagg ccgttaaggg tgtcaccgag     600
gaaaccacca ccgtgtgtca ccgcctgtac cacttcgctg aagaaggcgt actgcctttc     660
ccagcgatga acgtcaacga cgctgtcacc aagtccaagt tgataacaa gtacggcacc     720
cgccactccc tgatcgacgg catcaaccgc gccaccgaca tgctcatggg cggcaagaac     780
gtgcttgtct gcggttacgg tgatgtcggc aagggctgcg ctgaggcttt cgacggccag     840
ggcgctcgcg tcaaggtcac cgaagctgac ccaatcaacg ctcttcaggc tctgatggat     900
ggctactctg tggtcaccgt tgatgaggcc atcgaggacg ccgacatcgt gatcaccgcg     960
accggtaaca aggacatcat tccttcgag cagatgctca agatgaagga tcacgctctg    1020
ctgggcaaca tcgtcactt tgataatgag atcgatatgc attccctgtt gcaccgcgac    1080
gacgtcaccc gcaccacgat caagccacag gtcgacgagt tcaccttctc caccggtcgc    1140
tccatcatcg tgctgtctga aggccgtctg ctaaaccttg gcaacgccac cggacaccca    1200
tcatttgtca tgtccaactc tttcgccgat cagaccattg cgcagatcga actgttccaa    1260
aacgaaggac agtacgagaa cgaggtctac cgtctgccta aggttctcga cgaaaaggtg    1320
gcacgcatcc acgttgaggc tctcggcggt cagctcaccg aactgaccaa ggagcaggct    1380
gagtacatcg gcgttgacgt tgcaggtcca ttcaagccgg agcactaccg ctactaa        1437
```

<210> SEQ ID NO 145
<211> LENGTH: 478
<212> TYPE: PRT
<213> ORGANISM: Corynebacterium glutamicum

<400> SEQUENCE: 145

Met Ala Gln Val Met Asp Phe Lys Val Ala Asp Leu Ser Leu Ala Glu
1               5                   10                  15

Ala Gly Arg His Gln Ile Arg Leu Ala Glu Tyr Glu Met Pro Gly Leu
            20                  25                  30

Met Gln Leu Arg Lys Glu Phe Ala Asp Glu Gln Pro Leu Lys Gly Ala
        35                  40                  45

Arg Ile Ala Gly Ser Ile His Met Thr Val Gln Thr Ala Val Leu Ile
    50                  55                  60

Glu Thr Leu Thr Ala Leu Gly Ala Glu Val Arg Trp Ala Ser Cys Asn
65                  70                  75                  80

Ile Phe Ser Thr Gln Asp Glu Ala Ala Ala Ile Val Val Gly Ser
                85                  90                  95

Gly Thr Val Glu Glu Pro Ala Gly Val Pro Val Phe Ala Trp Lys Gly
            100                 105                 110

Glu Ser Leu Glu Glu Tyr Trp Trp Cys Ile Asn Gln Ile Phe Ser Trp
        115                 120                 125

Gly Asp Glu Leu Pro Asn Met Ile Leu Asp Asp Gly Gly Asp Ala Thr
    130                 135                 140

Met Ala Val Ile Arg Gly Arg Glu Tyr Glu Gln Ala Gly Leu Val Pro
145                 150                 155                 160

Pro Ala Glu Ala Asn Asp Ser Asp Glu Tyr Ile Ala Phe Leu Gly Met
                165                 170                 175

Leu Arg Glu Val Leu Ala Ala Glu Pro Gly Lys Trp Gly Lys Ile Ala
            180                 185                 190

Glu Ala Val Lys Gly Val Thr Glu Glu Thr Thr Thr Gly Val His Arg
        195                 200                 205

Leu Tyr His Phe Ala Glu Glu Gly Val Leu Pro Phe Pro Ala Met Asn
    210                 215                 220

Val Asn Asp Ala Val Thr Lys Ser Lys Phe Asp Asn Lys Tyr Gly Thr
225                 230                 235                 240

Arg His Ser Leu Ile Asp Gly Ile Asn Arg Ala Thr Asp Met Leu Met
                245                 250                 255

Gly Gly Lys Asn Val Leu Val Cys Gly Tyr Gly Asp Val Gly Lys Gly
            260                 265                 270

Cys Ala Glu Ala Phe Asp Gly Gln Gly Ala Arg Val Lys Val Thr Glu
        275                 280                 285

Ala Asp Pro Ile Asn Ala Leu Gln Ala Leu Met Asp Gly Tyr Ser Val
    290                 295                 300

Val Thr Val Asp Glu Ala Ile Glu Asp Ala Asp Ile Val Ile Thr Ala
305                 310                 315                 320

Thr Gly Asn Lys Asp Ile Ile Ser Phe Glu Gln Met Leu Lys Met Lys
                325                 330                 335

Asp His Ala Leu Leu Gly Asn Ile Gly His Phe Asp Asn Glu Ile Asp
            340                 345                 350

Met His Ser Leu Leu His Arg Asp Asp Val Thr Arg Thr Thr Ile Lys
        355                 360                 365

Pro Gln Val Asp Glu Phe Thr Phe Ser Thr Gly Arg Ser Ile Ile Val
    370                 375                 380

Leu Ser Glu Gly Arg Leu Leu Asn Leu Gly Asn Ala Thr Gly His Pro
385                 390                 395                 400

Ser Phe Val Met Ser Asn Ser Phe Ala Asp Gln Thr Ile Ala Gln Ile
            405                 410                 415

Glu Leu Phe Gln Asn Glu Gly Gln Tyr Glu Asn Glu Val Tyr Arg Leu
        420                 425                 430

Pro Lys Val Leu Asp Glu Lys Val Ala Arg Ile His Val Glu Ala Leu
    435                 440                 445

Gly Gly Gln Leu Thr Glu Leu Thr Lys Glu Gln Ala Glu Tyr Ile Gly
        450                 455                 460

Val Asp Val Ala Gly Pro Phe Lys Pro Glu His Tyr Arg Tyr
465                 470                 475

<210> SEQ ID NO 146
<211> LENGTH: 1458
<212> TYPE: DNA
<213> ORGANISM: Corynebacterium glutamicum

<400> SEQUENCE: 146
gtggtggatt cgtgcaactt cagactctca cggaggcgat ggaccaaaaa caactacaat      60
caagcagatc accttgtaca ccaccagaga aaaggcccac cctcagccat ggctatcagt     120
gttgttgatc tatttagcat cggtatcgga ccatcatcct cacataccgt cggcccatg      180 agagccgccc tcacgtatat ctctgaattt cccagctcac atgtcgatat cacgttgcac     240
ggatcccttg ccgccaccgg taaaggccac tgcactgacc gggcggtatt actgggtctg     300
gtgggatggg aaccaacgat agttcccatt gatgctgcac cctcacccgg cgcgccgatt     360
cctgcgaaag gttctgtgaa cgggccaaag gaacggtgt cgtattccct gacgtttgat      420
cctcatcctc ttccagaaca ccccaatgcc gttacctta aaggatcaac cacaaggact      480
tatttgtcgg tggtggtgg gttcattatg acgttggagg atttccggaa gctgacgat       540 atcggatcag gtgtgtcaac cattcatcca gaggcagagg tgccttgtcc ttttcagaag     600
agttcccaat tactcgcata tgggcgcgat tttgcggagg tcatgaagga taatgagcgc     660
ttaatccacg gggatcttgg cacagtggat gcccatttgg atcgagtgtg cagattatg      720 caggagtgcg tggcacaagg catcgcaacg cctgggattt accgggtgg gttgaatgtg     780 caacgtcggg cgccgcaggt acacgcgctg attagcaacg gggatacgtg tgagctgggt    840
gctgatcttg atgctgtgga gtgggtgaat ctgtacgcct ggcggtgaa tgaagaaaac     900 gccgctggtg gtcgtgtggt tactgctccg actaatggtg ctgcggggat tattccggcg    960
gtgatgcact atgcgcggga ttttttgaca ggttttgggg cggagcaggc gcggacgttt    1020
ttgtataccg cgggtgcggt gggcatcatc attaaggaaa atgcctcgat ctctggcgcg    1080
gaggtggggt gtcagggtga ggttggttca gcgtccgcga tggcggctgc cggttgtgt    1140 gcagtcttag gtggttctcc gcaacaggtg gaaaacgccg cggagattgc gttggagcac    1200
aatttgggat tgacgtgcga tccggtgggc gggttagtgc agattccgtg tattgaacgc    1260
aacgctattg ctgccatgaa gtccatcaat gcggcaaggc ttgcccggat tggtgatggc    1320
aacaatcgcg tgagtttgga tgatgtgtg gtcacgatgg ctgccaccgg tcgggacatg    1380
ttgaccaaat acaaggaaac gtcccttggt ggtttggcaa ccaccttggg cttcccggtg    1440
tcgatgacgg agtgttag                                                   1458

<210> SEQ ID NO 147

```
<211> LENGTH: 485
<212> TYPE: PRT
<213> ORGANISM: Corynebacterium glutamicum

<400> SEQUENCE: 147
```

| | | | | | | | | | | | | | | |
|---|---|---|---|---|---|---|---|---|---|---|---|---|---|---|
| Met | Val | Asp | Ser | Cys | Asn | Phe | Arg | Leu | Ser | Arg | Arg | Trp | Thr | Lys |
| 1 | | | | 5 | | | | | 10 | | | | | 15 |
| Asn | Asn | Tyr | Asn | Gln | Ala | Asp | His | Leu | Val | His | Gln | Arg | Lys | Gly |
| | | | 20 | | | | | 25 | | | | | 30 | |
| Pro | Pro | Ser | Ala | Met | Ala | Ile | Ser | Val | Val | Asp | Leu | Phe | Ser | Ile | Gly |
| | | 35 | | | | | 40 | | | | | 45 | | |
| Ile | Gly | Pro | Ser | Ser | His | Thr | Val | Gly | Pro | Met | Arg | Ala | Ala | Leu |
| 50 | | | | | 55 | | | | | 60 | | | | |
| Thr | Tyr | Ile | Ser | Glu | Phe | Pro | Ser | Ser | His | Val | Asp | Ile | Thr | Leu | His |
| 65 | | | | | 70 | | | | | 75 | | | | | 80 |
| Gly | Ser | Leu | Ala | Ala | Thr | Gly | Lys | Gly | His | Cys | Thr | Asp | Arg | Ala | Val |
| | | | | 85 | | | | | 90 | | | | | 95 | |
| Leu | Leu | Gly | Leu | Val | Gly | Trp | Glu | Pro | Thr | Ile | Val | Pro | Ile | Asp | Ala |
| | | | 100 | | | | | 105 | | | | | 110 | | |
| Ala | Pro | Ser | Pro | Gly | Ala | Pro | Ile | Pro | Ala | Lys | Gly | Ser | Val | Asn | Gly |
| | | 115 | | | | | 120 | | | | | 125 | | | |
| Pro | Lys | Gly | Thr | Val | Ser | Tyr | Ser | Leu | Thr | Phe | Asp | Pro | His | Pro | Leu |
| 130 | | | | | 135 | | | | | 140 | | | | | |
| Pro | Glu | His | Pro | Asn | Ala | Val | Thr | Phe | Lys | Gly | Ser | Thr | Thr | Arg | Thr |
| 145 | | | | | 150 | | | | | 155 | | | | | 160 |
| Tyr | Leu | Ser | Val | Gly | Gly | Gly | Phe | Ile | Met | Thr | Leu | Glu | Asp | Phe | Arg |
| | | | | 165 | | | | | 170 | | | | | 175 | |
| Lys | Leu | Asp | Asp | Ile | Gly | Ser | Gly | Val | Ser | Thr | Ile | His | Pro | Glu | Ala |
| | | | 180 | | | | | 185 | | | | | 190 | | |
| Glu | Val | Pro | Cys | Pro | Phe | Gln | Lys | Ser | Ser | Gln | Leu | Leu | Ala | Tyr | Gly |
| | | 195 | | | | | 200 | | | | | 205 | | | |
| Arg | Asp | Phe | Ala | Glu | Val | Met | Lys | Asp | Asn | Glu | Arg | Leu | Ile | His | Gly |
| | | | 210 | | | | | 215 | | | | | 220 | | |
| Asp | Leu | Gly | Thr | Val | Asp | Ala | His | Leu | Asp | Arg | Val | Trp | Gln | Ile | Met |
| 225 | | | | | 230 | | | | | 235 | | | | | 240 |
| Gln | Glu | Cys | Val | Ala | Gln | Gly | Ile | Ala | Thr | Pro | Gly | Ile | Leu | Pro | Gly |
| | | | | 245 | | | | | 250 | | | | | 255 | |
| Gly | Leu | Asn | Val | Gln | Arg | Arg | Ala | Pro | Gln | Val | His | Ala | Leu | Ile | Ser |
| | | | 260 | | | | | 265 | | | | | 270 | | |
| Asn | Gly | Asp | Thr | Cys | Glu | Leu | Gly | Ala | Asp | Leu | Asp | Ala | Val | Glu | Trp |
| | | 275 | | | | | 280 | | | | | 285 | | | |
| Val | Asn | Leu | Tyr | Ala | Leu | Ala | Val | Asn | Glu | Glu | Asn | Ala | Ala | Gly | Gly |
| | | | 290 | | | | | 295 | | | | | 300 | | |
| Arg | Val | Val | Thr | Ala | Pro | Thr | Asn | Gly | Ala | Ala | Gly | Ile | Ile | Pro | Ala |
| 305 | | | | | 310 | | | | | 315 | | | | | 320 |
| Val | Met | His | Tyr | Ala | Arg | Asp | Phe | Leu | Thr | Gly | Phe | Gly | Ala | Glu | Gln |
| | | | | 325 | | | | | 330 | | | | | 335 | |
| Ala | Arg | Thr | Phe | Leu | Tyr | Thr | Ala | Gly | Ala | Val | Gly | Ile | Ile | Lys |
| | | | 340 | | | | | 345 | | | | | 350 | | |
| Glu | Asn | Ala | Ser | Ile | Ser | Gly | Ala | Glu | Val | Gly | Cys | Gln | Gly | Glu | Val |
| | | | 355 | | | | | 360 | | | | | 365 | | |
| Gly | Ser | Ala | Ser | Ala | Met | Ala | Ala | Ala | Gly | Leu | Cys | Ala | Val | Leu | Gly |
| | | 370 | | | | | 375 | | | | | 380 | | | |
| Gly | Ser | Pro | Gln | Gln | Val | Glu | Asn | Ala | Ala | Glu | Ile | Ala | Leu | Glu | His |

```
                385                 390                 395                 400
Asn Leu Gly Leu Thr Cys Asp Pro Val Gly Gly Leu Val Gln Ile Pro
                405                 410                 415

Cys Ile Glu Arg Asn Ala Ile Ala Ala Met Lys Ser Ile Asn Ala Ala
                420                 425                 430

Arg Leu Ala Arg Ile Gly Asp Gly Asn Asn Arg Val Ser Leu Asp Asp
                435                 440                 445

Val Val Val Thr Met Ala Ala Thr Gly Arg Asp Met Leu Thr Lys Tyr
                450                 455                 460

Lys Glu Thr Ser Leu Gly Gly Leu Ala Thr Thr Leu Gly Phe Pro Val
465                 470                 475                 480

Ser Met Thr Glu Cys
                485
```

<210> SEQ ID NO 148
<211> LENGTH: 40
<212> TYPE: DNA
<213> ORGANISM: Artificial Sequence
<220> FEATURE:
<223> OTHER INFORMATION: primer

<400> SEQUENCE: 148
cggtacccgg ggatcgaaag ctcactgttg ttaccgcagg          40

<210> SEQ ID NO 149
<211> LENGTH: 40
<212> TYPE: DNA
<213> ORGANISM: Artificial Sequence
<220> FEATURE:
<223> OTHER INFORMATION: primer

<400> SEQUENCE: 149
cgttttccac ctgttacgaa atttcagcaa tctgtggtgg          40

<210> SEQ ID NO 150
<211> LENGTH: 23
<212> TYPE: DNA
<213> ORGANISM: Artificial Sequence
<220> FEATURE:
<223> OTHER INFORMATION: primer

<400> SEQUENCE: 150
aacaggtgga aaacgccgcg gag                           23

<210> SEQ ID NO 151
<211> LENGTH: 39
<212> TYPE: DNA
<213> ORGANISM: Artificial Sequence
<220> FEATURE:
<223> OTHER INFORMATION: primer

<400> SEQUENCE: 151
ccaagcttgc atgccattcg gtacgcgcta caccgcttg           39

<210> SEQ ID NO 152
<211> LENGTH: 25
<212> TYPE: DNA
<213> ORGANISM: Artificial Sequence
<220> FEATURE:
<223> OTHER INFORMATION: primer

<400> SEQUENCE: 152
caaccctggt cagccaactg agtag                         25

<210> SEQ ID NO 153
<211> LENGTH: 26
<212> TYPE: DNA
<213> ORGANISM: Artificial Sequence
<220> FEATURE:
<223> OTHER INFORMATION: primer

<400> SEQUENCE: 153
tgaaagcgat atcgatttgc tgcttg                                        26

<210> SEQ ID NO 154
<211> LENGTH: 36
<212> TYPE: DNA
<213> ORGANISM: Artificial Sequence
<220> FEATURE:
<223> OTHER INFORMATION: primer

<400> SEQUENCE: 154
cggtacccgg ggatcctcaa cctcctggcg tcagtt                             36

<210> SEQ ID NO 155
<211> LENGTH: 35
<212> TYPE: DNA
<213> ORGANISM: Artificial Sequence
<220> FEATURE:
<223> OTHER INFORMATION: primer

<400> SEQUENCE: 155
acaatgagtt tacgctcaac ctgcttgatt ctttc                              35

<210> SEQ ID NO 156
<211> LENGTH: 35
<212> TYPE: DNA
<213> ORGANISM: Artificial Sequence
<220> FEATURE:
<223> OTHER INFORMATION: primer

<400> SEQUENCE: 156
attccagctt gtcgtggtga acctgtaccc atttg                              35

<210> SEQ ID NO 157
<211> LENGTH: 36
<212> TYPE: DNA
<213> ORGANISM: Artificial Sequence
<220> FEATURE:
<223> OTHER INFORMATION: primer

<400> SEQUENCE: 157
ccaagcttgc atgccgatca agtcgcgttc ctgaac                             36

<210> SEQ ID NO 158
<211> LENGTH: 400
<212> TYPE: DNA
<213> ORGANISM: Artificial Sequence
<220> FEATURE:
<223> OTHER INFORMATION: DNA fragment

<400> SEQUENCE: 158
gcgtaaactc attgtagaag tcctgaacag cgtggaattt tcgcgtcagg gtggcgtaca   60
actcaactgg agaggctaaa tccttcatga gcgatgatcg taaggcaatt aaacgcgcac  120
taattagcgt gtatgacaag actggcctgg aggatctagc ccaggcactt caccgcgcga  180
acgtggaaat tgttttcacc ggatccactg cggcgaagat tgctgagctt ggtattcctg  240

```
ttaccccggt tgaggagctc accggtttcc ctgagtgcct tgagggccgt gtgaagacac      300
tgcatcctaa ggttcacgct ggcatcttgg cggacacccg caaggaagac cacctgcgtc      360
agctcaagga acttgaggtc gccccattcc agcttgtcgt                            400

<210> SEQ ID NO 159
<211> LENGTH: 20
<212> TYPE: DNA
<213> ORGANISM: Artificial Sequence
<220> FEATURE:
<223> OTHER INFORMATION: primer

<400> SEQUENCE: 159
cagcactgtg tttcctcgtc                                                   20

<210> SEQ ID NO 160
<211> LENGTH: 20
<212> TYPE: DNA
<213> ORGANISM: Artificial Sequence
<220> FEATURE:
<223> OTHER INFORMATION: primer

<400> SEQUENCE: 160
caggtccttc agaacctcag                                                   20

<210> SEQ ID NO 161
<211> LENGTH: 1224
<212> TYPE: DNA
<213> ORGANISM: Corynebacterium glutamicum

<400> SEQUENCE: 161
gtggctcagc caaccgccgt ccgtttgttc accagtgaat ctgtaactga gggacatcca       60
gacaaaatat gtgatgctat ttccgatacc attttggacg cgctgctcga aaaagatccg      120
cagtcgcgcg tcgcagtgga aactgtggtc accaccggaa tcgtccatgt tgttggcgag      180
gtccgtacca gcgcttacgt agagatccct caattagtcc gcaacaagct catcgaaatc      240
ggattcaact cctctgaggt tggattcgac ggacgcacct gtggcgtctc agtatctatc      300
ggtgagcagt cccaggaaat cgctgacggc gtggataact ccgacgaagc cgcaccaac       360 ggcgacgttg aagaagacga ccgcgcaggt gctggcgacc agggcctgat gttcggctac      420
gccaccaacg aaaccgaaga gtacatgcct cttcctatcg cgttggcgca ccgactgtca      480
cgtcgtctga cccaggttcg taaagagggc atcgttcctc acctgcgtcc agacggaaaa      540
acccaggtca ccttcgcata cgatgcgcaa gaccgcccta gccacctgga taccgtcgtc      600
atctccaccc agcacgaccc agaagttgac cgtgcatggt tggaaaccca gctgcgcgaa      660
cacgtcattg attgggtaat caagacgca ggcattgagg atctggcaac cggtgagatc       720
accgtgttga tcaacccttc aggttccttc attctgggtg gccccatggg tgatgcgggt      780
ctgaccggcc gcaagatcat cgtggatacc tacggtggca tggctcgcca tggtggtgga      840
gcattctccg gtaaggatcc aagcaaggtg gaccgctctg ctgcatacgc catgcgttgg      900
gtagcaaaga acatcgtggc agcaggcctt gctgatcgcg ctgaagttca ggttgcatac      960
gccattggac gcgcaaagcc agtcggactt tacgttgaaa cctttgacac caacaaggaa     1020
ggcctgagcg acgagcagat tcaggctgcc gtgttggagg tctttgacct gcgtccagca     1080
gcaattatcc gtgagcttga tctgcttcgt ccgatctacg ctgacactgc tgcctacggc     1140
cactttggtc gcactgattt ggaccttcct tgggaggcta tcgaccgcgt tgatgaactt     1200
cgcgcagccc tcaagttggc ctaa                                            1224
```

<210> SEQ ID NO 162
<211> LENGTH: 407
<212> TYPE: PRT
<213> ORGANISM: Corynebacterium glutamicum

<400> SEQUENCE: 162

Met Ala Gln Pro Thr Ala Val Arg Leu Phe Thr Ser Glu Ser Val Thr
1               5                   10                  15

Glu Gly His Pro Asp Lys Ile Cys Asp Ala Ile Ser Asp Thr Ile Leu
            20                  25                  30

Asp Ala Leu Leu Glu Lys Asp Pro Gln Ser Arg Val Ala Val Glu Thr
        35                  40                  45

Val Val Thr Thr Gly Ile Val His Val Val Gly Glu Val Arg Thr Ser
    50                  55                  60

Ala Tyr Val Glu Ile Pro Gln Leu Val Arg Asn Lys Leu Ile Glu Ile
65                  70                  75                  80

Gly Phe Asn Ser Ser Glu Val Gly Phe Asp Gly Arg Thr Cys Gly Val
                85                  90                  95

Ser Val Ser Ile Gly Glu Gln Ser Gln Glu Ile Ala Asp Gly Val Asp
            100                 105                 110

Asn Ser Asp Glu Ala Arg Thr Asn Gly Asp Val Glu Glu Asp Asp Arg
        115                 120                 125

Ala Gly Ala Gly Asp Gln Gly Leu Met Phe Gly Tyr Ala Thr Asn Glu
    130                 135                 140

Thr Glu Glu Tyr Met Pro Leu Pro Ile Ala Leu Ala His Arg Leu Ser
145                 150                 155                 160

Arg Arg Leu Thr Gln Val Arg Lys Glu Gly Ile Val Pro His Leu Arg
                165                 170                 175

Pro Asp Gly Lys Thr Gln Val Thr Phe Ala Tyr Asp Ala Gln Asp Arg
            180                 185                 190

Pro Ser His Leu Asp Thr Val Val Ile Ser Thr Gln His Asp Pro Glu
        195                 200                 205

Val Asp Arg Ala Trp Leu Glu Thr Gln Leu Arg Glu His Val Ile Asp
    210                 215                 220

Trp Val Ile Lys Asp Ala Gly Ile Glu Asp Leu Ala Thr Gly Glu Ile
225                 230                 235                 240

Thr Val Leu Ile Asn Pro Ser Gly Ser Phe Ile Leu Gly Gly Pro Met
                245                 250                 255

Gly Asp Ala Gly Leu Thr Gly Arg Lys Ile Ile Val Asp Thr Tyr Gly
            260                 265                 270

Gly Met Ala Arg His Gly Gly Gly Ala Phe Ser Gly Lys Asp Pro Ser
        275                 280                 285

Lys Val Asp Arg Ser Ala Ala Tyr Ala Met Arg Trp Val Ala Lys Asn
    290                 295                 300

Ile Val Ala Ala Gly Leu Ala Asp Arg Ala Glu Val Gln Val Ala Tyr
305                 310                 315                 320

Ala Ile Gly Arg Ala Lys Pro Val Gly Leu Tyr Val Glu Thr Phe Asp
                325                 330                 335

Thr Asn Lys Glu Gly Leu Ser Asp Glu Gln Ile Gln Ala Ala Val Leu
            340                 345                 350

Glu Val Phe Asp Leu Arg Pro Ala Ala Ile Ile Arg Glu Leu Asp Leu
        355                 360                 365

Leu Arg Pro Ile Tyr Ala Asp Thr Ala Ala Tyr Gly His Phe Gly Arg

```
            370                 375                 380
Thr Asp Leu Asp Leu Pro Trp Glu Ala Ile Asp Arg Val Asp Glu Leu
385                 390                 395                 400

Arg Ala Ala Leu Lys Leu Ala
            405

<210> SEQ ID NO 163
<211> LENGTH: 37
<212> TYPE: DNA
<213> ORGANISM: Artificial Sequence
<220> FEATURE:
<223> OTHER INFORMATION: primer

<400> SEQUENCE: 163
ccaagcttgc atgccgtggc tcagccaacc gccgtcc                      37

<210> SEQ ID NO 164
<211> LENGTH: 36
<212> TYPE: DNA
<213> ORGANISM: Artificial Sequence
<220> FEATURE:
<223> OTHER INFORMATION: primer

<400> SEQUENCE: 164
gagctcggta cccggttagg ccaacttgag ggctgc                       36

<210> SEQ ID NO 165
<211> LENGTH: 2262
<212> TYPE: DNA
<213> ORGANISM: Escherichia coli

<400> SEQUENCE: 165
atgacaatat tgaatcacac cctcggtttc cctcgcgttg gcctgcgtcg cgagctgaaa    60
aaagcgcaag aaagttattg ggcggggaac tccacgcgtg aagaactgct ggcggtaggg   120
cgtgaattgc gtgctcgtca ctgggatcaa caaaagcaag cgggtatcga cctgctgccg   180
gtgggcgatt ttgcctggta cgatcatgta ctgaccacca gtctgctgct gggtaacgtt   240
ccggcgcgtc atcagaacaa agatggttcg gtagatatcg acaccctgtt ccgtattggt   300
cgtggacgtg cgccgactgg cgaacctgcg gcggcagcgg aaatgaccaa atggtttaac   360
accaactatc actacatggt gccggagttc gttaaaggcc aacagttcaa actgacctgg   420
acgcagctgc tggacgaagt ggacgaggcg ctggcgctgg ccacaaggt gaaacctgtg   480 ctgctggggc cggttacctg gctgtggctg gggaaagtga aggtgaaca atttgaccgc   540 ctgagcctgc tgaacgacat tctgccggtt tatcagcaag tgctggcaga actggcgaaa   600
cgcggcatcg agtgggtaca gattgatgaa cccgcgctgg tactgaact accacaggcg   660 tggctggacg catacaaacc gcttacgac gcgctccagg acaggtgaa actgctgctg   720 accacctatt ttgaaggcgt aacgccaaat ctcgacacga ttactgcgct gcctgttcag   780
ggtctgcatg ttgacctcgt acatggtaaa gatgacgttg ctgaactgca caagcgcctg   840
ccttctgact ggttgctgtc tgcgggtctg atcaatggtc gtaacgtctg gcgcgccgat   900
cttaccgaga aatatgcgca aattaaggac attgtcggca acgtgattt gtgggtggca   960 tcttcctgct cgttgctgca cagccccatc gacctgagcg tggaaacgcg tcttgatgca  1020
gaagtgaaaa gctggtttgc cttcgcccta caaaaatgcc atgaactggc actgctgcgc  1080
gatgcgctga acagtggtga cacgcagct ctggcagagt ggagcgcccc gattcaggca  1140
cgtcgtcact ctacccgcgt acataatccg gcggtagaaa agcgtctggc ggcgatcacc  1200
```

```
gcccaggaca gccagcgtgc gaatgtctat gaagtgcgtg ctgaagccca gcgtgcgcgt    1260
tttaaactgc cagcgtggcc gaccaccacg attggttcct tcccgcaaac cacggaaatt    1320
cgtaccctgc gtctggattt caaaaagggc aatctcgacg ccaacaacta ccgcacgggc    1380
attgcggaac atatcaagca ggccattgtt gagcaggaac gtttgggact ggatgtgctg    1440
gtacatggcg aggccgagcg taatgacatg gtggaatact ttggcgagca cctcgacgga    1500
tttgtcttta cgcaaaacgg ttgggtacag agctacggtt cccgctgcgt gaagccaccg    1560
attgtcattg gtgacattag ccgcccggca ccgattaccg tggagtgggc gaagtatgcg    1620
caatcgctga ccgacaaacc ggtgaaaggg atgctgacgg ggccggtgac catactctgc    1680
tggtcgttcc gcgtgaaga tgtcagccgt gaaaccatcg ccaaacagat tgcgctggcg    1740
ctgcgtgatg aagtgccga tctggaagcc gctggaattg gcatcatcca gattgacgaa    1800
ccggcgctgc gcgaaggttt accgctgcgt cgtagcgact gggatgcgta tctccagtgg    1860
ggcgtagagg ccttccgtat caacgccgcc gtggcgaaag atgacacaca aatccacact    1920
cacatgtgtt attgcgagtt caacgacatc atggattcga ttgcggcgct ggacgcagac    1980
gtcatcacca tcgaaacctc gcgttccgac atggagttgc tggagtcgtt tgaagagttt    2040
gattatccaa atgaaatcgg tcctggcgtc tatgacattc actcgccaaa cgtaccgagc    2100
gtggaatgga ttgaagcctt gctgaagaaa gcggcaaaac gcattccggc agagcgcctg    2160
tgggtcaacc cggactgtgg cctgaaaacg cgcggctggc cagaaacccg cgcggcactg    2220
gcgaacatgg tgcaggcggc gcagaacttg cgtcgggggt aa                       2262
```

<210> SEQ ID NO 166
<211> LENGTH: 753
<212> TYPE: PRT
<213> ORGANISM: Escherichia coli

<400> SEQUENCE: 166

```
Met Thr Ile Leu Asn His Thr Leu Gly Phe Pro Arg Val Gly Leu Arg
1               5                   10                  15

Arg Glu Leu Lys Lys Ala Gln Glu Ser Tyr Trp Ala Gly Asn Ser Thr
            20                  25                  30

Arg Glu Glu Leu Leu Ala Val Gly Arg Glu Leu Arg Ala Arg His Trp
        35                  40                  45

Asp Gln Gln Lys Gln Ala Gly Ile Asp Leu Leu Pro Val Gly Asp Phe
    50                  55                  60

Ala Trp Tyr Asp His Val Leu Thr Thr Ser Leu Leu Gly Asn Val
65                  70                  75                  80

Pro Ala Arg His Gln Asn Lys Asp Gly Ser Val Asp Ile Asp Thr Leu
                85                  90                  95

Phe Arg Ile Gly Arg Gly Arg Ala Pro Thr Gly Glu Pro Ala Ala Ala
            100                 105                 110

Ala Glu Met Thr Lys Trp Phe Asn Thr Asn Tyr His Tyr Met Val Pro
        115                 120                 125

Glu Phe Val Lys Gly Gln Gln Phe Lys Leu Thr Trp Thr Gln Leu Leu
    130                 135                 140

Asp Glu Val Asp Glu Ala Leu Ala Leu Gly His Lys Val Lys Pro Val
145                 150                 155                 160

Leu Leu Gly Pro Val Thr Trp Leu Trp Leu Gly Lys Val Lys Gly Glu
                165                 170                 175

Gln Phe Asp Arg Leu Ser Leu Leu Asn Asp Ile Leu Pro Val Tyr Gln
```

```
              180                 185                 190
Gln Val Leu Ala Glu Leu Ala Lys Arg Gly Ile Glu Trp Val Gln Ile
            195                 200                 205
Asp Glu Pro Ala Leu Val Leu Glu Leu Pro Gln Ala Trp Leu Asp Ala
        210                 215                 220
Tyr Lys Pro Ala Tyr Asp Ala Leu Gln Gly Gln Val Lys Leu Leu Leu
225                 230                 235                 240
Thr Thr Tyr Phe Glu Gly Val Thr Pro Asn Leu Asp Thr Ile Thr Ala
                245                 250                 255
Leu Pro Val Gln Gly Leu His Val Asp Leu Val His Gly Lys Asp Asp
            260                 265                 270
Val Ala Glu Leu His Lys Arg Leu Pro Ser Asp Trp Leu Leu Ser Ala
        275                 280                 285
Gly Leu Ile Asn Gly Arg Asn Val Trp Arg Ala Asp Leu Thr Glu Lys
            290                 295                 300
Tyr Ala Gln Ile Lys Asp Ile Val Gly Lys Arg Asp Leu Trp Val Ala
305                 310                 315                 320
Ser Ser Cys Ser Leu Leu His Ser Pro Ile Asp Leu Ser Val Glu Thr
                325                 330                 335
Arg Leu Asp Ala Glu Val Lys Ser Trp Phe Ala Phe Ala Leu Gln Lys
            340                 345                 350
Cys His Glu Leu Ala Leu Leu Arg Asp Ala Leu Asn Ser Gly Asp Thr
        355                 360                 365
Ala Ala Leu Ala Glu Trp Ser Ala Pro Ile Gln Ala Arg Arg His Ser
    370                 375                 380
Thr Arg Val His Asn Pro Ala Val Glu Lys Arg Leu Ala Ala Ile Thr
385                 390                 395                 400
Ala Gln Asp Ser Gln Arg Ala Asn Val Tyr Glu Val Arg Ala Glu Ala
                405                 410                 415
Gln Arg Ala Arg Phe Lys Leu Pro Ala Trp Pro Thr Thr Thr Ile Gly
            420                 425                 430
Ser Phe Pro Gln Thr Thr Glu Ile Arg Thr Leu Arg Leu Asp Phe Lys
        435                 440                 445
Lys Gly Asn Leu Asp Ala Asn Asn Tyr Arg Thr Gly Ile Ala Glu His
        450                 455                 460
Ile Lys Gln Ala Ile Val Glu Gln Glu Arg Leu Gly Leu Asp Val Leu
465                 470                 475                 480
Val His Gly Glu Ala Glu Arg Asn Asp Met Val Glu Tyr Phe Gly Glu
                485                 490                 495
His Leu Asp Gly Phe Val Phe Thr Gln Asn Gly Trp Val Gln Ser Tyr
            500                 505                 510
Gly Ser Arg Cys Val Lys Pro Ile Val Ile Gly Asp Ile Ser Arg
        515                 520                 525
Pro Ala Pro Ile Thr Val Glu Trp Ala Lys Tyr Ala Gln Ser Leu Thr
        530                 535                 540
Asp Lys Pro Val Lys Gly Met Leu Thr Gly Pro Val Thr Ile Leu Cys
545                 550                 555                 560
Trp Ser Phe Pro Arg Glu Asp Val Ser Arg Glu Thr Ile Ala Lys Gln
                565                 570                 575
Ile Ala Leu Ala Leu Arg Asp Glu Val Ala Asp Leu Glu Ala Ala Gly
            580                 585                 590
Ile Gly Ile Ile Gln Ile Asp Glu Pro Ala Leu Arg Glu Gly Leu Pro
        595                 600                 605
```

```
Leu Arg Arg Ser Asp Trp Asp Ala Tyr Leu Gln Trp Gly Val Glu Ala
            610                 615                 620

Phe Arg Ile Asn Ala Ala Val Ala Lys Asp Asp Thr Gln Ile His Thr
625                 630                 635                 640

His Met Cys Tyr Cys Glu Phe Asn Asp Ile Met Asp Ser Ile Ala Ala
                645                 650                 655

Leu Asp Ala Asp Val Ile Thr Ile Glu Thr Ser Arg Ser Asp Met Glu
            660                 665                 670

Leu Leu Glu Ser Phe Glu Glu Phe Asp Tyr Pro Asn Glu Ile Gly Pro
        675                 680                 685

Gly Val Tyr Asp Ile His Ser Pro Asn Val Pro Ser Val Glu Trp Ile
    690                 695                 700

Glu Ala Leu Leu Lys Lys Ala Ala Lys Arg Ile Pro Ala Glu Arg Leu
705                 710                 715                 720

Trp Val Asn Pro Asp Cys Gly Leu Lys Thr Arg Gly Trp Pro Glu Thr
                725                 730                 735

Arg Ala Ala Leu Ala Asn Met Val Gln Ala Ala Gln Asn Leu Arg Arg
            740                 745                 750

Gly

<210> SEQ ID NO 167
<211> LENGTH: 3684
<212> TYPE: DNA
<213> ORGANISM: Escherichia coli

<400> SEQUENCE: 167
gtgagcagca aagtggaaca actgcgtgcg cagttaaatg aacgtattct ggtgctggac      60
ggcggtatgg gcaccatgat ccagagttat cgactgaacg aagccgattt cgtggtgaa     120
cgctttgccg actggccatg cgacctcaaa gcaacaacg acctgctggt actcagtaaa     180
ccggaagtga tcgccgctat ccacaacgcc tactttgaag cgggcgcgga tatcatcgaa     240
accaacacct tcaactccac gaccattgcg atggcggatt accagatgga atccctgtcg     300
gcggaaatca actttgcggc ggcgaaactg cgcgagctt gtgctgacga gtggaccgcg     360
cgcacgccag agaaaccgcg ctacgttgcc ggtgttctcg gcccgaccaa ccgcacggcg     420
tctatttctc cggacgtcaa cgatccggca tttcgtaata tcacttttga cgggctggtg     480
gcggcttatc gagagtccac caaagcgctg gtggaaggtg gcgcggatct gatcctgatt     540
gaaaccgttt cgacaccct aacgccaaa gcggcggtat ttgcggtgaa aacggagttt     600
gaagcgctgg gcgttgagct gccgattatg atctccggca ccatcaccga cgcctccggg     660
cgcacgctct ccgggcagac caccgaagca ttttacaact cattgcgcca cgccgaagct     720
ctgacctttg gcctgaactg tgcgctgggg cccgatgaac tgcgccagta cgtgcaggag     780
ctgtcacgga ttgcggaatg ctacgtcacc gcgcacccga acgccgggct acccaacgcc     840
tttggtgagt acgatctcga cgccgacacg atggcaaaac agatacgtga atgggcgcaa     900
gcgggttttc tcaatatcgt cggcggctgc tgtggcacca cgccacaaca tattgcagcg     960
atgagtcgtg cagtagaagg attagcgccg cgcaaactgc cggaaattcc cgtagcctgc    1020
cgtttgtccg gcctggagcc gctgaacatt ggcgaagata gcctgtttgt gaacgtgggt    1080
gaacgcacca acgtcaccgg ttccgctaag ttcaagcgcc tgatcaaaga agagaaatac    1140
agcgaggcgc tggatgtcgc gcgtcaacag gtggaaaacg cgcgcagat tatcgatatc    1200
aacatggatg aagggatgct cgatgccgaa gcggcgatgg tgcgttttct caatctgatt    1260
```

```
gccggtgaac cggatatcgc tcgcgtgccg attatgatcg actcctcaaa atgggacgtc    1320
attgaaaaag gtctgaagtg tatccagggc aaaggcattg ttaactctat ctcgatgaaa    1380
gagggcgtcg atgcctttat ccatcacgcg aaattgttgc gtcgctacgg tgcggcagtg    1440
gtggtaatgg cctttgacga acagggacag gccgatactc gcgcacggaa aatcgagatt    1500
tgccgtcggg cgtacaaaat cctcaccgaa gaggttggct tcccgccaga agatatcatc    1560
ttcgacccaa acatcttcgc ggtcgcaact ggcattgaag agcacaacaa ctacgcgcag    1620
gactttatcg gcgcgtgtga agacatcaaa cgcgaactgc cgcacgcgct gatttccggc    1680
ggcgtatcta acgtttcttt ctcgttccgt ggcaacgatc cggtgcgcga agccattcac    1740
gcagtgttcc tctactacgc tattcgcaat ggcatggata tggggatcgt caacgccggg    1800
caactggcga tttacgacga cctacccgct gaactgcgcg acgcggtgga agatgtgatt    1860
cttaatcgtc gcgacgatgg caccgagcgt ttactggagc ttgccgagaa atatcgcggc    1920
agcaaaaccg acgacaccgc caacgcccag caggcggagt ggcgctcgtg ggaagtgaat    1980
aaacgtctgg aatactcgct ggtcaaaggc attaccgagt ttatcgagca ggataccgaa    2040
gaagcccgcc agcaggctac gcgcccgatt gaagtgattg aaggcccgtt gatggacggc    2100
atgaatgtgg tcggcgacct gtttggcgaa gggaaaatgt tcctgccaca ggtggtcaaa    2160
tcggcgcgcg tcatgaaaca ggcggtggcc tacctcgaac cgtttattga agccagcaaa    2220
gagcagggca aaaccaacgg caagatggtg atcgccaccg tgaagggcga cgtccacgac    2280
atcggtaaaa atatcgttgg tgtggtgctg caatgtaaca actacgaaat tgtcgatctc    2340
ggcgttatgg tgcctgcgga aaaaattctc cgtaccgcta agaagtgaa tgctgatctg     2400 attggccttt cggggcttat cacgccgtcg ctggacgaga tggttaacgt ggcgaaagag    2460
atggagcgtc agggcttcac tattccgtta ctgattggcg gcgcgacgac ctcaaaagcg    2520
cacacggcgg tgaaaatcga gcagaactac agcggcccga cggtgtatgt gcagaatgcc    2580
tcgcgtaccg ttggtgtggt ggcggcgctg ctttccgata cccagcgtga tgattttgtc    2640
gctcgtaccc gcaaggagta cgaaaccgta cgtattcagc acgggcgcaa gaaaccgcgc    2700
acaccaccgg tcacgctgga agcggcgcgc gataacgatt tcgcttttga ctggcaggct    2760
tacacgccgc cggtggcgca ccgtctcggc gtgcaggaag tcgaagccag catcgaaacg    2820
ctgcgtaatt acatcgactg gacaccgttc tttatgacct ggtcgctggc cgggaagtat    2880
ccgcgcattc tggaagatga agtggtgggc gttgaggcgc agcggctgtt taaagacgcc    2940
aacgacatgc tggataaatt aagcgccgag aaaacgctga atccgcgtgg cgtggtgggc    3000
ctgttcccgg caaaccgtgt gggcgatgac attgaaatct accgtgacga aacgcgtacc    3060
catgtgatca acgtcagcca ccatctgcgt caacagaccg aaaaaacagg cttcgctaac    3120
tactgtctcg ctgacttcgt tgcgccgaag ctttctggta aagcagatta catcggcgca    3180
tttgccgtga ctggcgggct ggaagaggac gcactggctg atgcctttga agcgcagcac    3240
gatgattaca acaaaatcat ggtgaaagcg cttgccgacc gtttagccga agcctttgcg    3300
gagtatctcc atgagcgtgt gcgtaaagtc tactggggct atgcgccgaa cgagaacctc    3360
agcaacgaag agctgatccg cgaaaactac cagggcatcc gtccggcacc gggctatccg    3420
gcctgcccgg aacatacgga aaaagccacc atctgggagc tgctggaagt ggaaaaacac    3480
actggcatga aactcacaga atctttcgcc atgtggcccg tgcatcggt ttcgggttgg    3540 tacttcagcc acccggacag caagtactac gctgtagcac aaattcagcg cgatcaggtt    3600
```

```
gaagattatg cccgccgtaa aggtatgagc gttaccgaag ttgagcgctg gctggcaccg    3660
aatctggggt atgacgcgga ctga                                          3684
```

<210> SEQ ID NO 168
<211> LENGTH: 1227
<212> TYPE: PRT
<213> ORGANISM: Escherichia coli

<400> SEQUENCE: 168

```
Met Ser Ser Lys Val Glu Gln Leu Arg Ala Gln Leu Asn Glu Arg Ile
1               5                   10                  15

Leu Val Leu Asp Gly Gly Met Gly Thr Met Ile Gln Ser Tyr Arg Leu
            20                  25                  30

Asn Glu Ala Asp Phe Arg Gly Glu Arg Phe Ala Asp Trp Pro Cys Asp
        35                  40                  45

Leu Lys Gly Asn Asn Asp Leu Leu Val Leu Ser Lys Pro Glu Val Ile
    50                  55                  60

Ala Ala Ile His Asn Ala Tyr Phe Glu Ala Gly Ala Asp Ile Ile Glu
65                  70                  75                  80

Thr Asn Thr Phe Asn Ser Thr Thr Ile Ala Met Ala Asp Tyr Gln Met
                85                  90                  95

Glu Ser Leu Ser Ala Glu Ile Asn Phe Ala Ala Ala Lys Leu Ala Arg
            100                 105                 110

Ala Cys Ala Asp Glu Trp Thr Ala Arg Thr Pro Glu Lys Pro Arg Tyr
        115                 120                 125

Val Ala Gly Val Leu Gly Pro Thr Asn Arg Thr Ala Ser Ile Ser Pro
    130                 135                 140

Asp Val Asn Asp Pro Ala Phe Arg Asn Ile Thr Phe Asp Gly Leu Val
145                 150                 155                 160

Ala Ala Tyr Arg Glu Ser Thr Lys Ala Leu Val Glu Gly Gly Ala Asp
                165                 170                 175

Leu Ile Leu Ile Glu Thr Val Phe Asp Thr Leu Asn Ala Lys Ala Ala
            180                 185                 190

Val Phe Ala Val Lys Thr Glu Phe Glu Ala Leu Gly Val Glu Leu Pro
        195                 200                 205

Ile Met Ile Ser Gly Thr Ile Thr Asp Ala Ser Gly Arg Thr Leu Ser
    210                 215                 220

Gly Gln Thr Thr Glu Ala Phe Tyr Asn Ser Leu Arg His Ala Glu Ala
225                 230                 235                 240

Leu Thr Phe Gly Leu Asn Cys Ala Leu Gly Pro Asp Glu Leu Arg Gln
                245                 250                 255

Tyr Val Gln Glu Leu Ser Arg Ile Ala Glu Cys Tyr Val Thr Ala His
            260                 265                 270

Pro Asn Ala Gly Leu Pro Asn Ala Phe Gly Glu Tyr Asp Leu Asp Ala
        275                 280                 285

Asp Thr Met Ala Lys Gln Ile Arg Glu Trp Ala Gln Ala Gly Phe Leu
    290                 295                 300

Asn Ile Val Gly Gly Cys Cys Gly Thr Thr Pro Gln His Ile Ala Ala
305                 310                 315                 320

Met Ser Arg Ala Val Glu Gly Leu Ala Pro Arg Lys Leu Pro Glu Ile
                325                 330                 335

Pro Val Ala Cys Arg Leu Ser Gly Leu Glu Pro Leu Asn Ile Gly Glu
            340                 345                 350

Asp Ser Leu Phe Val Asn Val Gly Glu Arg Thr Asn Val Thr Gly Ser
```

```
                355                 360                 365
Ala Lys Phe Lys Arg Leu Ile Lys Glu Glu Lys Tyr Ser Glu Ala Leu
370                 375                 380

Asp Val Ala Arg Gln Gln Val Glu Asn Gly Ala Gln Ile Ile Asp Ile
385                 390                 395                 400

Asn Met Asp Glu Gly Met Leu Asp Ala Glu Ala Met Val Arg Phe
                405                 410                 415

Leu Asn Leu Ile Ala Gly Glu Pro Asp Ile Ala Arg Val Pro Ile Met
                420                 425                 430

Ile Asp Ser Ser Lys Trp Asp Val Ile Glu Lys Gly Leu Lys Cys Ile
                435                 440                 445

Gln Gly Lys Gly Ile Val Asn Ser Ile Ser Met Lys Glu Gly Val Asp
450                 455                 460

Ala Phe Ile His His Ala Lys Leu Leu Arg Arg Tyr Gly Ala Ala Val
465                 470                 475                 480

Val Val Met Ala Phe Asp Glu Gln Gly Gln Ala Asp Thr Arg Ala Arg
                485                 490                 495

Lys Ile Glu Ile Cys Arg Arg Ala Tyr Lys Ile Leu Thr Glu Glu Val
                500                 505                 510

Gly Phe Pro Pro Glu Asp Ile Ile Phe Asp Pro Asn Ile Phe Ala Val
                515                 520                 525

Ala Thr Gly Ile Glu Glu His Asn Asn Tyr Ala Gln Asp Phe Ile Gly
530                 535                 540

Ala Cys Glu Asp Ile Lys Arg Glu Leu Pro His Ala Leu Ile Ser Gly
545                 550                 555                 560

Gly Val Ser Asn Val Ser Phe Ser Phe Arg Gly Asn Asp Pro Val Arg
                565                 570                 575

Glu Ala Ile His Ala Val Phe Leu Tyr Tyr Ala Ile Arg Asn Gly Met
                580                 585                 590

Asp Met Gly Ile Val Asn Ala Gly Gln Leu Ala Ile Tyr Asp Asp Leu
                595                 600                 605

Pro Ala Glu Leu Arg Asp Ala Val Glu Asp Val Ile Leu Asn Arg Arg
610                 615                 620

Asp Asp Gly Thr Glu Arg Leu Leu Glu Leu Ala Glu Lys Tyr Arg Gly
625                 630                 635                 640

Ser Lys Thr Asp Asp Thr Ala Asn Ala Gln Gln Ala Glu Trp Arg Ser
                645                 650                 655

Trp Glu Val Asn Lys Arg Leu Glu Tyr Ser Leu Val Lys Gly Ile Thr
                660                 665                 670

Glu Phe Ile Glu Gln Asp Thr Glu Glu Ala Arg Gln Gln Ala Thr Arg
                675                 680                 685

Pro Ile Glu Val Ile Glu Gly Pro Leu Met Asp Gly Met Asn Val Val
                690                 695                 700

Gly Asp Leu Phe Gly Glu Gly Lys Met Phe Leu Pro Gln Val Val Lys
705                 710                 715                 720

Ser Ala Arg Val Met Lys Gln Ala Val Ala Tyr Leu Glu Pro Phe Ile
                725                 730                 735

Glu Ala Ser Lys Glu Gln Gly Lys Thr Asn Gly Lys Met Val Ile Ala
                740                 745                 750

Thr Val Lys Gly Asp Val His Asp Ile Gly Lys Asn Ile Val Gly Val
                755                 760                 765

Val Leu Gln Cys Asn Asn Tyr Glu Ile Val Asp Leu Gly Val Met Val
                770                 775                 780
```

```
Pro Ala Glu Lys Ile Leu Arg Thr Ala Lys Glu Val Asn Ala Asp Leu
785                 790                 795                 800

Ile Gly Leu Ser Gly Leu Ile Thr Pro Ser Leu Asp Glu Met Val Asn
                805                 810                 815

Val Ala Lys Glu Met Glu Arg Gln Gly Phe Thr Ile Pro Leu Leu Ile
            820                 825                 830

Gly Gly Ala Thr Thr Ser Lys Ala His Thr Ala Val Lys Ile Glu Gln
                835                 840                 845

Asn Tyr Ser Gly Pro Thr Val Tyr Val Gln Asn Ala Ser Arg Thr Val
            850                 855                 860

Gly Val Val Ala Ala Leu Leu Ser Asp Thr Gln Arg Asp Asp Phe Val
865                 870                 875                 880

Ala Arg Thr Arg Lys Glu Tyr Glu Thr Val Arg Ile Gln His Gly Arg
                885                 890                 895

Lys Lys Pro Arg Thr Pro Pro Val Thr Leu Glu Ala Ala Arg Asp Asn
            900                 905                 910

Asp Phe Ala Phe Asp Trp Gln Ala Tyr Thr Pro Val Ala His Arg
        915                 920                 925

Leu Gly Val Gln Glu Val Glu Ala Ser Ile Glu Thr Leu Arg Asn Tyr
    930                 935                 940

Ile Asp Trp Thr Pro Phe Phe Met Thr Trp Ser Leu Ala Gly Lys Tyr
945                 950                 955                 960

Pro Arg Ile Leu Glu Asp Glu Val Val Gly Val Ala Gln Arg Leu
            965                 970                 975

Phe Lys Asp Ala Asn Asp Met Leu Asp Lys Leu Ser Ala Glu Lys Thr
            980                 985                 990

Leu Asn Pro Arg Gly Val Val Gly Leu Phe Pro Ala Asn Arg Val Gly
        995                 1000                1005

Asp Asp Ile Glu Ile Tyr Arg Asp Glu Thr Arg Thr His Val Ile
    1010                1015                1020

Asn Val Ser His His Leu Arg Gln Gln Thr Glu Lys Thr Gly Phe
    1025                1030                1035

Ala Asn Tyr Cys Leu Ala Asp Phe Val Ala Pro Lys Leu Ser Gly
    1040                1045                1050

Lys Ala Asp Tyr Ile Gly Ala Phe Ala Val Thr Gly Gly Leu Glu
    1055                1060                1065

Glu Asp Ala Leu Ala Asp Ala Phe Glu Ala Gln His Asp Asp Tyr
    1070                1075                1080

Asn Lys Ile Met Val Lys Ala Leu Ala Asp Arg Leu Ala Glu Ala
    1085                1090                1095

Phe Ala Glu Tyr Leu His Glu Arg Val Arg Lys Val Tyr Trp Gly
    1100                1105                1110

Tyr Ala Pro Asn Glu Asn Leu Ser Asn Glu Glu Leu Ile Arg Glu
    1115                1120                1125

Asn Tyr Gln Gly Ile Arg Pro Ala Pro Gly Tyr Pro Ala Cys Pro
    1130                1135                1140

Glu His Thr Glu Lys Ala Thr Ile Trp Glu Leu Leu Glu Val Glu
    1145                1150                1155

Lys His Thr Gly Met Lys Leu Thr Glu Ser Phe Ala Met Trp Pro
    1160                1165                1170

Gly Ala Ser Val Ser Gly Trp Tyr Phe Ser His Pro Asp Ser Lys
    1175                1180                1185
```

```
Tyr Tyr Ala Val Ala Gln Ile Gln Arg Asp Gln Val Glu Asp Tyr
    1190                1195                1200

Ala Arg Arg Lys Gly Met Ser Val Thr Glu Val Glu Arg Trp Leu
    1205                1210                1215

Ala Pro Asn Leu Gly Tyr Asp Ala Asp
    1220                1225

<210> SEQ ID NO 169
<211> LENGTH: 3591
<212> TYPE: DNA
<213> ORGANISM: Corynebacterium glutamicum

<400> SEQUENCE: 169
gtgttgatcg cgacggcgc catgggcacc cagctccaag ctttgacct ggacgtggaa      60 aaggatttcc ttgatctgga ggggtgtaat gagattctca acgacacccg ccctgatgtg    120
ttgaggcaga ttcaccgcgc ctactttgag gcgggagctg acttggttga gaccaatact   180
tttggttgca acctgccgaa cttggcggat tatgacatcg ctgatcgttg ccgtgagctt   240
gcctacaagg gcactgcagt ggctagggaa gtggctgatg agatggggcc gggccgaaac   300
ggcatgcggc gtttcgtggt tggttccctg ggacctggaa cgaagcttcc atcgctgggc   360
catgcaccgt atgcagattt gcgtgggcac tacaaggaag cagcgcttgg catcatcgac   420
ggtggtggcg atgcctttt gattgagact gctcaggact tgcttcaggt caaggctgcg   480
gttcacggcg ttcaagatgc catggctgaa cttgatacat tcttgcccat tatttgccac   540
gtcaccgtag agaccaccgg caccatgctc atgggttctg agatcggtgc cgcgttgaca   600
gcgctgcagc cactgggtat cgacatgatt ggtctgaact gcgccaccgg cccagatgag   660
atgagcgagc acctgcgtta cctgtccaag cacgccgata ttcctgtgtc ggtgatgcct   720
aacgcaggtc ttcctgtcct gggtaaaaac ggtgcagaat acccacttga ggctgaggat   780
ttggcgcagg cgctggctgg attcgtctcc gaatatggcc tgtccatggt gggtggttgt   840
tgtggcacca cacctgagca catccgtgcg gtccgcgatg cggtggttgg tgttccagag   900 caggaaaacct ccacactgac caagatccct gcaggccctg ttgagcaggc ctcccgcgag   960
gtggagaaag aggactccgt cgcgtcgctg tacacctcgg tgccattgtc ccaggaaacc  1020
ggcatttcca tgatcggtga gcgcaccaac tccaacggtt ccaaggcatt ccgtgaggca  1080
atgctgtctg gcgattggga aaagtgtgtg atattgcca gcagcaaac ccgcgatggt  1140 gcacacatgc tggatctttg tgtggattac gtgggacgag acggcaccgc cgatatggcg  1200
accttggcag cacttcttgc taccagctcc actttgccaa tcatgattga ctccaccgag  1260
ccagaggtta ttcgcacagg ccttgagcac ttgggtggac gaagcatcgt taactccgtc  1320
aactttgaag acgcgatgg ccctgagtcc cgctaccagc gcatcatgaa actggtaaag  1380
cagcacggtg cggccgtggt tgcgctgacc attgatgagg aaggccaggc acgtaccgct  1440
gagcacaagg tgcgcattgc taaacgactg attgacgata tcaccggcag ctacggcctg  1500
gatatcaaag acatcgttgt ggactgcctg accttcccga tctctactgg ccaggaagaa  1560
accaggcgag atggcattga aaccatcgaa gccatccgcg agctgaagaa gctctaccca  1620
gaaatccaca ccaccctggg tctgtccaat atttccttcg gcctgaaccc tgctgcacgc  1680
caggttctta actctgtgtt cctcaatgag tgcattgagg ctggtctgga ctctgcgatt  1740
gcgcacagct ccaagatttt gccgatgaac cgcattgatg atcgccagcg cgaagtggcg  1800
ttggatatgg tctatgatcg ccgcaccgag gattacgatc cgctgcagga attcatgcag  1860
```

```
ctgtttgagg gcgtttctgc tgccgatgcc aaggatgctc gcgctgaaca gctggccgct    1920
atgcctttgt ttgagcgttt ggcacagcgc atcatcgacg gcgataagaa tggccttgag    1980
gatgatctgg aagcaggcat gaaggagaag tctcctattg cgatcatcaa cgaggacctt    2040
ctcaacggca tgaagaccgt gggtgagctg tttggttccg acagatgca gctgccattc     2100
gtgctgcaat cggcagaaac catgaaaact gcggtggcct atttggaacc gttcatggaa    2160
gaggaagcag aagctaccgg atctgcgcag cagagggca agggcaaaat cgtcgtggcc     2220
accgtcaagg gtgacgtgca cgatatcggc aagaacttgg tggacatcat tttgtccaac    2280
aacggttacg acgtggtgaa cttgggcatc aagcagccac tgtccgccat gttggaagca    2340
gcggaagaac acaaagcaga cgtcatcggc atgtcgggac ttcttgtgaa gtccaccgtg    2400
gtgatgaagg aaaaccttga ggagatgaac aacgccggcg catccaatta cccagtcatt    2460
ttgggtggcg ctgcgctgac gcgtacctac gtggaaaacg atctcaacga ggtgtacacc    2520
ggtgaggtgt actacgcccg tgatgctttc gagggcctgc gcctgatgga tgaggtgatg    2580
gcagaaaagc gtggtgaagg acttgatccc aactcaccag aagctattga gcaggcgaag    2640
aagaaggcgg aacgtaaggc tcgtaatgag cgttcccgca agattgccgc ggagcgtaaa    2700
gctaatgcgc ctcccgtgat tgttccggag cgttctgatg tctccaccga tactccaacc    2760
gcggcaccac cgttctgggg aacccgcatt gtcaagggtc tgcccttggc ggagttcttg    2820
ggcaaccttg atgagcgcgc cttgttcatg ggcagtggg gtctgaaatc cacccgcggc     2880
aacgagggtc caagctatga ggatttggtg aaactgaag gccgaccacg cctgcgctac     2940
tggctggatc gcctgaagtc tgagggcatt ttggaccacg tggccttggt gtatggctac    3000
ttcccagcgg tcgcggaagg cgatgacgtg gtgatcttgg aatccccgga tccacacgca    3060
gccgaacgca tgcgctttag cttcccacgc cagcagcgcg gcaggttctt gtgcatcgcg    3120
gatttcattc gcccacgcga gcaagctgtc aaggacggcc aagtggacgt catgccattc    3180
cagctggtca ccatgggtaa tcctattgct gatttcgcca acgagttgtt cgcagccaat    3240
gaataccgcg agtacttgga agttcacggc atcggcgtgc agctcaccga agcattggcc    3300
gagtactggc actcccgagt gcgcagcgaa ctcaagctga cgacggtgg atctgtcgct    3360
gattttgatc cagaagacaa gaccaagttc ttcgacctgg attaccgcgg cgcccgcttc    3420
tcctttggtt acggttcttg ccctgatctg gaagaccgcg caaagctggt ggaattgctc    3480
gagccaggcc gtatcggcgt ggagttgtcc gaggaactcc agctgcaccc agagcagtcc    3540
acagacgcgt ttgtgctcta ccacccagag gcaaagtact taacgtcta a              3591
```

<210> SEQ ID NO 170
<211> LENGTH: 1196
<212> TYPE: PRT
<213> ORGANISM: Corynebacterium glutamicum

<400> SEQUENCE: 170

```
Met Leu Ile Gly Asp Gly Ala Met Gly Thr Gln Leu Gln Gly Phe Asp
1               5                   10                  15

Leu Asp Val Glu Lys Asp Phe Leu Asp Leu Glu Gly Cys Asn Glu Ile
            20                  25                  30

Leu Asn Asp Thr Arg Pro Asp Val Leu Arg Gln Ile His Arg Ala Tyr
        35                  40                  45

Phe Glu Ala Gly Ala Asp Leu Val Glu Thr Asn Thr Phe Gly Cys Asn
    50                  55                  60

Leu Pro Asn Leu Ala Asp Tyr Asp Ile Ala Asp Arg Cys Arg Glu Leu
```

```
                65                  70                  75                  80
Ala Tyr Lys Gly Thr Ala Val Ala Arg Glu Val Ala Asp Glu Met Gly
                    85                  90                  95

Pro Gly Arg Asn Gly Met Arg Arg Phe Val Val Gly Ser Leu Gly Pro
                100                 105                 110

Gly Thr Lys Leu Pro Ser Leu Gly His Ala Pro Tyr Ala Asp Leu Arg
                115                 120                 125

Gly His Tyr Lys Glu Ala Ala Leu Gly Ile Ile Asp Gly Gly Gly Asp
            130                 135                 140

Ala Phe Leu Ile Glu Thr Ala Gln Asp Leu Leu Gln Val Lys Ala Ala
145                 150                 155                 160

Val His Gly Val Gln Asp Ala Met Ala Glu Leu Asp Thr Phe Leu Pro
                165                 170                 175

Ile Ile Cys His Val Thr Val Glu Thr Thr Gly Thr Met Leu Met Gly
            180                 185                 190

Ser Glu Ile Gly Ala Ala Leu Thr Ala Leu Gln Pro Leu Gly Ile Asp
            195                 200                 205

Met Ile Gly Leu Asn Cys Ala Thr Gly Pro Asp Glu Met Ser Glu His
        210                 215                 220

Leu Arg Tyr Leu Ser Lys His Ala Asp Ile Pro Val Ser Val Met Pro
225                 230                 235                 240

Asn Ala Gly Leu Pro Val Leu Gly Lys Asn Gly Ala Glu Tyr Pro Leu
                245                 250                 255

Glu Ala Glu Asp Leu Ala Gln Ala Leu Ala Gly Phe Val Ser Glu Tyr
                260                 265                 270

Gly Leu Ser Met Val Gly Gly Cys Cys Gly Thr Thr Pro Glu His Ile
            275                 280                 285

Arg Ala Val Arg Asp Ala Val Val Gly Val Pro Glu Gln Glu Thr Ser
            290                 295                 300

Thr Leu Thr Lys Ile Pro Ala Gly Pro Val Glu Gln Ala Ser Arg Glu
305                 310                 315                 320

Val Glu Lys Glu Asp Ser Val Ala Ser Leu Tyr Thr Ser Val Pro Leu
                325                 330                 335

Ser Gln Glu Thr Gly Ile Ser Met Ile Gly Glu Arg Thr Asn Ser Asn
                340                 345                 350

Gly Ser Lys Ala Phe Arg Glu Ala Met Leu Ser Gly Asp Trp Glu Lys
            355                 360                 365

Cys Val Asp Ile Ala Lys Gln Gln Thr Arg Asp Gly Ala His Met Leu
        370                 375                 380

Asp Leu Cys Val Asp Tyr Val Gly Arg Asp Gly Thr Ala Asp Met Ala
385                 390                 395                 400

Thr Leu Ala Ala Leu Leu Ala Thr Ser Ser Thr Leu Pro Ile Met Ile
                405                 410                 415

Asp Ser Thr Glu Pro Glu Val Ile Arg Thr Gly Leu Glu His Leu Gly
                420                 425                 430

Gly Arg Ser Ile Val Asn Ser Val Asn Phe Glu Asp Gly Asp Gly Pro
            435                 440                 445

Glu Ser Arg Tyr Gln Arg Ile Met Lys Leu Val Lys Gln His Gly Ala
        450                 455                 460

Ala Val Val Ala Leu Thr Ile Asp Glu Glu Gly Gln Ala Arg Thr Ala
465                 470                 475                 480

Glu His Lys Val Arg Ile Ala Lys Arg Leu Ile Asp Asp Ile Thr Gly
                485                 490                 495
```

```
Ser Tyr Gly Leu Asp Ile Lys Asp Ile Val Asp Cys Leu Thr Phe
            500                 505                 510

Pro Ile Ser Thr Gly Gln Glu Glu Thr Arg Arg Asp Gly Ile Glu Thr
            515                 520                 525

Ile Glu Ala Ile Arg Glu Leu Lys Lys Leu Tyr Pro Glu Ile His Thr
            530                 535                 540

Thr Leu Gly Leu Ser Asn Ile Ser Phe Gly Leu Asn Pro Ala Ala Arg
545                 550                 555                 560

Gln Val Leu Asn Ser Val Phe Leu Asn Glu Cys Ile Glu Ala Gly Leu
                565                 570                 575

Asp Ser Ala Ile Ala His Ser Ser Lys Ile Leu Pro Met Asn Arg Ile
            580                 585                 590

Asp Asp Arg Gln Arg Glu Val Ala Leu Asp Met Val Tyr Asp Arg Arg
            595                 600                 605

Thr Glu Asp Tyr Asp Pro Leu Gln Glu Phe Met Gln Leu Phe Glu Gly
            610                 615                 620

Val Ser Ala Ala Asp Ala Lys Asp Ala Arg Ala Glu Gln Leu Ala Ala
625                 630                 635                 640

Met Pro Leu Phe Glu Arg Leu Ala Gln Arg Ile Ile Asp Gly Asp Lys
                645                 650                 655

Asn Gly Leu Glu Asp Asp Leu Glu Ala Gly Met Lys Glu Lys Ser Pro
            660                 665                 670

Ile Ala Ile Ile Asn Glu Asp Leu Leu Asn Gly Met Lys Thr Val Gly
            675                 680                 685

Glu Leu Phe Gly Ser Gly Gln Met Gln Leu Pro Phe Val Leu Gln Ser
            690                 695                 700

Ala Glu Thr Met Lys Thr Ala Val Ala Tyr Leu Glu Pro Phe Met Glu
705                 710                 715                 720

Glu Glu Ala Glu Ala Thr Gly Ser Ala Gln Ala Glu Gly Lys Gly Lys
                725                 730                 735

Ile Val Val Ala Thr Val Lys Gly Asp Val His Asp Ile Gly Lys Asn
            740                 745                 750

Leu Val Asp Ile Ile Leu Ser Asn Asn Gly Tyr Asp Val Val Asn Leu
            755                 760                 765

Gly Ile Lys Gln Pro Leu Ser Ala Met Leu Glu Ala Ala Glu Glu His
            770                 775                 780

Lys Ala Asp Val Ile Gly Met Ser Gly Leu Leu Val Lys Ser Thr Val
785                 790                 795                 800

Val Met Lys Glu Asn Leu Glu Glu Met Asn Asn Ala Gly Ala Ser Asn
                805                 810                 815

Tyr Pro Val Ile Leu Gly Gly Ala Ala Leu Thr Arg Thr Tyr Val Glu
            820                 825                 830

Asn Asp Leu Asn Glu Val Tyr Thr Gly Glu Val Tyr Tyr Ala Arg Asp
            835                 840                 845

Ala Phe Glu Gly Leu Arg Leu Met Asp Glu Val Met Ala Glu Lys Arg
            850                 855                 860

Gly Glu Gly Leu Asp Pro Asn Ser Pro Glu Ala Ile Glu Gln Ala Lys
865                 870                 875                 880

Lys Lys Ala Glu Arg Lys Ala Arg Asn Glu Arg Ser Arg Lys Ile Ala
                885                 890                 895

Ala Glu Arg Lys Ala Asn Ala Ala Pro Val Ile Val Pro Glu Arg Ser
            900                 905                 910
```

```
Asp Val Ser Thr Asp Thr Pro Thr Ala Ala Pro Pro Phe Trp Gly Thr
            915                 920                 925

Arg Ile Val Lys Gly Leu Pro Leu Ala Glu Phe Leu Gly Asn Leu Asp
            930                 935                 940

Glu Arg Ala Leu Phe Met Gly Gln Trp Gly Leu Lys Ser Thr Arg Gly
945                 950                 955                 960

Asn Glu Gly Pro Ser Tyr Glu Asp Leu Val Glu Thr Glu Gly Arg Pro
                965                 970                 975

Arg Leu Arg Tyr Trp Leu Asp Arg Leu Lys Ser Glu Gly Ile Leu Asp
            980                 985                 990

His Val Ala Leu Val Tyr Gly Tyr  Phe Pro Ala Val Ala  Glu Gly Asp
            995                 1000                 1005

Asp Val  Val Ile Leu Glu Ser  Pro Asp Pro His Ala  Ala Glu Arg
    1010                 1015                 1020

Met Arg  Phe Ser Phe Pro Arg  Gln Gln Arg Gly Arg  Phe Leu Cys
    1025                 1030                 1035

Ile Ala  Asp Phe Ile Arg Pro  Arg Glu Gln Ala Val  Lys Asp Gly
    1040                 1045                 1050

Gln Val  Asp Val Met Pro Phe  Gln Leu Val Thr Met  Gly Asn Pro
    1055                 1060                 1065

Ile Ala  Asp Phe Ala Asn Glu  Leu Phe Ala Ala Asn  Glu Tyr Arg
    1070                 1075                 1080

Glu Tyr  Leu Glu Val His Gly  Ile Gly Val Gln Leu  Thr Glu Ala
    1085                 1090                 1095

Leu Ala  Glu Tyr Trp His Ser  Arg Val Arg Ser Glu  Leu Lys Leu
    1100                 1105                 1110

Asn Asp  Gly Gly Ser Val Ala  Asp Phe Asp Pro Glu  Asp Lys Thr
    1115                 1120                 1125

Lys Phe  Phe Asp Leu Asp Tyr  Arg Gly Ala Arg Phe  Ser Phe Gly
    1130                 1135                 1140

Tyr Gly  Ser Cys Pro Asp Leu  Glu Asp Arg Ala Lys  Leu Val Glu
    1145                 1150                 1155

Leu Leu  Glu Pro Gly Arg Ile  Gly Val Glu Leu Ser  Glu Glu Leu
    1160                 1165                 1170

Gln Leu  His Pro Glu Gln Ser  Thr Asp Ala Phe Val  Leu Tyr His
    1175                 1180                 1185

Pro Glu  Ala Lys Tyr Phe Asn  Val
    1190                 1195

<210> SEQ ID NO 171
<211> LENGTH: 981
<212> TYPE: DNA
<213> ORGANISM: Corynebacterium glutamicum

<400> SEQUENCE: 171
atgtccctaa cgaacatccc agcctcatct caatgggcaa ttagcgacgt tttgaagcgt       60
ccttcacccg gccgagtacc tttttctgtc gagtttatgc caccccgcga cgatgcagct      120
gaagagcgtc tttaccgcgc agcagaggtc ttccatgacc tcggtgcatc gtttgtctcc      180
gtgacttatg gtgctggcgg atcaacccgt gagagaacct cacgtattgc tcgacgatta      240
gcgaaacaac cgttgaccac tctggtgcac ctgaccctgg ttaaccacac tcgcgaagag      300
atgaaggcaa ttcttcggga ataccctaga gctgggatta aacaaacctgtt ggcgcttcga      360 ggagatccgc ctggagaccc attaggcgat tgggtgagca ccgatggagg actgaactat      420
```

```
gcctctgagc tcatcgatct tattaagtcc actcctgagt tccgggaatt cgacctcggt    480
atcgcctcct tccccgaagg gcatttccgg gcgaaaactc tagaagaaga caccaaatac    540
actctggcga agctgcgtgg aggggcagag tactccatca cgcagatgtt ctttgatgtg    600
gaagactacc tgcgacttcg tgatcgcctt gtcgctgcag accccattca tggtgcgaag    660
ccaatcattc ctggcatcat gcccattacg agcctgcggt ctgtgcgtcg acaggtcgaa    720
ctctctggtg ctcaattgcc gagccaacta gaagaatcac ttgttcgagc tgcaaacggc    780
aatgaagaag cgaacaaaga cgagatccgc aaggtgggca ttgaatattc caccaatatg    840
gcagagcgac tcattgccga aggtgcggaa gatctgcact tcatgacgct taacttcacc    900
cgtgcaaccc aagaagtgtt gtacaacctt ggcatggcgc ctgcttgggg agcagagcac    960
ggccaagacg cggtgcgtta a                                              981
```

<210> SEQ ID NO 172
<211> LENGTH: 326
<212> TYPE: PRT
<213> ORGANISM: Corynebacterium glutamicum

<400> SEQUENCE: 172

```
Met Ser Leu Thr Asn Ile Pro Ala Ser Ser Gln Trp Ala Ile Ser Asp
1               5                   10                  15

Val Leu Lys Arg Pro Ser Pro Gly Arg Val Pro Phe Ser Val Glu Phe
                20                  25                  30

Met Pro Pro Arg Asp Asp Ala Ala Glu Glu Arg Leu Tyr Arg Ala Ala
            35                  40                  45

Glu Val Phe His Asp Leu Gly Ala Ser Phe Val Ser Val Thr Tyr Gly
    50                  55                  60

Ala Gly Gly Ser Thr Arg Glu Arg Thr Ser Arg Ile Ala Arg Arg Leu
65                  70                  75                  80

Ala Lys Gln Pro Leu Thr Thr Leu Val His Leu Thr Leu Val Asn His
                85                  90                  95

Thr Arg Glu Glu Met Lys Ala Ile Leu Arg Glu Tyr Leu Glu Leu Gly
            100                 105                 110

Leu Thr Asn Leu Leu Ala Leu Arg Gly Asp Pro Pro Gly Asp Pro Leu
        115                 120                 125

Gly Asp Trp Val Ser Thr Asp Gly Gly Leu Asn Tyr Ala Ser Glu Leu
130                 135                 140

Ile Asp Leu Ile Lys Ser Thr Pro Glu Phe Arg Glu Phe Asp Leu Gly
145                 150                 155                 160

Ile Ala Ser Phe Pro Glu Gly His Phe Arg Ala Lys Thr Leu Glu Glu
                165                 170                 175

Asp Thr Lys Tyr Thr Leu Ala Lys Leu Arg Gly Gly Ala Glu Tyr Ser
            180                 185                 190

Ile Thr Gln Met Phe Phe Asp Val Glu Asp Tyr Leu Arg Leu Arg Asp
        195                 200                 205

Arg Leu Val Ala Ala Asp Pro Ile His Gly Ala Lys Pro Ile Ile Pro
    210                 215                 220

Gly Ile Met Pro Ile Thr Ser Leu Arg Ser Val Arg Arg Gln Val Glu
225                 230                 235                 240

Leu Ser Gly Ala Gln Leu Pro Ser Gln Leu Glu Ser Leu Val Arg
                245                 250                 255

Ala Ala Asn Gly Asn Glu Glu Ala Asn Lys Asp Glu Ile Arg Lys Val
            260                 265                 270
```

```
Gly Ile Glu Tyr Ser Thr Asn Met Ala Glu Arg Leu Ile Ala Glu Gly
            275                 280                 285

Ala Glu Asp Leu His Phe Met Thr Leu Asn Phe Thr Arg Ala Thr Gln
        290                 295                 300

Glu Val Leu Tyr Asn Leu Gly Met Ala Pro Ala Trp Gly Ala Glu His
305                 310                 315                 320

Gly Gln Asp Ala Val Arg
                325

<210> SEQ ID NO 173
<211> LENGTH: 1803
<212> TYPE: DNA
<213> ORGANISM: Saccharomyces cerevisiae

<400> SEQUENCE: 173
```

| | | | | | |
|---|---|---|---|---|---|
| atgaagatca | cagaaaaatt | agagcaacat | agacagacct | ctggcaagcc | cacttactca | 60 |
| ttcgagtact | tcgtcccgaa | gactacacaa | ggtgtacaga | acctgtatga | ccggatggac | 120 |
| cggatgtacg | aggcttcttt | gccccaattt | attgacatca | cctggaatgc | aggcggtgga | 180 |
| cggttgtcac | atctgtccac | ggacttggtt | gcgacagcgc | agtctgtgct | tggtttggaa | 240 |
| acgtgcatgc | accttacctg | caccaatatg | cccatttcga | tgattgacga | cgctttagaa | 300 |
| aacgcttatc | actccggttg | ccagaacatc | ctagcgctga | gaggagatcc | tcctagggac | 360 |
| gcagaaaact | ggactcccgt | tgaaggtggc | ttccagtatg | ccaaggactt | gattaagtat | 420 |
| atcaagtcca | agtacggtga | ccatttcgct | atcggcgttg | ccggctaccc | ggagtgccat | 480 |
| ccggagttgc | ctaacaaaga | cgtgaagctt | gatctcgagt | atttgaagca | gaagatcgac | 540 |
| gccggcggcg | acttcatcat | cactcagatg | ttttacgatg | ttgataattt | catcaactgg | 600 |
| tgttcccaag | ttagagctgc | gggcatggac | gtgcccatta | ttcccgggat | catgccgatc | 660 |
| actacctacg | cggccttctt | gagaagggcc | caatggggcc | aaatctccat | ccctcaacat | 720 |
| ttctcgtccc | gattggatcc | tatcaaggac | gatgacgagt | tggtccgtga | tatcggaact | 780 |
| aacttgatcg | tggaaatgtg | tcaaaaattg | ctcgacagtg | gttacgtttc | tcacttgcac | 840 |
| atctacacca | tgaacttgga | aaaagcgcct | ctcatgattc | tggaaagatt | gaacattcta | 900 |
| cctacggaat | cagagttcaa | tgcacatcca | ttggccgtgt | tgccatggag | aaaatctttg | 960 |
| aatccaaagc | gtaaaaacga | ggaagtcaga | cctatcttct | ggaagagaag | accttactcc | 1020 |
| tatgtcgcaa | gaacctctca | atgggccgtg | gacgaattcc | ccaacggtag | attcggtgat | 1080 |
| tcgtcttctc | ctgcgttcgg | tgacttggat | ctgtgtggtt | cagacttgat | caggcaatca | 1140 |
| gcgaacaaat | gtctcgaatt | atggtccacc | cctacttcca | tcaacgacgt | cgccttcttg | 1200 |
| gtcatcaact | acttgaatgg | aaacttgaag | tgtttacctt | ggagtgatat | ccccatcaat | 1260 |
| gatgaaataa | atccaatcaa | agcacacttg | attgagctga | ccagcattc | tatcatcact | 1320 |
| ataaactctc | aacctcaagt | caacggcatt | aggtccaatg | acaaaattca | tggttgggga | 1380 |
| cccaaggatg | gttacgttta | ccagaagcaa | tatttggaat | ttatgttgcc | caagactaag | 1440 |
| ttgcccaagt | tgattgacac | cttgaaaaac | aatgagttct | tgacctactt | cgccatcgac | 1500 |
| tctcaaggtg | acctgctaag | taatcatcca | gacaactcca | gtccaacgc | tgtgacttgg | 1560 |
| ggtatttcc | ccggcagaga | aattcttcaa | cctaccattg | tcgagaaaat | ttcgttctta | 1620 |
| gcgtggaagg | aggagttcta | tcatatcttg | aatgaatgga | actaaacat | gaataaatac | 1680 |
| gataaaccgc | atagtgccca | attcattcag | tccttgattg | acgattactg | cttggtcaat | 1740 |
| attgttgaca | atgactacat | ttctccagat | gatcaaatcc | attccatcct | actaagccta | 1800 | taa                                                          1803

<210> SEQ ID NO 174
<211> LENGTH: 600
<212> TYPE: PRT
<213> ORGANISM: Saccharomyces cerevisiae

<400> SEQUENCE: 174

Met Lys Ile Thr Glu Lys Leu Glu Gln His Arg Gln Thr Ser Gly Lys
1               5                   10                  15

Pro Thr Tyr Ser Phe Glu Tyr Phe Val Pro Lys Thr Thr Gln Gly Val
            20                  25                  30

Gln Asn Leu Tyr Asp Arg Met Asp Arg Met Tyr Glu Ala Ser Leu Pro
        35                  40                  45

Gln Phe Ile Asp Ile Thr Trp Asn Ala Gly Gly Arg Leu Ser His
    50                  55                  60

Leu Ser Thr Asp Leu Val Ala Thr Ala Gln Ser Val Leu Gly Leu Glu
65                  70                  75                  80

Thr Cys Met His Leu Thr Cys Thr Asn Met Pro Ile Ser Met Ile Asp
                85                  90                  95

Asp Ala Leu Glu Asn Ala Tyr His Ser Gly Cys Gln Asn Ile Leu Ala
            100                 105                 110

Leu Arg Gly Asp Pro Pro Arg Asp Ala Glu Asn Trp Thr Pro Val Glu
        115                 120                 125

Gly Gly Phe Gln Tyr Ala Lys Asp Leu Ile Lys Tyr Ile Lys Ser Lys
    130                 135                 140

Tyr Gly Asp His Phe Ala Ile Gly Val Ala Gly Tyr Pro Glu Cys His
145                 150                 155                 160

Pro Glu Leu Pro Asn Lys Asp Val Lys Leu Asp Leu Glu Tyr Leu Lys
                165                 170                 175

Gln Lys Ile Asp Ala Gly Gly Asp Phe Ile Ile Thr Gln Met Phe Tyr
            180                 185                 190

Asp Val Asp Asn Phe Ile Asn Trp Cys Ser Gln Val Arg Ala Ala Gly
        195                 200                 205

Met Asp Val Pro Ile Ile Pro Gly Ile Met Pro Ile Thr Thr Tyr Ala
    210                 215                 220

Ala Phe Leu Arg Arg Ala Gln Trp Gly Gln Ile Ser Ile Pro Gln His
225                 230                 235                 240

Phe Ser Ser Arg Leu Asp Pro Ile Lys Asp Asp Glu Leu Val Arg
                245                 250                 255

Asp Ile Gly Thr Asn Leu Ile Val Glu Met Cys Gln Lys Leu Leu Asp
            260                 265                 270

Ser Gly Tyr Val Ser His Leu His Ile Tyr Thr Met Asn Leu Glu Lys
        275                 280                 285

Ala Pro Leu Met Ile Leu Glu Arg Leu Asn Ile Leu Pro Thr Glu Ser
    290                 295                 300

Glu Phe Asn Ala His Pro Leu Ala Val Leu Pro Trp Arg Lys Ser Leu
305                 310                 315                 320

Asn Pro Lys Arg Lys Asn Glu Glu Val Arg Pro Ile Phe Trp Lys Arg
                325                 330                 335

Arg Pro Tyr Ser Tyr Val Ala Arg Thr Ser Gln Trp Ala Val Asp Glu
            340                 345                 350

Phe Pro Asn Gly Arg Phe Gly Asp Ser Ser Pro Ala Phe Gly Asp
        355                 360                 365

```
Leu Asp Leu Cys Gly Ser Asp Leu Ile Arg Gln Ser Ala Asn Lys Cys
    370                 375                 380

Leu Glu Leu Trp Ser Thr Pro Thr Ser Ile Asn Asp Val Ala Phe Leu
385                 390                 395                 400

Val Ile Asn Tyr Leu Asn Gly Asn Leu Lys Cys Leu Pro Trp Ser Asp
            405                 410                 415

Ile Pro Ile Asn Asp Glu Ile Asn Pro Ile Lys Ala His Leu Ile Glu
                420                 425                 430

Leu Asn Gln His Ser Ile Ile Thr Ile Asn Ser Gln Pro Gln Val Asn
            435                 440                 445

Gly Ile Arg Ser Asn Asp Lys Ile His Gly Trp Gly Pro Lys Asp Gly
    450                 455                 460

Tyr Val Tyr Gln Lys Gln Tyr Leu Glu Phe Met Leu Pro Lys Thr Lys
465                 470                 475                 480

Leu Pro Lys Leu Ile Asp Thr Leu Lys Asn Asn Glu Phe Leu Thr Tyr
            485                 490                 495

Phe Ala Ile Asp Ser Gln Gly Asp Leu Leu Ser Asn His Pro Asp Asn
                500                 505                 510

Ser Lys Ser Asn Ala Val Thr Trp Gly Ile Phe Pro Gly Arg Glu Ile
            515                 520                 525

Leu Gln Pro Thr Ile Val Glu Lys Ile Ser Phe Leu Ala Trp Lys Glu
    530                 535                 540

Glu Phe Tyr His Ile Leu Asn Glu Trp Lys Leu Asn Met Asn Lys Tyr
545                 550                 555                 560

Asp Lys Pro His Ser Ala Gln Phe Ile Gln Ser Leu Ile Asp Asp Tyr
            565                 570                 575

Cys Leu Val Asn Ile Val Asp Asn Asp Tyr Ile Ser Pro Asp Asp Gln
                580                 585                 590

Ile His Ser Ile Leu Leu Ser Leu
    595                 600

<210> SEQ ID NO 175
<211> LENGTH: 58
<212> TYPE: DNA
<213> ORGANISM: Artificial Sequence
<220> FEATURE:
<223> OTHER INFORMATION: primer

<400> SEQUENCE: 175
gcacttacct taactggtag gtgctttttt caattctgat tagaaaaact catcgagc      58

<210> SEQ ID NO 176
<211> LENGTH: 18
<212> TYPE: DNA
<213> ORGANISM: Artificial Sequence
<220> FEATURE:
<223> OTHER INFORMATION: primer

<400> SEQUENCE: 176
ggtacccggg gatcatgc                                                  18

<210> SEQ ID NO 177
<211> LENGTH: 40
<212> TYPE: DNA
<213> ORGANISM: Artificial Sequence
<220> FEATURE:
<223> OTHER INFORMATION: primer

<400> SEQUENCE: 177
```
cctacgttgc aggcgcaaat ggtacccggg gatcatgcta 40

<210> SEQ ID NO 178
<211> LENGTH: 55
<212> TYPE: DNA
<213> ORGANISM: Artificial Sequence
<220> FEATURE:
<223> OTHER INFORMATION: primer

<400> SEQUENCE: 178
cttaccttaa ctggtaggtg cttttttcaa ttctgattag aaaaactcat cgagc 55

<210> SEQ ID NO 179
<211> LENGTH: 2662
<212> TYPE: DNA
<213> ORGANISM: Artificial Sequence
<220> FEATURE:
<223> OTHER INFORMATION: DNA fragment

<400> SEQUENCE: 179
atttgcgcct gcaacgtagg ttgcgtggtg cttggagtgg tgaagctcca tgatttcagc 60
ggcgatgtgt ggctcgagag catcgtatgc gtagtcgagt tctgggagtt cgtatacagc 120
catgggtaaa aaatcctttc gtaggtttcc gcaccgagca tatacatctt ttgaaaatcc 180
gtcagatggc gcttcgcaaa agtacttggt gcgacacttc ccaatgatag gcctttttgt 240
tgatattgca acgaaatttt tcagccgacc tatttatcgg gtagtgggtc acaagcccgg 300
aataattggc agctaagtag ggttgaaggg cataaggctt cctcaatttt cgaaaggaac 360
attcctgtta tgactatcct gaaccatacc ctcggattcc cacgtgttgg ccttcgccgc 420
gagttgaaaa aggcccaaga gtcctactgg gctggcaatt caacccgcga agaactactt 480
gcggtcggca gggaactccg tgcgcgccac tgggaccagc agaaacaggc tgggatagat 540
ctgttgcccg tcggggattt cgcgtggtat gatcatgttt tgaccacctc actactcctg 600
ggtaatgtcc cggctcgcca ccagaataaa gacggttcag tcgatattga tacccttttt 660
cgcatcggtc gcggtcgagc cccaaccggt gagccggctg ccgccgcaga gatgaccaaa 720
tggttcaaca ctaattacca ttacatggtc cccgagttcg ttaagggaca acagttcaag 780
ctgacatgga cccagctatt ggacgaagtt gacgaagcgc tggcgctggg acataaagtt 840
aagcctgtgt tgcttggccc agtgacctgg ctctggctgg gtaaggtcaa gggcgagcaa 900
ttcgaccggt tgtccctgtt aaacgacatc ttgcccgtct accaacaagt gctcgctgag 960
ctggccaagc gtggtattga atgggtccaa attgatgagc cggctcttgt gcttgagtta 1020
ccgcaggctt ggctcgatgc gtacaagcca gcctacgatg ctctccaggg ccaggtgaaa 1080
ttgttgctga caacgtattt cgaggcgtc acgccaaacc tcgatacgat cactgcactc 1140
cccgtgcagg gcctgcacgt ggacctcgtg cacggtaaag atgatgtggc ggaacttcac 1200
aagcgactgc ctagtgattg gctgctaagt gccggattga tcaacggccg caacgtatgg 1260
cgagcagact tgaccgagaa atatgcccag attaaggaca tcgttggcaa gcgtgacctg 1320
tgggttgcct cttcttgttc ccttcttcac tcccccattg atctttccgt ggagacacgg 1380
ctcgacgctg aagtgaagtc gtggttcgca tttgctttac agaagtgcca tgaattggca 1440
ctcttgcgcg atgctctcaa tagcggtgac acggcagcgt tggctgagtg gtcagctcct 1500
atccaggcac gtcgtcactc caccagggtt cacaacccag ctgttgagaa cgcctggcg 1560
gccattactg cccaggatag ccaacgcgca aacgtttacg aagtgcgagc ggaagcgcag 1620

| | |
|---|---|
| cgagcaaggt ttaagctgcc agcatggccc accacaacta tcgggtcgtt tccacagacc | 1680 |
| accgaaattc gtacgctgag attagacttc aagaaaggga acctggatgc gaacaattac | 1740 |
| aggactggca tcgcggaaca catcaagcaa gctattgttg aacaggaacg cttgggactc | 1800 |
| gatgtactcg tacacggtga ggccgaacgc aacgacatgg tagagtattt cggtgaacat | 1860 |
| cttgatggtt ttgttttta c acaaaacggc tgggtccagt cctacggctc ccgatgcgta | 1920 |
| aagccaccta ttgttatcgg cgacatttct cgtcctgccc cgatcaccgt ggaatgggcg | 1980 |
| aaatacgccc aatctctgac cgataagcca gtcaaaggca tgctaaccgg accggtcact | 2040 |
| atcctgtgct ggtcgtttcc tcgtgaagat gtctcgcggg aaaccatcgc aaagcaaatc | 2100 |
| gcattggccc tgcgtgacga agtggcagac ctcgaagctg ctggcattgg catcatccag | 2160 |
| atcgatgagc cagcattgcg cgagggcctc ccgcttcgcc gcagcgactg ggatgcctat | 2220 |
| ctacagtggg gcgttgaggc attccgcatc aacgcagctg ttgcgaaaga tgatacgcaa | 2280 |
| atccacactc acatgtgtta ctgcgagttc aatgacatca tggactccat tgctgcactg | 2340 |
| gatgccgacg tcattaccat tgaaaccagt cgctctgata tggaactgct tgaaagcttc | 2400 |
| gaagagtttg attaccctaa cgaaatcgga ccgggagtgt atgacatcca ttccccaaat | 2460 |
| gtgccttcgg tggagtggat tgaagccctt ctcaaaaaag ccgcaaaacg gattcccgcg | 2520 |
| gaacggctct gggtgaaccc agattgtggc cttaagaccc gcggttggcc agaaacccgt | 2580 |
| gccgcccttg cgaacatggt gcaagctgca caaaaacctcc gccgtggcta gcgcacttac | 2640 |
| cttaactggt aggtgctttt tt | 2662 |

<210> SEQ ID NO 180
<211> LENGTH: 3991
<212> TYPE: DNA
<213> ORGANISM: Artificial Sequence
<220> FEATURE:
<223> OTHER INFORMATION: DNA fragment

<400> SEQUENCE: 180

| | |
|---|---|
| atttgcgcct gcaacgtagg ttgcgtggtg cttggagtgg tgaagctcca tgatttcagc | 60 |
| ggcgatgtgt ggctcgagag catcgtatgc gtagtcgagt tctgggagtt cgtatacagc | 120 |
| catgggtaaa aaatcctttc gtaggtttcc gcaccgagca tatacatctt ttgaaaatcc | 180 |
| gtcagatggc gcttcgcaaa agtacttggt gcgacacttc ccaatgatag gccttttgt | 240 |
| tgatattgca acgaaatttt tcagccgacc tatttatcgg gtagtgggtc acaagcccgg | 300 |
| aataattggc agctaagtag ggttgaaggg cataaggctt cctcaatttt cgaaaggaac | 360 |
| attcctgtta tgttgattgg tgatggggca atgggaactc aacttcaagg ctttgatcta | 420 |
| gatgtagaaa aagatttctt agatcttgag ggttgcaacg aaatcttgaa cgatacacgt | 480 |
| cccgatgtct tgcgccaaat tcaccgcgca tacttcgagg ctggcgccga cctcgtcgaa | 540 |
| actaatacat tcggttgcaa tttaccaaac ctcgctgatt acgatatcgc tgatcgctgt | 600 |
| agggaactag cttacaaggg cactgccgtg gcacgcgaag tggctgatga atgggtccg | 660 |
| ggacgaaacg ggatgcgccg ttttgttgtt ggctcgctgg gtccgggcac gaagctgccg | 720 |
| tcattgggac atgcgccata cgccgacttg agagggcact ataaggaagc cgcttttggga | 780 |
| atcatcgacg gcggtggcga cgcattcctt attgaaacgg cccaggatct gctccaagtg | 840 |
| aaagctgcag tacacggtgt acaggacgcg atggccgagt tggataccct ttttgccaatt | 900 |
| atctgccatg taaccgtgga gactaccggg accatgttga tgggctctga aattggcgct | 960 |
| gcattgacag cactccaacc actcgggatc gacatgatcg gtcttaactg cgccaccggc | 1020 |

```
cctgatgaga tgtctgaaca cttgcgttat ctgtccaaac acgccgacat cccggttagt    1080
gtgatgccaa acgccggact tccggtcctg gggaaaaatg gcgcagagta cccgctcgaa    1140
gccgaagatc ttgcgcaagc actagctgga ttcgtgagcg agtatggtct ttccatggtc    1200
ggcggatgct gtggaaccac cccagagcac atccgcgcag tgcgcgatgc agtcgttggc    1260
gttccagaac aggaaacctc cacgctcacc aagattccag ctggcccagt ggaacaagca    1320
tcccgcgaag ttgagaaaga ggactccgtg gcatccctgt acacctcagt tcctttgtca    1380
caagagactg gtatcagtat gatcggcgaa cgtaccaact caaacggcag caaagcgttc    1440
cgcgaagcga tgctgtccgg tgattgggag aagtgtgtgg atatcgccaa gcaacagacc    1500
cgcgatggtg ctcacatgct cgatctctgt gttgattatg tgggtcgcga cggaaccgct    1560
gatatgcgca ccctggctgc gcttttagcg acctcgtcaa ccctcccgat catgatcgat    1620
tctaccgagc ctgaagtgat tcgcaccggt ctggagcact gggtgggcg ttctatcgtt    1680 aactccgtga atttcgaaga tggcgacgga ccagaatccc ggtaccagcg tatcatgaag    1740
cttgtgaaac agcacggtgc cgcagtggtg gccctcacta tcgatgaaga aggccaggct    1800
cgcactgccg agcataaagt ccgcattgct aagcgactta ttgacgacat cacaggctcc    1860
tatggcctgg atatcaaaga cattgtagtt gactgtctca cctttccaat tctaccgga    1920 caagaagaga ctcggcgtga tggtattgaa accattgagg caatccgtga gctgaagaaa    1980
ctttaccccg aaatccatac cactttgggc ctgtcaaaca tttcgttcgg actaaaccca    2040
gccgcacgcc aggtccttaa ctctgttttt ttgaacgagt gcatcgaggc cggcttggat    2100
tccgccatcg cgcattcttc taagattctg ccaatgaatc gcattgacga ccgccagcga    2160
gaagtcgcac ttgacatggt ctacgacaga cgcacagagg attacgaccc ccttcaagag    2220
ttcatgcagc tgttcgaggg tgtgtcagcg gcagacgcta aggacgcacg cgccgaacag    2280
cttgcggcca tgcctctctt cgaaaggtta gcacagcgca ttatcgacgg tgataaaaat    2340
ggcctcgaag atgatctcga agcgggaatg aaagagaagt cccccatcgc aatcatcaac    2400
gaagatcttc tgaatggaat gaaaacggtt ggcgaactgt ttggttcggg tcaaatgcag    2460
ctgccgttcg tattgcagag tgcggaaaca atgaaaactg cggttgcata tctggaacct    2520
tttatggaag aagaagctga ggcaaccggt tccgctcagg ctgagggcaa aggtaagatc    2580
gttgttgcaa ctgtcaaggg cgacgtccat gacatcggaa agaatctcgt cgatatcatc    2640
ctaagcaata acggctacga cgtcgtgaac ctgggcatta acagcctct ttccgctatg    2700 ctagaagccg cagaagaaca caaagccgac gtgattgaa tgtccggcct cctggtcaag    2760
agcacggtcg tgatgaaaga aaatctggaa gaatgaaca acgccggagc gtccaattac    2820
ccggttattc tgggcggagc ggccctgacg cgcacctacg tggagaacga tctcaacgaa    2880
gtgtataccg gcgaggtgta ctacgcccgc gatgcgttcg agggattgcg actaatggat    2940
gaggttatgg cagaaaagcg tggcgagggc ctggatccaa atagtcccga ggctattgaa    3000
caagctaaga aaaagctga acgcaaggct cggaacgagc ggtcgcggaa gatcgccgca    3060
gagcgcaagg caaacgctgc gcccgtgatc gtacctgagc ggagcgacgt gtcgaccgac    3120
actcctacag cagcaccgcc attctggggc acccgcatcg tcaaaggctt gccgctggcc    3180
gaattccttg caacctaga cgagagggca ttgtttatgg ggcagtgggg cttgaaatct    3240
acgcggggta atgagggtcc atcgtatgag gatctcgtcg aaaccgaagg ccgaccacga    3300
ttgcgttact ggctggatcg cctcaagagc gaaggcatac ttgaccacgt ggcgttggtt    3360
```

| | |
|---|---|
| tacggttact ttcccgcggt agctgagggc gacgatgttg tcatcttaga gtctccagac | 3420 |
| cctcacgctg cagaacgaat gcgcttctcc ttccccgtc aacagcgcgg tcgctttctg | 3480 |
| tgcattgccg atttcattcg tccccgagag caagcggtga aggacggtca ggttgacgtg | 3540 |
| atgccgttcc agctcgtcac catgggaaat cctattgccg acttcgcaaa tgaactcttt | 3600 |
| gctgcaaacg aataccgtga gtatctcgaa gtccatggaa ttggcgtgca gttgaccgaa | 3660 |
| gcgctcgccg agtactggca cagccgcgtc cgctccgagc tgaagcttaa tgatggcgga | 3720 |
| agcgtggcgg acttcgaccc agaggacaag accaagtttt tcgatctcga ttaccgtggc | 3780 |
| gcacgttttt ccttcggtta tggctcctgc cctgacctcg aagatcgcgc caaactggtt | 3840 |
| gaactattag agccaggtcg aatcggtgta gaactctccg aggaattgca gctccatcct | 3900 |
| gaacagtcta ccgatgcttt tgttctgtat caccctgagg ccaagtactt caacgtgtag | 3960 |
| cgcacttacc ttaactggta ggtgcttttt t | 3991 |

<210> SEQ ID NO 181
<211> LENGTH: 1381
<212> TYPE: DNA
<213> ORGANISM: Artificial Sequence
<220> FEATURE:
<223> OTHER INFORMATION: DNA fragment

<400> SEQUENCE: 181

| | |
|---|---|
| atttgcgcct gcaacgtagg ttgcgtggtg cttggagtgg tgaagctcca tgatttcagc | 60 |
| ggcgatgtgt ggctcgagag catcgtatgc gtagtcgagt tctgggagtt cgtatacagc | 120 |
| catgggtaaa aaatccttc gtaggtttcc gcaccgagca tatacatctt ttgaaaatcc | 180 |
| gtcagatggc gcttcgcaaa agtacttggt gcgacacttc ccaatgatag gccttttgt | 240 |
| tgatattgca acgaaatttt tcagccgacc tatttatcgg gtagtgggtc acaagcccgg | 300 |
| aataattggc agctaagtag ggttgaaggg cataaggctt cctcaatttt cgaaaggaac | 360 |
| attcctgtta tgtcccttac caatattcca gcatcttcac agtgggcaat ctctgacgtt | 420 |
| ctgaagcgac cgagcccggg acgcgtgcct ttctctgtcg agtttatgcc accacgcgac | 480 |
| gatgctgccg aggaacgctt gtaccgtgcc gctgaagtat tccatgatct gggcgcctca | 540 |
| ttcgtttcgg tgacctacgg tgcgggtggc tctacgcgcg agcggacatc ccgcattgct | 600 |
| cgccgcctcg caaaacagcc cctcaccacc ctggtgcact taaccctcgt caatcatacc | 660 |
| agagaagaaa tgaaagcgat tcttcgggaa taccttgaat tgggcctaac gaatctgctg | 720 |
| gccctccgtg gtgatccacc gggcgatcct cttggagact gggtgtccac cgacggtggc | 780 |
| ctgaactatg cgtccgaatt gatcgacctg atcaagagca cacctgaatt tcgtgagttt | 840 |
| gatctcggta ttgcaagttt tcccgaaggc cacttccgtg caaagactct cgaagaggat | 900 |
| actaaataca ctttggcgaa gttgaggggc ggagcagaat acagtatcac tcagatgttc | 960 |
| ttcgacgtcg aggactactt gcgcctccga gatcgattgg tggccgctga ccctatccac | 1020 |
| ggtgcgaagc caatcatccc aggcatcatg cccattacgt cgctgcgtag cgtcaggcgc | 1080 |
| caggtagagc tttccggggc tcaactcccg tcgcagcttg aagagtccct ggtgcgagca | 1140 |
| gcgaacggga acgaagaagc aaacaaagat gaaatccgta aggttggcat cgagtattcc | 1200 |
| accaacatgg ccgagcgcct gattgccgag ggtgctgaag atctacactt tatgaccttg | 1260 |
| aacttcaccc gtgcgacaca agaggtcctg tataacttag gcatggctcc cgcctgggga | 1320 |
| gcagagcacg tcaagatgc tgttcgctag cgcacttacc ttaactggta ggtgcttttt | 1380 |
| t | 1381 |

<210> SEQ ID NO 182
<211> LENGTH: 2203
<212> TYPE: DNA
<213> ORGANISM: Artificial Sequence
<220> FEATURE:
<223> OTHER INFORMATION: DNA fragment

<400> SEQUENCE: 182

| | | | | | |
|---|---|---|---|---|---|
| atttgcgcct | gcaacgtagg | ttgcgtggtg | cttggagtgg | tgaagctcca | tgatttcagc | 60 |
| ggcgatgtgt | ggctcgagag | catcgtatgc | gtagtcgagt | tctgggagtt | cgtatacagc | 120 |
| catgggtaaa | aaatcctttc | gtaggtttcc | gcaccgagca | tatacatctt | ttgaaaatcc | 180 |
| gtcagatggc | gcttcgcaaa | agtacttggt | gcgacacttc | ccaatgatag | gcctttttgt | 240 |
| tgatattgca | acgaaatttt | tcagccgacc | tatttatcgg | gtagtgggtc | acaagcccgg | 300 |
| aataattggc | agctaagtag | ggttgaaggg | cataaggctt | cctcaatttt | cgaaaggaac | 360 |
| attcctgtta | tgaaaatcac | cgaaaagctt | gaacagcatc | gtcaaacctc | aggaaagcca | 420 |
| acttactctt | ttgagtactt | cgttccaaag | accacacagg | gtgtgcaaaa | cctgtacgat | 480 |
| cgtatggatc | gcatgtacga | agcttctttg | ccccagttta | ttgatatcac | ctggaatgcc | 540 |
| ggtggcggac | gcctatcgca | cctcagcact | gacctcgtcg | cgacagcaca | gtccgtgctg | 600 |
| ggcctcgaaa | cgtgcatgca | cctgacgtgt | acgaacatgc | ccatctcgat | gatcgacgat | 660 |
| gcgctcgaaa | atgcctatca | ctccggctgc | cagaacatcc | tggcactccg | tggcgaccca | 720 |
| cctcgggatg | cagagaactg | gaccoctgtc | gagggtggat | tccagtatgc | caaagatttg | 780 |
| attaagtaca | tcaagagcaa | atacggtgac | cacttcgcca | tcggtgtcgc | cggttaccca | 840 |
| gagtgccacc | ctgagttacc | gaacaaagat | gtgaagcttg | atttggaata | cctcaaacaa | 900 |
| aagattgatg | ctggcgggga | cttcatcatt | acccaaatgt | tctatgatgt | tgataacttc | 960 |
| atcaattggt | gttcacaagt | ccgcgctgcg | ggaatggacg | tcccaatcat | cccgggcatt | 1020 |
| atgcccatta | cgacctatgc | agcgttcctt | aggcgcgcac | agtggggtca | gatttccatt | 1080 |
| cctcagcatt | tttcttctcg | cctcgatccc | atcaaagacg | acgatgaact | tgtccgcgat | 1140 |
| atcggaacaa | acttgattgt | agagatgtgc | cagaaattgc | tggattctgg | ctacgttagc | 1200 |
| catttgcaca | tctataccat | gaatttggaa | aaagccccgc | tcatgattct | ggagcgactg | 1260 |
| aatatcttgc | caactgagtc | cgagtttaac | gctcacccgc | tagctgtcct | tccatggcga | 1320 |
| aagtctctca | accccaagcg | taaaaacgaa | gaggttcgcc | ctatcttctg | gaagcgtcgt | 1380 |
| ccatacagtt | acgtggcgcg | cacctcgcaa | tgggctgttg | atgaatttcc | caacggccgg | 1440 |
| tttggtgatt | cctcctcccc | agcattcggc | gatttggatc | tgtgcggctc | agatctgatc | 1500 |
| cgccaaagcg | ctaacaagtg | ccttgagtta | tggtcaaccc | caaccagtat | taacgacgtg | 1560 |
| gcatttcttg | tgatcaatta | cctgaacggc | aacctcaagt | gtctcccgtg | gtccgatatt | 1620 |
| ccgatcaacg | acgaaattaa | tcctatcaaa | gcccatctga | ttgaactgaa | tcagcactcc | 1680 |
| atcatcacca | tcaattcgca | accccaggta | aacggcatcc | gctctaatga | caagatccac | 1740 |
| gggtggggtc | caaagatgg | atatgtgtac | cagaaacaat | acctagagtt | tatgctccct | 1800 |
| aagaccaagc | ttcctaagct | tattgacacc | ctgaagaata | acgaattcct | cacttacttc | 1860 |
| gcaattgatt | cccagggcga | cctgttatca | aatcatccag | ataacagcaa | agtaacgca | 1920 |
| gtaacttggg | gtatcttccc | cggacgagag | attctacaac | cgaccatcgt | ggaaaagatc | 1980 |
| tctttcctgg | cgtggaagga | agaattctat | cacattctga | acgaatggaa | gcttaacatg | 2040 |

```
aacaaatacg acaagccgca ctcggcgcaa ttcatccaga gccttatcga cgactattgt    2100
ttggtgaaca ttgttgacaa cgactatatc tccccagatg accagatcca ctccatcctg    2160
ttgtccttgt agcgcactta ccttaactgg taggtgcttt ttt                      2203
```

<210> SEQ ID NO 183
<211> LENGTH: 1050
<212> TYPE: DNA
<213> ORGANISM: Corynebacterium glutamicum

<400> SEQUENCE: 183

```
ttggtggagg tgaataaatg ccagaggcag tcccaacaaa acactctcat cacactaaga      60
tacccaggca tgtccctaac gaacatccca gcctcatctc aatgggcaat tagcgacgtt     120
ttgaagcgtc cttcacccgg ccgagtacct ttttctgtcg agtttatgcc accccgcgat     180
gatgcagctg aagagcgtct ttaccgagca gcagaggtct tccatgacct cggtgcatcg     240
tttgtctccg tgacttatgg tgctggcgga tcaacccgtg agagaacctc acgtattgct     300
cgacgattag cgaaacaacc gttgaccact ctggtgcacc tgaccctggt taaccacact     360
cgcgaagaga tgaaggcaat tcttcgggaa tacctagagc tgggattaac aaacctgttg     420
gcgcttcgag gagatccgcc tggagaccca ttaggcgatt gggtgagcac cgatggagga     480
ctgaactacg cctctgagct catcgatctt attaagtcca ctcctgagtt ccgggaattc     540
gacctcggta tcgcctcctt ccccgaaggg catttccggg cgaaaactct agaagaagac     600
accaaataca ctctggcgaa gctgcgtgga ggtgcagagt actccatcac gcagatgttc     660
tttgatgtgg aagactacct gcgacttcgt gatcgccttg tcgctgcaga ccccattcat     720
ggcgcgaagc caatcattcc tggcatcatg cccattacga gcctgcggtc tgtgcgtcga     780
caggtcgaac tctctggtgc tcaattgccg agccaactag aagaatcact tgttcgagct     840
gcaaacggca atgaagaagc gaacaaagac gagatccgca aggtgggcat tgaatattcc     900
accaatatgg cagagcgact cattgccgaa ggtgcggaag atctgcactt catgacgctt     960
aacttcaccc gtgcaaccca agaagtgttg tacaaccttg gcatggcgcc tgcttgggga    1020
gcagagcacg gccaagacgc ggtgcgttaa                                     1050
```

<210> SEQ ID NO 184
<211> LENGTH: 349
<212> TYPE: PRT
<213> ORGANISM: Corynebacterium glutamicum

<400> SEQUENCE: 184

```
Leu Val Glu Val Asn Lys Cys Gln Arg Gln Ser Gln Gln Asn Thr Leu
1               5                   10                  15

Ile Thr Leu Arg Tyr Pro Gly Met Ser Leu Thr Asn Ile Pro Ala Ser
            20                  25                  30

Ser Gln Trp Ala Ile Ser Asp Val Leu Lys Arg Pro Ser Pro Gly Arg
        35                  40                  45

Val Pro Phe Ser Val Glu Phe Met Pro Pro Arg Asp Asp Ala Ala Glu
    50                  55                  60

Glu Arg Leu Tyr Arg Ala Ala Glu Val Phe His Asp Leu Gly Ala Ser
65                  70                  75                  80

Phe Val Ser Val Thr Tyr Gly Ala Gly Gly Ser Thr Arg Glu Arg Thr
                85                  90                  95

Ser Arg Ile Ala Arg Arg Leu Ala Lys Gln Pro Leu Thr Thr Leu Val
            100                 105                 110
```

```
His Leu Thr Leu Val Asn His Thr Arg Glu Glu Met Lys Ala Ile Leu
        115                 120                 125
Arg Glu Tyr Leu Glu Leu Gly Leu Thr Asn Leu Leu Ala Leu Arg Gly
        130                 135                 140
Asp Pro Pro Gly Asp Pro Leu Gly Asp Trp Val Ser Thr Asp Gly Gly
145                 150                 155                 160
Leu Asn Tyr Ala Ser Glu Leu Ile Asp Leu Ile Lys Ser Thr Pro Glu
                165                 170                 175
Phe Arg Glu Phe Asp Leu Gly Ile Ala Ser Phe Pro Glu Gly His Phe
                180                 185                 190
Arg Ala Lys Thr Leu Glu Glu Asp Thr Lys Tyr Thr Leu Ala Lys Leu
        195                 200                 205
Arg Gly Gly Ala Glu Tyr Ser Ile Thr Gln Met Phe Phe Asp Val Glu
        210                 215                 220
Asp Tyr Leu Arg Leu Arg Asp Arg Leu Val Ala Ala Asp Pro Ile His
225                 230                 235                 240
Gly Ala Lys Pro Ile Ile Pro Gly Ile Met Pro Ile Thr Ser Leu Arg
                245                 250                 255
Ser Val Arg Arg Gln Val Glu Leu Ser Gly Ala Gln Leu Pro Ser Gln
                260                 265                 270
Leu Glu Glu Ser Leu Val Arg Ala Ala Asn Gly Asn Glu Glu Ala Asn
        275                 280                 285
Lys Asp Glu Ile Arg Lys Val Gly Ile Glu Tyr Ser Thr Asn Met Ala
        290                 295                 300
Glu Arg Leu Ile Ala Glu Gly Ala Glu Asp Leu His Phe Met Thr Leu
305                 310                 315                 320
Asn Phe Thr Arg Ala Thr Gln Glu Val Leu Tyr Asn Leu Gly Met Ala
                325                 330                 335
Pro Ala Trp Gly Ala Glu His Gly Gln Asp Ala Val Arg
                340                 345
```

METHOD FOR PRODUCING OBJECTIVE SUBSTANCE

This application claims priority under 35 U.S.C. § 119 to U.S. Provisional Patent Application No. 62/591,910, filed Nov. 29, 2017, the entirety of which is incorporated by reference herein. Also, the Sequence Listing filed electronically herewith is hereby incorporated by reference (File name: 2018-11-26T_US-571_Seq_List; File size: 317 KB; Date recorded: 2018-11-26).

BACKGROUND OF THE INVENTION

Field of the Invention

The present invention relates to a method for producing an objective substance such as vanillin and vanillic acid by using a microorganism.

Brief Description of the Related Art

Vanillin is a major ingredient that provides the smell of vanilla, and is used as an aromatic in foods, drinks, perfumes, and so forth. Vanillin is usually produced by extraction from natural products or by chemical synthesis.

Bioengineering techniques have also been tried in production of vanillin. For example, vanillin has been tried to be produced by using various microorganisms and raw materials, such as eugenol, isoeugenol, ferulic acid, glucose, vanillic acid, coconut husk, or the like (Kaur B. and Chakraborty D., Biotechnological and molecular approaches for vanillin production: a review. Appl Biochem Biotechnol. 2013 February; 169(4):1353-72). In addition, other methods for producing vanillin using bioengineering techniques include producing vanillin as a glycoside (WO2013/022881 and WO2004/111254), producing vanillin from ferulic acid by using vanillin synthase (JP2015-535181), producing vanillic acid by fermentation of *Escherichia coli* and then enzymatically converting vanillic acid into vanillin (U.S. Pat. No. 6,372,461).

S-adenosylmethionine (SAM) is regenerated via the SAM cycle, which is a methylation cycle. S-adenosyl-L-homocysteine hydrolase, methionine synthase, methionine adenosyltransferase, and 5,10-methylenetetrahydrofolate reductase are all involved in the SAM cycle.

S-adenosyl-L-homocysteine hydrolase catalyzes the hydrolysis of S-adenosyl-L-homocysteine (SAH) to generate L-homocysteine and adenosine. Examples of the S-adenosyl-L-homocysteine hydrolase include an SahH protein, which is encoded by an sahH gene.

Methionine synthase catalyzes the methylation of L-homocysteine to generate L-methionine in the presence of a methyl group donor. Examples of the methionine synthase include MetE and MetH proteins, which are encoded by metE and metH genes, respectively.

Methionine adenosyltransferase catalyzes the conversion of L-methionine into SAM in the presence of ATP. Examples of the methionine adenosyltransferase include an MetK protein, which is encoded by an metK gene.

5,10-methylenetetrahydrofolate reductase catalyzes the reduction of 5,10-methylenetetrahydrofolate to generate 5-methyltetrahydrofolate (5-MTHF) in the presence of an electron donor. Examples of the 5,10-methylenetetrahydrofolate reductase include an MetF protein, which is encoded by an metF gene.

SUMMARY OF THE INVENTION

The present invention describes a novel technique for improving production of an objective substance such as vanillin and vanillic acid, and thereby provides a method for efficiently producing the objective substance.

It is an aspect of the present invention that a microorganism is able to produce an objective substance such as vanillin and vanillic acid in a significantly improved manner by modifying the microorganism so that the activity of an enzyme involved in SAM cycle, such as a SAM cycle enzyme, is increased.

That is, it is an aspect of the present invention to provide a method for producing an objective substance, the method comprising:

producing the objective substance by using a microorganism having an ability to produce the objective substance, wherein the microorganism has been modified so that the activity of an S-adenosylmethionine cycle enzyme is increased as compared with a non-modified strain, wherein the S-adenosylmethionine cycle enzyme is selected from the group consisting of methionine adenosyltransferase, methionine synthase, 5,10-methylenetetrahydrofolate reductase, and combinations thereof, and wherein the objective substance is selected from the group consisting of:

(X) metabolites the biosynthesis of which requires S-adenosylmethionine;

(Y) L-methionine; and (Z) combinations thereof, provided that the objective substance is selected from the metabolites (X) when only the activity of methionine adenosyltransferase is increased.

It is a further aspect of the present invention to provide the method as described above, wherein said producing comprises:

cultivating the microorganism in a culture medium containing a carbon source to produce and accumulate the objective substance in the culture medium.

It is a further aspect of the present invention to provide the method as described above, wherein said producing comprises:

converting a precursor of the objective substance into the objective substance by using the microorganism.

It is a further aspect of the present invention to provide the method as described above, wherein said using comprises:

cultivating the microorganism in a culture medium containing the precursor to produce and accumulate the objective substance in the culture medium.

It is a further aspect of the present invention to provide the method as described above, wherein said converting comprises:

allowing cells of the microorganism to act on the precursor in a reaction mixture to produce and accumulate the objective substance in the reaction mixture.

It is a further aspect of the present invention to provide the method as described above, wherein the cells are cells present in a culture broth of the microorganism, cells collected from the culture broth, cells present in a processed product of the culture broth, cells present in a processed product of the collected cells, or a combination of these.

It is a further aspect of the present invention to provide the method as described above, wherein the precursor is selected from the group consisting of protocatechuic acid, protocatechualdehyde, L-tryptophan, L-histidine, L-phenylalanine, L-tyrosine, L-arginine, L-ornithine, glycine, and combinations thereof.

It is a further aspect of the present invention to provide the method as described above, the method further comprising collecting the objective substance.

It is a further aspect of the present invention to provide the method as described above, wherein the methionine adenosyltransferase is encoded by an metK gene, the methionine synthase is encoded by an metH gene and/or an metE gene, and the 5,10-methylenetetrahydrofolate reductase is encoded by an metF gene.

It is a further aspect of the present invention to provide the method as described above, wherein:

the metK gene encodes a protein selected from the group consisting of:
(1a) a protein comprising the amino acid sequence of SEQ ID NO: 162,
(1b) a protein comprising the amino acid sequence of SEQ ID NO: 162 that includes substitution, deletion, insertion, and/or addition of 1 to 10 amino acid residues, and wherein said protein has methionine adenosyltransferase activity, and
(1c) a protein comprising an amino acid sequence having an identity of 90% or higher to the amino acid sequence of SEQ ID NO: 162, and wherein said protein has methionine adenosyltransferase activity;
the metH gene encodes a protein selected from the group consisting of:
(2a) a protein comprising the amino acid sequence of SEQ ID NO: 168 or 170,
(2b) a protein comprising the amino acid sequence of SEQ ID NO: 168 or 170 that includes substitution, deletion, insertion, and/or addition of 1 to 10 amino acid residues, and wherein said protein has methionine synthase activity, and
(2c) a protein comprising an amino acid sequence having an identity of 90% or higher to the amino acid sequence of SEQ ID NO: 168 or 170, and wherein said protein has methionine synthase activity;
the metE gene encodes a protein selected from the group consisting of:
(3a) a protein comprising the amino acid sequence of SEQ ID NO: 166,
(3b) a protein comprising the amino acid sequence of SEQ ID NO: 166 that includes substitution, deletion, insertion, and/or addition of 1 to 10 amino acid residues, and wherein said protein has methionine synthase activity, and
(3c) a protein comprising an amino acid sequence showing an identity of 90% or higher to the amino acid sequence of SEQ ID NO: 166, and wherein said protein has methionine synthase activity; and
the metF gene encodes a protein selected from the group consisting of:
(4a) a protein comprising the amino acid sequence of SEQ ID NO: 172, 174, or 184,
(4b) a protein comprising the amino acid sequence of SEQ ID NO: 172, 174, or 184 that includes substitution, deletion, insertion, and/or addition of 1 to 10 amino acid residues, and wherein said protein has 5,10-methylenetetrahydrofolate reductase activity, and
(4c) a protein comprising an amino acid sequence having an identity of 90% or higher to the amino acid sequence of SEQ ID NO: 172, 174, or 184, and wherein said protein has 5,10-methylenetetrahydrofolate reductase activity.

It is a further aspect of the present invention to provide the method as described above, wherein the activity of the S-adenosylmethionine cycle enzyme is increased by increasing the expression of a gene encoding the S-adenosylmethionine cycle enzyme.

It is a further aspect of the present invention to provide the method as described above, wherein the expression of the gene encoding the S-adenosylmethionine cycle enzyme is increased by increasing the copy number of the gene and/or modifying an expression control sequence of the gene.

It is a further aspect of the present invention to provide the method as described above, wherein the microorganism is a bacterium belonging to the family Enterobacteriaceae, a coryneform bacterium, or yeast.

It is a further aspect of the present invention to provide the method as described above, wherein the microorganism is a bacterium belonging to the genus *Corynebacterium*.

It is a further aspect of the present invention to provide the method as described above, wherein the microorganism is *Corynebacterium glutamicum*.

It is a further aspect of the present invention to provide the method as described above, wherein the microorganism is a bacterium belonging to the genus *Escherichia*.

It is a further aspect of the present invention to provide the method as described above, wherein the microorganism is *Escherichia coli*.

It is a further aspect of the present invention to provide the method as described above, wherein the metabolites (X) are selected from the group consisting of vanillin, vanillic acid, melatonin, ergothioneine, mugineic acid, ferulic acid, polyamine, guaiacol, 4-vinylguaiacol, 4-ethylguaiacol, creatine, and combinations thereof.

It is a further aspect of the present invention to provide the method as described above, wherein the microorganism has been further modified so that the activity of an enzyme that is involved in the biosynthesis of the objective substance is increased as compared with a non-modified strain.

It is a further aspect of the present invention to provide the method as described above, wherein the enzyme that is involved in the biosynthesis of the objective substance is selected from the group consisting of 3-deoxy-D-arabino-heptulosonic acid 7-phosphate synthase, 3-dehydroquinate synthase, 3-dehydroquinate dehydratase, 3-dehydroshikimate dehydratase, O-methyltransferase, aromatic aldehyde oxidoreductase, and combinations thereof.

It is a further aspect of the present invention to provide the method as described above, wherein the microorganism has been further modified so that the activity of phosphopantetheinyl transferase is increased as compared with a non-modified strain.

It is a further aspect of the present invention to provide the method as described above, wherein the microorganism has been further modified so that the activity of an enzyme that is involved in the by-production of a substance other than the objective substance is reduced as compared with a non-modified strain.

It is a further aspect of the present invention to provide the method as described above, wherein the enzyme that is involved in the by-production of a substance other than the objective substance is selected from the group consisting of vanillate demethylase, protocatechuate 3,4-dioxygenase, alcohol dehydrogenase, shikimate dehydrogenase, and combinations thereof.

It is a further aspect of the present invention to provide the method as described above, wherein the microorganism has been further modified so that the activity of an L-cysteine biosynthesis enzyme is increased as compared with a non-modified strain.

It is a further aspect of the present invention to provide the method as described above, wherein the L-cysteine biosynthesis enzyme is selected from the group consisting of proteins encoded by a cysI gene, cysX gene, cysH gene, cysD gene, cysN gene, cysY gene, cysZ gene, fpr2 gene, and combinations thereof.

It is a further aspect of the present invention to provide the method as described above, wherein the activity of the L-cysteine biosynthesis enzyme is increased by increasing the activity of a protein encoded by a cysR gene.

It is a further aspect of the present invention to provide the method as described above, wherein the microorganism has been further modified so that the activity of a protein encoded by an NCgl2048 gene is reduced as compared with a non-modified strain.

It is a further aspect of the present invention to provide the method as described above, wherein the microorganism has been further modified so that the activity of enolase is reduced as compared with a non-modified strain.

It is a further aspect of the present invention to provide the method as described above, wherein the microorganism has been further modified so that the activity of L-serine deaminase is reduced as compared with a non-modified strain.

It is a further aspect of the present invention to provide the method as described above, wherein the microorganism has been further modified so that the activity of AICAR formyltransferase/IMP cyclohydrolase is reduced as compared with a non-modified strain and/or so that a gene encoding AICAR formyltransferase/IMP cyclohydrolase has a mutation for improving the ability of the microorganism to produce the objective substance.

It is a further aspect of the present invention to provide the method as described above, wherein the activity of AICAR formyltransferase/IMP cyclohydrolase is reduced by modifying a gene encoding AICAR formyltransferase/IMP cyclohydrolase so as to have a mutation for improving the ability of the microorganism to produce the objective substance.

It is a further aspect of the present invention to provide the method as described above, wherein the mutation for improving the ability of the microorganism to produce the objective substance is a mutation replacing the serine residue at position 37 of the encoded AICAR formyltransferase/IMP cyclohydrolase with another amino acid residue.

It is a further aspect of the present invention to provide the method as described above, wherein said another amino acid residue is a phenylalanine residue.

It is a further aspect of the present invention to provide a method for producing vanillin, the method comprising:
producing vanillic acid by the method as described above; and
converting said vanillic acid to vanillin.

DETAILED DESCRIPTION OF THE EXEMPLARY EMBODIMENTS

<1> Microorganism

The microorganism as described herein is a microorganism having an ability to produce an objective substance, which microorganism has been modified so that the activity of an SAM cycle enzyme is increased. The ability to produce an objective substance can also be referred to as an "objective substance-producing ability".

<1-1> Microorganism Having Objective Substance-Producing Ability

The phrase "microorganism having an objective substance-producing ability" can refer to a microorganism that is able to produce an objective substance.

The phrase "microorganism having an objective substance-producing ability" can refer to a microorganism that is able to produce an objective substance by fermentation, if the microorganism is used in a fermentation method. That is, the phrase "microorganism having an objective substance-producing ability" can refer to a microorganism that is able to produce an objective substance from a carbon source. Specifically, the phrase "microorganism having an objective substance-producing ability" can refer to a microorganism that is able to, upon being cultured in a culture medium, such as a culture medium containing a carbon source, produce and accumulate the objective substance in the culture medium to such a degree that the objective substance can be collected from the culture medium.

Also, the phrase "microorganism having an objective substance-producing ability" can refer to a microorganism that is able to produce an objective substance by bioconversion, if the microorganism is used in a bioconversion method. That is, the phrase "microorganism having an objective substance-producing ability" can refer to a microorganism that is able to produce an objective substance from a precursor of the objective substance. Specifically, the phrase "microorganism having an objective substance-producing ability" can refer to a microorganism that is able to, upon being cultured in a culture medium containing a precursor of an objective substance, produce and accumulate the objective substance in the culture medium to such a degree that the objective substance can be collected from the culture medium. Also, specifically, the phrase "microorganism having an objective substance-producing ability" can refer to a microorganism that is able to, upon being allowed to act on a precursor of an objective substance in a reaction mixture, produce and accumulate the objective substance in the reaction mixture to such a degree that the objective substance can be collected from the reaction mixture.

The microorganism having an objective substance-producing ability can be able to produce and accumulate the objective substance in the culture medium or reaction mixture in an amount larger than that can be obtained with a non-modified strain. A non-modified strain can also be referred to as a "strain of a non-modified microorganism" or a "non-modified microorganism". The term "non-modified strain" or "strain of a non-modified microorganism" can refer to a control strain that has not been modified so that the activity of an SAM cycle enzyme is increased. The microorganism having an objective substance-producing ability can be able to accumulate the objective substance in the culture medium or reaction mixture in an amount of, for example, 0.01 g/L or more, 0.05 g/L or more, or 0.09 g/L or more.

The objective substance can be selected from L-methionine and metabolites the biosynthesis of which requires S-adenosylmethionine (SAM). Examples of the metabolites the biosynthesis of which requires SAM can include, for example, vanillin, vanillic acid, melatonin, ergothioneine, mugineic acid, ferulic acid, polyamine, guaiacol, 4-vinylguaiacol, 4-ethylguaiacol, and creatine. Examples of polyamine can include spermidine and spermine. The combination of the SAM cycle enzyme and the objective substance is not particularly limited, so long as the increased activity of the SAM cycle enzyme in a microorganism results in increased production of the objective substance. For example, when methionine adenosyltransferase is used alone as the SAM cycle enzyme, or when used in combination with other SAM cycle enzyme(s), the objective substance may be metabolites the biosynthesis of which requires SAM, that is, L-methionine may not be produced as the objective substance. Alternatively, for example, when methionine adenosyltransferase is not used as the SAM cycle enzyme, for example, when S-adenosyl-L-homocysteine hydrolase, methionine synthase, 5,10-methylenetetrahydrofolate reductase, or a combination of these is used, the objective substance may be L-methionine and/or the metabolites of which the biosynthesis requires SAM, that is, L-methionine may be produced as the objective substance.

The microorganism as described herein may be able to produce only one kind of objective substance, or may have an ability to produce two or more kinds of objective substances. Also, the microorganism may be able to produce an objective substance from one kind of precursor of the objective substance or from two or more kinds of precursors of the objective substance.

When the objective substance is a compound that can form a salt, the objective substance may be obtained as a free compound, a salt thereof, or a mixture of these. That is, the term "objective substance" can refer to an objective substance in a free form, a salt thereof, or a mixture thereof, unless otherwise stated. Examples of the salt can include, for example, sulfate salt, hydrochloride salt, carbonate salt, ammonium salt, sodium salt, and potassium salt. As the salt of the objective substance, one kind of salt may be employed, or two or more kinds of salts may be employed in combination.

A microorganism that can be used as a parent strain to construct the microorganism as described herein is not particularly limited. Examples of the microorganism can include bacteria and yeast.

Examples of the bacteria can include bacteria belonging to the family Enterobacteriaceae and coryneform bacteria.

Examples of bacteria belonging to the family Enterobacteriaceae can include bacteria belonging to the genus *Escherichia*, *Enterobacter*, *Pantoea*, *Klebsiella*, *Serratia*, *Envinia*, *Photorhabdus*, *Providencia*, *Salmonella*, *Morganella*, or the like. Specifically, bacteria classified into the family Enterobacteriaceae according to the taxonomy used in the NCBI (National Center for Biotechnology Information) database (ncbi.nlm.nih.gov/Taxonomy/Browser/wwwtax.cgi?id=91347) can be used.

The *Escherichia* bacteria are not particularly limited, and examples thereof can include those classified into the genus *Escherichia* according to the taxonomy known to those skilled in the field of microbiology. Examples of the *Escherichia* bacteria can include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria can include, for example, *Escherichia coli*. Specific examples of *Escherichia coli* can include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21 (DE3) strain; and derivative strains thereof.

The *Enterobacter* bacteria are not particularly limited, and examples can include those classified into the genus *Enterobacter* according to the taxonomy known to those skilled in the field of microbiology. Examples of the *Enterobacter* bacterium can include, for example, *Enterobacter agglomerans* and *Enterobacter aerogenes*. Specific examples of *Enterobacter agglomerans* can include, for example, the *Enterobacter agglomerans* ATCC 12287 strain. Specific examples of *Enterobacter aerogenes* can include, for example, the *Enterobacter aerogenes* ATCC 13048 strain, NBRC 12010 strain (Biotechnol. Bioeng., 2007, Mar. 27; 98(2):340-348), and AJ110637 strain (FERM BP-10955). Examples of the *Enterobacter* bacteria can also include, for example, the strains described in European Patent Application Laid-open (EP-A) No. 0952221. In addition, *Enterobacter agglomerans* can also include some strains classified as *Pantoea agglomerans*.

The *Pantoea* bacteria are not particularly limited, and examples can include those classified into the genus *Pantoea* according to the taxonomy known to those skilled in the field of microbiology. Examples of the *Pantoea* bacteria can include, for example, *Pantoea ananatis*, *Pantoea stewartii*, *Pantoea agglomerans*, and *Pantoea citrea*. Specific examples of *Pantoea ananatis* can include, for example, the *Pantoea ananatis* LMG20103 strain, AJ13355 strain (FERM BP-6614), AJ13356 strain (FERM BP-6615), AJ13601 strain (FERM BP-7207), SC17 strain (FERM BP-11091), SC17(0) strain (VKPM B-9246), and SC17sucA strain (FERM BP-8646). Some of *Enterobacter* bacteria and *Envinia* bacteria were reclassified into the genus *Pantoea* (Int. J. Syst. Bacteriol., 39, 337-345 (1989); Int. J. Syst. Bacteriol., 43, 162-173 (1993)). For example, some strains of *Enterobacter agglomerans* were recently reclassified into *Pantoea agglomerans*, *Pantoea ananatis*, *Pantoea stewartii*, or the like on the basis of nucleotide sequence analysis of 16S rRNA etc. (Int. J. Syst. Bacteriol., 39, 337-345 (1989)). The *Pantoea* bacteria can include those reclassified into the genus *Pantoea* as described above.

Examples of the Envinia bacteria can include Envinia *amylovora* and Envinia *carotovora*. Examples of the *Klebsiella* bacteria can include *Klebsiella planticola*.

Examples of coryneform bacteria can include bacteria belonging to the genus *Corynebacterium*, *Brevibacterium*, *Microbacterium*, or the like.

Specific examples of such coryneform bacteria can include the following species.

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of the coryneform bacteria can include the following strains.

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990

*Corynebacterium melassecola* ATCC 17965
*Corynebacterium efficiens* (*Corynebacterium thermoaminogenes*) AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The coryneform bacteria can include bacteria that had previously been classified into the genus *Brevibacterium*, but are now united into the genus *Corynebacterium* (Int. J. Syst. Bacteriol., 41, 255 (1991)). Moreover, *Corynebacterium stationis* can include bacteria that had previously been classified as *Corynebacterium ammoniagenes*, but are now re-classified into *Corynebacterium stationis* on the basis of nucleotide sequence analysis of 16S rRNA etc. (Int. J. Syst. Evol. Microbiol., 60, 874-879 (2010)).

The yeast may be budding or fission yeast. The yeast may be haploid, diploid, or more polyploid yeast. Examples of the yeast can include yeast belonging to the genus *Saccharomyces* such as *Saccharomyces cerevisiae*, the genus *Pichia* (also referred to as the genus *Wickerhamomyces*) such as *Pichia ciferrii*, *Pichia sydowiorum*, and *Pichia pastoris*, the genus *Candida* such as *Candida utilis*, the genus *Hansenula* such as *Hansenula polymorpha*, and the genus *Schizosaccharomyces* such as *Schizosaccharomyces pombe*.

These strains are available from, for example, the American Type Culture Collection (Address: P.O. Box 1549, Manassas, Va. 20108, United States of America, or atcc.org). That is, registration numbers are given to the respective strains, and the strains can be ordered using these registration numbers (refer to atcc.org). The registration numbers of the strains are listed in the catalogue of the American Type Culture Collection. These strains can also be obtained from, for example, the depositories at which the strains were deposited.

The microorganism may inherently have an objective substance-producing ability, or may have been modified so that it has an objective substance-producing ability. The microorganism having an objective substance-producing ability can be obtained by imparting an objective substance-producing ability to such a microorganism as mentioned above, or enhancing an objective substance-producing ability of such a microorganism as mentioned above.

Hereafter, specific examples of the methods for imparting or enhancing an objective substance-producing ability will be explained. Such modifications as exemplified below for imparting or enhancing an objective substance-producing ability may be employed independently, or may be used in an appropriate combination.

An objective substance can be generated by the action of an enzyme that is involved in the biosynthesis of the objective substance. Such an enzyme can also be referred to as "objective substance biosynthesis enzyme". Therefore, the microorganism may have an objective substance biosynthesis enzyme. In other words, the microorganism may have a gene encoding an objective substance biosynthesis enzyme. Such a gene can also be referred to as "objective substance biosynthesis gene". The microorganism may inherently have an objective substance biosynthesis gene, or may have been introduced with an objective substance biosynthesis gene. The methods for introducing a gene will be explained herein.

Also, an objective substance-producing ability of a microorganism can be improved by increasing the activity of an objective substance biosynthesis enzyme. That is, examples of the methods for imparting or enhancing an objective substance-producing ability can include a method of increasing the activity of an objective substance biosynthesis enzyme. That is, the microorganism may have been modified so that the activity of an objective substance biosynthesis enzyme is increased. The activity of one kind of objective substance biosynthesis enzyme may be increased, or the activities of two or more kinds of objective substance biosynthesis enzymes may be increased. The method for increasing the activity of a protein, such as an enzyme etc., will be described herein. The activity of a protein, such as an enzyme etc., can be increased by, for example, increasing the expression of a gene encoding the protein.

An objective substance can be generated from, for example, a carbon source and/or a precursor of the objective substance. Hence, examples of the objective substance biosynthesis enzyme can include, for example, enzymes that catalyze the conversion of the carbon source and/or the precursor into the objective substance. For example, 3-dehydroshikimic acid can be produced via a part of shikimate pathway, which may include steps catalyzed by 3-deoxy-D-arabino-heptulosonic acid 7-phosphate synthase (DAHP synthase), 3-dehydroquinate synthase, and 3-dehydroquinate dehydratase; 3-dehydroshikimic acid can be converted to protocatechuic acid by the action of 3-dehydroshikimate dehydratase (DHSD); protocatechuic acid can be converted to vanillic acid or protocatechualdehyde by the action of O-methyltransferase (OMT) or aromatic aldehyde oxidoreductase (also referred to as aromatic carboxylic acid reductase; ACAR), respectively; and vanillic acid or protocatechualdehyde can be converted to vanillin by the action of ACAR or OMT, respectively. That is, specific examples of the objective substance biosynthesis enzyme can include, for example, DAHP synthase, 3-dehydroquinate synthase, 3-dehydroquinate dehydratase, DHSD, OMT, and ACAR.

The term "3-deoxy-D-arabino-heptulosonic acid 7-phosphate synthase (DAHP synthase)" can refer to a protein that has the activity of catalyzing the reaction of converting D-erythrose 4-phosphate and phosphoenolpyruvic acid into 3-deoxy-D-arabino-heptulosonate 7-phosphate (DAHP) and phosphate (EC 2.5.1.54). This activity can also be referred to as a "DAHP synthase activity". A gene encoding a DAHP synthase can also be referred to as a "DAHP synthase gene". Examples of a DAHP synthase can include AroF, AroG, and AroH proteins, which are encoded by aroF, aroG, and aroH genes, respectively. Among these, the AroG protein may function as the major DAHP synthase. Examples of a DAHP synthase such as the AroF, AroG, and AroH proteins can include those native to various organisms such as Enterobacteriaceae bacteria and coryneform bacteria. Specific examples of a DAHP synthase can include the AroF, AroG, and AroH proteins native to *E. coli*. The nucleotide sequence of the aroG gene native to the *E. coli* K-12 MG1655 strain is shown as SEQ ID NO: 1, and the amino acid sequence of the AroG protein encoded by this gene is shown as SEQ ID NO: 2.

The DAHP synthase activity can be measured by, for example, incubating the enzyme with substrates, such as D-erythrose 4-phosphate and phosphoenolpyruvic acid, and measuring the enzyme- and substrate-dependent generation of DAHP.

The term "3-dehydroquinate synthase" can refer to a protein that has the activity of catalyzing the reaction of dephosphorylating DAHP to generate 3-dehydroquinic acid (EC 4.2.3.4). This activity can also be referred to as a "3-dehydroquinate synthase activity". A gene encoding a 3-dehydroquinate synthase can also be referred to as a "3-dehydroquinate synthase gene". Examples of a 3-dehydroquinate synthase can include an AroB protein, which is encoded by an aroB gene. Examples of a 3-dehydroquinate synthase such as the AroB protein can include those native to various organisms such as Enterobacteriaceae bacteria and coryneform bacteria. Specific examples of a 3-dehydroquinate synthase can include the AroB protein native to *E. coli*. The nucleotide sequence of the aroB gene native to the *E. coli* K-12 MG1655 strain is shown as SEQ ID NO: 3, and the amino acid sequence of the AroB protein encoded by this gene is shown as SEQ ID NO: 4.

The 3-dehydroquinate synthase activity can be measured by, for example, incubating the enzyme with a substrate, such as DAHP, and measuring the enzyme- and substrate-dependent generation of 3-dehydroquinic acid.

The term "3-dehydroquinate dehydratase" can refer to a protein that has the activity of catalyzing the reaction of dehydrating 3-dehydroquinic acid to generate 3-dehydroshikimic acid (EC 4.2.1.10). This activity can also be referred to as a "3-dehydroquinate dehydratase activity". A gene encoding a 3-dehydroquinate dehydratase can also be referred to as a "3-dehydroquinate dehydratase gene". Examples of a 3-dehydroquinate dehydratase can include an AroD protein, which is encoded by an aroD gene. Examples of a 3-dehydroquinate dehydratase such as the AroD protein can include those native to various organisms such as Enterobacteriaceae bacteria and coryneform bacteria. Specific examples of a 3-dehydroquinate dehydratase can include the AroD protein native to *E. coli*. The nucleotide sequence of the aroD gene native to the *E. coli* K-12 MG1655 strain is shown as SEQ ID NO: 5, and the amino acid sequence of the AroD protein encoded by this gene is shown as SEQ ID NO: 6.

The 3-dehydroquinate dehydratase activity can be measured by, for example, incubating the enzyme with a substrate, such as 3-dehydroquinic acid, and measuring the enzyme- and substrate-dependent generation of 3-dehydroshikimic acid.

The term "3-dehydroshikimate dehydratase (DHSD)" can refer to a protein that has the activity of catalyzing the reaction of dehydrating 3-dehydroshikimic acid to generate protocatechuic acid (EC 4.2.1.118). This activity can also be referred to as a "DHSD activity". A gene encoding a DHSD can also be referred to as a "DHSD gene". Examples of a DHSD can include an AsbF protein, which is encoded by an asbF gene. Examples of a DHSD such as the AsbF protein can include those native to various organisms such as *Bacillus thuringiensis, Neurospora crassa*, and *Podospora pauciseta*. The nucleotide sequence of the asbF gene native to the *Bacillus thuringiensis* BMB171 strain is shown as SEQ ID NO: 7, and the amino acid sequence of the AsbF protein encoded by this gene is shown as SEQ ID NO: 8.

The DHSD activity can be measured by, for example, incubating the enzyme with a substrate, such as 3-dehydroshikimic acid, and measuring the enzyme- and substrate-dependent generation of protocatechuic acid.

The expression of a gene encoding an enzyme of the shikimate pathway, such as a DAHP synthase, 3-dehydroquinate synthase, and 3-dehydroquinate dehydratase, is repressed by the tyrosine repressor TyrR, which is encoded by a tyrR gene. Therefore, the activity of an enzyme of the shikimate pathway can also be increased by reducing the activity of the tyrosine repressor TyrR. Examples of the tyrosine repressor TyrR can include those native to various organisms such as Enterobacteriaceae bacteria and coryneform bacteria. Specific examples of the tyrosine repressor TyrR can include the TyrR protein native to *E. coli*. The nucleotide sequence of the tyrR gene native to the *E. coli* K-12 MG1655 strain is shown as SEQ ID NO: 9, and the amino acid sequence of the TyrR protein encoded by this gene is shown as SEQ ID NO: 10.

The term "O-methyltransferase (OMT)" can refer to a protein that has the activity of catalyzing the reaction of methylating hydroxyl group of a substance in the presence of a methyl group donor (EC 2.1.1.68 etc.). This activity can also be referred to as an "OMT activity". A gene encoding OMT can also be referred to as an "OMT gene". OMT can have a required substrate specificity depending on the specific biosynthesis pathway via which an objective substance is produced in the method as described herein. For example, when an objective substance is produced via the conversion of protocatechuic acid into vanillic acid, OMT that is specific for at least protocatechuic acid can be used. Also, for example, when an objective substance is produced via the conversion of protocatechualdehyde into vanillin, OMT that is specific for at least protocatechualdehyde can be used. That is, specifically, the term "O-methyltransferase (OMT)" can refer to a protein that has the activity of catalyzing the reaction of methylating protocatechuic acid and/or protocatechualdehyde in the presence of a methyl group donor to generate vanillic acid and/or vanillin, that is, methylation of hydroxyl group at the meta-position. OMT may be specific for both protocatechuic acid and protocatechualdehyde as the substrate, but is not necessarily limited thereto. Examples of the methyl group donor can include S-adenosylmethionine (SAM). Examples of an OMT can include OMTs native to various organisms, such as OMT native to *Homo sapiens* (Hs) (GenBank Accession No. NP_000745 and NP_009294), OMT native to *Arabidopsis thaliana* (GenBank Accession Nos. NP_200227 and NP_009294), OMT native to *Fragaria×ananassa* (GenBank Accession No. AAF28353), and other various OMTs native to mammals, plants, and microorganisms exemplified in WO2013/022881A1. Four kinds of transcript variants and two kinds of OMT isoforms are known for the OMT gene native to *Homo sapiens*. The nucleotide sequences of these four transcript variants (transcript variants 1-4, GenBank Accession No. NM_000754.3, NM_001135161.1, NM_001135162.1, and NM_007310.2) are shown as SEQ ID NOS: 11 to 14, the amino acid sequence of the longer OMT isoform (MB-COMT, GenBank Accession No. NP_000745.1) is shown as SEQ ID NO: 15, and the amino acid sequence of the shorter OMT isoform (S-COMT, GenBank Accession No. NP_009294.1) is shown as SEQ ID NO: 16. SEQ ID NO: 16 corresponds to SEQ ID NO: 15 of which the N-terminal 50 amino acid residues are truncated. Examples of an OMT further can include OMTs native to Bacteroidetes bacteria, that is, bacteria belonging to the phylum Bacteroidetes. Examples of the Bacteroidetes bacteria can include bacteria belonging to the genus *Niastella, Terrimonas, Chitinophaga*, or the like (International Journal of Systematic and Evolutionary Microbiology (2007), 57, 1828-1833). Examples of the *Niastella* bacteria can include

*Niastella koreensis*. The nucleotide sequence of the OMT gene native to *Niastella koreensis* is shown as SEQ ID NO: 130, and the amino acid sequence of OMT encoded by this gene is shown as SEQ ID NO: 131.

OMT may also catalyze the reaction of methylating protocatechuic acid and/or protocatechualdehyde to generate isovanillic acid and/or isovanillin, that is, methylation of hydroxyl group at the para-position, as a side reaction. OMT may selectively catalyze the methylation of a hydroxyl group at the meta-position. The expression "selectively catalyzing the methylation of hydroxyl group at the meta-position" can mean that OMT selectively generates vanillic acid from protocatechuic acid and/or that OMT selectively generates vanillin from protocatechualdehyde. The expression "selectively generating vanillic acid from protocatechuic acid" can mean that OMT generates vanillic acid in an amount of, for example, 3 times or more, 5 times or more, 10 times or more, 15 times or more, 20 times or more, 25 times or more, or 30 times or more of that of isovanillic acid in terms of molar ratio, when OMT is allowed to act on protocatechuic acid. The expression "selectively generating vanillic acid from protocatechuic acid" can also mean that OMT generates vanillic acid in an amount of, for example, 60% or more, 65% or more, 70% or more, 75% or more, 80% or more, 85% or more, 90% or more, or 95% or more, with respect to the total amount of vanillic acid and isovanillic acid in terms of molar ratio, when OMT is allowed to act on protocatechuic acid. This ratio, that is, the ratio of the amount of vanillic acid with respect to the total amount of vanillic acid and isovanillic acid, can also be referred to as "VA/(VA+iVA) ratio". Also, the phrase "selectively generating vanillin from protocatechualdehyde" can mean that OMT generates vanillin in an amount of, for example, 3 times or more, 5 times or more, 10 times or more, 15 times or more, 20 times or more, 25 times or more, or 30 times or more of that of isovanillin in terms of molar ratio, when OMT is allowed to act on protocatechualdehyde. The expression "selectively generating vanillin from protocatechualdehyde" can also mean that OMT generates vanillin in an amount of, for example, 60% or more, 65% or more, 70% or more, 75% or more, 80% or more, 85% or more, 90% or more, or 95% or more, with respect to the total amount of vanillin and isovanillin in terms of molar ratio, when OMT is allowed to act on protocatechualdehyde. This ratio, that is, the ratio of the amount of vanillin with respect to the total amount of vanillin and isovanillin, can also be referred to as "Vn/(Vn+iVn) ratio". Examples of OMT that selectively catalyzes the methylation of hydroxyl group at the meta-position can include OMT having a "specific mutation", which is described herein.

OMT having the "specific mutation" can also be referred to as a "mutant OMT". A gene encoding a mutant OMT can also be referred to as a "mutant OMT gene".

OMT not having the "specific mutation" can also be referred to as a "wild-type OMT". A gene encoding a wild-type OMT can also be referred to as a "wild-type OMT gene". The term "wild-type" referred to herein is used for convenience to distinguish the "wild-type" OMT from the "mutant" OMT, and the "wild-type" OMT is not limited to those obtained as natural substances, and can include any OMT not having the "specific mutation". Examples of the wild-type OMT can include, for example, OMTs exemplified above. In addition, all conservative variants of OMTs exemplified above should be included in wild-type OMTs, provided that such conservative variants do not have the "specific mutation".

Examples of the "specific mutation" can include the mutations present in the mutant OMTs described in WO2013/022881A1. That is, examples of the "specific mutation" can include a mutation that the leucine residue at position 198 of the wild-type OMT (L198) is replaced with an amino acid residue having a hydrophobic index (hydropathy index) lower than that of leucine residue, and a mutation that the glutamate residue at position 199 of the wild-type OMT (E199) is replaced with an amino acid residue having either a neutral or positive side-chain charge at pH 7.4. The mutant OMT may have either one or both of these mutations.

Examples of the "amino acid residue having a hydrophobic index (hydropathy index) lower than that of leucine residue" can include Ala, Arg, Asn, Asp, Cys, Glu, Gln, Gly, His, Lys, Met, Phe, Pro, Ser, Thr, Trp, and Tyr. As the "amino acid residue showing a hydrophobic index (hydropathy index) lower than that of leucine residue", especially, an amino acid residue selected from Ala, Arg, Asn, Asp, Glu, Gln, Gly, His, Lys, Met, Pro, Ser, Thr, Trp, and Tyr is a particular example, and Tyr is a more particular example.

The "amino acid residue having either a neutral or positive side-chain charge at pH 7.4" can include Ala, Arg, Asn, Cys, Gln, Gly, His, Ile, Leu, Lys, Met, Phe, Pro, Ser, Thr, Trp, Tyr, and Val. As the "amino acid residue having either a neutral or positive side-chain charge at pH 7.4", Ala or Gln is a particular example.

The terms "L198" and "E199" in an arbitrary wild-type OMT can refer to "an amino acid residue corresponding to the leucine residue at position 198 of the amino acid sequence shown as SEQ ID NO: 16" and "an amino acid residue corresponding to the glutamate residue at position 199 of the amino acid sequence shown as SEQ ID NO: 16", respectively. The positions of these amino acid residues represent relative positions, and their absolute positions may shift due to deletion, insertion, addition, and so forth of amino acid residue(s). For example, if one amino acid residue is deleted or inserted at a position on the N-terminus side of position X in the amino acid sequence shown as SEQ ID NO: 16, the amino acid residue originally at position X is relocated at position X-1 or X+1, however, it is still regarded as the "amino acid residue corresponding to the amino acid residue at position X of the amino acid sequence shown as SEQ ID NO: 16". Furthermore, although "L198" and "E199" are typically leucine residue and glutamate residue, respectively, they may not be leucine residue and glutamate residue, respectively. That is, when "L198" and "E199" are not leucine residue and glutamate residue, respectively, the "specific mutation" can include a mutation that those amino acid residues each are replaced with any of the aforementioned amino acid residues.

In the amino acid sequence of an arbitrary OMT, which amino acid residue is the amino acid residue corresponding to "L198" or "E199" can be determined by aligning the amino acid sequence of the arbitrary OMT and the amino acid sequence of SEQ ID NO: 16. The alignment can be performed by, for example, using known gene analysis software. Specific examples of such software can include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

Examples of the "specific mutation" further can include mutations at the following amino acid residues: D21, L31, M36, S42, L67, Y90, and P144. The "specific mutation" can be a mutation at one amino acid residue, or can be a combination of mutations at two or more amino acid residues. That is, the "specific mutation" may include, for example, mutations at one or more of the following amino acid residues: D21, L31, M36, S42, L67, Y90, and P144.

In the aforementioned notation for defining amino acid residues, the numbers represent the positions in the amino acid sequence shown as SEQ ID NO: 131, and the letters at the left side of the numbers represent the amino acid residues at the respective positions in the amino acid sequence shown as SEQ ID NO: 131, that is, the amino acid residues before modification at the respective positions. That is, for example, "D21" represents D (Asp) residue at position 21 in the amino acid sequence shown as SEQ ID NO: 131. These amino acid residues in an arbitrary wild-type OMT each can refer to "an amino acid residue corresponding to the indicated amino acid residue in the amino acid sequence shown as SEQ ID NO: 131". That is, for example, "D21" in an arbitrary wild-type OMT represents an amino acid residue corresponding to D (Asp) residue at position 21 in the amino acid sequence shown as SEQ ID NO: 131.

In each of the aforementioned mutations, the amino acid residue after modification may be any amino acid residue other than the amino acid residue before modification. Examples of the amino acid residue after modification can include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gln), provided that the amino acid residues after modification is other than the amino acid residue before modification. As the amino acid residues after modification, there may be selected those effective for production of an objective substance, such as those resulting in an increase in the VA/(VA+iVA) ratio and/or Vn/(Vn+iVn) ratio of OMT.

Specific examples of the "specific mutation" can include the following mutations: D21Y, L31H, M36(K, V), S42C, L67F, Y90(A, C, G, S), and P144(E, G, S, V, Y). That is, the mutations at amino acid residues D21, L31, M36, S42, L67, Y90, and P144 may be, for example, the mutations D21Y, L31H, M36(K, V), S42C, L67F, Y90(A, C, G, S), and P144(E, G, S, V, Y), respectively. The "specific mutation" can include, for example, one or more of the following mutations: D21Y, L31H, M36(K, V), S42C, L67F, Y90(A, C, G, S), and P144(E, G, S, V, Y).

In the aforementioned notation for defining mutations, the numbers and the letters at the left side of the numbers represent the same as described above. In the aforementioned notation for defining mutations, the letters at the right side of the numbers represent the amino acid residues after modification at the respective positions. That is, for example, "D21Y" represents a mutation for replacing D (Asp) residue at position 21 in the amino acid sequence shown as SEQ ID NO: 131 with Y (Tyr) residue. Also, for example, M36(K, V) represents a mutation for replacing M (Met) residue at position 36 in the amino acid sequence shown as SEQ ID NO: 131 with K (Lys) or V (Val) residue. These mutations in an arbitrary wild-type OMT each can refer to "a mutation corresponding to the indicated mutation in the amino acid sequence shown as SEQ ID NO: 131". A "mutation corresponding to a mutation at the amino acid residue at position X in the amino acid sequence shown in SEQ ID NO: 131" should be read as a mutation at an amino acid residue corresponding to the amino acid residue at position X in the amino acid sequence shown in SEQ ID NO: 131". That is, for example, "D21Y" in an arbitrary wild-type OMT represents a mutation for replacing an amino acid residue corresponding to D (Asp) residue at position 21 in the amino acid sequence shown as SEQ ID NO: 131 with Y (Tyr) residue.

Combinations of mutations are not particularly limited. Specific examples of combinations of mutations can include D21Y/M36K/L67F, D21Y/M36K/L67F/Y90A, L31H/M36K/L67F/P144V, L31H/L67F/Y90A, M36K/S42C/L67F, M36K/L67F, M36K/L67F/Y90A, M36K/L67F/Y90A/P144E, M36K/L67F/Y90C, M36K/L67F/Y90C/P144V, M36K/L67F/Y90G, M36K/L67F/Y90S/P144G, M36K/L67F/P144S, M36K/L67F/P144Y, M36K/Y90A/P144V, M36K/P144E, and M36V/L67F/P144S. That is, the "specific mutation" may include, for example, any of these combinations.

In the aforementioned notation for defining combinations, the numbers and the letters at the left and right sides of the numbers represent the same as described above. In the aforementioned notation for defining combinations, two or more mutations noted together and inserted with "/" represent a double or more multiple mutation. That is, for example, "M36K/P144E" represents a double mutation of M36K and P144E.

The descriptions regarding the mutations at "L198" or "E199", such as those for defining the absolute positions thereof, can be applied mutatis mutandis to other "specific mutations" such as the mutations at amino acid residues corresponding to D21, L31, M36, S42, L67, Y90, and P144, provided that the amino acid sequence shown in SEQ ID NO: 131 is used as the reference sequence of the wild-type OMT for the other "specific mutations".

A mutant OMT gene can be obtained by, for example, modifying a wild-type OMT gene so that OMT encoded thereby has the "specific mutation". The wild-type OMT gene to be modified can be obtained by, for example, cloning from an organism having the wild-type OMT gene, or chemical synthesis. Alternatively, a mutant OMT gene can also be obtained without using a wild-type OMT gene. For example, a mutant OMT gene may be directly obtained by, for example, cloning from an organism having the mutant OMT gene, or chemical synthesis. The obtained mutant OMT gene may be used as it is, or may be further modified before use. The wild-type OMT gene to be modified or the mutant OMT gene may or may not be derived from the host, such as a microorganism from which the microorganism as described herein is derived.

Genes can be modified by using a known method. For example, an objective mutation can be introduced into a target site of DNA by the site-specific mutagenesis method. Examples of the site-specific mutagenesis method can include a method using PCR (Higuchi, R., 61, in PCR Technology, Erlich, H. A. Eds., Stockton Press (1989); Carter P., Meth. In Enzymol., 154, 382 (1987)), and a method of using a phage (Kramer, W. and Frits, H. J., Meth. in Enzymol., 154, 350 (1987); Kunkel, T. A. et al., Meth. in Enzymol., 154, 367 (1987)).

The OMT activity can be measured by, for example, incubating the enzyme with a substrate, such as protocatechuic acid or protocatechualdehyde, in the presence of SAM, and measuring the enzyme- and substrate-dependent generation of the corresponding product, such as vanillic acid or vanillin (WO2013/022881A1). Furthermore, by measuring the generation of the corresponding by-product, such as isovanillic acid or isovanillin, under the same conditions, and comparing the generation of the by-product with the generation of the product, it can be determined whether OMT selectively generates the product.

The term "aromatic aldehyde oxidoreductase (aromatic carboxylic acid reductase; ACAR)" can refer to a protein that has an activity of catalyzing the reaction of reducing vanillic acid and/or protocatechuic acid in the presence of an electron donor and ATP to generate vanillin and/or protocatechualdehyde (EC 1.2.99.6 etc.). This activity can also be referred to as an "ACAR activity". A gene encoding an ACAR can also be referred to as an "ACAR gene". ACAR may generally use both vanillic acid and protocatechuic acid as the substrate, but is not necessarily limited thereto. That is, ACAR can have a required substrate specificity depending on the specific biosynthesis pathway via which an objective substance is produced in the method as described herein. For example, when an objective substance is produced via the conversion of vanillic acid into vanillin, ACAR that is specific for at least vanillic acid can be used. Also, for example, when an objective substance is produced via the conversion of protocatechuic acid into protocatechualdehyde, ACAR that is specific for at least protocatechuic acid can be used. Examples of the electron donor can include NADH and NADPH. Examples of an ACAR can include ACARs native to various organisms such as *Nocardia* sp. strain NRRL 5646, *Actinomyces* sp., *Clostridium thermoaceticum, Aspergillus niger, Corynespora melonis, Coriolus* sp., and *Neurospora* sp. (J. Biol. Chem., 2007, Vol. 282, No. 1, pp. 478-485). The *Nocardia* sp. strain NRRL 5646 has been classified into *Nocardia iowensis*. Examples of an ACAR further can include ACARs native to other *Nocardia* bacteria such as *Nocardia brasiliensis* and *Nocardia vulneris*. The nucleotide sequence of the ACAR gene native to the *Nocardia brasiliensis* ATCC 700358 strain is shown as SEQ ID NO: 17, and the amino acid sequence of ACAR encoded by this gene is shown as SEQ ID NO: 18. The nucleotide sequence of an example of variant ACAR gene native to the *Nocardia brasiliensis* ATCC 700358 strain is shown as SEQ ID NO: 19, and the amino acid sequence of ACAR encoded by this gene is shown as SEQ ID NO: 20.

The ACAR activity can be measured by, for example, incubating the enzyme with a substrate, such as vanillic acid or protocatechuic acid, in the presence of ATP and NADPH, and measuring the enzyme- and substrate-dependent oxidation of NADPH (modification of the method described in J. Biol. Chem., 2007, Vol. 282, No. 1, pp. 478-485).

ACAR can be made into an active enzyme by phosphopantetheinylation (J. Biol. Chem., 2007, Vol. 282, No. 1, pp. 478-485). Therefore, ACAR activity can also be increased by increasing the activity of an enzyme that catalyzes phosphopantetheinylation of a protein, which can also be referred to as a "phosphopantetheinylation enzyme". That is, examples of the methods for imparting or enhancing an objective substance-producing ability can include a method of increasing the activity of a phosphopantetheinylation enzyme. That is, the microorganism can be modified so that the activity of a phosphopantetheinylation enzyme is increased. Examples of the phosphopantetheinylation enzyme can include phosphopantetheinyl transferase (PPT).

The term "phosphopantetheinyl transferase (PPT)" can refer to a protein that has an activity of catalyzing the reaction of phosphopantetheinylating ACAR in the presence of a phosphopantetheinyl group donor. This activity can also be referred to as a "PPT activity". A gene encoding a PPT can also be referred to as a "PPT gene". Examples of the phosphopantetheinyl group donor can include coenzyme A (CoA). Examples of a PPT can include an EntD protein, which is encoded by an entD gene. Examples of a PPT such as the EntD protein can include those native to various organisms. Specific examples of a PPT can include the EntD protein native to *E. coli*. The nucleotide sequence of the entD gene native to the *E. coli* K-12 MG1655 strain is shown as SEQ ID NO: 21, and the amino acid sequence of the EntD protein encoded by this gene is shown as SEQ ID NO: 22. Specific examples of a PPT can also include PPT native to *Nocardia brasiliensis*, PPT native to *Nocardia farcinica* IFM10152 (J. Biol. Chem., 2007, Vol. 282, No. 1, pp. 478-485), and PPT native to *Corynebacterium glutamicum* (App. Env. Microbiol. 2009, Vol. 75, No. 9, pp. 2765-2774). The nucleotide sequence of the PPT gene native to the *C. glutamicum* ATCC 13032 strain is shown as SEQ ID NO: 23, and the amino acid sequence of PPT encoded by this gene is shown as SEQ ID NO: 24.

The PPT activity can be measured on the basis of, for example, enhancement of the ACAR activity observed when the enzyme is incubated with ACAR in the presence of CoA (J. Biol. Chem., 2007, Vol. 282, No. 1, pp. 478-485).

Melatonin can be produced from L-tryptophan. That is, examples of the objective substance biosynthesis enzyme can also include, for example, L-tryptophan biosynthesis enzymes and enzymes that catalyze the conversion of L-tryptophan into melatonin. Examples of the L-tryptophan biosynthesis enzymes can include common biosynthesis enzymes of aromatic amino acids, such as 3-deoxy-D-arabinoheptulosonate-7-phosphate synthase (aroF, aroG, aroH), 3-dehydroquinate synthase (aroB), 3-dehydroquinate dehydratase (aroD), shikimate dehydrogenase (aroF), shikimate kinase (aroK, aroL), 5-enolpyruvylshikimate-3-phosphate synthase (aroA), and chorismate synthase (aroC); as well as anthranilate synthase (trpED), and tryptophan synthase (trpAB). Shown in the parentheses after the names of the enzymes are examples of the names of the genes encoding the enzymes (the same shall apply to the same occasions hereafter). L-tryptophan can be converted successively to hydroxytryptophan, serotonin, N-acetylserotonin, and melatonin by the action of tryptophan 5-hydroxylase (EC 1.14.16.4), 5-hydroxytryptophan decarboxylase (EC 4.1.1.28), aralkylamine N-acetyltransferase (AANAT; EC 2.3.1.87), and acetylserotonin O-methyltransferase (EC 2.1.1.4). That is, examples of enzymes that catalyze the conversion of L-tryptophan into melatonin can include these enzymes. Notably, acetylserotonin O-methyltransferase is an example of OMT that catalyzes the reaction of methylating N-acetylserotonin to generate melatonin, using SAM as the methyl donor.

Ergothioneine can be produced from L-histidine. That is, examples of the objective substance biosynthesis enzyme can also include, for example, L-histidine biosynthesis enzymes and enzymes that catalyze the conversion of L-histidine into ergothioneine. Examples of the L-histidine biosynthesis enzymes can include ATP phosphoribosyltransferase (hisG), phosphoribosyl-AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD). L-histidine can be converted successively to hercynine, hercynyl-gamma-L-glutamyl-L-cysteine sulfoxide, hercynyl-L-cysteine sulfoxide, and ergothioneine by the action of the EgtB, EgtC, EgtD, and EgtE proteins, which are encoded by the egtB, egtC, egtD, and egtE genes, respectively. Hercynine can also be converted to hercynyl-L-cysteine sulfoxide by the action of the Egt1 protein, which is encoded by the egt1 gene. That is, examples of the enzymes that catalyze the conversion of L-histidine into ergothioneine can include these enzymes. Notably, EgtD is an S-adenosyl-1-methionine (SAM)-dependent histidine N,N,N-methyltransferase that catalyzes the reaction of methylating histidine to generate hercynine, using SAM as the methyl donor.

Guaiacol can be produced from vanillic acid. Hence, the aforementioned descriptions concerning objective substance biosynthesis enzymes for vanillic acid can be applied mutatis mutandis to objective substance biosynthesis enzymes for guaiacol. Vanillic acid can be converted to guaiacol by the action of vanillic acid decarboxylase (VDC). That is, examples of the objective substance biosynthesis enzyme can also include VDC.

Ferulic acid, 4-vinylguaiacol, and 4-ethylguaiacol can be produced from L-phenylalanine or L-tyrosine. That is, examples of the objective substance biosynthesis enzyme can also include, for example, L-phenylalanine biosynthesis enzymes, L-tyrosine biosynthesis enzymes, and enzymes that catalyze the conversion of L-phenylalanine or L-tyrosine into ferulic acid, 4-vinylguaiacol, or 4-ethylguaiacol. Examples of the L-phenylalanine biosynthesis enzymes can include the common biosynthesis enzymes of aromatic amino acids exemplified above, as well as chorismate mutase (pheA), prephenate dehydratase (pheA), and tyrosine amino transferase (tyrB). Chorismate mutase and prephenate dehydratase may be encoded by the pheA gene as a bifunctional enzyme. Examples of the L-tyrosine biosynthesis enzymes can include the common biosynthesis enzymes of aromatic amino acids exemplified above, as well as chorismate mutase (tyrA), prephenate dehydrogenase (tyrA), and tyrosine amino transferase (tyrB). Chorismate mutase and prephenate dehydrogenase may be encoded by the tyrA gene as a bifunctional enzyme. L-phenylalanine can be converted to cinnamic acid by the action of phenylalanine ammonia lyase (PAL; EC 4.3.1.24), and then to p-coumaric acid by the action of cinnamic acid 4-hydroxylase (C4H; EC 1.14.13.11). Also, L-tyrosine can be converted to p-coumaric acid by the action of tyrosine ammonia lyase (TAL; EC 4.3.1.23). p-Coumaric acid can be converted successively to caffeic acid, ferulic acid, 4-vinylguaiacol, and 4-ethylguaiacol by the action of hydroxycinnamic acid 3-hydroxylase (C3H), O-methyltransferase (OMT), ferulic acid decarboxylase (FDC), and vinylphenol reductase (VPR), respectively. That is, examples of enzymes that catalyze the conversion of L-phenylalanine or L-tyrosine into ferulic acid, 4-vinylguaiacol, or 4-ethylguaiacol can include these enzymes. For producing ferulic acid, 4-vinylguaiacol, or 4-ethylguaiacol, OMT that uses at least caffeic acid can be used.

Polyamines can be produced from L-arginine or L-ornithine. That is, examples of the objective substance biosynthesis enzyme can also include, for example, L-arginine biosynthesis enzymes, L-ornithine biosynthesis enzymes, and enzymes that catalyze the conversion of L-arginine or L-ornithine into a polyamine. Examples of the L-ornithine biosynthesis enzymes can include N-acetylglutamate synthase (argA), N-acetylglutamate kinase (argB), N-acetylglutamyl phosphate reductase (argC), acetylornithine transaminase (argD), and acetylornithine deacetylase (argE). Examples of the L-arginine biosynthesis enzymes can include the L-ornithine biosynthesis enzymes exemplified above, as well as carbamoyl phosphate synthetase (carAB), ornithine carbamoyl transferase (argF, argI), argininosuccinate synthetase (argG), argininosuccinate lyase (argH). L-arginine can be converted to agmatine by the action of arginine decarboxylase (speA; EC 4.1.1.19), and then to putrescine by the action of agmatine ureohydrolase (speB; EC 3.5.3.11). Also, L-ornithine can be converted to putrescine by the action of ornithine decarboxylase (speC; EC 4.1.1.17). Putrescine can be converted to spermidine by the action of spermidine synthase (speE; EC 2.5.1.16), and then to spermine by the action of spermine synthase (EC 2.5.1.22). Agmatine can also be converted to aminopropylagmatine by the action of agmatine/triamine aminopropyl transferase, and then to spermidine by the action of aminopropylagmatine ureohydrolase. That is, examples of the enzymes that catalyze the conversion of L-arginine or L-ornithine into a polyamine can include these enzymes. Notably, spermidine synthase, spermine synthase, and agmatine/triamine aminopropyl transferase each catalyze the reaction of transferring a propylamine group from decarboxylated S-adenosyl methionine (dcSAM), which can be generated from SAM by decarboxylation, into the corresponding substrate.

Creatine can be produced from L-arginine and glycine. That is, examples of the objective substance biosynthesis enzyme can also include, for example, L-arginine biosynthesis enzymes, glycine biosynthesis enzymes, and enzymes that catalyze the conversion of L-arginine and glycine into creatine. L-arginine and glycine can be combined to generate guanidinoacetate and ornithine by the action of arginine:glycine amidinotransferase (AGAT, EC 2.1.4.1); and guanidinoacetate can be methylated to generate creatine by the action of guanidinoacetate N-methyltransferase (GAMT, EC 2.1.1.2), using SAM as the methyl donor. That is, examples of the enzymes that catalyze the conversion of L-arginine and glycine into creatine can include these enzymes.

Mugineic acid can be produced from SAM. That is, examples of the objective substance biosynthesis enzyme can also include, for example, enzymes that catalyze the conversion of SAM into mugineic acid. One molecule of nicotianamine can be synthesized from three molecules of SAM by the action of nicotianamine synthase (EC 2.5.1.43). Nicotianamine can be converted successively to 3"-deamino-3"-oxonicotianamine, 2'-deoxymugineic-acid, and mugineic-acid by the action of nicotianamine aminotransferase (EC 2.6.1.80), 3"-deamino-3"-oxonicotianamine reductase (EC 1.1.1.285), and 2'-deoxymugineic-acid 2'-dioxygenase (EC 1.14.11.24), respectively. That is, examples of the enzymes that catalyze the conversion of SAM into mugineic acid can include these enzymes.

L-Methionine can be produced from L-cysteine. That is, examples of the objective substance biosynthesis enzyme can also include, for example, L-cysteine biosynthesis enzymes and enzymes that catalyze the conversion of L-cysteine into L-methionine. Examples of the L-cysteine biosynthesis enzymes can include the CysIXHDNYZ proteins, Fpr2 protein, and CysK protein described herein. Examples of the enzymes that catalyze the conversion of L-cysteine into L-methionine can include cystathionine-gamma-synthase and cystathionine-beta-lyase.

Examples of the methods for imparting or enhancing an objective substance-producing ability can also include a method of increasing the activity of an uptake system of a substance other than an objective substance, such as a substance generated as an intermediate during production of an objective substance and a substance used as a precursor of an objective substance. That is, the microorganism may have been modified so that the activity of such an uptake system is increased. The term "uptake system of a substance" can refer to a protein having a function of incorporating the substance from the outside of a cell into the cell. This activity can also be referred to as an "uptake activity of a substance". A gene encoding such an uptake system can also be referred to as an "uptake system gene". Examples of such an uptake system can include a vanillic acid uptake system and a protocatechuic acid uptake system. Examples of the vanillic acid uptake system can include a VanK protein, which is encoded by a vanK gene (M. T. Chaudhry, et al., Microbiology, 2007, 153:857-865). The nucleotide sequence of the vanK gene (NCgl2302) native to the *C. glutamicum* ATCC 13869 strain is shown as SEQ ID NO: 25, and the amino acid sequence of the VanK protein encoded by this gene is shown as SEQ ID NO: 26. Examples of the protocatechuic acid uptake system gene can include a PcaK protein, which is encoded by a pcaK gene (M. T. Chaudhry, et al., Microbiology, 2007, 153:857-865). The nucleotide sequence of the pcaK gene (NCgl1031) native to the *C. glutamicum* ATCC 13869 strain is shown as SEQ ID NO: 27, and the amino acid sequence of the PcaK protein encoded by this gene is shown as SEQ ID NO: 28.

The uptake activity of a substance can be measured according to, for example, a known method (M. T. Chaudhry, et al., Microbiology, 2007. 153:857-865).

Examples of the methods for imparting or enhancing an objective substance-producing ability further can include a method of reducing the activity of an enzyme that is involved in the by-production of a substance other than an objective substance. Such a substance other than an objective substance can also be referred to as a "byproduct". Such an enzyme can also be referred to as a "byproduct generation enzyme". Examples of the byproduct generation enzyme can include, for example, enzymes that are involved in the utilization of an objective substance, and enzymes that catalyze a reaction branching away from the biosynthetic pathway of an objective substance to generate a substance other than the objective substance. The method for reducing the activity of a protein, such as an enzyme etc., will be described herein. The activity of a protein, such as an enzyme etc., can be reduced by, for example, disrupting a gene that encodes the protein. For example, it has been reported that, in coryneform bacteria, vanillin is metabolized in the order of vanillin→vanillic acid→protocatechuic acid, and utilized (Current Microbiology, 2005, Vol. 51, pp. 59-65). That is, specific examples of the byproduct generation enzyme can include an enzyme that catalyzes the conversion of vanillin into protocatechuic acid and enzymes that catalyze further metabolization of protocatechuic acid. Examples of such enzymes can include vanillate demethylase, protocatechuate 3,4-dioxygenase, and various enzymes that further decompose the reaction product of protocatechuate 3,4-dioxygenase to succinyl-CoA and acetyl-CoA (Appl. Microbiol. Biotechnol., 2012, Vol. 95, p 77-89). In addition, vanillin can be converted into vanillyl alcohol by the action of alcohol dehydrogenase (Kunjapur A M. et al., J. Am. Chem. Soc., 2014, Vol. 136, p 11644-11654.; Hansen E H. et al., App. Env. Microbiol., 2009, Vol. 75, p 2765-2774.). That is, specific examples of the byproduct generation enzyme can also include alcohol dehydrogenase (ADH). In addition, 3-dehydroshikimic acid, which is an intermediate of the biosynthetic pathway of vanillic acid and vanillin, can also be converted into shikimic acid by the action of shikimate dehydrogenase. That is, specific examples of the byproduct generation enzyme can also include shikimate dehydrogenase.

The term "vanillate demethylase" can refer to a protein having an activity for catalyzing the reaction of demethylating vanillic acid to generate protocatechuic acid. This activity can also be referred to as a "vanillate demethylase activity". A gene encoding vanillate demethylase can also be referred to as a "vanillate demethylase gene". Examples of a vanillate demethylase can include VanAB proteins, which are encoded by vanAB genes (Current Microbiology, 2005, Vol. 51, pp. 59-65). The vanA gene and vanB gene encode the subunit A and subunit B of vanillate demethylase, respectively. To reduce the vanillate demethylase activity, both the vanAB genes may be disrupted or the like, or only one of the two may be disrupted or the like. The nucleotide sequences of the vanAB genes native to the *C. glutamicum* ATCC 13869 strain are shown as SEQ ID NOS: 29 and 31, and the amino acid sequences of the VanAB proteins encoded by these genes are shown as SEQ ID NOS: 30 and 32, respectively. The vanAB genes typically constitute the vanABK operon together with the vanK gene. Therefore, in order to reduce the vanillate demethylase activity, the vanABK operon may be totally disrupted or the like, for example, deleted. In such a case, the vanK gene may be introduced to a host again. For example, when vanillic acid present outside cells is used, and the vanABK operon is totally disrupted or the like, for example, deleted, it is preferable to introduce the vanK gene anew.

The vanillate demethylase activity can be measured by, for example, incubating the enzyme with a substrate such as vanillic acid, and measuring the enzyme- and substrate-dependent generation of protocatechuic acid (J Bacteriol, 2001, Vol. 183, p 32'76-3281).

The term "protocatechuate 3,4-dioxygenase" can refer to a protein having an activity for catalyzing the reaction of oxidizing protocatechuic acid to generate beta-Carboxy-cis, cis-muconic acid. This activity can also be referred to as a "protocatechuate 3,4-dioxygenase activity". A gene encoding protocatechuate 3,4-dioxygenase can also be referred to as a "protocatechuate 3,4-dioxygenase gene". Examples of a protocatechuate 3,4-dioxygenase can include PcaGH proteins, which are encoded by pcaGH genes (Appl. Microbiol. Biotechnol., 2012, Vol. 95, p 77-89). The pcaG gene and pcaH gene encode the alpha subunit and beta subunit of protocatechuate 3,4-dioxygenase, respectively. To reduce the protocatechuate 3,4-dioxygenase activity, both the pcaGH genes may be disrupted or the like, or only one of the two may be disrupted or the like. The nucleotide sequences of the pcaGH genes native to the *C. glutamicum* ATCC 13032 strain are shown as SEQ ID NOS: 33 and 35, and the amino acid sequences of the PcaGH proteins encoded by these genes are shown as SEQ ID NOS: 34 and 36, respectively.

The protocatechuate 3,4-dioxygenase activity can be measured by, for example, incubating the enzyme with a substrate, such as protocatechuic acid, and measuring the enzyme- and substrate-dependent oxygen consumption (Meth. Enz., 1970, Vol. 17A, p 526-529).

The term "alcohol dehydrogenase (ADH)" can refer to a protein that has an activity for catalyzing the reaction of reducing an aldehyde in the presence of an electron donor to generate an alcohol (EC 1.1.1.1, EC 1.1.1.2, EC 1.1.1.71, etc.). This activity can also be referred to as an "ADH activity". A gene encoding an ADH can also be referred to as an "ADH gene". Examples of the electron donor can include NADH and NADPH.

As ADH, one having an activity for catalyzing the reaction of reducing vanillin in the presence of an electron donor to generate vanillyl alcohol is a particular example. This activity can also be especially referred to as a "vanillyl alcohol dehydrogenase activity". Furthermore, ADH having the vanillyl alcohol dehydrogenase activity can also be especially referred to as a "vanillyl alcohol dehydrogenase".

Examples of an ADH can include a YqhD protein, NCgl0324 protein, NCgl0313 protein, NCgl2709 protein, NCgl0219 protein, and NCgl2382 protein, which are encoded by a yqhD gene, NCgl0324 gene, NCgl0313 gene, NCgl2709 gene, NCgl0219 gene, and NCgl2382 gene, respectively. The yqhD gene and the NCgl0324 gene encode vanillyl alcohol dehydrogenase. The yqhD gene can be found in, for example, bacteria belonging to the family Enterobacteriaceae such as *E. coli*. The NCgl0324 gene, NCgl0313 gene, NCgl2709 gene, NCgl0219 gene, and NCgl2382 gene can be found in, for example, coryneform bacteria such as *C. glutamicum*. The nucleotide sequence of the yqhD gene native to the *E. coli* K-12 MG1655 strain is shown as SEQ ID NO: 37, and the amino acid sequence of the YqhD protein encoded by this gene is shown as SEQ ID NO: 38. The nucleotide sequences of the NCgl0324 gene, NCgl0313 gene, and NCgl2709 gene native to the *C. glutamicum* ATCC 13869 strain are shown as SEQ ID NOS: 39, 41, and 43, respectively, and the amino acid sequences of the proteins encoded by these genes are shown as SEQ ID NOS: 40, 42, and 44, respectively. The nucleotide sequences of the NCgl0219 gene and NCgl2382 gene native to the *C. glutamicum* ATCC 13032 strain are shown as SEQ ID NOS: 45 and 47, respectively, and the amino acid sequences of the proteins encoded by these genes are shown as SEQ ID NOS: 46 and 48, respectively. The activity of one kind of ADH may be reduced, or the activities of two or more kinds of ADHs may be reduced. For example, the activity or activities of one or more of the NCgl0324 protein, NCgl2709 protein, and NCgl0313 protein may be reduced. Particularly, at least the activity of NCgl0324 protein may be reduced.

The ADH activity can be measured by, for example, incubating the enzyme with a substrate, that is, an aldehyde such as vanillin, in the presence of NADPH or NADH, and measuring the enzyme- and substrate-dependent oxidation of NADPH or NADH.

The term "shikimate dehydrogenase" can refer to a protein that has the activity of catalyzing the reaction of reducing 3-dehydroshikimic acid in the presence of an electron donor to generate shikimic acid (EC 1.1.1.25). This activity can also be referred to as a "shikimate dehydrogenase activity". A gene encoding a shikimate dehydrogenase can also be referred to as a "shikimate dehydrogenase gene". Examples of the electron donor can include NADH and NADPH. Examples of a shikimate dehydrogenase can include an AroE protein, which is encoded by an aroE gene. The nucleotide sequence of the aroE gene native to the *E. coli* K-12 MG1655 strain is shown as SEQ ID NO: 49, and the amino acid sequence of the AroE protein encoded by this gene is shown as SEQ ID NO: 50.

The shikimate dehydrogenase activity can be measured by, for example, incubating the enzyme with a substrate, such as 3-dehydroshikimic acid, in the presence of NADPH or NADH, and measuring the enzyme- and substrate-dependent oxidation of NADPH or NADH.

Examples of the methods for imparting or enhancing an objective substance-producing ability further can include a method of increasing the activity of an L-cysteine biosynthesis enzyme.

The term "L-cysteine biosynthesis enzyme" can refer to a protein that is involved in L-cysteine biosynthesis. A gene encoding the L-cysteine biosynthesis enzyme can also be referred to as an "L-cysteine biosynthesis gene". Examples of the L-cysteine biosynthesis enzyme can include proteins that are involved in sulfur utilization. Examples of the proteins that are involved in sulfur utilization can include CysIXHDNYZ proteins and an Fpr2 protein, which are encoded by cysIXHDNYZ genes and an fpr2 gene, respectively. The CysIXHDNYZ proteins are involved specifically in the reduction of inorganic sulfur compounds such as sulfate and sulfite. Fpr2 protein may be involved specifically in electron transport for the reduction of sulfite. Examples of the L-cysteine biosynthesis enzyme can also include O-acetylserine (thiol)-lyase. Examples of O-acetylserine (thiol)-lyase can include a CysK protein, which is encoded by a cysK gene. Examples of L-cysteine biosynthesis enzyme can include those native to various organisms such as Enterobacteriaceae bacteria and coryneform bacteria. Specific examples of L-cysteine biosynthesis enzyme can include the CysIXHDNYZ proteins, Fpr2 protein, and CysK protein native to *C. glutamicum*. The nucleotide sequences of the cysIXHDNYZ genes and fpr2 gene native to the *C. glutamicum* ATCC 13869 strain are shown as SEQ ID NOS: 88, 90, 92, 94, 96, 98, 100, and 102, respectively, and the amino acid sequences of the proteins encoded by these genes are shown as SEQ ID NOS: 89, 91, 93, 95, 97, 99, 101, and 103, respectively. The activity of one kind of L-cysteine biosynthesis enzyme may be increased, or the activities of two or more kinds of L-cysteine biosynthesis enzymes may be increased. For example, the activities of one or more of the CysIXHDNYZ proteins, Fpr2 protein, and CysK protein may be increased, or the activities of one or more of the CysIXHDNYZ proteins and Fpr2 protein may be increased.

The activity of an L-cysteine biosynthesis enzyme can be increased by, for example, increasing the expression of a gene encoding the L-cysteine biosynthesis enzyme, that is, an L-cysteine biosynthesis gene such as the cysIXHDNYZ genes, fpr2 gene, and cysK gene.

The expression of an L-cysteine biosynthesis gene can be increased by, for example, modifying, such as increasing or reducing, the activity of an expression regulator of the gene. That is, the expression of an L-cysteine biosynthesis gene can be increased by, for example, increasing the activity of a positive expression regulator, such as an activator, of the gene. Also, the expression of an L-cysteine biosynthesis gene can be increased by, for example, reducing the activity of a negative expression regulator, such as a repressor, of the gene. Such a regulator can also be referred to as a "regulator protein". A gene encoding such a regulator can also be referred to as a "regulator gene".

Examples of such an activator can include a CysR protein and an SsuR protein, which are encoded by a cysR gene and an ssuR gene, respectively. An increased activity of the CysR protein may result in an increased expression of one or more of the cysIXHDNYZ genes, fpr2 gene, and ssuR gene. Also, an increased activity of the SsuR protein may result in an increased expression of gene(s) involved in utilization of organic sulfur compounds. Examples of such an activator can include those native to various organisms such as Enterobacteriaceae bacteria and coryneform bacteria. Specific examples of such an activator can include the CysR protein and SsuR protein native to *C. glutamicum*. The nucleotide sequences of the cysR gene (NCgl0120) and ssuR gene native to the *C. glutamicum* ATCC 13869 strain are shown as SEQ ID NOS: 104 and 106, respectively, and the amino acid sequences of the proteins encoded by these genes are shown as SEQ ID NOS: 105 and 107, respectively. The activity or activities of either one or both of the CysR protein and SsuR protein may be increased. For example, the activity of at least the CysR protein may be increased. The activity of such an activator can be increased by, for example, increasing the expression of a gene encoding the activator.

Examples of such a repressor can include the McbR protein, which is encoded by the mcbR gene. A reduced activity of the McbR protein may result in an increased expression of one or more of the cysR gene and ssuR gene, and thereby may further result in an increased expression of one or more of the cysIXHDNYZ genes and fpr2 gene. The activity of such a repressor can be reduced by, for example, reducing the expression of a gene encoding the repressor or by disrupting a gene encoding the repressor.

That is, specifically, the activity of an L-cysteine biosynthesis enzyme can be increased by, for example, increasing the expression of one or more of the cysIXHDNYZ genes, fpr2 gene, cysR gene, and ssuR gene. Therefore, the phrase "the activity of an L-cysteine biosynthesis enzyme is increased" can mean that, for example, the expression of one or more of the cysIXHDNYZ genes, fpr2 gene, cysR gene, and ssuR gene is increased. For example, the expression of at least the cysR gene may be increased. Also, for example, the expression of all of these genes may be increased. The expression of one or more of the cysIXHDNYZ genes, fpr2 gene, and ssuR gene may be increased by increasing the expression of the cysR gene.

Examples of the methods for imparting or enhancing an objective substance-producing ability further can include a method of reducing the activity of the NCgl2048 protein.

The term "NCgl2048 protein" can refer to a protein encoded by an NCgl2048 gene. Examples of an NCgl2048 protein can include those native to various organisms such as Enterobacteriaceae bacteria and coryneform bacteria. Specific examples of an NCgl2048 protein can include the NCgl2048 protein native to *C. glutamicum*. The nucleotide sequence of the NCgl2048 gene native to the *C. glutamicum* ATCC 13869 strain is shown as SEQ ID NO: 119, and the amino acid sequence of the protein encoded by this gene is shown as SEQ ID NO: 120. Incidentally, the original function of the NCgl2048 protein regarding conservative variants described herein can mean the function of the protein having the amino acid sequence shown as SEQ ID NO: 120, or may also mean a property that a reduction in the activity of the protein in a microorganism provides an increased production of an objective substance.

Examples of the methods for imparting or enhancing an objective substance-producing ability further can include a method of reducing the activity of enolase.

The term "enolase" can refer to a protein that has the activity of catalyzing the reaction of dehydrating 2-phospho-D-glyceric acid to generate phosphoenolpyruvic acid (EC 4.2.1.11). This activity can also be referred to as an "enolase activity". Enolase can also be referred to as "phosphopyruvate hydratase". A gene encoding an enolase can also be referred to as an "enolase gene". Examples of an enolase can include an Eno protein, which is encoded by an eno gene. Examples of an enolase such as the Eno protein can include those native to various organisms such as Enterobacteriaceae bacteria and coryneform bacteria. Specific examples of an enolase can include the Eno protein native to *C. glutamicum*. The nucleotide sequence of the eno gene (NCgl0935) native to the *C. glutamicum* ATCC 13869 strain is shown as SEQ ID NO: 128, and the amino acid sequence of the Eno protein encoded by this gene is shown as SEQ ID NO: 129.

The enolase activity can be measured by, for example, incubating the enzyme with a substrate, such as 2-phospho-D-glyceric acid, and measuring the enzyme- and substrate-dependent generation of phosphoenolpyruvic acid.

Examples of the methods for imparting or enhancing an objective substance-producing ability further can include a method of reducing the activity of L-serine deaminase.

The term "L-serine deaminase" can refer to a protein that has the activity of catalyzing the reaction of converting L-serine into pyruvic acid and ammonia (EC 4.3.1.17). This activity can also be referred to as an "L-serine deaminase activity". L-serine deaminase can also be referred to as "L-serine ammonia-lyase". A gene encoding an L-serine deaminase can also be referred to as a "L-serine deaminase gene". Examples of an L-serine deaminase can include an SdaA protein, which is encoded by an sdaA gene. Examples of an L-serine deaminase such as the SdaA protein can include those native to various organisms such as Enterobacteriaceae bacteria and coryneform bacteria. Specific examples of an L-serine deaminase can include the SdaA protein native to *C. glutamicum*. The nucleotide sequence of the sdaA gene (NCgl1583) native to the *C. glutamicum* ATCC 13869 strain is shown as SEQ ID NO: 146, and the amino acid sequence of the SdaA protein encoded by this gene is shown as SEQ ID NO: 147.

The L-serine deaminase activity can be measured by, for example, incubating the enzyme with a substrate, such as L-serine, and measuring the enzyme- and substrate-dependent generation of pyruvic acid or ammonia.

Examples of the methods for imparting or enhancing an objective substance-producing ability further can include a method of reducing the activity of AICAR formyltransferase/IMP cyclohydrolase or modifying a gene encoding AICAR formyltransferase/IMP cyclohydrolase so as to have the "specific mutation" described herein.

The term "AICAR formyltransferase/IMP cyclohydrolase" can refer to AICAR formyltransferase and/or IMP cyclohydrolase, that is, either one or both of AICAR formyltransferase and IMP cyclohydrolase. The term "AICAR formyltransferase" can refer to a protein that has the activity of catalyzing the reaction of converting 5-amino-1-(5-phospho-D-ribosyl)imidazole-4-carboxamide (AICAR) and 10-formyltetrahydrofolate into 5-formamido-1-(5-phospho-D-ribosyl)imidazole-4-carboxamide (FAICAR) and tetrahydrofolate (EC 2.1.2.3). This activity can also be referred to as an "AICAR formyltransferase activity". The term "IMP cyclohydrolase" can refer to a protein that has the activity of catalyzing the reaction of dehydrating FAICAR to generate IMP (EC 3.5.4.10). This activity can also be referred to as an "IMP cyclohydrolase activity". A gene encoding an AICAR formyltransferase/IMP cyclohydrolase can also be referred to as an "AICAR formyltransferase/IMP cyclohydrolase gene". AICAR formyltransferase and IMP cyclohydrolase may be encoded as a bifunctional enzyme. Hence, the term "AICAR formyltransferase/IMP cyclohydrolase" can specifically refer to a bifunctional AICAR formyltransferase/IMP cyclohydrolase, i.e. a protein having both the AICAR formyltransferase activity and IMP cyclohydrolase activity. Examples of an AICAR formyltransferase/IMP cyclohydrolase can include a PurH protein, which is a bifunctional AICAR formyltransferase/IMP cyclohydrolase encoded by a purH gene. Examples of an AICAR formyltransferase/IMP cyclohydrolase such as the PurH protein can include those native to various organisms such as Enterobacteriaceae bacteria and coryneform bacteria. Specific examples of an AICAR formyltransferase/IMP cyclohydrolase can include the PurH protein native to *C. glutamicum*. The nucleotide sequence of the purH gene (NCgl0827) native to the *C. glutamicum* ATCC 13869 strain is shown as SEQ ID NO: 134, and the amino acid sequence of the PurH protein encoded by this gene is shown as SEQ ID NO: 135.

The AICAR formyltransferase/IMP cyclohydrolase activity can be measured by, for example, incubating the enzyme with a substrate, such as AICAR and 10-formyltetrahydrofolate for AICAR formyltransferase; FAICAR for IMP cyclohydrolase, and measuring the enzyme- and substrate-dependent generation of the corresponding product, such as FAICAR or tetrahydrofolate for AICAR formyltransferase; IMP for IMP cyclohydrolase. Generation of tetrahydrofolate can be measured on the basis of absorbance at 298 nm (Rayl E A, et al (1996) JBC 271:2225-33). Furthermore, the AICAR formyltransferase activity and the IMP cyclohydrolase activity can be collectively measured by, for example, incubating the enzyme with the substrate for AICAR formyltransferase, such as AICAR and 10-formyltetrahydrofolate, and measuring the enzyme- and substrate-dependent generation of the product for IMP cyclohydrolase, such as IMP. It is sufficient that AICAR formyltransferase/IMP cyclohydrolase has the AICAR formyltransferase/IMP cyclohydrolase activity that is measured under at least one appropriate condition. In other words, it is sufficient that the microorganism is modified so that the activity of AICAR formyltransferase/IMP cyclohydrolase is reduced when the activity is measured under at least one appropriate condition. Incidentally, it is also sufficient that all the other proteins referred to herein have the respective activities that are each measured under at least one appropriate condition.

Methods for reducing the activity of a protein such as AICAR formyltransferase/IMP cyclohydrolase will be explained herein. The activity of AICAR formyltransferase/IMP cyclohydrolase can be reduced by, for example, attenuating the expression of a gene encoding AICAR formyltransferase/IMP cyclohydrolase, or disrupting a gene encoding AICAR formyltransferase/IMP cyclohydrolase. Furthermore, in an embodiment, the activity of AICAR formyltransferase/IMP cyclohydrolase may also be reduced by, for example, modifying a gene encoding AICAR formyltransferase/IMP cyclohydrolase so as to have the "specific mutation". Such methods for reducing the activity of AICAR formyltransferase/IMP cyclohydrolase may be used independently or in an arbitrary combination.

The microorganism may be modified so that a gene encoding AICAR formyltransferase/IMP cyclohydrolase has the "specific mutation".

The "specific mutation" is a mutation that results in improving an objective substance-producing ability of the microorganism. The term "specific mutation" in reference to the AICAR formyltransferase/IMP cyclohydrolase gene can refer to a change in the nucleotide sequence of the AICAR formyltransferase/IMP cyclohydrolase gene. The "specific mutation" can provide a change in the amino acid sequence of the encoded AICAR formyltransferase/IMP cyclohydrolase. Accordingly, the term "specific mutation" may also be used for AICAR formyltransferase/IMP cyclohydrolase as a term referring to a change in the amino acid sequence of AICAR formyltransferase/IMP cyclohydrolase provided by the "specific mutation" in the AICAR formyltransferase/IMP cyclohydrolase gene. That is, the phrase "an AICAR formyltransferase/IMP cyclohydrolase gene has the "specific mutation"" may be read as that AICAR formyltransferase/IMP cyclohydrolase encoded by the gene has the "specific mutation".

AICAR formyltransferase/IMP cyclohydrolase having the "specific mutation" can also be referred to as a "mutant AICAR formyltransferase/IMP cyclohydrolase". A gene encoding a mutant AICAR formyltransferase/IMP cyclohydrolase, that is, an AICAR formyltransferase/IMP cyclohydrolase gene having the "specific mutation", can also be referred to as "mutant AICAR formyltransferase/IMP cyclohydrolase gene".

AICAR formyltransferase/IMP cyclohydrolase not having the "specific mutation" can also be referred to as a "wild-type AICAR formyltransferase/IMP cyclohydrolase". A gene encoding a wild-type AICAR formyltransferase/IMP cyclohydrolase, that is, an AICAR formyltransferase/IMP cyclohydrolase gene not having the "specific mutation", can also be referred to as a "wild-type AICAR formyltransferase/IMP cyclohydrolase gene". Examples of the wild-type AICAR formyltransferase/IMP cyclohydrolase gene or wild-type AICAR formyltransferase/IMP cyclohydrolase can include, for example, the AICAR formyltransferase/IMP cyclohydrolase genes or AICAR formyltransferases/IMP cyclohydrolases exemplified above and conservative variants thereof.

The "specific mutation" is not particularly limited, so long as the mutation improves an objective substance-producing ability of the microorganism. The "specific mutation" may be, for example, a mutation for reducing the activity of AICAR formyltransferase/IMP cyclohydrolase. The "specific mutation" may also be, for example, a mutation for increasing the intracellular concentration of AICAR.

Specific examples of the "specific mutation" can include a mutation that the serine residue at position 37 (S37) of the encoded AICAR formyltransferase/IMP cyclohydrolase is replaced with another amino acid residue.

In the mutation at "S37", the amino acid residue after the modification may be any amino acid residue other than the amino acid residue before the modification, which is at least other than a serine residue, so long as the mutation improves an objective substance-producing ability of the microorganism. Examples of the amino acid residue after modification can include K (Lys), R (Arg), H (His), A (Ala), V (Val), L (Leu), I (Ile), G (Gly), T (Thr), P (Pro), F (Phe), W (Trp), Y (Tyr), C (Cys), M (Met), D (Asp), E (Glu), N (Asn), and Q (Gln). Particular examples of the amino acid residue after modification can include F (Phe). That is, particular examples of the "specific mutation" can include a mutation for replacing S37 with F (S37F mutation).

The term "S37" in an arbitrary wild-type AICAR formyltransferase/IMP cyclohydrolase can refer to an amino acid residue corresponding to the serine residue at position 37 of the amino acid sequence shown as SEQ ID NO: 135. The descriptions regarding the mutations at "L198" or "E199" for OMT, such as those for defining the absolute positions thereof, can be applied mutatis mutandis to the mutation at "S37" for AICAR formyltransferase/IMP cyclohydrolase, provided that the amino acid sequence shown in SEQ ID NO: 135" is used as the reference sequence of the wild-type protein.

A mutant AICAR formyltransferase/IMP cyclohydrolase gene can be obtained by, for example, modifying a wild-type AICAR formyltransferase/IMP cyclohydrolase gene so that AICAR formyltransferase/IMP cyclohydrolase encoded thereby has the "specific mutation". The wild-type AICAR formyltransferase/IMP cyclohydrolase gene to be modified can be obtained by, for example, cloning from an organism having the wild-type AICAR formyltransferase/IMP cyclohydrolase gene, or chemical synthesis. Alternatively, a mutant AICAR formyltransferase/IMP cyclohydrolase gene can also be obtained without using a wild-type AICAR formyltransferase/IMP cyclohydrolase gene. For example, a mutant AICAR formyltransferase/IMP cyclohydrolase gene may be directly obtained by, for example, cloning from an organism having the mutant AICAR formyltransferase/IMP cyclohydrolase gene, or chemical synthesis. The obtained mutant AICAR formyltransferase/IMP cyclohydrolase gene may be used as it is, or may be further modified before use. Genes can be modified by using a known method. For example, an objective mutation can be introduced into a target site of DNA by the site-specific mutagenesis method. The wild-type AICAR formyltransferase/IMP cyclohydrolase gene to be modified or the mutant AICAR formyltransferase/IMP cyclohydrolase gene may or may not be derived from the host, such as a microorganism from which the microorganism as described herein is derived.

Methods for modifying a microorganism so that the AICAR formyltransferase/IMP cyclohydrolase gene has the "specific mutation" are not particularly limited. The phrase "a microorganism is modified so that a gene encoding AICAR formyltransferase/IMP cyclohydrolase has the "specific mutation"" may specifically mean that the microorganism is modified so as to have a mutant AICAR formyltransferase/IMP cyclohydrolase gene instead of a native wild-type AICAR formyltransferase/IMP cyclohydrolase gene. The phrase "a microorganism has a mutant AICAR formyltransferase/IMP cyclohydrolase gene instead of a native wild-type AICAR formyltransferase/IMP cyclohydrolase gene" can mean that the microorganism has the mutant AICAR formyltransferase/IMP cyclohydrolase gene while it no longer has the normally-functional native wild-type AICAR formyltransferase/IMP cyclohydrolase gene, that is, the native wild-type AICAR formyltransferase/IMP cyclohydrolase gene has been modified so as not to normally function. It is sufficient that the native wild-type AICAR formyltransferase/IMP cyclohydrolase gene has been modified in such a manner that an objective substance-producing ability of the microorganism is improved. The phrase "native wild-type AICAR formyltransferase/IMP cyclohydrolase gene" can refer to a wild-type AICAR formyltransferase/IMP cyclohydrolase gene inherently present in the microorganism. A microorganism can be modified so that the AICAR formyltransferase/IMP cyclohydrolase gene has the "specific mutation" by, for example, introducing a mutant AICAR formyltransferase/IMP cyclohydrolase gene into the microorganism. In such a case, the native wild-type AICAR formyltransferase/IMP cyclohydrolase gene on the chromosome or the like of the microorganism should be modified, e.g. disrupted or deleted, in such a manner that an objective substance-producing ability of the microorganism is improved in combination with the introduction of the mutant AICAR formyltransferase/IMP cyclohydrolase gene. For example, the native wild-type AICAR formyltransferase/IMP cyclohydrolase gene may be replaced with the mutant AICAR formyltransferase/IMP cyclohydrolase gene, or may be disrupted or deleted independently from the introduction of the mutant AICAR formyltransferase/IMP cyclohydrolase gene. Alternatively, the microorganism can also be modified so that the AICAR formyltransferase/IMP cyclohydrolase gene has the "specific mutation" by, for example, introducing the "specific mutation" into a wild-type AICAR formyltransferase/IMP cyclohydrolase gene, such as the native wild-type AICAR formyltransferase/IMP cyclohydrolase gene, on the chromosome or the like of the microorganism. A mutation can be introduced into a gene on a chromosome or the like by, for example, natural mutation, mutagenesis treatment, or genetic engineering.

The protein of which the activity is to be modified can be appropriately chosen depending on the type of the biosynthesis pathway via which an objective substance is produced in the method as described herein and on the types and activities of the proteins inherently possessed by the microorganism. For example, when vanillin is produced by bioconversion of protocatechuic acid, it may be preferable to enhance the activity or activities of one or more of OMT, ACAR, PPT, and the protocatechuic acid uptake system. Also, when vanillin is produced by bioconversion of protocatechualdehyde, it may be preferable to enhance the activity of OMT.

The genes and proteins used for breeding a microorganism having an objective substance-producing ability may have, for example, the above-exemplified or other known nucleotide sequences and amino acid sequences, respectively. Also, the genes and proteins used for breeding a microorganism having an objective substance-producing ability may be conservative variants of the genes and proteins exemplified above, such as genes and proteins having the above-exemplified or other known nucleotide sequences and amino acid sequences, respectively. Specifically, for example, the genes used for breeding a microorganism having an objective substance-producing ability may each be a gene encoding a protein having the amino acid sequence exemplified above or the amino acid sequence of a known protein, but including substitution, deletion, insertion, and/or addition of one or several some amino acid residues at one or several positions, so long as the original function of the protein, such as enzymatic activity, transporter activity, etc., is maintained. Furthermore, for example, the genes used for breeding a microorganism having an objective substance-producing ability may each be a gene encoding a protein having an amino acid sequence showing a homology of, for example, 50% or more, 65% or more, 80% or more, 90% or more, 95% or more, 97% or more, or 99% or more, to the total amino acid sequence of the amino acid sequence exemplified above or the amino acid sequence of a known protein, so long as the original function of the protein is maintained. As for conservative variants of genes and proteins, the descriptions concerning conservative variants of the SAM cycle enzyme gene and SAM cycle enzyme described herein can be applied mutatis mutandis.

<1-2> Increase in SAM Cycle Enzyme Activity

The microorganism as described herein has been modified so that the activity of an SAM cycle enzyme is increased. Specifically, the microorganism has been modified so that the activity of an SAM cycle enzyme is increased as compared with a strain of a non-modified microorganism. By modifying a microorganism so that the activity of an SAM cycle enzyme is increased, an objective substance-producing ability of the microorganism can be improved, that is, the production of an objective substance by using the microorganism can be increased. Also, by modifying a microorganism so that the activity of an SAM cycle enzyme is increased, an ability of the microorganism for generating or regenerating SAM may possibly be improved. That is, specifically, an increase in an objective substance-producing ability of a microorganism may be due to an increase in an ability of the microorganism to generate or regenerate SAM.

The microorganism as described herein can be obtained by modifying a microorganism having an objective substance-producing ability so that the activity of an SAM cycle enzyme is increased. The microorganism can also be obtained by modifying a microorganism so that the activity of an SAM cycle enzyme is increased, and then imparting an objective substance-producing ability to the microorganism or enhancing an objective substance-producing ability of the microorganism. In addition, the microorganism may acquire an objective substance-producing ability as a result of a modification that results in increasing the activity of an SAM cycle enzyme, or as a result of a combination of a modification that results in increasing the activity of an SAM cycle enzyme and other modification(s) for imparting or enhancing an objective substance-producing ability. The modifications for constructing the microorganism can be performed in an arbitrary order.

The term "S-adenosylmethionine cycle enzyme (SAM cycle enzyme)" can refer to an enzyme that is involved in the SAM cycle. A gene encoding a SAM cycle enzyme can also be referred to as a "SAM cycle enzyme gene". The SAM cycle enzyme can be S-adenosyl-L-homocysteine hydrolase, methionine synthase, methionine adenosyltransferase, or 5,10-methylenetetrahydrofolate reductase. In an embodiment, the SAM cycle enzyme may be methionine adenosyltransferase, methionine synthase, or 5,10-methylenetetrahydrofolate reductase. In such an embodiment, the activity of S-adenosyl-L-homocysteine hydrolase may additionally be increased. The activity of one SAM cycle enzyme may be increased, or the activities of two or more of the SAM cycle enzymes may be increased.

The term "S-adenosyl-L-homocysteine hydrolase" can refer to a protein that has the activity of catalyzing the reaction of hydrolyzing S-adenosyl-L-homocysteine (SAH) to generate L-homocysteine and adenosine (EC 3.3.1.1). This activity can also be referred to as an "S-adenosyl-L-homocysteine hydrolase activity". S-adenosyl-L-homocysteine hydrolase can also be referred to as "adenosylhomocysteinase". A gene encoding an S-adenosyl-L-homocysteine hydrolase can also be referred to as an "S-adenosyl-L-homocysteine hydrolase gene". Examples of an S-adenosyl-L-homocysteine hydrolase can include an SahH protein, which is encoded by an sahH gene. Examples of an S-adenosyl-L-homocysteine hydrolase such as the SahH protein can include those native to various organisms such as yeast, Streptomyces bacteria, and coryneform bacteria. Specific examples of an S-adenosyl-L-homocysteine hydrolase can include the SahH protein native to *C. glutamicum*. The nucleotide sequence of the sahH gene (NCgl0719) native to the *C. glutamicum* ATCC 13869 strain is shown as SEQ ID NO: 144, and the amino acid sequence of the SahH protein encoded by this gene is shown as SEQ ID NO: 145.

The term "methionine synthase" can refer to a protein that has the activity of catalyzing the reaction of methylating L-homocysteine to generate L-methionine in the presence of a methyl group donor (EC 2.1.1.13, EC 2.1.1.14, etc.). This activity can also be referred to as a "methionine synthase activity". A gene encoding a methionine synthase can also be referred to as a "methionine synthase gene". Examples of the methyl group donor used by methionine synthase can include 5-methyltetrahydropteroyl-mono-L-glutamate (synonym: 5-methyltetrahydrofolate; 5-MTHF) and those having two more L-glutamate residues, such as 5-methyltetrahydropteroyl-tri-L-glutamate. Examples of a methionine synthase can include MetE and MetH proteins, which are encoded by metE and metH genes, respectively. MetE protein may be a vitamin-B12-independent methionine synthase. MetH protein may be a vitamin-B12-dependent methionine synthase. Examples of a methionine synthase such as the MetE and MetH proteins can include those native to various organisms such as Enterobacteriaceae bacteria and coryneform bacteria. Specific examples of methionine synthase can include the MetE and MetH proteins native to *E. coli*. The nucleotide sequences of the metE and metH genes native to the *E. coli* K-12 MG1655 are shown as SEQ ID NOS: 165 and 167, respectively, and the amino acid sequences of the proteins encoded by these genes are shown as SEQ ID NOS: 166 and 168, respectively. The nucleotide sequence of the metH gene (cg1701) native to the *C. glutamicum* ATCC 13032 strain is shown as SEQ ID NO: 169, and the amino acid sequence of the MetH protein encoded by this gene is shown as SEQ ID NO: 170. Incidentally, coryneform bacteria such as *Corynebacterium glutamicum* has NCgl2048 gene, which encodes a protein homologous to both MetE and MetH proteins native to *E. coli*. While the protein encoded by NCgl2048 gene is annotated as methionine synthase in some databases, this protein is excluded from "methionine synthase" as referred to herein.

The term "methionine adenosyltransferase" can refer to a protein that has the activity of catalyzing the reaction of converting L-methionine into SAM in the presence of ATP (EC 2.5.1.6). This activity can also be referred to as a "methionine adenosyltransferase activity". A gene encoding a methionine adenosyltransferase can also be referred to as "methionine adenosyltransferase gene". Examples of a methionine adenosyltransferase can include an MetK protein, which is encoded by an metK gene. Examples of a methionine adenosyltransferase such as the MetK protein can include those native to various organisms such as Enterobacteriaceae bacteria and coryneform bacteria. Specific examples of a methionine adenosyltransferase can include MetK protein native to *C. glutamicum*. The nucleotide sequence of the metK gene (NCgl1541) native to the *C. glutamicum* ATCC 13869 strain is shown as SEQ ID NO: 161, and the amino acid sequence of the MetK protein encoded by this gene is shown as SEQ ID NO: 162.

The term "5,10-methylenetetrahydrofolate reductase" can refer to a protein that has the activity of catalyzing the reaction of reducing 5,10-methylenetetrahydrofolate to generate 5-methyltetrahydrofolate (5-MTHF) in the presence of an electron donor (EC 1.5.1.20). This activity can also be referred to as a "5,10-methylenetetrahydrofolate reductase activity". A gene encoding a 5,10-methylenetetrahydrofolate reductase can also be referred to as "5,10-methylenetetrahydrofolate reductase gene". Examples of a 5,10-methylenetetrahydrofolate reductase can include an MetF protein, which is encoded by an metF gene. Examples of the electron donor can include NADH and NADPH. Examples of a 5,10-methylenetetrahydrofolate reductase such as the MetF protein can include those native to various organisms such as yeast, Enterobacteriaceae bacteria, and coryneform bacteria. Specific examples of a 5,10-methylenetetrahydrofolate reductase can include the MetF proteins native to *C. glutamicum* and *S. cerevisiae*. The nucleotide sequence of the metF gene (NCgl2091) native to the *C. glutamicum* ATCC 13869 strain is shown as SEQ ID NO: 183, and the amino acid sequence of the MetF protein encoded by this gene is shown as SEQ ID NO: 184. The nucleotide sequence of the metF gene (MET13) native to the *S. cerevisiae* S288c strain is shown as SEQ ID NO: 173, and the amino acid sequence of the MetF protein encoded by this gene is shown as SEQ ID NO: 174. Specific examples of 5,10-methylenetetrahydrofolate reductase also can include a partial MetF protein native to *C. glutamicum* used in the Examples section. The nucleotide sequence of a partial metF gene encoding this partial MetF protein is shown as SEQ ID NO: 171, and the amino acid sequence of this partial MetF protein is shown as SEQ ID NO: 172. The terms "metF gene" and "MetF protein" can include these partial metF gene and MetF protein, as well as full-length ones.

That is, the SAM cycle enzyme gene may be, for example, a gene having or including the nucleotide sequence shown as SEQ ID NOs: 144, 161, 165, 167, 169, 171, 173, or 183. Also, the SAM cycle enzyme may be, for example, a protein having or including the amino acid sequence shown as SEQ ID NO: 145, 162, 166, 168, 170, 172, 174, or 184.

The SAM cycle enzyme gene may be a variant of any of the SAM cycle enzyme genes exemplified above, such as the sahH, metE, metH, metK, and metF genes, so long as the original function thereof is maintained. Similarly, the SAM cycle enzyme may be a variant of any of the SAM cycle enzymes exemplified above, such as the SahH, MetE, MetH, MetK, and MetF proteins, so long as the original function thereof is maintained. A variant that maintains the original function thereof can also be referred to as a "conservative variant". A gene defined with the above-mentioned gene name and a protein defined with the above-mentioned protein name can include not only the genes and proteins exemplified above, respectively, but also can include conservative variants thereof. Namely, for example, the term "metK gene (or NCgl1541 gene)" can includes not only the metK gene exemplified above, such as the metK gene having the nucleotide sequence shown as SEQ ID NO: 161, but also can include conservative variants thereof. Similarly, the term "MetK protein (or NCgl1541 protein)" can include not only the MetK protein exemplified above, such as the MetK protein having the amino acid sequence shown as SEQ ID NO: 162, but also can include conservative variants thereof. Examples of the conservative variants can include, for example, homologues and artificially modified versions of the genes and proteins exemplified above.

The phrase "the original function is maintained" means that a variant of the gene or protein has a function, such as activity or property corresponding to the function, such as activity or property, of the original gene or protein. The phrase "the original function is maintained" in reference to a gene can mean that a variant of the gene encodes a protein that maintains the original function. That is, the phrase "the original function is maintained" in reference to the SAM cycle enzyme gene can mean that the variant of the gene encodes a SAM cycle enzyme. The phrase "the original function is maintained" in reference to the SAM cycle enzyme can mean that the variant of the protein has the corresponding SAM cycle enzyme activity, such as the S-adenosyl-L-homocysteine hydrolase activity for S-adenosyl-L-homocysteine hydrolase; the methionine synthase activity for methionine synthase; the methionine adenosyltransferase activity for methionine adenosyltransferase; and the 5,10-methylenetetrahydrofolate reductase activity for 5,10-methylenetetrahydrofolate reductase.

The S-adenosyl-L-homocysteine hydrolase activity can be measured by, for example, incubating the enzyme with a substrate, such as S-adenosyl-L-homocysteine and DTNB (5,5'-Dithiobis(2-nitrobenzoic acid), and measuring the product, such as homocysteine-dependent generation of TNB (5-Mercapto-2-nitrobenzoic acid) on the basis of absorbance at 412 nm (J Mol Microbiol Biotechnol 2008, 15: 277-286).

The methionine synthase activity can be measured by, for example, incubating the enzyme with a substrate, such as L-homocysteine in the presence of a methyl group donor, and measuring the enzyme- and substrate-dependent generation of L-methionine.

The methionine adenosyltransferase activity can be measured by, for example, incubating the enzyme with a substrate, such as L-serine, and measuring the enzyme- and substrate-dependent generation of pyruvic acid or ammonia.

The 5,10-methylenetetrahydrofolate reductase activity can be measured by, for example, incubating the enzyme with a substrate, such as 5,10-methylenetetrahydrofolate, in the presence of an electron donor, and measuring the enzyme- and substrate-dependent generation of 5-MTHF.

The SAM cycle enzyme can have the corresponding SAM cycle enzyme activity, that is, the S-adenosyl-L-homocysteine hydrolase activity for S-adenosyl-L-homocysteine hydrolase; the methionine synthase activity for methionine synthase; the methionine adenosyltransferase activity for methionine adenosyltransferase; and the 5,10-methylenetetrahydrofolate reductase activity for 5,10-methylenetetrahydrofolate reductase, which is measured under at least one appropriate condition. In other words, it is sufficient that the microorganism is modified so that the activity of an SAM cycle enzyme is increased when the activity is measured under at least one appropriate condition. Incidentally, it is also sufficient that all the other proteins referred to herein can have the respective activities that are each measured under at least one appropriate condition.

Hereafter, examples of the conservative variants will be explained.

Homologues of the SAM cycle enzyme gene or homologues of the SAM cycle enzymes can be easily determined from public databases by, for example, BLAST search or FASTA search, using any of the nucleotide sequences of the SAM cycle enzyme genes exemplified above or any of the amino acid sequences of the SAM cycle enzymes exemplified above as a query sequence. Furthermore, homologues of the SAM cycle enzyme gene can be obtained by, for example, PCR using a chromosome of an organism such as coryneform bacteria as the template, and oligonucleotides prepared on the basis of any of the nucleotide sequences of the SAM cycle enzyme genes exemplified above as primers.

The SAM cycle enzyme gene may be a gene encoding a protein having any of the aforementioned amino acid sequences, such as the amino acid sequence shown as SEQ ID NO: 145, 162, 166, 168, 170, 172, 174, or 184, including substitution, deletion, insertion, and/or addition of one or several amino acid residues at one or several positions, so long as the original function is maintained. For example, the encoded protein may have an extended or deleted N-terminus and/or C-terminus. Although the number meant by the phrase "one or several" may differ depending on the positions of amino acid residues in the three-dimensional structure of the protein or the types of amino acid residues, specifically, it can be, for example, 1 to 50, 1 to 40, 1 to 30, 1 to 20, 1 to 10, 1 to 5, or 1 to 3.

The aforementioned substitution, deletion, insertion, and/or addition of one or several amino acid residues are each a conservative mutation that maintains the original function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, or the like of amino acid residues as mentioned above can include a naturally occurring mutation due to an individual difference, or a difference of species of the organism from which the gene is derived (mutant or variant).

Furthermore, the SAM cycle enzyme gene may be a gene encoding a protein having an amino acid sequence showing a homology of, for example, 50% or more, 65% or more, 80% or more, 90% or more, 95% or more, 97% or more, or 99% or more, to the total amino acid sequence of any of the aforementioned amino acid sequences, so long as the original function is maintained. In addition, in this specification, "homology" is equivalent to "identity".

Furthermore, the SAM cycle enzyme gene may be a gene, such as a DNA, that is able to hybridize under stringent conditions with a probe that can be prepared from any of the aforementioned nucleotide sequences, for example the nucleotide sequence shown as SEQ ID NO: 144, 161, 165, 167, 169, 171, 173, or 183, such as a sequence complementary to the whole sequence or a partial sequence of any of the aforementioned nucleotide sequences, so long as the original function is maintained. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, 80%, 90%, 95%, 97%, or 99% homologous, hybridize to each other, and DNAs less homologous than the above do not hybridize to each other, or conditions of washing of typical Southern hybridization, that is, conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, in particular, the washing conditions of the hybridization may be, for example, 50° C., 2×SSC and 0.1% SDS.

Furthermore, since properties concerning degeneracy of codons can change depending on the host, the SAM cycle enzyme gene can include substitution of respective equivalent codons for arbitrary codons. That is, the SAM cycle enzyme gene may be a variant of any of the SAM cycle enzyme genes exemplified above due to the degeneracy of the genetic code. For example, the SAM cycle enzyme gene may be modified so that it has optimal codons according to codon frequencies in the chosen host.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison, i.e. alignment, for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other. The term "identity" between amino acid sequences may specifically mean an identity calculated by blastp with default scoring parameters (i.e. Matrix, BLOSUM62; Gap Costs, Existence=11, Extension=1; Compositional Adjustments, Conditional compositional score matrix adjustment), unless otherwise stated. The term "identity" between nucleotide sequences may specifically mean an identity calculated by blastn with default scoring parameters (i.e. Match/Mismatch Scores=1, −2; Gap Costs=Linear), unless otherwise stated.

The aforementioned descriptions concerning conservative variants of the genes and proteins can be applied mutatis mutandis to variants of arbitrary proteins such as objective substance biosynthesis enzymes and genes encoding them.

<1-3> Methods for Increasing Activity of Protein

Hereinafter, the methods for increasing the activity of a protein such as the SAM cycle enzyme will be explained.

The phrase "the activity of a protein is increased" can mean that the activity of the protein is increased as compared with a non-modified strain, that is, as compared with a strain of a non-modified microorganism. Specifically, the phrase "the activity of a protein is increased" can mean that the activity of the protein per cell is increased as compared with that of a non-modified strain. The term "non-modified strain" or "strain of a non-modified microorganism" can refer to a control strain that has not been modified so that the activity of an objective protein is increased. Examples of the non-modified strain can include a wild-type strain and parent strain. Specific examples of the non-modified strain can include the respective type strains of the species of microorganisms. Specific examples of the non-modified strain can also include strains exemplified above in relation to the description of microorganisms. That is, in an embodiment, the activity of a protein may be increased as compared with a type strain, that is, the type strain of the species to which the microorganism as described herein belongs. In another embodiment, the activity of a protein may also be increased as compared with the *C. glutamicum* ATCC 13869 strain. In another embodiment, the activity of a protein may also be increased as compared with the *C. glutamicum* ATCC 13032 strain. In another embodiment, the activity of a protein may also be increased as compared with the *E. coli* K-12 MG1655 strain. The phrase "the activity of a protein is increased" may also be expressed as "the activity of a protein is enhanced". More specifically, the phrase "the activity of a protein is increased" can mean that the number of molecules of the protein per cell is increased, and/or the function of each molecule of the protein is increased, as compared with those of a non-modified strain. That is, the term "activity" in the phrase "the activity of a protein is increased" is not limited to the catalytic activity of the protein, but can also mean the transcription amount of a gene encoding the protein, that is, the amount of mRNA, or the translation amount of a gene encoding the protein, that is, the amount of the protein. Furthermore, the phrase "the activity of a protein is increased" can include not only when the activity of an objective protein is increased in a strain inherently having the activity of the objective protein, but also when the activity of an objective protein is imparted to a strain not inherently having the activity of the objective protein. Furthermore, so long as the activity of the protein is eventually increased, the activity of an objective protein inherently present in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.2 times or more, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The phrase "the expression of a gene is increased" can mean that the expression of the gene is increased as compared with a non-modified strain, such as a wild-type strain and parent strain. Specifically, the phrase "the expression of a gene is increased" can mean that the expression amount of the gene per cell is increased as compared with that of a non-modified strain. More specifically, the phrase "the expression of a gene is increased" can mean that the transcription amount of the gene, that is, the amount of mRNA, is increased, and/or the translation amount of the gene, that is, the amount of the protein expressed from the gene, is increased. The phrase "the expression of a gene is increased" can also be referred to as "the expression of a gene is enhanced". The expression of a gene may be increased to, for example, 1.2 times or more, 1.5 times or more, 2 times or more, or 3 times or more of that of a non-modified strain. Furthermore, the phrase "the expression of a gene is increased" can include not only when the expression amount of an objective gene is increased in a strain that inherently expresses the objective gene, but also when the gene is introduced into a strain that does not inherently express the objective gene, and is expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy of a gene may be introduced, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome, such as a gene, unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector can have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of a vector autonomously replicable in Enterobacteriaceae bacteria such as *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (Takara Bio), pACYC series vectors, and the broad host spectrum vector RSF1010. Specific examples of a vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVK9 described in WO2007/046389; pVS7 described in WO2013/069634; and pVC7 described in Japanese Patent Laid-open (Kokai) No. 9-070291.

When a gene is introduced, it is sufficient that the gene is able to be expressed by the chosen host. Specifically, it is sufficient that the gene is present in a host so that it is expressed under the control of a promoter that functions in the host. The term "promoter that functions in a host" can refer to a promoter that shows a promoter activity in the host. The promoter may be a promoter derived from the host, or may be a heterogenous promoter. The promoter may be the native promoter of the gene to be introduced, or a promoter of another gene. As the promoter, for example, such a stronger promoter as described herein may also be used.

A terminator for termination of gene transcription may be located downstream of the gene. The terminator is not particularly limited so long as it functions in the chosen host. The terminator may be a terminator derived from the host, or may be a heterogenous terminator. The terminator may be the native terminator of the gene to be introduced, or a terminator of another gene. Specific examples of the terminator can include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by a host. For example, all the genes may be carried by a single expression vector or a chromosome. Furthermore, the genes may be separately carried by two or more expression vectors, or separately carried by a single or two or more expression vectors and a chromosome. An operon made up of two or more genes may also be introduced. When "introducing two or more genes", for example, the respective genes encoding two or more kinds of proteins, such as enzymes; the respective genes encoding two or more subunits that make up a single protein complex, such as an enzyme complex, or a combination of these can be introduced.

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a variant of a gene may be obtained by modifying the gene. A gene can be modified by a known technique. For example, an objective mutation can be introduced into an objective site of DNA by the site-specific mutation method. That is, the coding region of a gene can be modified by the site-specific mutation method so that a specific site of the encoded protein includes substitution, deletion, insertion, and/or addition of amino acid residues. Examples of the site-specific mutation method can include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be totally synthesized.

In addition, when a protein functions as a complex made up of a plurality of subunits, a part or all of the subunits may be modified, so long as the activity of the protein is eventually increased. That is, for example, when the activity of a protein is increased by increasing the expression of a gene, the expression of a part or all of the genes that encode the respective subunits may be enhanced. It is typically preferable to enhance the expression of all of the genes encoding the subunits. Furthermore, the subunits making up the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, a promoter, a Shine-Dalgarno (SD) sequence (also referred to as ribosome-binding site (RBS)), and a spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" can refer to a promoter providing an improved transcription of a gene compared with the inherent wild-type promoter of the gene. Examples of stronger promoters can include, for example, the known high expression promoters such as T7 promoter, trp promoter, lac promoter, thr promoter, tac promoter, trc promoter, tet promoter, araBAD promoter, rpoH promoter, msrA promoter, Pm1 promoter (derived from the genus *Bifidobacterium*), PR promoter, and PL promoter. Examples of stronger promoters usable in coryneform bacteria can include, for example, the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), P2 promoter (position 942-1034 of SEQ ID NO: 108), and P3 promoter (SEQ ID NO: 111), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of a highly active-type promoter can include various tac-like promoters (Katashkina J I et al., Russian Federation Patent Application No. 2006134574). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence, which can also be referred to as ribosome binding site (RBS), for the gene on a chromosome with a stronger SD sequence. The term "stronger SD sequence" can refer to a SD sequence that provides an improved translation of mRNA compared with the inherent wild-type SD sequence of the gene. Examples of stronger SD sequences can include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modification.

The translation efficiency of a gene can also be improved by, for example, modifying codons. For example, the translation efficiency of the gene can be improved by replacing a rare codon present in the gene with a more frequently used synonymous codon. That is, the gene to be introduced may be modified, for example, so as to contain optimal codons according to the frequencies of codons observed in the chosen host. Codons can be replaced by, for example, the site-specific mutation method for introducing an objective mutation into an objective site of DNA. Alternatively, a gene fragment in which objective codons are replaced may be entirely synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as described above may be used independently or in an arbitrary combination.

Furthermore, the modification that increases the activity of a protein can also be attained by, for example, enhancing the specific activity of the enzyme. Enhancement of the specific activity can also include desensitization to feedback inhibition. That is, when a protein is subject to feedback inhibition by a metabolite, the activity of the protein can be increased by mutating a gene or protein in the chosen host to be desensitized to the feedback inhibition. The phrase "being desensitized to feedback inhibition" can include complete elimination of the feedback inhibition, and attenuation of the feedback inhibition, unless otherwise stated. Also, the phrase "being desensitized to feedback inhibition", that is, when feedback inhibition is eliminated or attenuated, can also be referred to as "tolerant to feedback inhibition". A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, and/or addition of one or several amino acid residues at one or several positions of the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain, such as a wild-type strain or parent strain. Examples of the method for evaluating the amount of mRNA can include Northern hybridization, RT-PCR, microarray, RNA-seq, and so forth (Sambrook, J., et al., Molecular Cloning: A Laboratory Manual/Third Edition, Cold Spring Harbor Laboratory Press, Cold Spring Harbor (USA), 2001). The amount of mRNA may be increased to, for example, 1.2 times or more, 1.5 times or more, 2 times or more, or 3 times or more of that of a non-modified strain.

An increase in the amount of a protein can be confirmed by Western blotting using antibodies (Sambrook, J., et al., Molecular Cloning: A Laboratory Manual/Third Edition, Cold Spring Harbor Laboratory Press, Cold Spring Harbor (USA), 2001). The amount of the protein, such as the number of molecules of the protein per cell, may be increased to, for example, 1.2 times or more, 1.5 times or more, 2 times or more, or 3 times or more of that of a non-modified strain.

The aforementioned methods for increasing the activity of a protein can be applied to enhancement of the activities of arbitrary proteins such as an objective substance biosynthesis enzyme, phosphopantetheinylation enzyme, and uptake system of a substance, and enhancement of the expression of arbitrary genes such as genes encoding those arbitrary proteins, besides enhancement of the activity of the SAM cycle enzyme.

<1-4> Method for Reducing Activity of Protein

Hereafter, the methods for reducing the activity of a protein will be explained.

The phrase "the activity of a protein is reduced" means that the activity of the protein is reduced as compared with a non-modified strain, that is, as compared with a strain of a non-modified microorganism. Specifically, the phrase "the activity of a protein is reduced" can mean that the activity of the protein per cell is reduced as compared with that of a non-modified strain. The term "non-modified strain" or "strain of a non-modified microorganism" can refer to a control strain that has not been modified so that the activity of an objective protein is reduced. Examples of the non-modified strain can include a wild-type strain and parent strain. Specific examples of the non-modified strain can include the respective type strains of the species of microorganisms. Specific examples of the non-modified strain can also include strains exemplified above in relation to the description of microorganisms. That is, in an embodiment, the activity of a protein may be reduced as compared with a type strain, that is, the type strain of the species to which the microorganism as described herein belongs. In another embodiment, the activity of a protein may also be reduced as compared with the C. glutamicum ATCC 13869 strain. In another embodiment, the activity of a protein may also be reduced as compared with the C. glutamicum ATCC 13032 strain. In another embodiment, the activity of a protein may also be reduced as compared with the E. coli K-12 MG1655 strain. The phrase "the activity of a protein is reduced" can also include when the activity of the protein has completely disappeared. More specifically, the phrase "the activity of a protein is reduced" can mean that the number of molecules of the protein per cell is reduced, and/or the function of each molecule of the protein is reduced, as compared with those of a non-modified strain. That is, the term "activity" in the phrase "the activity of a protein is reduced" is not limited to the catalytic activity of the protein, but can also mean the transcription amount of a gene encoding the protein, that is, the amount of mRNA, or the translation amount of a gene encoding the protein, that is, the amount of the protein. The phrase "the number of molecules of the protein per cell is reduced" can also include when the protein does not exist at all. The phrase "the function of each molecule of the protein is reduced" can also include when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The phrase "the expression of a gene is reduced" can mean that the expression of the gene is reduced as compared with a non-modified strain, such as a wild-type strain and parent strain. Specifically, the phrase "the expression of a gene is reduced" can mean that the expression of the gene per cell is reduced as compared with that of a non-modified strain. More specifically, the phrase "the expression of a gene is reduced" can mean that the transcription amount of the gene, that is, the amount of mRNA, is reduced, and/or the translation amount of the gene, that is, the amount of the protein expressed from the gene, is reduced. The phrase "the expression of a gene is reduced" can also include when the gene is not expressed at all. The phrase "the expression of a gene is reduced" can also be referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of these. The expression of a gene can be reduced by modifying an expression control sequence of the gene, such as a promoter, a Shine-Dalgarno (SD) sequence (also referred to as ribosome-binding site (RBS)), and a spacer region between RBS and the start codon of the gene. When an expression control sequence is modified, one or more nucleotides, two or more nucleotides, or three or more nucleotides, of the expression control sequence are modified. For example, the transcription efficiency of a gene can be reduced by, for example, replacing the promoter of the gene on a chromosome with a weaker promoter. The term "weaker promoter" can refer to a promoter providing an attenuated transcription of a gene compared with the inherent wild-type promoter of the gene. Examples of weaker promoters can include, for example, inducible promoters. That is, an inducible promoter may function as a weaker promoter under a non-induced condition, such as in the absence of the corresponding inducer. Examples of weaker promoters can also include, for example, P4 and P8 promoters (position 872-969 of SEQ ID NO: 109 and position 901-1046 of SEQ ID NO: 110, respectively). Furthermore, a part of or the entire expression control sequence may be deleted. The expression of a gene can also be reduced by, for example, manipulating a factor responsible for expression control. Examples of the factor responsible for expression control can include low molecules responsible for transcription or translation control, such as inducers, inhibitors, etc., proteins responsible for transcription or translation control, such as transcription factors etc., nucleic acids responsible for transcription or translation control, such as siRNA etc., and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described herein.

The modification for reducing the activity of a protein can also be attained by, for example, disrupting a gene encoding the protein. The phrase "a gene is disrupted" can mean that a gene is modified so that a protein that can normally function is not produced. The phrase "a protein that normally functions is not produced" can include when the protein is not produced at all from the gene, and when the protein of which the function, such as activity or property, per molecule is reduced or eliminated is produced from the gene.

Disruption of a gene can be attained by, for example, deleting the gene on a chromosome. The term "deletion of a gene" can refer to deletion of a partial or the entire region of the coding region of the gene. Furthermore, the whole of a gene including sequences upstream and downstream from the coding region of the gene on a chromosome may be deleted. The region to be deleted may be any region, such as an N-terminal region (i.e. a region encoding an N-terminal region of a protein), an internal region, or a C-terminal region (i.e. a region encoding a C-terminal region of a protein), so long as the activity of the protein can be reduced. Deletion of a longer region will typically more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, it is preferred that reading frames of the sequences upstream and downstream from the region to be deleted are not the same. Inconsistency of reading frames may cause a frameshift downstream of the region to be deleted.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence will typically more surely inactivate the gene. It is preferred that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof can include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modifying a gene so as to encode a protein of which the amino acid sequence is deleted. The phrase "deletion of the amino acid sequence of a protein" can refer to deletion of a partial or the entire region of the amino acid sequence of the protein. In addition, the phrase "deletion of the amino acid sequence of a protein" can mean that the original amino acid sequence disappears in the protein, and can also include when the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or the entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be applied mutatis mutandis to the position and length of the region to be deleted in deletion of the amino acid sequence of a protein.

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene can include a gene of which a partial or the entire region of the coding region is deleted, a gene including a missense mutation, a gene including a nonsense mutation, a gene including a frame shift mutation, and a gene including insertion of a transposon or marker gene. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in an arbitrary combination.

When a protein functions as a complex made up of a plurality of subunits, a part or all of the subunits may be modified, so long as the activity of the protein is eventually reduced. That is, for example, a part or all of the genes that encode the respective subunits may be disrupted or the like. Furthermore, when there is a plurality of isozymes of a protein, a part or all of the activities of the isozymes may be reduced, so long as the activity of the protein is eventually reduced. That is, for example, a part or all of the genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA can include Northern hybridization, RT-PCR, microarray, RNA-seq, and so forth (Sambrook, J., et al., Molecular Cloning: A Laboratory Manual/Third Edition, Cold Spring Harbor Laboratory Press, Cold Spring Harbor (USA), 2001). The amount of mRNA may be reduced to, for example, 50% or less, 20% or less, 10% or less, 5% or less, or 0%, of that of a non-modified strain.

A reduction in the amount of a protein can be confirmed by Western blotting using antibodies (Sambrook, J., et al., Molecular Cloning: A Laboratory Manual/Third Edition, Cold Spring Harbor Laboratory Press, Cold Spring Harbor (USA) 2001). The amount of the protein, such as the number of molecules of the protein per cell, may be reduced to, for example, 50% or less, 20% or less, 10% or less, 5% or less, or 0%, of that of a non-modified strain.

Disruption of a gene can be confirmed by determining the nucleotide sequence of a part of or the entire gene, restriction enzyme map, full length, or the like of the gene depending on the means used for the disruption.

The aforementioned methods for reducing the activity of a protein can be applied to reduction in the activities of arbitrary proteins such as a byproduct generation enzyme, and reduction in the expression of arbitrary genes such as genes encoding those arbitrary proteins.

<2> Method for Producing Objective Substance

The method as described herein is a method for producing an objective substance by using the microorganism as described herein.

<2-1> Fermentation Method

An objective substance can be produced by, for example, fermentation of the microorganism as described herein. That is, an embodiment of the method as described herein may be a method for producing an objective substance by fermentation of the microorganism. This embodiment can also be referred to as a "fermentation method". Also, the step of producing an objective substance by fermentation of the microorganism can also be referred to as a "fermentation step".

The fermentation step can be performed by cultivating the microorganism as described herein. Specifically, in the fermentation method, an objective substance can be produced from a carbon source. That is, the fermentation step may be, for example, a step of cultivating the microorganism in a culture medium, such as a culture medium containing a carbon source, to produce and accumulate the objective substance in the culture medium. That is, the fermentation method may be a method for producing an objective substance that comprises the step of cultivating the microorganism in a culture medium, such as a culture medium containing a carbon source, to produce and accumulate the objective substance in the culture medium. Also, in other words, the fermentation step may be, for example, a step of producing the objective substance from a carbon source by using the microorganism.

The culture medium to be used is not particularly limited, so long as the microorganism can proliferate in it and produce an objective substance. As the culture medium, for example, a typical culture medium used for the culture of microorganisms such as bacteria and yeast can be used. The culture medium may contain carbon source, nitrogen source, phosphate source, and sulfur source, as well as other medium components such as various organic components and inorganic components as required. The types and concentrations of the medium components can be appropriately determined according to various conditions such as the type of the chosen microorganism.

The carbon source is not particularly limited, so long as the microorganism can utilize it and produce an objective substance. Specific examples of the carbon source can include, for example, saccharides such as glucose, fructose, sucrose, lactose, galactose, xylose, arabinose, blackstrap molasses, hydrolysates of starches, and hydrolysates of biomass; organic acids such as acetic acid, citric acid, succinic acid, and gluconic acid; alcohols such as ethanol, glycerol, and crude glycerol; and fatty acids. As the carbon source, in particular, plant-derived materials can be used. Examples of the plant can include, for example, corn, rice, wheat, soybean, sugarcane, beet, and cotton. Examples of the plant-derived materials can include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the microorganism. As the carbon source, one kind of carbon source may be used, or two or more kinds of carbon sources may be used in combination.

The concentration of the carbon source in the culture medium is not particularly limited, so long as the microorganism can proliferate and produce an objective substance. The concentration of the carbon source in the culture medium may be as high as possible and within such a range that production of the objective substance is not inhibited. The initial concentration of the carbon source in the culture medium may be, for example, 5 to 30% (w/v), or 10 to 20% (w/v). Furthermore, the carbon source may be added to the culture medium as required. For example, the carbon source may be added to the culture medium in proportion to decrease or depletion of the carbon source accompanying progress of the fermentation. While the carbon source may be temporarily depleted so long as an objective substance can be eventually produced, it may be preferable to perform the culture so that the carbon source is not depleted or the carbon source does not continue to be depleted.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas and aqueous ammonia used for pH adjustment may also be used as a nitrogen source. As the nitrogen source, one nitrogen source may be used, or two or more nitrogen sources may be used in combination.

Specific examples of the phosphate source can include, for example, phosphate salts such as potassium dihydrogenphosphate and dipotassium hydrogenphosphate, and phosphoric acid polymers such as pyrophosphoric acid. As the phosphate source, one phosphate source may be used, or two or more phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, one sulfur source may be used, or two or more sulfur sources may be used in combination.

Specific examples of other various organic and inorganic components can include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

Furthermore, when an auxotrophic mutant strain that requires a nutrient such as amino acids for growth thereof is used, the culture medium may preferably contain such a required nutrient. Furthermore, the culture medium may contain a component used for production of an objective substance. Specific examples of such a component can include, for example, methyl group donors such as SAM and precursors thereof such as methionine.

Culture conditions are not particularly limited, so long as the microorganism can proliferate, and an objective substance is produced. The culture can be performed with, for example, typical conditions used for culture of microorganisms such as bacteria and yeast. The culture conditions may be appropriately determined according to various conditions such as the type of the chosen microorganism.

The culture can be performed by using a liquid medium. At the time of the culture, for example, the microorganism cultured on a solid medium such as agar medium may be directly inoculated into a liquid medium, or the microorganism cultured in a liquid medium as seed culture may be inoculated into a liquid medium for main culture. That is, the culture may be performed separately as seed culture and main culture. In such a case, the culture conditions of the seed culture and the main culture may or may not be the same. It is sufficient that an objective substance is produced at least during the main culture. The amount of the microorganism present in the culture medium at the time of the start of the culture is not particularly limited. For example, a seed culture broth showing an OD660 of 4 to 100 may be inoculated to a culture medium for main culture in an amount of 0.1 to 100 mass %, or 1 to 50 mass %, at the time of the start of the culture.

The culture can be performed as batch culture, fed-batch culture, continuous culture, or a combination of these. The culture medium used at the start of the culture can also be referred to as a "starting medium". The culture medium added to the culture system (e.g. fermentation tank) in the fed-batch culture or the continuous culture can also be referred to as a "feed medium". To add a feed medium to the culture system in the fed-batch culture or the continuous culture can also be referred to as "feed". Furthermore, when the culture is performed separately as seed culture and main culture, the culture schemes of the seed culture and the main culture may or may not be the same. For example, both the seed culture and the main culture may be performed as batch culture. Alternatively, for example, the seed culture may be performed as batch culture, and the main culture may be performed as fed-batch culture or continuous culture.

The various components, such as the carbon source, may be present in the starting medium, feed medium, or both. That is, the various components, such as the carbon source, may be added to the culture medium independently or in an arbitrary combination during the culture. These components may be added once or a plurality of times, or may be continuously added. The types of the components present in the starting medium may or may not be the same as the types of the components present in the feed medium. Furthermore, the concentrations of the components present in the starting medium may or may not be the same as the concentrations of the components present in the feed medium. Furthermore, two or more kinds of feed media containing components of different types and/or different concentrations may be used. For example, when feeding is intermittently performed two or more times, the types and/or concentrations of components present in the feed medium may or may not be the same for each feeding.

The culture can be performed, for example, under an aerobic condition. The term "aerobic condition" can refer to a condition where the dissolved oxygen concentration in the culture medium is 0.33 ppm or higher, or 1.5 ppm or higher. The oxygen concentration can be controlled to be, for example, 1 to 50%, or about 5%, of the saturated oxygen concentration. The culture can be performed, for example, with aeration or shaking. The pH of the culture medium may be, for example, 3 to 10, or 4.0 to 9.5. The pH of the culture medium can be adjusted during the culture as required. The pH of the culture medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., or 25 to 37° C. The culture time may be, for example, 10 to 120 hours. The culture may be continued, for example, until the carbon source present in the culture medium is consumed, or until the activity of the microorganism is lost.

By cultivating the microorganism under such conditions as described above, an objective substance is accumulated in the culture medium.

Production of an objective substance can be confirmed by known methods used for detection or identification of compounds. Examples of such methods can include, for example, HPLC, UPLC, LC/MS, GC/MS, and NMR. These methods may be independently used, or may be used in an appropriate combination. These methods can also be used for determining the concentrations of various components present in the culture medium.

The produced objective substance can be appropriately collected. That is, the fermentation method may further comprise a step of collecting the objective substance. This step can also be referred to as a "collection step". The collection step may be a step of collecting the objective substance from the culture broth, specifically from the culture medium. The objective substance can be collected by known methods used for separation and purification of compounds. Examples of such methods can include, for example, ion-exchange resin method, membrane treatment, precipitation, extraction, distillation, and crystallization. The objective substance can be collected specifically by extraction with an organic solvent such as ethyl acetate or by steam distillation. These methods may be independently used, or may be used in an appropriate combination.

Furthermore, when an objective substance precipitates in the culture medium, it can be collected by, for example, centrifugation or filtration. The objective substance precipitated in the culture medium and the objective substance dissolved in the culture medium may be isolated together after the objective substance dissolved in the culture medium is crystallized.

The collected objective substance may contain, for example, other component(s) such as microbial cells, medium components, moisture, and by-product metabolites of the microorganism, in addition to the objective substance. Purity of the collected objective substance may be, for example, 30% (w/w) or higher, 50% (w/w) or higher, 70% (w/w) or higher, 80% (w/w) or higher, 90% (w/w) or higher, or 95% (w/w) or higher.

<2-2> Bioconversion Method

An objective substance can also be produced by, for example, bioconversion using the microorganism as described herein. That is, another embodiment of the method as described herein may be a method for producing an objective substance by bioconversion using the microorganism. This embodiment can also be referred to as a "bioconversion method". Also, the step of producing an objective substance by bioconversion using the microorganism can also be referred to as a "bioconversion step".

Specifically, in the bioconversion method, an objective substance can be produced from a precursor of the objective substance. More specifically, in the bioconversion method, an objective substance can be produced by converting a precursor of the objective substance into the objective substance by using the microorganism. That is, the bioconversion step may be a step of converting a precursor of an objective substance into the objective substance by using the microorganism.

A precursor of an objective substance can also be referred to simply as a "precursor". Examples of the precursor can include substances of which conversion into an object substance requires SAM. Specific examples of the precursor can include intermediates of the biosynthesis pathway of an object substance, such as those recited in relation to the descriptions of the objective substance biosynthesis enzymes, provided that conversion of the intermediates into the object substance requires SAM. More specific examples of the precursor can include, for example, protocatechuic acid, protocatechualdehyde, L-tryptophan, L-histidine, L-phenylalanine, L-tyrosine, L-arginine, L-ornithine, and glycine. Protocatechuic acid may be used as a precursor for producing, for example, vanillin, vanillic acid, or guaiacol. Protocatechualdehyde may be used as a precursor for producing, for example, vanillin. L-tryptophan may be used as a precursor for producing, for example, melatonin. L-histidine may be used as a precursor for producing, for example, ergothioneine. L-phenylalanine and L-tyrosine each may be used as a precursor for producing, for example, ferulic acid, 4-vinylguaiacol, or 4-ethylguaiacol. L-arginine and L-ornithine each may be used as a precursor for producing, for example, a polyamine. L-arginine and glycine each may be used as a precursor for producing, for example, creatine. As the precursor, one kind of precursor may be used, or two or more kinds of precursors may be used in combination. In cases where the precursor is a compound that can form a salt, the precursor may be used as a free compound, a salt thereof, or a mixture thereof. That is, the term "precursor" can refer to a precursor in a free form, a salt thereof, or a mixture thereof, unless otherwise stated. Examples of the salt can include, for example, sulfate salt, hydrochloride salt, carbonate salt, ammonium salt, sodium salt, and potassium salt. As the salt of the precursor, one kind of salt may be employed, or two or more kinds of salts may be employed in combination.

As the precursor, a commercial product may be used, or one appropriately prepared and obtained may be used. That is, the bioconversion method may further comprise a step of producing a precursor. The method for producing a precursor is not particularly limited, and for example, known methods can be used. A precursor can be produced by, for example, a chemical synthesis method, enzymatic method, bioconversion method, fermentation method, extraction method, or a combination of these. That is, for example, a precursor of an objective substance can be produced from a further precursor thereof using an enzyme that catalyzes the conversion of such a further precursor into the precursor of an objective substance, which enzyme can also be referred to as a "precursor biosynthesis enzyme". Furthermore, for example, a precursor of an objective substance can be produced from a carbon source or such a further precursor by using a microorganism having a precursor-producing ability. The phrase "microorganism having a precursor-producing ability" can refer to a microorganism that is able to generate a precursor of an objective substance from a carbon source or a further precursor thereof. For example, examples of the method for producing protocatechuic acid according to an enzymatic method or bioconversion method can include the method of converting para-cresol into protocatechuic acid using *Pseudomonas putida* KS-0180 (Japanese Patent Laid-open (Kokai) No. 7-75589), the method of converting para-hydroxybenzoic acid into protocatechuic acid using an NADH-dependent para-hydroxybenzoic acid hydroxylase (Japanese Patent Laid-open (Kokai) No. 5-244941), the method of producing protocatechuic acid by cultivating a transformant harboring a gene that is involved in the reaction of generating protocatechuic acid from terephthalic acid in a culture medium containing terephthalic acid (Japanese Patent Laid-open (Kokai) No. 2007-104942), and the method of producing protocatechuic acid from a precursor thereof by using a microorganism having protocatechuic acid-producing ability and having a reduced activity of protocatechuic acid 5-oxidase or being deficient in that activity (Japanese Patent Laid-open (Kokai) No. 2010-207094). Furthermore, examples of the method for producing protocatechuic acid by fermentation can include the method of producing protocatechuic acid by using a bacterium of the genus *Brevibacterium* and acetic acid as a carbon source (Japanese Patent Laid-open (Kokai) No. 50-89592), the method of producing protocatechuic acid by using a bacterium of the genus *Escherichia* or *Klebsiella* introduced with a gene encoding 3-dihydroshikimate dehydrogenase and glucose as a carbon source (U.S. Pat. No. 5,272,073). Furthermore, protocatechualdehyde can be produced by using protocatechuic acid as a precursor according to an enzymatic method using ACAR or a bioconversion method using a microorganism having ACAR. The produced precursor can be used for the bioconversion method as it is, or after being subjected to an appropriate treatment such as concentration, dilution, drying, dissolution, fractionation, extraction, and purification, as required. That is, as the precursor, for example, a purified product purified to a desired extent may be used, or a material containing a precursor may be used. The material containing a precursor is not particularly limited so long as the microorganism can use the precursor. Specific examples of the material containing a precursor can include a culture broth obtained by cultivating a microorganism having a precursor-producing ability, a culture supernatant separated from the culture broth, and processed products thereof such as concentrated products, such as concentrated liquid, thereof and dried products thereof.

In an embodiment, the bioconversion step can be performed by, for example, cultivating the microorganism as described herein. This embodiment can also be referred to as a "first embodiment of the bioconversion method". That is, the bioconversion step may be, for example, a step of cultivating the microorganism in a culture medium containing a precursor of an objective substance to convert the precursor into the objective substance. The bioconversion step may be, specifically, a step of cultivating the microorganism in a culture medium containing a precursor of an objective substance to produce and accumulate the objective substance in the culture medium.

The culture medium to be used is not particularly limited, so long as the culture medium contains a precursor of an objective substance, and the microorganism can proliferate in it and produce the objective substance. Culture conditions are not particularly limited, so long as the microorganism can proliferate, and an objective substance is produced. The descriptions concerning the culture mentioned for the fermentation method, such as those concerning the culture medium and culture conditions, can be applied mutatis mutandis to the culture in the first embodiment of the bioconversion method, except that the culture medium contains the precursor in the first embodiment.

The precursor may be present in the culture medium over the whole period of the culture, or may be present in the culture medium during only a partial period of the culture. That is, the phrase "cultivating a microorganism in a culture medium containing a precursor" does not necessarily mean that the precursor is present in the culture medium over the whole period of the culture. For example, the precursor may or may not be present in the culture medium from the start of the culture. When the precursor is not present in the culture medium at the time of the start of the culture, the precursor is added to the culture medium after the start of the culture. Timing of the addition can be appropriately determined according to various conditions such as the length of the culture period. For example, after the microorganism sufficiently grows, the precursor may be added to the culture medium. Furthermore, in any case, the precursor may be added to the culture medium as required. For example, the precursor may be added to the culture medium in proportion to decrease or depletion of the precursor accompanying generation of an objective substance. Methods for adding the precursor to the culture medium are not particularly limited. For example, the precursor can be added to the culture medium by feeding a feed medium containing the precursor to the culture medium. Furthermore, for example, the microorganism as described herein and a microorganism having a precursor-producing ability can be co-cultured to allow the microorganism having a precursor-producing ability to produce the precursor in the culture medium, and thereby add the precursor to the culture medium. For the phrase "a component is added to a culture medium", the indicated "a component" may include a component that is generated or regenerated in the culture medium. These methods of addition may be independently used, or may be used in an appropriate combination. The concentration of the precursor in the culture medium is not particularly limited so long as the microorganism can use the precursor as a raw material of an objective substance. The concentration of the precursor in the culture medium, for example, may be 0.1 g/L or higher, 1 g/L or higher, 2 g/L or higher, 5 g/L or higher, 10 g/L or higher, or 15 g/L or higher, or may be 200 g/L or lower, 100 g/L or lower, 50 g/L or lower, or 20 g/L or lower, or may be within a range defined with a combination thereof, in terms of the weight of the free compound. The precursor may or may not be present in the culture medium at a concentration within the range exemplified above over the whole period of the culture. For example, the precursor may be present in the culture medium at a concentration within the range exemplified above at the time of the start of the culture, or it may be added to the culture medium so that a concentration within the range exemplified above is attained after the start of the culture. When the culture is performed separately as a seed culture and main culture, it is sufficient that an objective substance is produced at least during the main culture. Hence, it is sufficient that the precursor is present in the culture medium at least during the main culture, that is, over the whole period of the main culture or during a partial period of the main culture, and that is, the precursor may or may not be present in the culture medium during the seed culture. In such cases, terms regarding the culture, such as "culture period (period of culture)" and "start of culture", can be read as those regarding the main culture.

In another embodiment, the bioconversion step can also be performed by, for example, using cells of the microorganism as described herein. This embodiment can also be referred to as a "second embodiment of the bioconversion method". That is, the bioconversion step may be, for example, a step of converting a precursor of an objective substance in a reaction mixture into the objective substance by using cells of the microorganism. The bioconversion step may be, specifically, a step of allowing cells of the microorganism to act on a precursor of an objective substance in a reaction mixture to generate and accumulate the objective substance in the reaction mixture. The bioconversion step performed by using such cells can also be referred to as a "conversion reaction".

Cells of the microorganism can be obtained by cultivating the microorganism. The culture method for obtaining the cells is not particularly limited so long as the microorganism can proliferate. At the time of the culture for obtaining the cells, the precursor may or may not be present in the culture medium. Also, at the time of the culture for obtaining the cells, an objective substance may or may not be produced in the culture medium. The descriptions concerning the culture mentioned for the fermentation method, such as those concerning the culture medium and culture conditions, can be applied mutatis mutandis to the culture for obtaining the cells used for the second embodiment of the bioconversion method.

The cells may be used for the conversion reaction while being present in the culture broth (specifically, culture medium), or after being collected from the culture broth (specifically, culture medium). The cells may also be used for the conversion reaction after being subjected to a treatment as required. That is, examples of the cells can include a culture broth containing the cells, the cells collected from the culture broth, and a processed product thereof. In other words, examples of the cells can include cells present in a culture broth of the microorganism, cells collected from the culture broth, or cells present in a processed product thereof. Examples of the processed product can include products obtained by subjecting the cells to a treatment. Specific examples of the processed product can include products obtained by subjecting a culture broth containing the cells to a treatment, or subjecting the cells collected from the culture broth to a treatment. Cells in these forms may be independently used, or may be used in an appropriate combination.

The method for collecting the cells from the culture medium is not particularly limited, and for example, known methods can be used. Examples of such methods can include, for example, spontaneous precipitation, centrifugation, and filtration. A flocculant may also be used. These methods may be independently used, or may be used in an appropriate combination. The collected cells can be washed as required by using an appropriate medium. The collected cells can be re-suspended as required by using an appropriate medium. Examples of the medium usable for washing or suspending the cells can include, for example, aqueous media (aqueous solvents) such as water and aqueous buffer.

Examples of the treatment of the cells can include, for example, dilution, condensation, immobilization on a carrier such as acrylamide and carrageenan, freezing and thawing treatment, and treatment for increasing permeability of cell membranes. Permeability of cell membranes can be increased by, for example, using a surfactant or organic solvent. These treatments may be independently used, or may be used in an appropriate combination.

The cells used for the conversion reaction are not particularly limited so long as the cells have the objective substance-producing ability. It is preferred that the cells maintain their metabolic activities. The phrase "the cells maintain their metabolic activities" can mean that the cells have an ability to utilize a carbon source to generate or regenerate a substance required for producing an objective substance. Examples of such a substance can include, for example, ATP, electron donors such as NADH and NADPH, and methyl group donors such as SAM. The cells may or may not have proliferation ability.

The conversion reaction can be carried out in an appropriate reaction mixture. Specifically, the conversion reaction can be carried out by allowing the cells and the precursor to coexist in an appropriate reaction mixture. The conversion reaction may be carried out by the batch method or may be carried out by the column method. In the case of the batch method, the conversion reaction can be carried out by, for example, mixing the cells of the microorganism and the precursor in a reaction mixture present in a reaction vessel. The conversion reaction may be carried out statically, or may be carried out with stirring or shaking the reaction mixture. In the case of the column method, the conversion reaction can be carried out by, for example, passing a reaction mixture containing the precursor through a column filled with immobilized cells. Examples of the reaction mixture can include those based on an aqueous medium (aqueous solvent) such as water and aqueous buffer.

The reaction mixture may contain components other than the precursor as required, in addition to the precursor. Examples of the components other than the precursor can include ATP, electron donors such as NADH and NADPH, methyl group donors such as SAM, metal ions, buffering agents, surfactants, organic solvents, carbon sources, phosphate sources, and other various medium components. That is, for example, a culture medium containing the precursor may also be used as a reaction mixture. That is, the descriptions concerning the culture medium mentioned for the first embodiment of the bioconversion method may also be applied mutatis mutandis to the reaction mixture in the second embodiment of the bioconversion method. The types and concentrations of the components present in the reaction mixture may be determined according to various conditions such as the type of the precursor to be used and the form of the cells to be used.

Conditions of the conversion reaction, such as dissolved oxygen concentration, pH of the reaction mixture, reaction temperature, reaction time, concentrations of various components, etc., are not particularly limited so long as an objective substance is generated. The conversion reaction can be performed with, for example, typical conditions used for substance conversion using microbial cells such as resting cells. The conditions of the conversion reaction may be determined according to various conditions such as the type of chosen microorganism. The conversion reaction can be performed, for example, under an aerobic condition. The term "aerobic condition" can refer to a condition where the dissolved oxygen concentration in the reaction mixture is 0.33 ppm or higher, or 1.5 ppm or higher. The oxygen concentration can be controlled to be, for example, 1 to 50%, or about 5%, of the saturated oxygen concentration. The pH of the reaction mixture may be, for example, typically 6.0 to 10.0, or 6.5 to 9.0. The reaction temperature may be, for example, typically 15 to 50° C., 15 to 45° C., or 20 to 40° C. The reaction time may be, for example, 5 minutes to 200 hours. In the case of the column method, the loading rate of the reaction mixture may be, for example, such a rate that the reaction time falls within the range of the reaction time exemplified above. Furthermore, the conversion reaction can also be performed with, for example, a culture condition, such as typical conditions used for culture of microorganisms such as bacteria and yeast. During the conversion reaction, the cells may or may not proliferate. That is, the descriptions concerning the culture conditions for the first embodiment of the bioconversion method may also be applied mutatis mutandis to the conditions of the conversion reaction in the second embodiment of the bioconversion method, except that the cells may or may not proliferate in the second embodiment. In such a case, the culture conditions for obtaining the cells and the conditions of the conversion reaction may be the same or different. The concentration of the precursor in the reaction mixture, for example, may be 0.1 g/L or higher, 1 g/L or higher, 2 g/L or higher, 5 g/L or higher, 10 g/L or higher, or 15 g/L or higher, or may be 200 g/L or lower, 100 g/L or lower, 50 g/L or lower, or 20 g/L or lower, or may be within a range defined with a combination thereof, in terms of the weight of the free compound. The density of the cells in the reaction mixture, for example, may be 1 or higher, or may be 300 or lower, or may be within a range defined with a combination thereof, in terms of the optical density (OD) at 600 nm.

During the conversion reaction, the cells, the precursor, and the other components may be added to the reaction mixture independently or in any arbitrary combination thereof. For example, the precursor may be added to the reaction mixture in proportion to decrease or depletion of the precursor accompanying generation of an objective substance. These components may be added once or a plurality of times, or may be continuously added.

Methods for adding the various components such as the precursor to the reaction mixture are not particularly limited. These components each can be added to the reaction mixture by, for example, directly adding them to the reaction mixture. Furthermore, for example, the microorganism as described herein and a microorganism having a precursor-producing ability can be co-cultured to allow the microorganism having a precursor-producing ability to produce the precursor in the reaction mixture, and thereby add the precursor to the reaction mixture. Furthermore, for example, components such as ATP, electron donors, and methyl group donors each may be generated or regenerated in the reaction mixture, may be generated or regenerated in the cells of the microorganism, or may be generated or regenerated by a coupling reaction between different cells. For example, when cells of the microorganism maintain the metabolic activities thereof, they can generate or regenerate components such as ATP, electron donors, and methyl group donors within them by using a carbon source. For example, specifically, the microorganism may have an enhanced ability for generating or regenerating SAM, and the generated or regenerated SAM by it may be used for the conversion reaction. The generation or regeneration of SAM may further be enhanced in combination with any other method for generating or regenerating SAM. In addition, examples of the method for generating or regenerating ATP can include, for example, the method of supplying ATP from a carbon source by using a *Corynebacterium* bacterium (Hori, H. et al., Appl. Microbiol. Biotechnol., 48(6):693-698 (1997)), the method of regenerating ATP by using yeast cells and glucose (Yamamoto, S et al., Biosci. Biotechnol. Biochem., 69(4): 784-789 (2005)), the method of regenerating ATP using phosphoenolpyruvic acid and pyruvate kinase (C. Aug'e and Ch. Gautheron, Tetrahedron Lett., 29:789-790 (1988)), and the method of regenerating ATP by using polyphosphoric acid and polyphosphate kinase (Murata, K. et al., Agric. Biol. Chem., 52(6):1471-1477 (1988)). For the phrase "a component is added to a reaction mixture", the indicated "a component" may include a component that is generated or regenerated in the reaction mixture.

Furthermore, the reaction conditions may be constant from the start to the end of the conversion reaction, or they may vary during the conversion reaction. The phrase "the reaction conditions vary during the conversion reaction" can include not only when the reaction conditions are temporally changed, but also when the reaction conditions are spatially changed. The phrase "the reaction conditions are spatially changed" can mean that, for example, when the conversion reaction is performed by the column method, the reaction conditions such as reaction temperature and cell density differ depending on position in the flow.

A culture broth (specifically, culture medium) or reaction mixture containing an objective substance is obtained by carrying out the bioconversion step as described above. Confirmation of the production of the objective substance and collection of the objective substance can be carried out in the same manners as those for the fermentation method described above. That is, the bioconversion method may further comprise the collection step, such as a step of collecting the objective substance from the culture broth (specifically, culture medium) or reaction mixture. The collected objective substance may contain, for example, other component(s) such as microbial cells, medium components, reaction mixture components, moisture, and by-product metabolites of the microorganism, in addition to the objective substance. Purity of the collected objective substance may be, for example, 30% (w/w) or higher, 50% (w/w) or higher, 70% (w/w) or higher, 80% (w/w) or higher, 90% (w/w) or higher, or 95% (w/w) or higher.

<2-3> Method for Producing Vanillin and Other Objective Substances

When an objective substance is produced by using the microorganism as described herein, that is, by the fermentation method or bioconversion method, the thus-produced objective substance can further be converted to another objective substance. The present invention thus provides a method for producing a second objective substance, the method comprising steps of producing a first objective substance by using the microorganism, that is, by the fermentation method or bioconversion method, and converting the thus-produced first objective substance to the second objective substance.

For example, when vanillic acid is produced by using the microorganism as described herein, that is, by the fermentation method or bioconversion method, the thus-produced vanillic acid can further be converted to vanillin. The present invention thus provides a method for producing vanillin, the method comprising steps of producing vanillic acid by using the microorganism, that is, by the fermentation method or bioconversion method, and converting the thus-produced vanillic acid into vanillin. This method can also be referred to as a "vanillin production method".

Vanillic acid produced by using the microorganism can be used for the conversion into vanillin as it is, or after being subjected to an appropriate treatment such as concentration, dilution, drying, dissolution, fractionation, extraction, and purification, as required. That is, as vanillic acid, for example, a purified product purified to a desired extent may be used, or a material containing vanillic acid may be used. The material containing vanillic acid is not particularly limited so long as a component that catalyzes the conversion, such as a microorganism and an enzyme, can use vanillic acid. Specific examples of the material containing vanillic acid can include a culture broth or reaction mixture containing vanillic acid, a supernatant separated from the culture broth or reaction mixture, and processed products thereof such as concentrated products (such as concentrated liquid) thereof and dried products thereof.

The method for converting vanillic acid into vanillin is not particularly limited.

Vanillic acid can be converted into vanillin by, for example, a bioconversion method using a microorganism having ACAR. The microorganism having ACAR may or may not be modified so that the activity of an SAM cycle enzyme is increased. The descriptions concerning the microorganism as described herein can be applied mutatis mutandis to the microorganism having ACAR, except that the microorganism having ACAR has ACAR and may or may not be modified so that the activity of an SAM cycle enzyme is increased. The microorganism having ACAR may be modified so that the activity or activities of one or more of ACAR, PPT, and the vanillic acid uptake system is/are enhanced. In addition, the descriptions concerning the bioconversion method for producing an objective substance using the microorganism can be applied mutatis mutandis to the bioconversion method for converting vanillic acid into vanillin using a microorganism having ACAR.

Vanillic acid can also be converted into vanillin by, for example, an enzymatic method using ACAR.

ACAR can be produced by allowing a host having an ACAR gene to express the ACAR gene. ACAR can also be produced with a cell-free protein expression system.

A host having an ACAR gene can also be referred to as a "host having ACAR". The host having an ACAR gene may be a host inherently having the ACAR gene or may be a host modified to have the ACAR gene. Examples of the host inherently having an ACAR gene can include organisms from which ACARs exemplified above are derived. Examples of the host modified to have an ACAR gene can include hosts into which the ACAR gene has been introduced. Also, a host inherently having an ACAR gene may be modified so that the expression of ACAR is increased. The host to be used for expression of ACAR is not particularly limited, so long as the host can express an ACAR that can function. Examples of the host can include, for example, microorganisms such as bacteria and yeast (fungi), plant cells, insect cells, and animal cells.

An ACAR gene can be expressed by cultivating a host having the ACAR gene. The culture method is not particularly limited so long as the host having the ACAR gene can proliferate and express ACAR. The descriptions concerning the culture for the fermentation method can be applied mutatis mutandis to the culture of the host having the ACAR gene. As necessarily, expression of the ACAR gene can be induced. As a result of cultivation, a culture broth containing ACAR can be obtained. ACAR can be accumulated in cells of the host and/or the culture medium.

ACAR present in the cells of the host, the culture medium, or the like may be used as it is for the enzymatic reaction, or ACAR purified therefrom may be used for the enzymatic reaction. Purification can be performed to a desired extent. That is, as ACAR, purified ACAR may be used, or a fraction containing ACAR may be used. Such a fraction is not particularly limited, so long as ACAR present therein can act on vanillic acid. Examples of such a fraction can include, a culture broth of a host having an ACAR gene, that is a host having ACAR; cells collected from the culture broth; processed products of the cells such as cell disruptant, cell lysate, cell extract, and immobilized cells such as those immobilized with acrylamide, carrageenan, or the like; a culture supernatant collected from the culture broth; partially purified products thereof, that is, a crude product; and combinations thereof. These fractions may be used independently, or in combination with purified ACAR.

The enzymatic reaction can be performed by allowing ACAR to act on vanillic acid. Conditions of the enzymatic reaction are not particularly limited so long as vanillin is generated. The enzymatic reaction can be performed with, for example, typical conditions used for substance conversion using an enzyme or microbial cells such as resting cells. For example, the descriptions concerning the conversion reaction in the second embodiment of the bioconversion method may also be applied mutatis mutandis to the enzymatic reaction in the vanillin production method.

A reaction mixture containing vanillin is obtained by carrying out the conversion as described above. Confirmation of the production of vanillin and collection of vanillin can be carried out in the same manners as those for the fermentation method described above. That is, the vanillin production method may further comprise a step of collecting vanillin from the reaction mixture. The collected vanillin may contain, for example, other component(s) such as microbial cells, medium components, reaction mixture components, ACAR, moisture, and by-product metabolites of the microorganism, in addition to vanillin. Purity of the collected vanillin may be, for example, 30% (w/w) or higher, 50% (w/w) or higher, 70% (w/w) or higher, 80% (w/w) or higher, 90% (w/w) or higher, or 95% (w/w) or higher.

Vanillic acid can also be converted to guaiacol by, for example, a bioconversion method using a microorganism having VDC or an enzymatic method using VDC. Ferulic acid can be converted to 4-vinylguaiacol by, for example, a bioconversion method using a microorganism having FDC or an enzymatic method using FDC. 4-vinylguaiacol can be converted to 4-ethylguaiacol by, for example, a bioconversion method using a microorganism having VPR or an enzymatic method using VPR. Ferulic acid can also be converted to 4-ethylguaiacol by a combination of these methods. Specifically, ferulic acid can be converted to 4-ethylguaiacol by, for example, using FDC or a microorganism having FDC in combination with VPR or a microorganism having VPR simultaneously or sequentially, or using a microorganism having both FDC and VPR. The aforementioned descriptions concerning the vanillin production method can be applied mutatis mutandis to methods for producing other objective substances.

EXAMPLES

Hereafter, the present invention will be more specifically explained with reference to the following non-limiting examples.

Example 1: Vanillic Acid Production by C. glutamicum Strain Having Enhanced Expression of metK Gene Encoding Methionine Adenosyltransferase In this example, a strain having enhanced expression of the NCgl1541 gene (metK) encoding methionine adenosyltransferase was constructed from the Corynebacterium glutamicum 2256 strain (ATCC 13869) as a parent strain, and vanillic acid production was performed with the constructed strain.

<1> Construction of Strain Deficient in Vanillate Demethylase Genes (FKS0165 Strain)

It has been reported that, in coryneform bacteria, vanillin is metabolized in the order of vanillin→vanillic acid→protocatechuic acid, and utilized (Current Microbiology, 2005, Vol. 51, pp. 59-65). The conversion reaction from vanillic acid to protocatechuic acid is catalyzed by vanillate demethylase. The vanA gene and vanB gene encode the subunit A and subunit B of vanillate demethylase, respectively. The vanK gene encodes the vanillic acid uptake system, and constitutes the vanABK operon together with the vanAB genes (M. T. Chaudhry, et al., Microbiology, 2007, 153:857-865). Therefore, a strain deficient in utilization ability of an objective substance such as vanillin and vanillic acid (FKS0165 strain) was first constructed from C. glutamicum 2256 strain by deleting the vanABK operon. The procedure is shown below.

<1-1> Construction of Plasmid pBS4SΔvanABK56 for Deletion of vanABK Genes

PCR was performed by using the genomic DNA of the C. glutamicum 2256 strain as the template, and the synthetic DNAs of SEQ ID NOS: 51 and 52 as the primers to obtain a PCR product containing an N-terminus side coding region of the vanA gene. Separately, PCR was also performed by using the genomic DNA of the C. glutamicum 2256 strain as the template, and the synthetic DNAs of SEQ ID NOS: 53 and 54 as the primers to obtain a PCR product containing a C-terminus side coding region of the vanK gene. The sequences of SEQ ID NOS: 52 and 53 are partially complementary to each other. Then, the PCR product containing the N-terminus side coding region of the vanA gene and the PCR product containing the C-terminus side coding region of the vanK gene were mixed in approximately equimolar amounts, and inserted into the pBS4S vector (WO2007/046389) treated with BamHI and PstI by using In Fusion HD Cloning Kit (Clontech). With this DNA, competent cells of *Escherichia coli* JM109 (Takara Bio) were transformed, and the cells were applied to the LB agar medium (5 g/L yeast extract, 10 g/L tryptone, 10 g/L NaCl, 15 g/L agar) containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one into which the target PCR product was inserted was designated as pBS4SΔvanABK56.

<1-2> Construction of FKS0165 Strain pBS4SΔvanABK56 obtained above does not contain the region enabling autonomous replication of the plasmid in cells of coryneform bacteria. Therefore, if coryneform bacteria are transformed with this plasmid, a strain in which this plasmid is incorporated into the genome by homologous recombination appears as a transformant, although it occurs at an extremely low frequency. Therefore, pBS4SΔvanABK56 was introduced into the *C. glutamicum* 2256 strain by the electric pulse method. The cells were applied to the CM-Dex agar medium (5 g/L of glucose, 10 g/L of polypeptone, 10 g/L of yeast extract, 1 g/L of KH$_2$PO$_4$, 0.4 g/L of MgSO$_4$·7H$_2$O, 0.01 g/L of FeSO$_4$·7H$_2$O, 0.01 g/L of MnSO$_4$·7H$_2$O, 3 g/L of urea, 1.2 g/L of soybean hydrolysate, 10 μg/L of biotin, 15 g/L of agar, adjusted to pH 7.5 with NaOH) containing 25 μg/mL of kanamycin, and cultured at 31.5° C. It was confirmed by PCR that the grown strain was a once-recombinant strain in which pBS4SΔvanABK56 was incorporated into the genome by homologous recombination. This once-recombinant strain had both the wild-type vanABK genes, and the deficient-type vanABK genes.

The once-recombinant strain was cultured overnight in the CM-Dex liquid medium (having the same composition as that of the CM-Dex agar medium except that it does not contain agar), and the culture broth was applied to the S10 agar medium (100 g/L of sucrose, 10 g/L of polypeptone, 10 g/L of yeast extract, 1 g/L of KH$_2$PO$_4$, 0.4 g/L of MgSO$_4$·7H$_2$O, 0.01 g/L of FeSO$_4$·7H$_2$O, 0.01 g/L of MnSO$_4$·4-5H$_2$O, 3 g/L of urea, 1.2 g/L of soybean protein hydrolysate solution, 10 μg/L of biotin, 20 g/L of agar, adjusted to pH 7.5 with NaOH, and autoclaved at 120° C. for 20 minutes), and cultured at 31.5° C. Among the colonies that appeared, a strain that showed kanamycin susceptibility was purified on the CM-Dex agar medium. By preparing genomic DNA from the purified strain, and using it to perform PCR with the synthetic DNAs of SEQ ID NOS: 55 and 56 as the primers, deletion of the vanABK genes was confirmed, and the strain was designated as FKS0165 strain.

<2> Construction of Strain Deficient in Alcohol Dehydrogenase Homologue Genes (FKFC14 Strain)

Subsequently, by using the *Corynebacterium glutamicum* FKS0165 strain as a parent strain, there was constructed a strain FKFC14, which is deficient in alcohol dehydrogenase homologue genes, i.e. NCgl0324 gene (adhC), NCgl0313 gene (adhE), and NCgl2709 gene (adhA), via the following procedure.

<2-1> Construction of FKFC5 Strain (FKS0165ΔNCgl0324 Strain)

<2-1-1> Construction of Plasmid pBS4SΔ2256adhC for Deletion of NCgl0324 Gene

PCR was performed by using the genomic DNA of the *C. glutamicum* 2256 strain as the template, and the synthetic DNAs of SEQ ID NOS: 57 and 58 as the primers to obtain a PCR product containing an N-terminus side coding region of the NCgl0324 gene. Separately, PCR was performed by using the genomic DNA of the *C. glutamicum* 2256 strain as the template, and the synthetic DNAs of SEQ ID NOS: 59 and 60 as the primers to obtain a PCR product containing a C-terminus side coding region of the NCgl0324 gene. The sequences of SEQ ID NOS: 58 and 59 are partially complementary to each other. Then, approximately equimolar amounts of the PCR product containing the N-terminus side coding region of the NCgl0324 gene and the PCR product containing the C-terminus side coding region of the NCgl0324 gene were mixed, and inserted into the pBS4S vector (WO2007/046389) treated with BamHI and PstI by using In Fusion HD Cloning Kit (Clontech). With this DNA, competent cells of *Escherichia coli* JM109 (Takara Bio) were transformed, and the cells were applied to the LB agar medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256adhC.

<2-1-2> Construction of FKFC5 Strain (FKS0165ΔNCgl0324 Strain)

Since pBS4SΔ2256adhC obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhC was introduced into the *C. glutamicum* FKS0165 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhC was incorporated into the genome by homologous recombination. This once-recombinant strain had both the wild-type NCgl0324 gene, and the deficient-type NCgl0324 gene.

The once-recombinant strain was cultured overnight in the CM-Dex liquid medium, the culture broth was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 61 and 62 as the primers to confirm deletion of the NCgl0324 gene, and the strain was designated as FKFC5 strain.

<2-2> Construction of FKFC11 Strain (2256ΔvanABKΔNCgl0324ΔNCgl0313 Strain)

<2-2-1> Construction of Plasmid pBS4SΔ2256adhE for Deletion of NCgl0313 Gene

PCR was performed by using the genomic DNA of the *C. glutamicum* 2256 strain as the template, and the synthetic DNAs of SEQ ID NOS: 63 and 64 as the primers to obtain a PCR product containing an N-terminus side coding region of the NCgl0313 gene. Separately, PCR was performed by using the genomic DNA of the *C. glutamicum* 2256 strain as the template, and the synthetic DNAs of SEQ ID NOS: 65 and 66 as the primers to obtain a PCR product containing a C-terminus side coding region of the NCgl0313 gene. The sequences of SEQ ID NOS: 64 and 65 are partially complementary to each other. Then, approximately equimolar amounts of the PCR product containing the N-terminus side coding region of the NCgl0313 gene and the PCR product containing the C-terminus side coding region of the NCgl0313 gene were mixed, and inserted into the pBS4S vector (WO2007/046389) treated with BamHI and PstI by using In Fusion HD Cloning Kit (Clontech). With this DNA, competent cells of *Escherichia coli* JM109 (Takara Bio) were transformed, and the cells were applied to the LB agar medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256adhE.

<2-2-2> Construction of FKFC11 Strain (2256ΔvanABKΔNCgl0324ΔNCgl0313 Strain)

Since pBS4SΔ2256adhE obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhE was introduced into the *C. glutamicum* FKFC5 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhE was incorporated into the genome by homologous recombination. This once-recombinant strain had both the wild-type NCgl0313 gene, and the deficient-type NCgl0313 gene.

The once-recombinant strain was cultured overnight in the CM-Dex liquid medium, the culture broth was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 67 and 68 as the primers to confirm deletion of the NCgl0313 gene, and the strain was designated as FKFC11 strain.

<2-3> Construction of FKFC14 Strain (2256ΔvanABKΔNCgl0324ΔNCgl0313ΔNCgl2709 Strain)

<2-3-1> Construction of Plasmid pBS4SΔ2256adhA for Deletion of NCgl2709 Gene

PCR was performed by using the genomic DNA of the *C. glutamicum* 2256 strain as the template, and the synthetic DNAs of SEQ ID NOS: 69 and 70 as the primers to obtain a PCR product containing an N-terminus side coding region of the NCgl2709 gene. Separately, PCR was performed by using the genomic DNA of the *C. glutamicum* 2256 strain as the template, and the synthetic DNAs of SEQ ID NOS: 71 and 72 as the primers to obtain a PCR product containing a C-terminus side coding region of the NCgl2709 gene. The sequences of SEQ ID NOS: 70 and 71 are partially complementary to each other. Then, approximately equimolar amounts of the PCR product containing the N-terminus side coding region of the NCgl2709 gene and the PCR product containing the C-terminus side coding region of the NCgl2709 gene were mixed, and inserted into the pBS4S vector treated with BamHI and PstI by using In Fusion HD Cloning Kit (Clontech). With this DNA, competent cells of *Escherichia coli* JM109 (Takara Bio) were transformed, and the cells were applied to the LB agar medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256adhA.

<2-3-2> Construction of FKFC14 Strain (2256ΔvanABKΔNCgl0324ΔNCgl0313ΔNCgl2709 Strain)

Since pBS4SΔ2256adhA obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256adhA was introduced into the *C. glutamicum* FKFC11 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256adhA was incorporated into the genome by homologous recombination. This once-recombinant strain had both the wild-type NCgl2709 gene, and the deficient-type NCgl2709 gene.

The once-recombinant strain was cultured overnight in the CM-Dex liquid medium, the culture broth was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 73 and 74 as the primers to confirm deletion of the NCgl2709 gene, and the strain was designated as FKFC14 strain.

<3> Construction of Strain Deficient in Protocatechuic Acid Dioxygenase Genes (FKFC14ΔpcaGH Strain)

Subsequently, by using the *Corynebacterium glutamicum* FKFC14 strain as a parent strain, there was constructed a strain FKFC14ΔpcaGH, which is deficient in NCgl2314 gene (pcaG) and NCgl2315 gene (pcaH) encoding the alpha subunit and beta subunit of protocatechuate 3,4-dioxygenase, by outsourcing. The FKFC14ΔpcaGH strain can also be constructed via the following procedure.

<3-1> Construction of Plasmid pBS4SΔ2256pcaGH for Deletion of NCgl2314 and NCgl2315 Genes NCgl2314 and NCgl2315 genes are adjacent to each other, and therefore these genes can be deleted all together. PCR is performed by using the genomic DNA of the *C. glutamicum* 2256 strain as the template, and the synthetic DNAs of SEQ ID NOS: 75 and 76 as the primers to obtain a PCR product containing an upstream region of the NCgl2315 gene. Separately, PCR is performed by using the genomic DNA of the *C. glutamicum* 2256 strain as the template, and the synthetic DNAs of SEQ ID NOS: 77 and 78 as the primers to obtain a PCR product containing a downstream region of the NCgl2314 gene. The sequences of SEQ ID NOS: 76 and 77 are partially complementary to each other. Then, approximately equimolar amounts of the PCR product containing the upstream region of the NCgl2315 gene and the PCR product containing the downstream region of the NCgl2314 gene are mixed, and inserted into the pBS4S vector (WO2007/046389) treated with BamHI and PstI by using In Fusion HD Cloning Kit (Clontech). With this DNA, competent cells of *Escherichia coli*

JM109 (Takara Bio) are transformed, and the cells are applied to the LB agar medium containing 100 µM IPTG, 40 µg/mL of X-Gal, and 40 µg/mL of kanamycin, and cultured overnight. Then, white colonies that appeared are picked up, and separated into single colonies to obtain transformants. Plasmids are extracted from the obtained transformants, and one in which the target PCR product is inserted is designated as pBS4SΔ2256pcaGH.

<3-2> Construction of FKFC14ΔpcaGH Strain

Since pBS4SΔ2256pcaGH obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256pcaGH is introduced into the *C. glutamicum* FKFC14 strain by the electric pulse method. The cells are applied to the CM-Dex agar medium containing 25 µg/mL of kanamycin, and cultured at 31.5° C. It is confirmed by PCR that the grown strain is a once-recombinant strain in which pBS4SΔ2256pcaGH is incorporated into the genome by homologous recombination. This once-recombinant strain has both the wild-type NCgl2314 and NCgl2315 genes, and the deficient-type NCgl2314 and NCgl2315 genes.

The once-recombinant strain is cultured overnight in the CM-Dex liquid medium, the culture medium is applied to the S10 agar medium, and culture is performed at 31.5° C. Among the colonies that appear, a strain that shows kanamycin susceptibility is purified on the CM-Dex agar medium. Genomic DNA is prepared from the purified strain, and used to perform PCR with the synthetic DNAs of SEQ ID NOS: 79 and 80 as the primers to confirm deletion of the NCgl2314 and NCgl2315 genes, and the strain is designated as FKFC14ΔpcaGH strain.

<4> Construction of Ep2_0055 Strain (FKFC14ΔpcaGH P2::NCgl0120 P8::NCgl2048 P4::NCgl0935 Strain P3::NCgl0719)

<4-1> Construction of Ap1_0007 Strain (FKFC14ΔpcaGH P2::NCgl0120 Strain)

Subsequently, by using the *Corynebacterium glutamicum* FKFC14ΔpcaGH strain as a parent strain, there was constructed a strain Ap1_0007, in which the promoter region of NCgl0120 gene (cysR) encoding a Crp family expression regulatory protein has been replaced with the P2 promoter to enhance the expression of this gene, by outsourcing. The nucleotide sequence of a genomic region containing the P2 promoter in this strain is shown as SEQ ID NO: 108, wherein position 942-1034 corresponds to the P2 promoter. The Ap1_0007 strain can also be constructed via the following procedure.

<4-1-1> Construction of Plasmid pBS4SP2::NCgl0120 for Substitution of NCgl0120 Gene Promoter PCR is performed by using the genomic DNA of the *C. glutamicum* 2256 strain as the template, and the synthetic DNAs of SEQ ID NOS: 81 and 82 as the primers to obtain a PCR product containing an upstream region of the NCgl0120 gene. Separately, PCR is performed by using the genomic DNA of the *C. glutamicum* 2256 strain as the template, and the synthetic DNAs of SEQ ID NOS: 83 and 84 as the primers to obtain a PCR product containing an N-terminus side coding region of the NCgl0120 gene. In addition, a DNA fragment of SEQ ID NO: 85 containing P2 promoter region is obtained by artificial gene synthesis. And then, PCR is performed by using the DNA fragment of SEQ ID NO: 85 as the template, and the synthetic DNAs of SEQ ID NOS: 86 and 87 as the primers to obtain a PCR product containing the P2 promoter. The sequences of SEQ ID NOS: 82 and 86 are partially complementary to each other, and the sequences of SEQ ID NOS: 83 and 87 are partially complementary to each other. Then, approximately equimolar amounts of the PCR product containing the upstream region of the NCgl0120 gene, the PCR product containing the N-terminus side coding region of the NCgl0120 gene, and the PCR product containing the P2 promoter are mixed, and inserted into the pBS4S vector (WO2007/046389) treated with BamHI and PstI by using In Fusion HD Cloning Kit (Clontech). With this DNA, competent cells of *Escherichia coli* JM109 (Takara Bio) are transformed, and the cells are applied to the LB agar medium containing 100 µM IPTG, 40 µg/mL of X-Gal, and 40 µg/mL of kanamycin, and cultured overnight. Then, white colonies that appeared are picked up, and separated into single colonies to obtain transformants. Plasmids are extracted from the obtained transformants, and one in which the target PCR product is inserted is designated as pBS4SP2::NCgl0120.

<4-1-2> Construction of Ap1_0007 Strain

Since pBS4SP2::NCgl0120 obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SP2::NCgl0120 is introduced into the *C. glutamicum* FKFC14ΔpcaGH strain by the electric pulse method. The cells are applied to the CM-Dex agar medium containing 25 µg/mL of kanamycin, and cultured at 31.5° C. It is confirmed by PCR that the grown strain is a once-recombinant strain in which pBS4SP2::NCgl0120 is incorporated into the genome by homologous recombination.

The once-recombinant strain is cultured overnight in the CM-Dex liquid medium, the culture medium is applied to the S10 agar medium, and culture is performed at 31.5° C. Among the colonies that appear, a strain that shows kanamycin susceptibility is purified on the CM-Dex agar medium. Genomic DNA is prepared from the purified strain, and used to perform nucleotide sequence analysis to confirm that P2 promoter is located upstream of the NCgl0120 gene, and the strain is designated as Ap1_0007 strain.

<4-2> Construction of Bp1_0112 Strain (FKFC14ΔpcaGH P2::NCgl0120 P8::NCgl2048 Strain)

Subsequently, by using the *Corynebacterium glutamicum* Ap1_0007 strain as a parent strain, there was constructed a strain Bp1_0112, in which the promoter region of NCgl2048 gene has been replaced with the P8 promoter to attenuate the expression of this gene, by outsourcing. The nucleotide sequence of a genomic region containing the P8 promoter in this strain is shown as SEQ ID NO: 110, wherein position 901-1046 corresponds to the P8 promoter. The Bp1_0112 strain can also be constructed via the following procedure.

<4-2-1> Construction of Plasmid pBS4SP8::NCgl2048 for Substitution of NCgl2048 Gene Promoter PCR is performed by using the genomic DNA of the *C. glutamicum* 2256 strain as the template, and the synthetic DNAs of SEQ ID NOS: 112 and 113 as the primers to obtain a PCR product containing an upstream region of the NCgl2048 gene. Separately, PCR is performed by using the genomic DNA of the *C. glutamicum* 2256 strain as the template, and the synthetic DNAs of SEQ ID NOS: 114 and 115 as the primers to obtain a PCR product containing an N-terminus side coding region of the NCgl2048 gene. In addition, a DNA fragment of SEQ ID NO: 116 containing P8 promoter region is obtained by artificial gene synthesis. And then, PCR is performed by using the DNA fragment of SEQ ID NO: 116 as the template, and the synthetic DNAs of SEQ ID NOS: 117 and 118 as the primers to obtain a PCR product containing the P8 promoter. The sequences of SEQ ID NOS: 113 and 117 are partially complementary to each other, and the sequences of SEQ ID NOS: 114 and 118 are partially complementary to each other. Then, approximately equimolar amounts of the PCR product containing the upstream region of the NCgl2048 gene, the PCR product containing the N-terminus side coding region of the NCgl2048 gene, and the PCR product containing the P8 promoter are mixed, and inserted into the pBS4S vector (WO2007/046389) treated with BamHI and PstI by using In Fusion HD Cloning Kit (Clontech). With this DNA, competent cells of *Escherichia coli* JM109 (Takara Bio) are transformed, and the cells are applied to the LB agar medium containing 100 μM IPTG, 40 μg/mL of X-Gal, and 40 μg/mL of kanamycin, and cultured overnight. Then, white colonies that appeared are picked up, and separated into single colonies to obtain transformants. Plasmids are extracted from the obtained transformants, and one in which the target PCR product is inserted is designated as pBS4SP8::NCgl2048.

<4-2-2> Construction of Bp1_0112 Strain

Since pBS4SP8::NCgl2048 obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SP8::NCgl2048 is introduced into the *C. glutamicum* Ap1_0007 strain by the electric pulse method. The cells are applied to the CM-Dex agar medium containing 25 μg/mL of kanamycin, and cultured at 31.5° C. It is confirmed by PCR that the grown strain is a once-recombinant strain in which pBS4SP8::NCgl2048 is incorporated into the genome by homologous recombination.

The once-recombinant strain is cultured overnight in the CM-Dex liquid medium, the culture medium is applied to the S10 agar medium, and culture is performed at 31.5° C. Among the colonies that appear, a strain that shows kanamycin susceptibility is purified on the CM-Dex agar medium. Genomic DNA is prepared from the purified strain, and used to perform nucleotide sequence analysis to confirm that P8 promoter is located upstream of the NCgl2048 gene, and the strain is designated as Bp1_0112 strain.

<4-3> Construction of Dp2_0340 Strain (FKFC14ΔpcaGH P2::NCgl0120 P8::NCgl2048 P4::NCgl0935 Strain)

Subsequently, by using the *Corynebacterium glutamicum* Bp1_0112 strain as a parent strain, there was constructed a strain Dp2_0340, in which the promoter region of NCgl0935 gene (eno) encoding enolase has been replaced with the P4 promoter to attenuate the expression of this gene, by outsourcing. The nucleotide sequence of a genomic region containing the P4 promoter in this strain is shown as SEQ ID NO: 109, wherein position 872-969 corresponds to the P4 promoter. The Dp2_0340 strain can also be constructed via the following procedure.

<4-3-1> Construction of Plasmid pBS4SP4::NCgl0935 for Substitution of NCgl0935 Gene Promoter PCR is performed by using the genomic DNA of the *C. glutamicum* 2256 strain as the template, and the synthetic DNAs of SEQ ID NOS: 121 and 122 as the primers to obtain a PCR product containing an upstream region of the NCgl0935 gene. Separately, PCR is performed by using the genomic DNA of the *C. glutamicum* 2256 strain as the template, and the synthetic DNAs of SEQ ID NOS: 123 and 124 as the primers to obtain a PCR product containing an N-terminus side coding region of the NCgl0935 gene. In addition, a DNA fragment of SEQ ID NO: 125 containing P4 promoter region is obtained by artificial gene synthesis. And then, PCR is performed by using the DNA fragment of SEQ ID NO: 125 as the template, and the synthetic DNAs of SEQ ID NOS: 126 and 127 as the primers to obtain a PCR product containing the P4 promoter. The sequences of SEQ ID NOS: 122 and 126 are partially complementary to each other, and the sequences of SEQ ID NOS: 123 and 127 are partially complementary to each other. Then, approximately equimolar amounts of the PCR product containing the upstream region of the NCgl0935 gene, the PCR product containing the N-terminus side coding region of the NCgl0935 gene, and the PCR product containing the P4 promoter are mixed, and inserted into the pBS4S vector (WO2007/046389) treated with BamHI and PstI by using In Fusion HD Cloning Kit (Clontech). With this DNA, competent cells of *Escherichia coli* JM109 (Takara Bio) are transformed, and the cells are applied to the LB agar medium containing 100 μM IPTG, 40 μg/mL of X-Gal, and 40 μg/mL of kanamycin, and cultured overnight. Then, white colonies that appeared are picked up, and separated into single colonies to obtain transformants. Plasmids are extracted from the obtained transformants, and one in which the target PCR product is inserted is designated as pBS4SP4::NCgl0935.

<4-3-2> Construction of Dp2_0340 Strain

Since pBS4SP4::NCgl0935 obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SP4::NCgl0935 is introduced into the *C. glutamicum* Bp1_0112 strain by the electric pulse method. The cells are applied to the CM-Dex agar medium containing 25 μg/mL of kanamycin, and cultured at 31.5° C. It is confirmed by PCR that the grown strain is a once-recombinant strain in which pBS4SP4::NCgl0935 is incorporated into the genome by homologous recombination.

The once-recombinant strain is cultured overnight in the CM-Dex liquid medium, the culture medium is applied to the S10 agar medium, and culture is performed at 31.5° C. Among the colonies that appear, a strain that shows kanamycin susceptibility is purified on the CM-Dex agar medium. Genomic DNA is prepared from the purified strain, and used to perform nucleotide sequence analysis to confirm that P4 promoter is located upstream of the NCgl0935 gene, and the strain is designated as Dp2_0340 strain.

<4-4> Construction of Ep2_0055 Strain (FKFC14ΔpcaGH P2::NCgl0120 P8::NCgl2048 P4::NCgl0935 P3::NCgl0719 Strain)

Subsequently, by using the *Corynebacterium glutamicum* Dp2_0340 strain as a parent strain, there was constructed a strain Ep2_0055, in which the promoter region of NCgl0719 gene (sahH) encoding S-adenosyl-L-homocysteine hydrolase has been replaced with the P3 promoter, by outsourcing. The nucleotide sequence the P3 promoter is shown as SEQ ID NO: 111. The Ep2_0055 strain can also be constructed via the following procedure.

<4-4-1> Construction of Plasmid pBS4SP3::NCgl0719 for Substitution of NCgl0719 Gene Promoter PCR is performed by using the genomic DNA of the *C. glutamicum* 2256 strain as the template, and the synthetic DNAs of SEQ ID NOS: 138 and 139 as the primers to obtain a PCR product containing an upstream region of the NCgl0719 gene. Separately, PCR is performed by using the genomic DNA of the *C. glutamicum* 2256 strain as the template, and the synthetic DNAs of SEQ ID NOS: 140 and 141 as the primers to obtain a PCR product containing an N-terminus side coding region of the NCgl0719 gene. In addition, a DNA fragment of SEQ ID NO: 111 containing P3 promoter region is obtained by artificial gene synthesis. And then, PCR is performed by using the DNA fragment of SEQ ID NO: 111 as the template, and the synthetic DNAs of SEQ ID NOS: 142 and 143 as the primers to obtain a PCR product containing the P3 promoter. The sequences of SEQ ID NOS: 139 and 142 are partially complementary to each other, and the sequences of SEQ ID NOS: 140 and 143 are partially complementary to each other. Then, approximately equimolar amounts of the PCR product containing the upstream region of the NCgl0719 gene, the PCR product containing the N-terminus side coding region of the NCgl0719 gene, and the PCR product containing the P3 promoter are mixed, and inserted into the pBS4S vector (WO2007/046389) treated with BamHI and PstI by using In Fusion HD Cloning Kit (Clontech). With this DNA, competent cells of *Escherichia coli* JM109 (Takara Bio) are transformed, and the cells are applied to the LB agar medium containing 100 μM IPTG, 40 μg/mL of X-Gal, and 40 μg/mL of kanamycin, and cultured overnight. Then, white colonies that appeared are picked up, and separated into single colonies to obtain transformants. Plasmids are extracted from the obtained transformants, and one in which the target PCR product is inserted is designated as pBS4SP3::NCgl0719.

<4-4-2> Construction of Ep2_0055 Strain

Since pBS4SP3::NCgl0719 obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SP3::NCgl0719 is introduced into the *C. glutamicum* Dp2_0340 strain by the electric pulse method. The cells are applied to the CM-Dex agar medium containing 25 μg/mL of kanamycin, and cultured at 31.5° C. It is confirmed by PCR that the grown strain is a once-recombinant strain in which pBS4SP3::NCgl0719 is incorporated into the genome by homologous recombination.

The once-recombinant strain is cultured overnight in the CM-Dex liquid medium, the culture medium is applied to the S10 agar medium, and culture is performed at 31.5° C. Among the colonies that appear, a strain that shows kanamycin susceptibility is purified on the CM-Dex agar medium. Genomic DNA is prepared from the purified strain, and used to perform nucleotide sequence analysis to confirm that P3 promoter is located upstream of the NCgl0719 gene, and the strain is designated as Ep2_0055 strain.

<4-5> Construction of Ep2_0055ΔsdaA Strain (FKFC14ΔpcaGHΔsdaA P2::NCgl0120 P8::NCgl2048 P4::NCgl0935 P3::NCgl0719 Strain)

Subsequently, by using the *Corynebacterium glutamicum* Ep2_0055 strain as a parent strain, there was constructed a strain Ep2_0055ΔsdaA, which is deficient in NCgl1583 gene (sdaA) encoding L-serine deaminase.

<4-5-1> Construction of Plasmid pBS4SΔ2256sdaA for Deletion of sdaA Gene

PCR was performed by using the genomic DNA of the *C. glutamicum* 2256 strain as the template, and the synthetic DNAs of SEQ ID NOS: 148 and 149 as the primers to obtain a PCR product containing an N-terminus side coding region of the sdaA gene. Separately, PCR was performed by using the genomic DNA of the *C. glutamicum* 2256 strain as the template, and the synthetic DNAs of SEQ ID NOS: 150 and 151 as the primers to obtain a PCR product containing a C-terminus side coding region of the sdaA gene. The sequences of SEQ ID NOS: 149 and 150 are partially complementary to each other. Then, approximately equimolar amounts of the PCR product containing the N-terminus side coding region of the sdaA gene and the PCR product containing the C-terminus side coding region of the sdaA gene were mixed, and inserted into the pBS4S vector treated with BamHI and PstI by using In Fusion HD Cloning Kit (Clontech). With this DNA, competent cells of *Escherichia coli* JM109 (Takara Bio) were transformed, and the cells were applied to the LB agar medium containing 100 μM IPTG, 40 μg/mL of X-Gal, and 40 μg/mL of kanamycin, and cultured overnight. Then, white colonies that appeared were picked up, and separated into single colonies to obtain transformants. Plasmids were extracted from the obtained transformants, and one in which the target PCR product was inserted was designated as pBS4SΔ2256sdaA.

<4-5-2> Construction of Ep2_0055ΔsdaA Strain (FKFC14ΔpcaGHΔsdaA P2::NCgl0120 P8::NCgl2048 P4::NCgl0935 P3::NCgl0719 Strain)

Since pBS4SΔ2256sdaA obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256sdaA was introduced into the *C. glutamicum* Ep2_0055 strain by the electric pulse method. The cells were applied to the CM-Dex agar medium containing 25 μg/mL of kanamycin, and cultured at 31.5° C. It was confirmed by PCR that the grown strain was a once-recombinant strain in which pBS4SΔ2256sdaA was incorporated into the genome by homologous recombination. This once-recombinant strain had both the wild-type sdaA gene, and the deficient-type sdaA gene.

The once-recombinant strain was cultured overnight in the CM-Dex liquid medium, the culture broth was applied to the S10 agar medium, and culture was performed at 31.5° C. Among the colonies that appeared, a strain that showed kanamycin susceptibility was purified on the CM-Dex agar medium. Genomic DNA was prepared from the purified strain, and used to perform PCR with the synthetic DNAs of SEQ ID NOS: 152 and 153 as the primers to confirm deletion of the sdaA gene, and the strain was designated as Ep2_0055ΔsdaA strain.

<4-6> Construction of Ep2_0055ΔsdaA purH(S37F) Strain (FKFC14ΔpcaGHΔsdaA purH(S37F) P2::NCgl0120 P8::NCgl2048 P4::NCgl0935 P3::NCgl0719 Strain)

The *Corynebacterium glutamicum* FKFC14ΔpcaGH strain as a parent strain was subjected to mutagenesis with irradiation of UV to thereby construct a strain FKFC14ΔpcaGH purH(S37F). Subsequently, the *Corynebacterium glutamicum* Ep2_0055ΔsdaA strain as a parent strain was subjected to gene recombination using the genome DNA of the FKFC14ΔpcaGH purH(S37F) strain to thereby construct a strain Ep2_0055ΔsdaA purH(S37F). The FKFC14ΔpcaGH purH(S37F) and Ep2_0055ΔsdaA purH(S37F) strains harbor purH(S37F) gene, which is a mutant purH gene, instead of the wild-type purH gene. The purH (S37F) gene encodes PurH(S37F) protein, which has a mutation that the serine residue at position 37 is replaced with a phenylalanine residue. The nucleotide sequence of the corresponding wild-type purH gene is shown as SEQ ID NO: 134, and the amino acid sequence of the corresponding wild-type purH protein is shown as SEQ ID NO: 135. The nucleotide sequence of the purH(S37F) gene is shown as SEQ ID NO: 136, and the amino acid sequence of the purH(S37F) protein is shown as SEQ ID NO: 137. The Ep2_0055ΔsdaA purH(S37F) strain can also be constructed via the following procedure.

<4-6-1> Construction of Plasmid pBS4SΔ2256purH(S37F) for Introduction of purH(S37F) Mutation PCR is performed by using the genomic DNA of the C. glutamicum 2256 strain as the template, and the synthetic DNAs of SEQ ID NOS: 154 and 155 as the primers to obtain a PCR product containing an N-terminus side coding region of the purH gene. Separately, PCR is performed by using the genomic DNA of the C. glutamicum 2256 strain as the template, and the synthetic DNAs of SEQ ID NOS: 156 and 157 as the primers to obtain a PCR product containing a C-terminus side coding region of the purH gene. In addition, a DNA fragment of SEQ ID NO: 158 is obtained by artificial gene synthesis. The sequences of SEQ ID NOS: 155 and 158 are partially complementary to each other, and the sequences of SEQ ID NOS: 156 and 158 are partially complementary to each other. Then, approximately equimolar amounts of the PCR product containing the N-terminus side coding region of the purH gene, the DNA fragment of SEQ ID NO: 158, and the PCR product containing the C-terminus side coding region of the purH gene are mixed, and inserted into the pBS4S vector treated with BamHI and PstI by using In Fusion HD Cloning Kit (Clontech). With this DNA, competent cells of Escherichia coli JM109 (Takara Bio) are transformed, and the cells are applied to the LB agar medium containing 100 μM IPTG, 40 μg/mL of X-Gal, and 40 μg/mL of kanamycin, and cultured overnight. Then, white colonies that appeared are picked up, and separated into single colonies to obtain transformants. Plasmids are extracted from the obtained transformants, and one in which the target PCR product is inserted is designated as pBS4SΔ2256purH(S37F).

<4-6-2> Construction of Ep2_0055ΔsdaA purH(S37F) Strain (FKFC14ΔpcaGHΔsdaA purH(S37F) P2::NCgl0120 P8::NCgl2048 P4::NCgl0935 P3::NCgl0719 Strain)

Since pBS4SΔ2256purH(S37F) obtained above does not contain the region enabling autonomous replication of the plasmid in cells of coryneform bacteria, if coryneform bacteria are transformed with this plasmid, a strain in which this plasmid is incorporated into the genome by homologous recombination appears as a transformant, although it occurs at an extremely low frequency. Therefore, pBS4SΔ2256purH(S37F) is introduced into the C. glutamicum Ep2_0055ΔsdaA strain by the electric pulse method. The cells are applied to the CM-Dex agar medium containing 25 μg/mL of kanamycin, and cultured at 31.5° C. It is confirmed by PCR that the grown strain is a once-recombinant strain in which pBS4SΔ2256purH(S37F) is incorporated into the genome by homologous recombination. This once-recombinant strain had both the wild-type purH gene, and the S37F type purH gene.

The once-recombinant strain is cultured overnight in the CM-Dex liquid medium, the culture broth is applied to the S10 agar medium, and culture is performed at 31.5° C. Among the colonies that appeared, a strain that showed kanamycin susceptibility is purified on the CM-Dex agar medium. Genomic DNA is prepared from the purified strain, and used to perform PCR with the synthetic DNAs of SEQ ID NOS: 159 and 160 as the primers to confirm introduction of the purH(S37F) gene, and the strain is designated as Ep2_0055ΔsdaA purH(S37F) strain.

<5> Construction of Plasmid pVK9::PcspB-Omt312 for Expression of Mutant OMT Gene of Niastella koreensis The plasmid pVK9::PcspB-omt312 was obtained by outsourcing. The plasmid pVK9::PcspB-omt312 harbors a mutant OMT gene of Niastella koreensis codon-optimized for the codon usage of C. glutamicum. This mutant OMT gene encodes a mutant OMT that corresponds to the wild-type OMT of Niastella koreensis provided that a double mutation M36K/L67F has been introduced, specifically, methionine residue (M) at position 36 has been replaced with lysine residue (K) due to codon change from ATG to AAG, and leucine residue (L) at position 67 has been replaced with phenylalanine residue (F) due to codon change from TTG to TTT. This mutant OMT gene can also be referred to as "omt312 gene" and this mutant OMT can also be referred to as "OMT312". The nucleotide sequence of pVK9::PcspB-omt312 is shown as SEQ ID NO: 132, wherein omt312 gene corresponds to position 4880-5545. The amino acid sequence of OMT312 is shown as SEQ ID NO: 133. pVK9::PcspB-omt312 can also be constructed by artificial gene synthesis.

<6> Construction of Plasmid pVS7::Plac-metK for Expression of metK Gene

The plasmid pVS7::Plac-metK harbors metK gene of the C. glutamicum 2256 strain (ATCC 13869). The nucleotide sequence of the metK gene is shown as SEQ ID NO: 161, and the amino acid sequence of the MetK protein is shown as SEQ ID NO: 162. The plasmid pVS7::Plac-metK was constructed via the following procedure.

PCR was performed by using the genomic DNA of the C. glutamicum 2256 strain as the template, and the synthetic DNAs of SEQ ID NOS: 163 and 164 as the primers to obtain a PCR product containing the metK gene. Then, the PCR product was inserted into the pVS7 vector (WO2013/069634) treated with BamHI and PstI by using In Fusion HD Cloning Kit (Clontech). The pVS7 vector is a shuttle-vector for coryneform bacteria and Escherichia coli. With this DNA, competent cells of Escherichia coli JM109 (Takara Bio) were transformed, and the cells were applied to the LB agar medium containing 100 μM IPTG, 40 μg/mL of X-Gal, and 50 μg/mL of spectinomycin, and cultured overnight. Then, white colonies that appeared were picked up, and separated into single colonies to obtain transformants. Plasmids were extracted from the obtained transformants, and one in which the target PCR product was inserted was designated as pVS7::Plac-metK.

<7> Construction of Vanillic Acid-Producing Strain

A mixture of the plasmid pVK9::PcspB-omt312 and the pVS7 vector, and a mixture of the plasmid pVK9::PcspB-omt312 and the plasmid pVS7::Plac-metK were each introduced into the C. glutamicum Ep2_0055ΔsdaA purH(S37F) strain by the electric pulse method. The cells were applied to the CM-Dex agar medium containing 25 μg/mL of kanamycin and 50 μg/mL of spectinomycin, and cultured at 31.5° C. The grown strains were designated as Ep2_0055ΔsdaA purH(S37F)/pVK9::PcspB-omt312+pVS7 and Ep2_0055ΔsdaA purH(S37F)/pVK9::PcspB-omt312+pVS7::Plac-metK, respectively.

These strains were each inoculated into 4 mL of the CM-Dex liquid medium containing 25 μg/mL of kanamycin and 50 μg/mL of spectinomycin contained in a test tube, and cultured at 31.5° C. with shaking for about 16 hr. A 0.8 mL aliquot of the obtained culture broth was mixed with 0.8 mL of 40% glycerol aqueous solution to obtain a glycerol stock, and stored at −80° C.

<8> Vanillic Acid Production by *C. glutamicum* Ep2_0055ΔsdaA purH(S37F)/pVK9::PcspB-Omt312+pVS7 and Ep2_0055ΔsdaA purH(S37F)/pVK9::PcspB-Omt312+pVS7::Plac-metK Strains A 5 μL aliquot of each of the glycerol stocks of the Ep2_0055ΔsdaA purH(S37F)/pVK9::PcspB-omt312+pVS7 and Ep2_0055ΔsdaA purH(S37F)/pVK9::PcspB-omt312+pVS7::Plac-metK strains was inoculated into 0.5 mL of the CM-Dex w/o mameno medium (5 g/L of glucose, 10 g/L of Polypeptone, 10 g/L of Yeast Extract, 1 g/L of $KH_2PO_4$, 0.4 g/L of $MgSO_4 \cdot 7H_2O$, 0.01 g/L of $FeSO_4 \cdot 7H_2O$, 0.01 g/L of $MnSO_4 \cdot 7H_2O$, 3 g/L of urea, 10 μg/L of biotin, adjusted to pH 7.5 with KOH) containing 25 μg/mL of kanamycin and 50 μg/mL of spectinomycin contained in 2.0 mL DEEP WELL PLATE, and cultured at 30° C. with shaking for 16 hr as preculture. A 0.1 mL aliquot of the obtained preculture broth was inoculated into 0.4 mL of a vanillic acid production medium (75 g/L of glucose, 0.6 g/L of $MgSO_4 \cdot 7H_2O$, 6.3 g/L of $(NH_4)_2SO_4$, 2.5 g/L of $KH_2PO_4$, 12.5 mg/L of $FeSO_4 \cdot 7H_2O$, 12.5 mg/L of $MnSO_4 \cdot 4-5H_2O$, 2.5 g/L of Yeast Extract, 150 μg/L of Vitamin B1, 150 μg/L of Biotin, 6.9 g/L of Protocatechuic acid, adjusted to pH 7 with KOH, and then mixed with 30 g/L of $CaCO_3$ (sterilized with hot air at 180° C. for 3 hours)) containing 25 μg/mL of kanamycin and 50 μg/mL of spectinomycin contained in 2.0 mL DEEP WELL PLATE, and cultured at 30° C. with shaking for 24 hr.

At the completion of the culture, the concentration of vanillic acid in the medium was analyzed by using Ultra Performance Liquid Chromatography NEXERA X2 System (SHIMADZU) with the following conditions. In addition, the optical density (OD) was measured at 600 nm by using Spectra Max 190 (Molecular Devices).

Conditions of UPLC analysis

Column: KINETEX 2.6 μm XB-C18, 150×30 mm (Phenomenex)

Oven temperature: 40° C.

Mobile phase (A): 0.1% Trifluoroacetic acid

Mobile phase (B): 0.1% Trifluoroacetic acid/80% acetonitrile

Gradient program (time, A (%), B (%)): (0, 90, 10)→(3, 80, 20)

Flow rate: 1.5 ml/min

The results are shown in Table 1. The vanillic acid concentration in the medium observed for the Ep2_0055ΔsdaA purH(S37F)/pVK9::PcspB-omt312+pVS7::Plac-metK strain was about 1.04 times as high as that observed for the Ep2_0055ΔsdaA purH(S37F)/pVK9::PcspB-omt312+pVS7 strain. Also, the vanillic acid productivity per OD observed for the Ep2_0055ΔsdaA purH(S37F)/pVK9::PcspB-omt312+pVS7::Plac-metK strain was about 1.03 times as high as that observed for the Ep2_0055ΔsdaA purH(S37F)/pVK9::PcspB-omt312+pVS7 strain.

TABLE 1

Vanillic acid production by *C. glutamicum* vanillic acid-producing strains

| Strain | OD | Concentration of generated vanillic acid (mg/L) | Productivity of vanillic acid (mg/L, h, final OD) |
|---|---|---|---|
| Ep2_0055ΔsdaA purH(S37F)/ pVK9::PcspB-omt312 + pVS7 | 33.2 ± 2.2 | 820 ± 9.8 | 1.06 ± 0.059 |
| Ep2_0055ΔsdaA purH(S37F)/ pVK9::PcspB-omt312 + pVS7::Plac-metK | 32.4 ± 1.8 | 850 ± 8.0 | 1.09 ± 0.071 |

Example 2: Vanillic Acid Production by *C. glutamicum* Strain Having Enhanced Expression of metE Gene Encoding Methionine Synthase In this example, a strain having an enhanced expression of metE gene encoding methionine synthase was constructed from the *Corynebacterium glutamicum* 2256 strain (ATCC 13869) as a parent strain, and vanillic acid production was performed with the constructed strain.

<1> Construction of *C. glutamicum* Ns1_0003 Strain (FKFC14ΔpcaGH P2::NCgl0120 P8::NCgl2048 P4::NCgl0935 P3::NCgl0719 purH(S37F) Strain)

The *Corynebacterium glutamicum* Ns1_0003 strain, which corresponds to the *C. glutamicum* Ep2_0055 strain provided that the Ns1_0003 strain harbors the purH(S37F) gene, was obtained by outsourcing. The Ns1_0003 strain can also be constructed via the following procedure.

By using the Ep2_0055 strain as a parent strain, the wild-type purH gene thereof is replaced with the purH (S37F) gene in the same manner as described in Example 1<4-6-2>, and the obtained strain harboring the purH(S37F) gene is designated as Ns1_0003 strain.

<2> Construction of Plasmid pZK1::PcspB-OMT312-PmsrA-MetE-EC for Co-Expression of Mutant OMT Gene and metE Gene <2-1> Construction of Plasmid pZK1::PcspB-OMT312 pZK1::PcspB-OMT312 was constructed from pVK9::PcspB-omt312 in order to introduce the tcg0610 terminator sequence from *Corynebacterium glutamicum* ATCC 13032 and remove a known tn10 transposon targeting site. PCR was performed using synthetic DNAs of SEQ ID NOS: 175 and 176 as primers and pVK9::PcspB-omt312 as the template. This PCR product was then phosphorylated using T4 polynucleotide kinase (New England Biolabs) and the resulting phosphorylated blunt ends were self-ligated using a Quick Ligation Kit (New England Biolabs). The resulting ligation mix was transformed into *Escherichia coli* 10-beta competent cells (New England Biolabs). The transformed cell mix was applied to LB agar medium containing 25 μg/mL of kanamycin, and cultured overnight. Single colonies were picked into liquid LB medium containing kanamycin and grown overnight, and plasmids were extracted.

Sanger sequencing was performed to confirm that the sequence of the resulting plasmids was as expected, and a plasmid with the correct sequence was designated pZK1::PcspB-OMT312.

<2-2> Construction of Plasmid pZK1::PcspB-OMT312-PmsrA-MetE-EC

PCR was performed by using synthetic DNAs of SEQ ID NOS: 177 and 178 as primers and pZK1::PcspB-OMT312 as the template to amplify a vector backbone. A synthetic DNA of SEQ ID NO: 179 containing the cspB promoter, the metE gene from *Escherichia coli*, and the terminator tcg0610 from *Corynebacterium glutamicum* ATCC 13032 was obtained by outsourcing. The codon bias was optimized by weighted random selections using a *Corynebacterium glutamicum* ATCC 13032 codon usage table. This synthetic DNA was cloned into the vector backbone using a Gibson Assembly Cloning Kit (New England Biolabs) according to the manufacturer's protocols. The resulting assembly mix was transformed into *Escherichia coli* 10-beta competent cells (New England Biolabs). The transformed cell mix was applied to LB agar medium containing 25 μg/mL of kanamycin, and cultured overnight. Single colonies were picked into liquid LB medium containing kanamycin and grown overnight, and plasmids were extracted. Sanger sequencing was performed to confirm that the sequence of the resulting plasmids was as expected, and a plasmid with the correct sequence was designated pZK1::PcspB-OMT312-PmsrA-MetE-EC.

<3> Construction of Vanillic Acid-Producing Strain

*Corynebacterium glutamicum* vanillic acid-producing strains, Ns1_0003_Rg (Ns1_0003/pZK1::PcspB-omt312) and Ph2_0011_Rg (Ns1_0003/pZK1::PcspB-OMT312-PmsrA-MetE-EC), were obtained by outsourcing. These strains can also be constructed via the following procedure.

The plasmid pZK1::PcspB-omt312 and the plasmid pZK1::PcspB-OMT312-PmsrA-MetE-EC are each introduced into the *C. glutamicum* Ns1_0003 strain by the electric pulse method. The cells are applied to the CM-Dex agar medium containing 25 μg/mL of kanamycin, and cultured at 31.5° C. The grown strains are designated as Ns1_0003_Rg and Ph2_0011_Rg, respectively.

These strains are each inoculated into 4 mL of the CM-Dex liquid medium containing 25 μg/mL of kanamycin contained in a test tube, and cultured at 31.5° C. with shaking for about 16 hr. A 0.8 mL aliquot of the obtained culture broth was mixed with 0.8 mL of 40% glycerol aqueous solution to obtain a glycerol stock, and stored at −80° C.

<4> Vanillic Acid Production by *C. glutamicum* Ns1_0003_Rg and pH2_0011_Rg Strains A 5 μL aliquot of each of the glycerol stocks of the Ns1_0003_Rg and Ph2_0011_Rg strains was inoculated into 0.5 mL of the CM-Dex w/o mameno medium containing 25 μg/mL of kanamycin contained in 2.0 mL DEEP WELL PLATE, and cultured at 30° C. with shaking for 16 hr as preculture. A 0.1 mL aliquot of the obtained preculture broth was inoculated into 0.4 mL of the vanillic acid production medium containing 25 μg/mL of kanamycin contained in 2.0 mL DEEP WELL PLATE, and cultured at 30° C. with shaking for 24 hr.

At the completion of the culture, the concentration of vanillic acid in the medium was analyzed by using Ultra Performance Liquid Chromatography NEXERA X2 System (SHIMADZU) with the same conditions as described in Example 1<8>. In addition, the optical density (OD) was measured at 600 nm by using Spectra Max 190 (Molecular Devices).

The results are shown in Table 2. The vanillic acid concentration in the medium observed for the Ph2_0011_Rg strain was about 1.28 times as high as that observed for the Ns1_0003_Rg strain. Also, the vanillic acid productivity per OD observed for the Ph2_0011_Rg strain was about 1.25 times as high as that observed for the Ns1_0003_Rg strain.

TABLE 2

Vanillic acid production by *C. glutamicum* vanillic acid-producing strains

| Strain | OD | Concentration of generated vanillic acid (mg/L) | Productivity of vanillic acid (mg/L, h, final OD) |
|---|---|---|---|
| Ns1_0003_Rg | 30.6 ± 0.0 | 633 ± 3.1 | 0.86 ± 0.004 |
| Ph2_0011_Rg | 31.2 ± 0.9 | 808 ± 5.6 | 1.08 ± 0.023 |

Example 3: Vanillic Acid Production by *C. glutamicum* Strain Having Enhanced Expression of metH Gene Encoding Methionine Synthase In this example, a strain having an enhanced expression of metH gene encoding methionine synthase was constructed from the *Corynebacterium glutamicum* 2256 strain (ATCC 13869) as a parent strain, and vanillic acid production was performed with the constructed strain.

<1> Construction of Plasmid pZK1::PcspB-OMT312-PmsrA-MetH-CG for Co-Expression of Mutant OMT Gene and metH Gene PCR was performed by using synthetic DNAs of SEQ ID NOS: 177 and 178 as primers and pZK1::PcspB-OMT312 as the template to amplify a vector backbone. A synthetic DNA of SEQ ID NO: 180 containing the cspB promoter, the metH gene (cg1701) from *Corynebacterium glutamicum*, and the terminator tcg0610 from *Corynebacterium glutamicum* ATCC 13032 was obtained by outsourcing. The codon bias was optimized by weighted random selections using a *Corynebacterium glutamicum* ATCC 13032 codon usage table. This synthetic DNA was cloned into the vector backbone using a Gibson Assembly Cloning Kit (New England Biolabs) according to the manufacturer's protocols. The resulting assembly mix was transformed into *Escherichia coli* 10-beta competent cells (New England Biolabs). The transformed cell mix was applied to LB agar medium containing 25 μg/mL of kanamycin, and cultured overnight. Single colonies were picked into liquid LB medium containing kanamycin and grown overnight, and plasmids were extracted. Sanger sequencing was performed to confirm that the sequence of the resulting plasmids was as expected, and a plasmid with the correct sequence was designated pZK1::PcspB-OMT312-PmsrA-MetH-CG.

<2> Construction of Vanillic Acid-Producing Strain

*Corynebacterium glutamicum* vanillic acid-producing strains, Ns1_0003_Rg (Ns1_0003/pZK1::PcspB-omt312) and Ph2_0003_Rg (Ns1_0003/pZK1::PcspB-OMT312-PmsrA-MetH-CG), were obtained by outsourcing. These strains can also be constructed via the following procedure.

The plasmid pZK1::PcspB-omt312 and the plasmid pZK1::PcspB-OMT312-PmsrA-MetH-CG are each introduced into the *C. glutamicum* Ns1_0003 strain by the electric pulse method. The cells are applied to the CM-Dex agar medium containing 25 μg/mL of kanamycin, and cultured at 31.5° C. The grown strains are designated as Ns1_0003_Rg and Ph2_0003_Rg, respectively.

These strains are each inoculated into 4 mL of the CM-Dex liquid medium containing 25 μg/mL of kanamycin contained in a test tube, and cultured at 31.5° C. with shaking for about 16 hr. A 0.8 mL aliquot of the obtained culture broth was mixed with 0.8 mL of 40% glycerol aqueous solution to obtain a glycerol stock, and stored at −80° C.

<4> Vanillic Acid Production by *C. glutamicum* Ns1_0003_Rg and pH2_0003_Rg Strains A 5 µL aliquot of each of the glycerol stocks of the Ns1_0003_Rg and Ph2_0003_Rg strains was inoculated into 0.5 mL of the CM-Dex w/o mameno medium containing 25 µg/mL of kanamycin contained in 2.0 mL DEEP WELL PLATE, and cultured at 30° C. with shaking for 16 hr as preculture. A 0.1 mL aliquot of the obtained preculture broth was inoculated into 0.4 mL of the vanillic acid production medium containing 25 µg/mL of kanamycin contained in 2.0 mL DEEP WELL PLATE, and cultured at 30° C. with shaking for 24 hr.

At the completion of the culture, the concentration of vanillic acid in the medium was analyzed by using Ultra Performance Liquid Chromatography NEXERA X2 System (SHIMADZU) with the same conditions as described in Example 1<8>. In addition, the optical density (OD) was measured at 600 nm by using Spectra Max 190 (Molecular Devices).

The results are shown in Table 3. The vanillic acid concentration in the medium observed for the Ph2_0003_Rg strain was about 1.15 times as high as that observed for the Ns1_0003_Rg strain. Also, the vanillic acid productivity per OD observed for the Ph2_0003_Rg strain was about 1.16 times as high as that observed for the Ns1_0003_Rg strain.

TABLE 3

Vanillic acid production by *C. glutamicum* vanillic acid-producing strains

| Strain | OD | Concentration of generated vanillic acid (mg/L) | Productivity of vanillic acid (mg/L, h, final OD) |
|---|---|---|---|
| Ns1_0003_Rg | 30.6 ± 0.0 | 633 ± 3.1 | 0.86 ± 0.004 |
| Ph2_0003_Rg | 30.2 ± 0.4 | 725 ± 7.3 | 1.00 ± 0.022 |

Example 4: Vanillic Acid Production by *C. glutamicum* Strain Having Enhanced Expression of metF Gene Encoding 5,10-Methylenetetrahydrofolate Reductase In this example, a strain having an enhanced expression of metF gene encoding 5,10-methylenetetrahydrofolate reductase was constructed from the *Corynebacterium glutamicum* 2256 strain (ATCC 13869) as a parent strain, and vanillic acid production was performed with the constructed strain.

<1> Construction of Plasmids pZK1::PcspB-OMT312-PmsrA-MetF-CG and pZK1::PcspB-OMT312-PmsrA-MetF-SC for Co-Expression of Mutant OMT Gene and metE Gene <1-1> Construction of Plasmid pZK1::PcspB-OMT312-PmsrA-MetF-CG PCR was performed by using synthetic DNAs of SEQ ID NOS: 177 and 178 as primers and pZK1::PcspB-OMT312 as the template to amplify a vector backbone. A synthetic DNA of SEQ ID NO: 181 containing the cspB promoter, the metF gene (NCgl2091, partial) from *Corynebacterium glutamicum*, and the terminator tcg0610 from *Corynebacterium glutamicum* ATCC 13032 was obtained by outsourcing. The codon bias was optimized by weighted random selections using a *Corynebacterium glutamicum* ATCC 13032 codon usage table. This metF gene encodes the amino acid sequence shown as SEQ ID NO: 172, which is a partial amino acid sequence of the MetF protein of the *C. glutamicum* ATCC 13869 strain. This synthetic DNA was cloned into the vector backbone using a Gibson Assembly Cloning Kit (New England Biolabs) according to the manufacturer's protocols. The resulting assembly mix was transformed into *Escherichia coli* 10-beta competent cells (New England Biolabs). The transformed cell mix was applied to LB agar medium containing 25 µg/mL of kanamycin, and cultured overnight. Single colonies were picked into liquid LB medium containing kanamycin and grown overnight, and plasmids were extracted. Sanger sequencing was performed to confirm that the sequence of the resulting plasmids was as expected, and a plasmid with the correct sequence was designated pZK1::PcspB-OMT312-PmsrA-MetF-CG.

<1-2> Construction of the Plasmid pZK1::PcspB-OMT312-PmsrA-MetF-SC

PCR was performed by using synthetic DNAs of SEQ ID NOS: 177 and 178 as primers and pZK1::PcspB-OMT312 as the template to amplify a vector backbone. A synthetic DNA of SEQ ID NO: 182 containing the cspB promoter, the metF gene (MET13) from *Saccharomyces cerevisiae*, and the terminator tcg0610 from *Corynebacterium glutamicum* ATCC 13032 was obtained by outsourcing. The codon bias was optimized by weighted random selections using a *Corynebacterium glutamicum* ATCC 13032 codon usage table. This synthetic DNA was cloned into the vector backbone using a Gibson Assembly Cloning Kit (New England Biolabs) according to the manufacturer's protocols. The resulting assembly mix was transformed into *Escherichia coli* 10-beta competent cells (New England Biolabs). The transformed cell mix was applied to LB agar medium containing 25 µg/mL of kanamycin, and cultured overnight. Single colonies were picked into liquid LB medium containing kanamycin and grown overnight, and plasmids were extracted. Sanger sequencing was performed to confirm that the sequence of the resulting plasmids was as expected, and a plasmid with the correct sequence was designated pZK1::PcspB-OMT312-PmsrA-MetF-SC.

<2> Construction of Vanillic Acid-Producing Strain

*Corynebacterium glutamicum* vanillic acid-producing strains, Ns1_0003_Rg (Ns1_0003/pZK1::PcspB-omt312), Ph2_0028_Rg (Ns1_0003/pZK1::PcspB-OMT312-PmsrA-MetF-CG), and Ph2_0009_Rg (Ns1_0003/pZK1::PcspB-OMT312-PmsrA-MetF-SC), were obtained by outsourcing. These strains can also be constructed via the following procedure.

The plasmid pZK1::PcspB-omt312, the plasmid pZK1::PcspB-OMT312-PmsrA-MetF-CG, and the plasmid pZK1::PcspB-OMT312-PmsrA-MetF-SC are each introduced into the *C. glutamicum* Ns1_0003 strain by the electric pulse method. The cells are applied to the CM-Dex agar medium containing 25 µg/mL of kanamycin, and cultured at 31.5° C. The grown strains are designated as Ns1_0003_Rg, Ph2_0028_Rg, and Ph2_0009_Rg, respectively.

These strains are each inoculated into 4 mL of the CM-Dex liquid medium containing 25 µg/mL of kanamycin contained in a test tube, and cultured at 31.5° C. with shaking for about 16 hr. A 0.8 mL aliquot of the obtained culture broth was mixed with 0.8 mL of 40% glycerol aqueous solution to obtain a glycerol stock, and stored at −80° C.

<4> Vanillic Acid Production by *C. glutamicum* Ns1_0003_Rg, pH2_0028_Rg, and pH2_0009_Rg Strains A 5 µL aliquot of each of the glycerol stocks of the Ns1_0003_Rg, Ph2_0028_Rg, and Ph2_0009_Rg strains was inoculated into 0.5 mL of the CM-Dex w/o mameno medium containing 25 µg/mL of kanamycin contained in 2.0 mL DEEP WELL PLATE, and cultured at 30° C. with shaking for 16 hr as preculture. A 0.1 mL aliquot of the obtained preculture broth was inoculated into 0.4 mL of the vanillic acid production medium containing 25 μg/mL of kanamycin contained in 2.0 mL DEEP WELL PLATE, and cultured at 30° C. with shaking for 24 hr.

At the completion of the culture, the concentration of vanillic acid in the medium was analyzed by using Ultra Performance Liquid Chromatography NEXERA X2 System (SHIMADZU) with the same conditions as described in Example 1<8>. In addition, the optical density (OD) was measured at 600 nm by using Spectra Max 190 (Molecular Devices).

The results are shown in Table 4. The vanillic acid concentration in the medium observed for the Ph2_0028_Rg strain was about 1.25 times as high as that observed for the Ns1_0003_Rg strain. Also, the vanillic acid productivity per OD observed for the Ph2_0028_Rg strain was about 1.26 times as high as that observed for the Ns1_0003_Rg strain. The vanillic acid concentration in the medium observed for the Ph2_0009_Rg strain was about 1.34 times as high as that observed for the Ns1_0003_Rg strain. Also, the vanillic acid productivity per OD observed for the Ph2_0009_Rg strain was about 1.21 times as high as that observed for the Ns1_0003_Rg strain.

TABLE 4

Vanillic acid production by C. glutamicum vanillic acid-producing strains

| Strain | OD | Concentration of generated vanillic acid (mg/L) | Productivity of vanillic acid (mg/L, h, final OD) |
|---|---|---|---|
| Ns1_0003_Rg | 30.6 ± 0.0 | 633 ± 3.1 | 0.86 ± 0.004 |
| Ph2_0028_Rg | 30.4 ± 0.4 | 791 ± 5.6 | 1.09 ± 0.011 |
| Ph2_0009_Rg | 33.8 ± 1.3 | 845 ± 18.0 | 1.04 ± 0.061 |

INDUSTRIAL APPLICABILITY

According to the present invention, an ability of a microorganism for producing an objective substance such as vanillin and vanillic acid can be improved, and the objective substance can be efficiently produced.

EXPLANATION OF SEQUENCE LISTING

SEQ ID NOS:
1: Nucleotide sequence of aroG gene of *Escherichia coli* MG1655
2: Amino acid sequence of AroG protein of *Escherichia coli* MG1655
3: Nucleotide sequence of aroB gene of *Escherichia coli* MG1655
4: Amino acid sequence of AroB protein of *Escherichia coli* MG1655
5: Nucleotide sequence of aroD gene of *Escherichia coli* MG1655
6: Amino acid sequence of AroD protein of *Escherichia coli* MG1655
7: Nucleotide sequence of asbF gene of *Bacillus thuringiensis* BMB171
8: Amino acid sequence of AsbF protein of *Bacillus thuringiensis* BMB171
9: Nucleotide sequence of tyrR gene of *Escherichia coli* MG1655
10: Amino acid sequence of TyrR protein of *Escherichia coli* MG1655
11-14: Nucleotide sequences of transcript variants 1 to 4 of OMT gene of *Homo sapiens*
15: Amino acid sequence of OMT isoform (MB-COMT) of *Homo sapiens*
16: Amino acid sequence of OMT isoform (S-COMT) of *Homo sapiens*
17: Nucleotide sequence of ACAR gene of *Nocardia brasiliensis*
18: Amino acid sequence of ACAR protein of *Nocardia brasiliensis*
19: Nucleotide sequence of ACAR gene of *Nocardia brasiliensis*
20: Amino acid sequence of ACAR protein of *Nocardia brasiliensis*
21: Nucleotide sequence of entD gene of *Escherichia coli* MG1655
22: Amino acid sequence of EntD protein of *Escherichia coli* MG1655
23: Nucleotide sequence of PPT gene of *Corynebacterium glutamicum* ATCC 13032
24: Amino acid sequence of PPT protein of *Corynebacterium glutamicum* ATCC 13032
25: Nucleotide sequence of vanK gene of *Corynebacterium glutamicum* 2256 (ATCC 13869)
26: Amino acid sequence of VanK protein of *Corynebacterium glutamicum* 2256 (ATCC 13869)
27: Nucleotide sequence of pcaK gene of *Corynebacterium glutamicum* 2256 (ATCC 13869)
28: Amino acid sequence of PcaK protein of *Corynebacterium glutamicum* 2256 (ATCC 13869)
29: Nucleotide sequence of vanA gene of *Corynebacterium glutamicum* 2256 (ATCC 13869)
30: Amino acid sequence of VanA protein of *Corynebacterium glutamicum* 2256 (ATCC 13869)
31: Nucleotide sequence of vanB gene of *Corynebacterium glutamicum* 2256 (ATCC 13869)
32: Amino acid sequence of VanB protein of *Corynebacterium glutamicum* 2256 (ATCC 13869)
33: Nucleotide sequence of pcaG gene of *Corynebacterium glutamicum* ATCC 13032
34: Amino acid sequence of PcaG protein of *Corynebacterium glutamicum* ATCC 13032
35: Nucleotide sequence of pcaH gene of *Corynebacterium glutamicum* ATCC 13032
36: Amino acid sequence of PcaH protein of *Corynebacterium glutamicum* ATCC 13032
37: Nucleotide sequence of yqhD gene of *Escherichia coli* MG1655
38: Amino acid sequence of YqhD protein of *Escherichia coli* MG1655
39: Nucleotide sequence of NCgl0324 gene of *Corynebacterium glutamicum* 2256 (ATCC 13869)
40: Amino acid sequence of NCgl0324 protein of *Corynebacterium glutamicum* 2256 (ATCC 13869)
41: Nucleotide sequence of NCgl0313 gene of *Corynebacterium glutamicum* 2256 (ATCC 13869)
42: Amino acid sequence of NCgl0313 protein of *Corynebacterium glutamicum* 2256 (ATCC 13869)
43: Nucleotide sequence of NCgl2709 gene of *Corynebacterium glutamicum* 2256 (ATCC 13869)
44: Amino acid sequence of NCgl2709 protein of *Corynebacterium glutamicum* 2256 (ATCC 13869)
45: Nucleotide sequence of NCgl0219 gene of *Corynebacterium glutamicum* ATCC 13032

46: Amino acid sequence of NCgl0219 protein of *Corynebacterium glutamicum* ATCC 13032
47: Nucleotide sequence of NCgl2382 gene of *Corynebacterium glutamicum* ATCC 13032
48: Amino acid sequence of NCgl2382 protein of *Corynebacterium glutamicum* ATCC 13032
49: Nucleotide sequence of aroE gene of *Escherichia coli* MG1655
50: Amino acid sequence of AroE protein of *Escherichia coli* MG1655
51-84: Primers
85: Nucleotide sequence of DNA fragment containing P2 promoter region
86 and 87: Primers
88: Nucleotide sequence of cysI gene of *Corynebacterium glutamicum* 2256 (ATCC 13869)
89: Amino acid sequence of CysI protein of *Corynebacterium glutamicum* 2256 (ATCC 13869)
90: Nucleotide sequence of cysX gene of *Corynebacterium glutamicum* 2256 (ATCC 13869)
91: Amino acid sequence of CysX protein of *Corynebacterium glutamicum* 2256 (ATCC 13869)
92: Nucleotide sequence of cysH gene of *Corynebacterium glutamicum* 2256 (ATCC 13869)
93: Amino acid sequence of CysH protein of *Corynebacterium glutamicum* 2256 (ATCC 13869)
94: Nucleotide sequence of cysD gene of *Corynebacterium glutamicum* 2256 (ATCC 13869)
95: Amino acid sequence of CysD protein of *Corynebacterium glutamicum* 2256 (ATCC 13869)
96: Nucleotide sequence of cysN gene of *Corynebacterium glutamicum* 2256 (ATCC 13869)
97: Amino acid sequence of CysN protein of *Corynebacterium glutamicum* 2256 (ATCC 13869)
98: Nucleotide sequence of cysY gene of *Corynebacterium glutamicum* 2256 (ATCC 13869)
99: Amino acid sequence of CysY protein of *Corynebacterium glutamicum* 2256 (ATCC 13869)
100: Nucleotide sequence of cysZ gene of *Corynebacterium glutamicum* 2256 (ATCC 13869)
101: Amino acid sequence of CysZ protein of *Corynebacterium glutamicum* 2256 (ATCC 13869)
102: Nucleotide sequence of fpr2 gene of *Corynebacterium glutamicum* 2256 (ATCC 13869)
103: Amino acid sequence of Fpr2 protein of *Corynebacterium glutamicum* 2256 (ATCC 13869)
104: Nucleotide sequence of cysR gene of *Corynebacterium glutamicum* 2256 (ATCC 13869)
105: Amino acid sequence of CysR protein of *Corynebacterium glutamicum* 2256 (ATCC 13869)
106: Nucleotide sequence of ssuR gene of *Corynebacterium glutamicum* 2256 (ATCC 13869)
107: Amino acid sequence of SsuR protein of *Corynebacterium glutamicum* 2256 (ATCC 13869)
108: Nucleotide sequence containing P2 promoter
109: Nucleotide sequence containing P4 promoter
110: Nucleotide sequence containing P8 promoter
111: Nucleotide sequence containing P3 promoter
112-115: Primers
116: Nucleotide sequence of DNA fragment containing P8 promoter region
117 and 118: Primers
119: Nucleotide sequence of NCgl2048 gene of *Corynebacterium glutamicum* 2256 (ATCC 13869)
120: Amino acid sequence of NCgl2048 protein of *Corynebacterium glutamicum* 2256 (ATCC 13869)
121-124: Primers
125: Nucleotide sequence of DNA fragment containing P4 promoter region
126 and 127: Primers
128: Nucleotide sequence of eno gene of *Corynebacterium glutamicum* 2256 (ATCC 13869)
129: Amino acid sequence of Eno protein of *Corynebacterium glutamicum* 2256 (ATCC 13869)
130: Nucleotide sequence of OMT gene of *Niastella koreensis*
131: Amino acid sequence of OMT of *Niastella koreensis*
132: Nucleotide sequence of pVK9::PcspB-omt312
133: Amino acid sequence of OMT312
134: Nucleotide sequence of purH gene of *Corynebacterium glutamicum* 2256 (ATCC 13869)
135: Amino acid sequence of PurH protein of *Corynebacterium glutamicum* 2256 (ATCC 13869)
136: Nucleotide sequence of purH(S37F) gene (mutant purH gene)
137: Amino acid sequence of purH(S37F) protein (mutant purH protein)
138-143: Primers
144: Nucleotide sequence of sahH gene of *Corynebacterium glutamicum* 2256 (ATCC 13869)
145: Amino acid sequence of SahH protein of *Corynebacterium glutamicum* 2256 (ATCC 13869)
146: Nucleotide sequence of sdaA gene of *Corynebacterium glutamicum* 2256 (ATCC 13869)
147: Amino acid sequence of SdaA protein of *Corynebacterium glutamicum* 2256 (ATCC 13869)
148-157: Primers
158: Nucleotide sequence of DNA fragment
159 and 160: Primers
161: Nucleotide sequence of metK gene of *Corynebacterium glutamicum* 2256 (ATCC 13869)
162: Amino acid sequence of MetK protein of *Corynebacterium glutamicum* 2256 (ATCC 13869)
163 and 164: Primers
165: Nucleotide sequence of metE gene of *Escherichia coli* MG1655
166: Amino acid sequence of MetE protein of *Escherichia coli* MG1655
167: Nucleotide sequence of metH gene of *Escherichia coli* MG1655
168: Amino acid sequence of MetH protein of *Escherichia coli* MG1655
169: Nucleotide sequence of metH gene of *Corynebacterium glutamicum* ATCC 13032
170: Amino acid sequence of MetH protein of *Corynebacterium glutamicum* ATCC 13032
171: Nucleotide sequence of partial metF gene of *Corynebacterium glutamicum* 2256 (ATCC 13869)
172: Amino acid sequence of partial MetF protein of *Corynebacterium glutamicum* 2256 (ATCC 13869)
173: Nucleotide sequence of metF gene of *Saccharomyces cerevisiae* S288c
174: Amino acid sequence of MetF protein of *Saccharomyces cerevisiae* S288c
175-178: Primers
179-182: Nucleotide sequences of DNA fragment
183: Nucleotide sequence of metF gene of *Corynebacterium glutamicum* 2256 (ATCC 13869)
184: Amino acid sequence of MetF protein of *Corynebacterium glutamicum* 2256 (ATCC 13869)

The invention claimed is:

1. A method for producing an objective substance, the method comprising:
producing the objective substance by using a microorganism having an ability to produce the objective substance,
wherein the microorganism has been modified so that the activity of an S-adenosylmethionine cycle enzyme is increased as compared with a non-modified microorganism,
wherein the microorganism is a coryneform bacterium,
wherein the S-adenosylmethionine cycle enzyme is a combination of methionine adenosyltransferase and 5,10-methylenetetrahydrofolate reductase, and optionally may include methionine synthase; and
wherein the objective substance is selected from metabolites the biosynthesis of which requires S-adenosylmethionine selected from the group consisting of vanillin, vanillic acid, mugineic acid, ferulic acid, polyamine, guaiacol, 4-vinylguaiacol, 4-ethylguaiacol, creatine, and combinations thereof;
wherein said producing comprises:
cultivating the microorganism in a culture medium comprising a carbon source so that the objective substance is produced and accumulates in the culture medium, or
converting a precursor of the objective substance into the objective substance by:
cultivating the microorganism in a culture medium comprising the precursor so that the objective substance is produced and accumulates in the culture medium, or
allowing cells of the microorganism to act on the precursor in a reaction mixture so that the objective substance is produced and accumulates in the reaction mixture.

2. The method according to claim 1, wherein the cells are present in a culture broth of the microorganism, collected from a culture broth of the microorganism, present in a processed product of a culture broth of the microorganism, present in a processed product of the cells collected from a culture broth of the microorganism, or a combination thereof.

3. The method according to claim 1, wherein the precursor is selected from the group consisting of protocatechuic acid, protocatechualdehyde, L-tryptophan, L-histidine, L-phenylalanine, L-tyrosine, L-arginine, L-ornithine, glycine, and combinations thereof.

4. The method according to claim 1, the method further comprising collecting the objective substance.

5. The method according to claim 1, wherein the methionine adenosyltransferase is encoded by an metK gene, the methionine synthase is encoded by an metH gene and/or an metE gene, and the 5,10-methylenetetrahydrofolate reductase is encoded by an metF gene.

6. The method according to claim 5, wherein:
the metK gene encodes a protein selected from the group consisting of:
(1a) a protein comprising the amino acid sequence of SEQ ID NO: 162,
(1b) a protein comprising the amino acid sequence of SEQ ID NO: 162 that includes substitution, deletion, insertion, and/or addition of 1 to 10 amino acid residues, and wherein said protein has methionine adenosyltransferase activity, and
(1c) a protein comprising an amino acid sequence having an identity of 90% or higher to the amino acid sequence of SEQ ID NO: 162, and wherein said protein has methionine adenosyltransferase activity;
the metH gene encodes a protein selected from the group consisting of:
(2a) a protein comprising the amino acid sequence of SEQ ID NO: 168 or 170,
(2b) a protein comprising the amino acid sequence of SEQ ID NO: 168 or 170 that includes substitution, deletion, insertion, and/or addition of 1 to 10 amino acid residues, and wherein said protein has methionine synthase activity, and
(2c) a protein comprising an amino acid sequence having an identity of 90% or higher to the amino acid sequence of SEQ ID NO: 168 or 170, and wherein said protein has methionine synthase activity;
the metE gene encodes a protein selected from the group consisting of:
(3a) a protein comprising the amino acid sequence of SEQ ID NO: 166,
(3b) a protein comprising the amino acid sequence of SEQ ID NO: 166 that includes substitution, deletion, insertion, and/or addition of 1 to 10 amino acid residues, and wherein said protein has methionine synthase activity, and
(3c) a protein comprising an amino acid sequence showing an identity of 90% or higher to the amino acid sequence of SEQ ID NO: 166, and wherein said protein has methionine synthase activity; and
the metF gene encodes a protein selected from the group consisting of:
(4a) a protein comprising the amino acid sequence of SEQ ID NO: 172, 174, or 184,
(4b) a protein comprising the amino acid sequence of SEQ ID NO: 172, 174, or 184 that includes substitution, deletion, insertion, and/or addition of 1 to 10 amino acid residues, and wherein said protein has 5,10-methylenetetrahydrofolate reductase activity, and
(4c) a protein comprising an amino acid sequence having an identity of 90% or higher to the amino acid sequence of SEQ ID NO: 172, 174, or 184, and wherein said protein has 5,10-methylenetetrahydrofolate reductase activity.

7. The method according to claim 1, wherein the activity of the S-adenosylmethionine cycle enzyme is increased by increasing the expression of a gene encoding the S-adenosylmethionine cycle enzyme.

8. The method according to claim 7, wherein the expression of the gene encoding the S-adenosylmethionine cycle enzyme is increased by increasing the copy number of the gene and/or modifying an expression control sequence of the gene.

9. The method according to claim 1, wherein the microorganism is a bacterium belonging to the genus *Corynebacterium*.

10. The method according to claim 9, wherein the microorganism is *Corynebacterium glutamicum*.

11. The method according to claim 1, wherein the microorganism has been further modified so that the activity of an enzyme that is involved in the biosynthesis of the objective substance is increased as compared with a non-modified microorganism.

12. The method according to claim 11, wherein the enzyme that is involved in the biosynthesis of the objective substance is selected from the group consisting of 3-deoxy-D-arabino-heptulosonic acid 7-phosphate synthase, 3-dehydroquinate synthase, 3-dehydroquinate dehydratase, 3-dehydroshikimate dehydratase, O-methyltransferase, aromatic aldehyde oxidoreductase, and combinations thereof.

13. The method according to claim 1, wherein the microorganism has been further modified so that the activity of phosphopantetheinyl transferase is increased as compared with a non-modified microorganism.

14. The method according to claim 1, wherein the microorganism has been further modified so that the activity of an enzyme that is involved in the by-production of a substance other than the objective substance is reduced as compared with a non-modified microorganism.

15. The method according to claim 14, wherein the enzyme that is involved in the by-production of a substance other than the objective substance is selected from the group consisting of vanillate demethylase, protocatechuate 3,4-dioxygenase, alcohol dehydrogenase, shikimate dehydrogenase, and combinations thereof.

16. The method according to claim 1, wherein the microorganism has been further modified so that the activity of an L-cysteine biosynthesis enzyme is increased as compared with a non-modified microorganism.

17. The method according to claim 16, wherein the L-cysteine biosynthesis enzyme is selected from the group consisting of proteins encoded by a cysI gene, cysX gene, cysH gene, cysD gene, cysN gene, cysY gene, cysZ gene, fpr2 gene, and combinations thereof.

18. The method according to claim 16, wherein the activity of the L-cysteine biosynthesis enzyme is increased by increasing the activity of a protein encoded by a cysR gene.

19. The method according to claim 1, wherein the microorganism has been further modified so that the activity of a protein encoded by an NCgl2048 gene is reduced as compared with a non-modified microorganism.

20. The method according to claim 1, wherein the microorganism has been further modified so that the activity of enolase is reduced as compared with a non-modified microorganism.

21. A method for producing vanillin, the method comprising:
producing vanillic acid by the method according to claim 1; and
converting said vanillic acid to vanillin.

* * * * *